(12) United States Patent
Dudley et al.

(10) Patent No.: US 9,132,089 B2
(45) Date of Patent: *Sep. 15, 2015

(54) PHARMACEUTICAL COMPOSITION AND METHOD FOR TREATING HYPOGONADISM

(71) Applicants: Besins Healthcare Inc., Herndon, VA (US); Unimed Pharmaceuticals, LLC, Marietta, GA (US)

(72) Inventors: Robert E. Dudley, Kenilworth, IL (US); Dominique Drouin, Verrieres le Buisson (FR)

(73) Assignees: BESINS HEALTHCARE INC., Herndon, VA (US); UNIMED PHARMACEUTICALS, LLC, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/942,245

(22) Filed: Jul. 15, 2013

(65) Prior Publication Data

US 2013/0303501 A1    Nov. 14, 2013

Related U.S. Application Data

(63) Continuation of application No. 10/867,445, filed on Jun. 14, 2004, now abandoned, which is a continuation of application No. 10/248,267, filed on Jan. 3, 2003, now abandoned, which is a continuation of application No. 09/651,777, filed on Aug. 30, 2000, now Pat. No. 6,503,894.

(51) Int. Cl.
| | |
|---|---|
| *A61K 31/568* | (2006.01) |
| *A61K 31/565* | (2006.01) |
| *A61K 31/475* | (2006.01) |
| *A61K 31/485* | (2006.01) |
| *A61K 31/52* | (2006.01) |
| *A61K 31/557* | (2006.01) |
| *A61K 47/10* | (2006.01) |
| *A61K 47/12* | (2006.01) |
| *A61K 47/14* | (2006.01) |
| *A61K 9/06* | (2006.01) |
| *A61K 9/00* | (2006.01) |
| *A61K 31/5685* | (2006.01) |

(52) U.S. Cl.
CPC ............ *A61K 9/06* (2013.01); *A61K 9/0014* (2013.01); *A61K 31/565* (2013.01); *A61K 31/568* (2013.01); *A61K 47/10* (2013.01); *A61K 47/12* (2013.01); *A61K 47/14* (2013.01); *A61K 31/5685* (2013.01)

(58) Field of Classification Search
CPC ........... A61K 2300/00; A61K 31/568; A61K 31/5685; A61K 47/10; A61K 9/006; A61K 31/565; A61K 31/415; A61K 31/475; A61K 31/485; A61K 31/52; A61K 31/557; A61K 47/12; A61K 47/14; A61K 9/0014; A61K 9/06

See application file for complete search history.

(56) References Cited

U.S. PATENT DOCUMENTS

| | | |
|---|---|---|
| 2,155,658 A | 4/1939 | Herrman et al. |
| 3,068,188 A | 12/1962 | Beste et al. |
| 3,121,042 A | 2/1964 | Ercoli |
| 3,164,520 A | 1/1965 | Huber |
| 3,218,283 A | 11/1965 | Miller |
| 3,887,699 A | 6/1975 | Yolles |
| 3,888,995 A | 6/1975 | Katz et al. |
| 3,913,789 A | 10/1975 | Miller |
| 3,939,111 A | 2/1976 | Schollenberger et al. |
| 3,989,816 A | 11/1976 | Rajadhyaksha |
| 4,009,254 A | 2/1977 | Renold |
| 4,078,060 A | 3/1978 | Benson et al. |
| 4,083,973 A | 4/1978 | Van der Vies |
| 4,161,948 A | 7/1979 | Bichon |
| 4,197,316 A | 4/1980 | Yu et al. |
| 4,299,826 A | 11/1981 | Luedders |
| 4,346,709 A | 8/1982 | Schmitt |
| 4,424,363 A | 1/1984 | Plath et al. |
| 4,440,777 A | 4/1984 | Zupan |
| 4,442,094 A | 4/1984 | Atkinson et al. |
| 4,447,562 A | 5/1984 | Ivani |
| 4,478,822 A | 10/1984 | Haslam et al. |
| 4,496,455 A | 1/1985 | Linder et al. |
| 4,496,556 A | 1/1985 | Orentreich |
| 4,557,934 A | 12/1985 | Cooper |
| 4,563,473 A | 1/1986 | Hofman et al. |
| 4,615,697 A | 10/1986 | Robinson |
| 4,631,188 A | 12/1986 | Stoy et al. |

(Continued)

FOREIGN PATENT DOCUMENTS

| | | |
|---|---|---|
| AU | 4998490 | 9/1990 |
| AU | 9141391 | 6/1992 |

(Continued)

OTHER PUBLICATIONS

U.S. Appl. No. 13/965,499, Aug. 2013, Dudley et al.*

(Continued)

*Primary Examiner* — Kara R McMillian

(74) *Attorney, Agent, or Firm* — Lisa V. Mueller; Michael Best & Friedrich LLP

(57) ABSTRACT

A pharmaceutical composition useful for treating hypogonadism is disclosed. The composition comprises an androgenic or anabolic steroid, a C1-C4 alcohol, a penetration enhancer such as isopropyl myristate, and water. Also disclosed is a method for treating hypogonadism utilizing the composition.

7 Claims, 40 Drawing Sheets

(56) References Cited

U.S. PATENT DOCUMENTS

| | | |
|---|---|---|
| 4,663,157 A | 5/1987 | Brock |
| 4,670,254 A | 6/1987 | Kamishita |
| 4,683,242 A | 7/1987 | Poser |
| 4,690,775 A | 9/1987 | Schott et al. |
| 4,695,465 A | 9/1987 | Kigasawa et al. |
| 4,699,779 A | 10/1987 | Palinczar |
| 4,704,282 A | 11/1987 | Campbell et al. |
| 4,725,439 A | 2/1988 | Campbell et al. |
| 4,745,160 A | 5/1988 | Churchill et al. |
| 4,767,627 A | 8/1988 | Caldwell et al. |
| 4,780,320 A | 10/1988 | Baker |
| 4,788,062 A | 11/1988 | Gale et al. |
| 4,791,099 A | 12/1988 | Aroonsakul |
| 4,820,724 A | 4/1989 | Nimni |
| 4,855,305 A | 8/1989 | Cohen |
| 4,861,764 A | 8/1989 | Samour et al. |
| 4,863,911 A | 9/1989 | Anderson et al. |
| 4,863,970 A | 9/1989 | Patel et al. |
| 4,867,982 A | 9/1989 | Campbell et al. |
| 4,906,169 A | 3/1990 | Chien et al. |
| 4,919,937 A | 4/1990 | Mauvais-Jarvis et al. |
| 4,920,203 A | 4/1990 | Tang et al. |
| 4,946,870 A | 8/1990 | Partain et al. |
| 4,954,487 A | 9/1990 | Cooper et al. |
| 4,981,696 A | 1/1991 | Loomis et al. |
| 4,994,265 A | 2/1991 | White |
| 5,013,553 A | 5/1991 | Southard et al. |
| 5,023,252 A | 6/1991 | Hseih |
| 5,026,692 A | 6/1991 | Jubo et al. |
| 5,036,100 A | 7/1991 | Deboeck et al. |
| 5,053,227 A | 10/1991 | Chiang et al. |
| 5,059,603 A | 10/1991 | Rubin |
| 5,071,657 A | 12/1991 | Oloff et al. |
| 5,073,545 A | 12/1991 | Arima et al. |
| 5,116,828 A | 5/1992 | Miura et al. |
| 5,122,519 A | 6/1992 | Ritter |
| 5,152,997 A | 10/1992 | Ebert et al. |
| 5,200,190 A | 4/1993 | Azuma et al. |
| 5,208,013 A | 5/1993 | Klein |
| 5,223,261 A | 6/1993 | Nelson et al. |
| 5,231,087 A | 7/1993 | Thornfeldt |
| 5,231,382 A | 7/1993 | Tanaka |
| 5,232,703 A | 8/1993 | Blank |
| 5,238,933 A | 8/1993 | Catz et al. |
| 5,238,944 A | 8/1993 | Wick et al. |
| 5,256,652 A | 10/1993 | El-Rashidy |
| 5,324,521 A | 6/1994 | Gertner et al. |
| 5,326,566 A | 7/1994 | Thornfeldt |
| 5,326,790 A | 7/1994 | Thornfeldt |
| 5,332,577 A | 7/1994 | Gertner et al. |
| 5,340,584 A | 8/1994 | Spicer et al. |
| 5,340,585 A | 8/1994 | Pike et al. |
| 5,340,586 A | 8/1994 | Pike et al. |
| 5,346,901 A | 9/1994 | Bell et al. |
| 5,362,497 A | 11/1994 | Yamada et al. |
| 5,362,886 A | 11/1994 | Berglund |
| 5,413,794 A | 5/1995 | Suzuki et al. |
| 5,436,634 A | 7/1995 | Kanazawa |
| 5,446,025 A | 8/1995 | Lu |
| 5,446,070 A | 8/1995 | Mantelle |
| 5,460,820 A | 10/1995 | Ebert et al. |
| 5,482,970 A | 1/1996 | Kim et al. |
| 5,487,898 A | 1/1996 | Lu et al. |
| 5,550,107 A | 8/1996 | Labrie |
| 5,589,498 A | 12/1996 | Mohr |
| 5,607,691 A | 3/1997 | Hale et al. |
| 5,610,150 A | 3/1997 | Labrie |
| 5,629,019 A | 5/1997 | Lee et al. |
| 5,629,021 A | 5/1997 | Wright |
| 5,639,743 A | 6/1997 | Kaswan et al. |
| 5,641,504 A | 6/1997 | Lee et al. |
| 5,643,899 A | 7/1997 | Elias et al. |
| 5,648,350 A | 7/1997 | DeLignieres |
| 5,651,973 A | 7/1997 | Moo-Young et al. |
| 5,654,337 A | 8/1997 | Roentsch et al. |
| 5,656,286 A | 8/1997 | Miranda et al. |
| 5,662,925 A | 9/1997 | Ebert et al. |
| 5,665,377 A | 9/1997 | Gonella |
| 5,676,956 A | 10/1997 | Duffy et al. |
| 5,676,968 A | 10/1997 | Lipp et al. |
| 5,686,112 A | 11/1997 | Liedtke |
| 5,693,335 A | 12/1997 | Xia et al. |
| 5,708,038 A | 1/1998 | Davis |
| 5,716,638 A | 2/1998 | Touitou |
| 5,719,197 A | 2/1998 | Kanios et al. |
| 5,723,114 A | 3/1998 | Thornfeldt et al. |
| 5,725,874 A | 3/1998 | Oda et al. |
| 5,730,987 A | 3/1998 | Omar |
| 5,731,303 A | 3/1998 | Hsieh |
| 5,731,339 A | 3/1998 | Lowrey |
| 5,744,162 A | 4/1998 | Okabe et al. |
| 5,760,096 A | 6/1998 | Thornfeldt et al. |
| 5,769,274 A | 6/1998 | Behar |
| 5,770,606 A | 6/1998 | El Rashidy et al. |
| 5,776,923 A | 7/1998 | Labrie |
| 5,780,050 A | 7/1998 | Jain et al. |
| 5,783,208 A | 7/1998 | Venkateshwaran et al. |
| 5,785,991 A | 7/1998 | Burkoth et al. |
| 5,788,983 A | 8/1998 | Chien et al. |
| 5,788,984 A | 8/1998 | Guenther et al. |
| 5,807,568 A | 9/1998 | Cody et al. |
| 5,807,849 A | 9/1998 | Labrie |
| 5,807,957 A | 9/1998 | Samour et al. |
| 5,837,289 A | 11/1998 | Grasela et al. |
| 5,844,103 A | 12/1998 | Au et al. |
| 5,847,128 A | 12/1998 | Martin et al. |
| 5,849,729 A | 12/1998 | Zoumas et al. |
| 5,855,905 A | 1/1999 | Oettel et al. |
| 5,855,920 A | 1/1999 | Chein |
| 5,859,006 A | 1/1999 | Daugan |
| 5,863,560 A | 1/1999 | Osborne |
| 5,874,074 A | 2/1999 | Smith |
| RE36,138 E | 3/1999 | Suzuki et al. |
| 5,877,216 A | 3/1999 | Place et al. |
| 5,880,117 A | 3/1999 | Arnold |
| 5,881,926 A | 3/1999 | Ross |
| 5,882,676 A | 3/1999 | Lee et al. |
| 5,891,462 A | 4/1999 | Carrara |
| 5,894,019 A | 4/1999 | Hesse et al. |
| 5,902,603 A | 5/1999 | Chen et al. |
| 5,906,830 A | 5/1999 | Farinas et al. |
| 5,908,619 A | 6/1999 | Scholz |
| 5,908,638 A | 6/1999 | Huber et al. |
| 5,926,953 A | 7/1999 | Behar |
| 5,932,227 A | 8/1999 | Higo et al. |
| 5,935,949 A | 8/1999 | White |
| 5,942,545 A | 8/1999 | Samour et al. |
| 5,952,000 A | 9/1999 | Venkateshwaran |
| 5,955,455 A | 9/1999 | Labrie |
| 5,962,021 A | 10/1999 | Hughes, Jr. et al. |
| 5,968,919 A | 10/1999 | Samour et al. |
| 5,972,377 A | 10/1999 | Jona et al. |
| 5,981,542 A | 11/1999 | Bigg et al. |
| 6,007,837 A | 12/1999 | Enscore et al. |
| 6,010,716 A | 1/2000 | Saunal et al. |
| 6,019,988 A | 2/2000 | Parab et al. |
| 6,019,997 A | 2/2000 | Scholz et al. |
| 6,024,974 A | 2/2000 | Li |
| 6,036,977 A | 3/2000 | Drizen et al. |
| 6,037,346 A | 3/2000 | Doherty, Jr. et al. |
| 6,046,244 A | 4/2000 | Buyuktimkin et al. |
| 6,051,555 A | 4/2000 | Hadley |
| 6,071,531 A | 6/2000 | Jona et al. |
| 6,075,028 A | 6/2000 | Graham |
| 6,077,841 A | 6/2000 | Sui et al. |
| 6,087,362 A | 7/2000 | El-Rashidy |
| 6,087,368 A | 7/2000 | Macor et al. |
| 6,103,765 A | 8/2000 | Neal |
| 6,117,446 A | 9/2000 | Place |
| 6,124,461 A | 9/2000 | Shoemaker |
| 6,127,363 A | 10/2000 | Doherty et al. |
| 6,132,760 A | 10/2000 | Hedenstrom et al. |
| 6,133,320 A | 10/2000 | Yallampalli et al. |
| 6,139,873 A | 10/2000 | Hughes, Jr. et al. |

(56) References Cited

U.S. PATENT DOCUMENTS

| | | |
|---|---|---|
| 6,143,746 A | 11/2000 | Daugan et al. |
| 6,146,662 A | 11/2000 | Jao et al. |
| 6,156,753 A | 12/2000 | Doherty et al. |
| 6,165,491 A | 12/2000 | Grasset et al. |
| 6,172,088 B1 | 1/2001 | Simpkins et al. |
| 6,187,750 B1 | 2/2001 | Chein |
| 6,190,693 B1 | 2/2001 | Kafrissen et al. |
| 6,200,591 B1 | 3/2001 | Hussain et al. |
| 6,200,593 B1 | 3/2001 | Place |
| 6,207,694 B1 | 3/2001 | Murad |
| 6,221,379 B1 | 4/2001 | Place |
| 6,224,573 B1 | 5/2001 | Yeager et al. |
| 6,225,299 B1 | 5/2001 | Golbs et al. |
| 6,228,852 B1 | 5/2001 | Shaak |
| 6,238,284 B1 | 5/2001 | Dittgen et al. |
| 6,241,529 B1 | 6/2001 | Place |
| 6,248,363 B1 | 6/2001 | Patel et al. |
| 6,251,436 B1 | 6/2001 | Drizen et al. |
| 6,266,560 B1 | 7/2001 | Zhang et al. |
| 6,267,984 B1 | 7/2001 | Beste et al. |
| 6,267,985 B1 | 7/2001 | Chen et al. |
| 6,277,884 B1 | 8/2001 | de Tejada |
| 6,284,234 B1 | 9/2001 | Niemiec et al. |
| 6,284,263 B1 | 9/2001 | Place |
| 6,294,192 B1 | 9/2001 | Patel et al. |
| 6,294,550 B1 | 9/2001 | Place et al. |
| 6,299,900 B1 | 10/2001 | Reed et al. |
| 6,306,841 B1 | 10/2001 | Place et al. |
| 6,309,663 B1 | 10/2001 | Patel et al. |
| 6,319,913 B1 | 11/2001 | Mak et al. |
| 6,323,242 B1 | 11/2001 | Mueller |
| 6,331,543 B1 | 12/2001 | Garvey et al. |
| 6,342,246 B2 | 1/2002 | Johnson et al. |
| 6,342,250 B1 | 1/2002 | Masters |
| 6,395,744 B1 | 5/2002 | Adams et al. |
| 6,436,950 B1 | 8/2002 | Achari et al. |
| 6,469,016 B1 | 10/2002 | Place et al. |
| 6,472,425 B1 | 10/2002 | Garvey et al. |
| 6,503,894 B1 | 1/2003 | Dudley |
| 6,506,765 B2 | 1/2003 | Gupta et al. |
| 6,562,369 B2 | 5/2003 | Luo et al. |
| 6,562,370 B2 | 5/2003 | Luo et al. |
| 6,579,865 B2 | 6/2003 | Mak et al. |
| 6,582,724 B2 | 6/2003 | Hsu et al. |
| 6,586,000 B2 | 7/2003 | Luo et al. |
| 6,593,313 B2 | 7/2003 | Place et al. |
| 6,696,484 B2 | 2/2004 | Liao et al. |
| 6,743,448 B2 | 6/2004 | Kryger |
| 6,818,226 B2 | 11/2004 | Reed et al. |
| 6,980,566 B2 | 12/2005 | Melick et al. |
| 7,030,104 B2 | 4/2006 | Gray et al. |
| 7,097,853 B1 | 8/2006 | Garbe et al. |
| 7,320,968 B2 | 1/2008 | Gyurik |
| 7,611,727 B2 | 11/2009 | Taravella et al. |
| 8,466,136 B2 | 6/2013 | Malladi et al. |
| 8,466,137 B2 | 6/2013 | Malladi et al. |
| 8,466,138 B2 | 6/2013 | Malladi et al. |
| 2001/0018073 A1 | 8/2001 | Dittgen et al. |
| 2001/0023261 A1 | 9/2001 | Ryoo et al. |
| 2001/0033870 A1 | 10/2001 | Luo et al. |
| 2001/0036483 A1 | 11/2001 | Luo et al. |
| 2001/0051166 A1 | 12/2001 | Luo et al. |
| 2001/0051656 A1 | 12/2001 | Place et al. |
| 2002/0004065 A1 | 1/2002 | Kanios |
| 2002/0013304 A1 | 1/2002 | Wilson et al. |
| 2002/0034554 A1 | 3/2002 | Hsu et al. |
| 2002/0128176 A1 | 9/2002 | Forssmann et al. |
| 2002/0183296 A1 | 12/2002 | Dudley et al. |
| 2003/0018085 A1 | 1/2003 | Raoof |
| 2003/0022877 A1 | 1/2003 | Dudley |
| 2003/0027804 A1 | 2/2003 | van der Hoop |
| 2003/0050292 A1 | 3/2003 | Dudley et al. |
| 2003/0087885 A1 | 5/2003 | Masini-Eteve et al. |
| 2003/0139384 A1 | 7/2003 | Dudley |
| 2003/0175329 A1 | 9/2003 | Azarnoff et al. |
| 2003/0232072 A1 | 12/2003 | Dudley et al. |
| 2004/0001881 A1 | 1/2004 | Selzer et al. |
| 2004/0002482 A1 | 1/2004 | Dudley et al. |
| 2004/0028725 A1 | 2/2004 | Morgan et al. |
| 2004/0044086 A1 | 3/2004 | Schulze |
| 2004/0072810 A1 | 4/2004 | Masini-Eteve et al. |
| 2004/0110732 A1 | 6/2004 | Masini-Eteve et al. |
| 2004/0198706 A1 | 10/2004 | Carrara et al. |
| 2005/0020552 A1 | 1/2005 | Aschkenasy et al. |
| 2005/0025833 A1 | 2/2005 | Aschkenasy et al. |
| 2005/0042268 A1 | 2/2005 | Aschkenasy et al. |
| 2005/0049233 A1 | 3/2005 | Dudley |
| 2005/0054623 A1 | 3/2005 | Dudley |
| 2005/0112181 A1 | 5/2005 | Dudley et al. |
| 2005/0113353 A1 | 5/2005 | Dudley et al. |
| 2005/0118242 A1 | 6/2005 | Dudley et al. |
| 2005/0142173 A1 | 6/2005 | Dudley et al. |
| 2005/0152956 A1 | 7/2005 | Dudley |
| 2005/0158388 A1 | 7/2005 | Le Nestour et al. |
| 2005/0222106 A1 | 10/2005 | Bracht |
| 2005/0276842 A1 | 12/2005 | Zhang et al. |
| 2006/0088579 A1 | 4/2006 | Shastri et al. |
| 2006/0105041 A1 | 5/2006 | Masini-Eteve |
| 2006/0211664 A1 | 9/2006 | Dudley |
| 2006/0280783 A1 | 12/2006 | Dipietro et al. |
| 2007/0065494 A1 | 3/2007 | Anigbogu et al. |
| 2007/0082039 A1 | 4/2007 | Jones et al. |
| 2007/0088012 A1 | 4/2007 | Seo |
| 2007/0154533 A1 | 7/2007 | Dudley |
| 2007/0189977 A1 | 8/2007 | Zhang et al. |
| 2007/0190124 A1 | 8/2007 | Zhang et al. |
| 2007/0196323 A1 | 8/2007 | Zhang et al. |
| 2007/0196453 A1 | 8/2007 | Zhang et al. |
| 2007/0237822 A1 | 10/2007 | Malladi |
| 2007/0254036 A1 | 11/2007 | Brennan et al. |
| 2008/0058299 A1 | 3/2008 | Dudley |
| 2008/0220068 A1 | 9/2008 | Masini-Eteve et al. |
| 2008/0261937 A1 | 10/2008 | Dudley et al. |
| 2008/0317844 A1 | 12/2008 | Dudley |
| 2009/0011041 A1 | 1/2009 | Musaeva et al. |
| 2009/0258063 A1 | 10/2009 | Udagawa et al. |
| 2010/0048526 A1 | 2/2010 | Taravella et al. |
| 2011/0172196 A1 | 7/2011 | Dudley |
| 2011/0201586 A1 | 8/2011 | Dudley |
| 2011/0306582 A1 | 12/2011 | Dudley |
| 2012/0028948 A1 | 2/2012 | Malladi et al. |
| 2012/0058981 A1 | 3/2012 | Dudley |

FOREIGN PATENT DOCUMENTS

| | | |
|---|---|---|
| CA | 2141690 | 3/1994 |
| CA | 2220358 | 11/1996 |
| CA | 2419573 | 3/2002 |
| CA | 2420895 | 3/2002 |
| CA | 2451725 | 1/2003 |
| CA | 2502607 | 5/2004 |
| CA | 2624788 | 4/2007 |
| CN | 1470239 | 1/2004 |
| DE | 3836862 | 5/1990 |
| DE | 19825856 | 12/1999 |
| EP | 0043738 | 1/1982 |
| EP | 0183492 | 6/1986 |
| EP | 0189861 | 8/1986 |
| EP | 0196769 | 10/1986 |
| EP | 0248885 | 12/1987 |
| EP | 0271983 | 6/1988 |
| EP | 0332147 | 9/1989 |
| EP | 0364211 | 4/1990 |
| EP | 0386960 | 9/1990 |
| EP | 0491076 | 6/1992 |
| EP | 0513832 | 11/1992 |
| EP | 0581587 | 2/1994 |
| EP | 0483105 | 6/1995 |
| EP | 0672422 | 9/1995 |
| EP | 0698393 | 2/1996 |
| EP | 0197753 | 10/1996 |
| EP | 0737477 | 10/1996 |
| EP | 0857488 | 8/1998 |
| EP | 0552405 | 11/1998 |

(56) References Cited

FOREIGN PATENT DOCUMENTS

| | | |
|---|---|---|
| EP | 0563813 | 12/1999 |
| EP | 1043020 | 1/2000 |
| EP | 1005831 | 6/2000 |
| EP | 0815871 | 7/2002 |
| EP | 0811381 | 5/2003 |
| EP | 1634583 | 3/2006 |
| EP | 2450041 | 5/2012 |
| FR | 2518879 | 7/1983 |
| FR | 2519252 | 7/1983 |
| GB | 916778 | 1/1963 |
| GB | 941634 | 1/1963 |
| GB | 1158283 | 7/1969 |
| GB | 2109231 | 6/1983 |
| JP | 01138288 | 5/1989 |
| JP | 62011675 | 8/1994 |
| JP | H7-82147 | 3/1995 |
| JP | H9-176049 | 7/1997 |
| JP | H10-087488 | 4/1998 |
| JP | 2000-212080 | 8/2000 |
| JP | 2002087964 | 3/2002 |
| JP | 2002212105 | 7/2002 |
| KR | 2002013248 | 5/1999 |
| RU | 2122396 | 11/1998 |
| WO | WO8703473 | 6/1987 |
| WO | WO9207586 | 5/1992 |
| WO | WO9207590 | 5/1992 |
| WO | WO9215289 | 9/1992 |
| WO | WO9325168 | 12/1993 |
| WO | WO9408590 | 4/1994 |
| WO | WO9409778 | 5/1994 |
| WO | WO9421230 | 9/1994 |
| WO | WO9421271 | 9/1994 |
| WO | WO9424125 | 10/1994 |
| WO | WO9428902 | 12/1994 |
| WO | WO9629988 | 3/1996 |
| WO | WO9616644 | 6/1996 |
| WO | WO9616657 | 6/1996 |
| WO | WO9620699 | 7/1996 |
| WO | WO9627372 | 9/1996 |
| WO | WO9636339 | 11/1996 |
| WO | WO9637201 | 11/1996 |
| WO | WO9703985 | 2/1997 |
| WO | WO9724148 | 7/1997 |
| WO | WO 97/29735 | 8/1997 |
| WO | WO9739743 | 10/1997 |
| WO | WO9740792 | 11/1997 |
| WO | WO9741865 | 11/1997 |
| WO | WO9743989 | 11/1997 |
| WO | WO9806404 | 2/1998 |
| WO | WO9808547 | 3/1998 |
| WO | WO9817215 | 4/1998 |
| WO | WO9818417 | 5/1998 |
| WO | WO9824451 | 6/1998 |
| WO | WO9830198 | 7/1998 |
| WO | WO9831368 | 7/1998 |
| WO | WO9832465 | 7/1998 |
| WO | WO9834621 | 8/1998 |
| WO | WO9837871 | 9/1998 |
| WO | WO9840076 | 9/1998 |
| WO | WO9850016 | 11/1998 |
| WO | WO9855076 | 12/1998 |
| WO | WO9913812 | 3/1999 |
| WO | WO9920257 | 4/1999 |
| WO | WO9921558 | 5/1999 |
| WO | WO9924041 | 5/1999 |
| WO | WO9932107 | 7/1999 |
| WO | WO9933859 | 7/1999 |
| WO | WO9966870 | 12/1999 |
| WO | WO9966909 | 12/1999 |
| WO | WO0001351 | 1/2000 |
| WO | WO0006144 | 2/2000 |
| WO | WO0024362 | 5/2000 |
| WO | WO0040230 | 7/2000 |
| WO | WO0045795 | 8/2000 |
| WO | WO0066870 | 8/2000 |
| WO | WO0067708 | 11/2000 |
| WO | WO0074684 | 12/2000 |
| WO | WO0076522 | 12/2000 |
| WO | WO0105400 | 1/2001 |
| WO | WO0143775 | 6/2001 |
| WO | WO0151053 | 7/2001 |
| WO | WO0152823 | 7/2001 |
| WO | WO0154699 | 8/2001 |
| WO | WO0164146 | 9/2001 |
| WO | WO0164167 | 9/2001 |
| WO | WO0172307 | 10/2001 |
| WO | WO0176608 | 10/2001 |
| WO | WO0211768 | 2/2002 |
| WO | WO0217926 | 3/2002 |
| WO | WO0217927 | 3/2002 |
| WO | WO0217967 | 3/2002 |
| WO | WO03002123 | 1/2003 |
| WO | WO03088974 | 10/2003 |
| WO | WO2004037173 | 5/2004 |
| WO | WO2005076899 | 8/2005 |
| WO | WO2006023526 | 3/2006 |
| WO | WO2006027278 | 3/2006 |
| WO | WO2006113227 | 10/2006 |
| WO | WO2006113505 | 10/2006 |
| WO | WO2007044976 | 4/2007 |
| WO | WO2007119151 | 10/2007 |

OTHER PUBLICATIONS

Notice of Opposition of Unimed Pharmaceuticals LLC et al.'s European Patent No. 1937276 dated Aug. 21, 2013 by Andreas Oser.
Brookfield DV-II+ Pro EXTRA Programmable Rheometer Operating Instructions Manual No. M/09-166, (Dec. 2007) p. 1-79.
Physicians' Desk Reference, Medical Economics Co., 55th edition (2001) pp. 304, 339, 535-538, 3218-3220, Androgel 1% and Testoderm TTS.
Physicians' Desk Reference, Thomson PDR, 58th edition (2004) p. 337, 3239-3241, Androgel 1%.
Labeling for ANDROGEL 1% (testosterone gel) Product (2002).
Labeling for TESTIM 1% (testosterone gel) CIII Product (2002).
U.S. Appl. No. 13/430,862, filed Mar. 27, 2012.
U.S. Appl. No. 13/648,694, filed Oct. 10, 2012.
U.S. Appl. No. 13/781,849, filed Mar. 1, 2013.
U.S. Appl. No. 13/831,189, filed Mar. 14, 2013.
U.S. Appl. No. 13/831,207, filed Mar. 14, 2013.
U.S. Appl. No. 13/831,217, filed Mar. 14, 2013.
U.S. Appl. No. 13/831,231, filed Mar. 14, 2013.
U.S. Appl. No. 13/902,035, filed May 24, 2013.
U.S. Appl. No. 13/180,327, Sep. 17, 2012 Final Rejection, 27 pages.
U.S. Appl. No. 13/180,327, Feb. 19, 2013 Notice of Allowance, 16 pages.
U.S. Appl. No. 13/253,848, Aug. 30, 2012 Non-Final Rejection, 34 pages.
U.S. Appl. No. 13/253,848, Feb. 20, 2013 Notice of Allowance, 14 pages.
U.S. Appl. No. 13/253,867, Aug. 31, 2012 Final Rejection, 28 pages.
U.S. Appl. No. 13/253,867, Mar. 4, 2013 Notice of Allowance, 15 pages.
U.S. Appl. No. 13/275,232, Sep. 17, 2012 Final Rejection, 30 pages.
U.S. Appl. No. 13/902,035, Aug. 2, 2013 Non-final Office Action, 29 pages.
U.S. Appl. No. 13/831,217, Jun. 26, 2013 Non-final Office Action, 27 pages.
U.S. Appl. No. 13/831,231, Jun. 24, 2013 Non-final Office Action, 33 pages.
U.S. Appl. No. 13/831,189, Jun. 20, 2013 Non-final Office Action, 25 pages.
U.S. Appl. No. 13/831,207, Jun. 27, 2013 Non-final Office Action, 26 pages.
U.S. Appl. No. 13/180,316, Feb. 21, 2013 Notice of Allowance, 15 pages.
"Dermally applied testosterone gel ('androgen') appears effective and well tolerated," In Pharma (Feb. 1999) 1175, p. 12.
"Observation study of T-gel (1%) in treatment of adolescent boys with hypogonadism," http://clinicaltrials.gov/NCT00193661 (2006).

(56) References Cited

OTHER PUBLICATIONS

"Products filed for marketing approval: androgel," Pharma Business (Jul./Aug. 1999) 29:72-73.
"Testosterone gel shows promise in phase III trial," AIDS Alert (1999) 14:67.
"Unimed files NDA for androgel in USA," Pharma Market Letter (May 10, 1999) 26(19):23.
Banker et al., Modern Pharmaceutics, 3rd Edition (1996) Marcel Dekker, New York, p. 716.
Bennett, D., "It's no myth, scientists say—there really is a male menopause," Weekly World News (Jul. 18, 2000) 13.
Goldstat, R. et al., "Transdermal testosterone therapy improves well-being, mood, and sexual function in premenopausal women," Menopause (2003) 10(5):390-398.
Lobel, B. et al., "Contraception in men: efficacy and immediate toxicity—a study of 18 cases," Acta Urologica Belgica (1989) 57(1):117-124.
Mooney, M. et al., "Built to survive: a comprehensive guide to the medical use of anabolic therapies, nutrition, supplementation, and exercise for HIV(+) men and women," Program for Wellness Restoration (PoWeR) Anabolic Hormone Guidelines, Library of Congress (1999) Table of Contents, 63-85.
Moynihan, R., "Drug maker urges group to lobby FDA on testosterone for women," BMJ (2004) 329:1255.
Seki, T. et al., Percutaneous absorption enhancer applied ot membrane permeation-controlled transdermal delivery of nicardipine hydrochloride in drug design and delivery (1989) 4:69-75.
Sitruk-Ware, R., "Transdermal delivery of steroids," Contraception (1989) 39(1):1-20.
Ullis, K., Super T: The Complete Guide to Creating an Effective, Safe and Natural Testosterone Supplement Program for Men and Women, Simon & Schuster, New York (1999) Table of Contents.
U.S. Appl. No. 13/965,499, filed Aug. 13, 2013.
2232508, Mar. 16, 1999, Unimed Pharmaceuticals, LLC.
U.S. Appl. No. 09/703,753, filed Nov. 1, 2000, (abandoned).
U.S. Appl. No. 09/892,981, filed Jun. 27, 2001, (abandoned).
U.S. Appl. No. 10/033,101, filed Oct. 19, 2001, (abandoned).
U.S. Appl. No. 10/046,454, filed Oct. 19, 2001, (abandoned).
U.S. Appl. No. 10/098,232, filed Mar. 15, 2002, (abandoned).
U.S. Appl. No. 10/099,725, filed Mar. 15, 2002, (abandoned).
U.S. Appl. No. 10/153,468, filed May 21, 2002, (abandoned).
U.S. Appl. No. 10/248,267, filed Jan. 3, 2003, (abandoned).
U.S. Appl. No. 10/273,484, filed Oct. 18, 2002, (abandoned).
U.S. Appl. No. 10/456,868, filed Jun. 6, 2003.
U.S. Appl. No. 10/531,526, filed Feb. 8, 2006.
U.S. Appl. No. 10/787,071, filed Feb. 25, 2004, (abandoned).
U.S. Appl. No. 10/825,540, filed Apr. 15, 2004, (abandoned).
U.S. Appl. No. 10/828,678, filed Apr. 20, 2004, (abandoned).
U.S. Appl. No. 10/829,618, filed Apr. 20, 2004.
U.S. Appl. No. 10/867,435, filed Jun. 14, 2004.
U.S. Appl. No. 10/867,445, filed Jun. 14, 2004.
U.S. Appl. No. 10/925,421, filed Aug. 24, 2004.
U.S. Appl. No. 11/399,642, filed Apr. 6, 2006.
U.S. Appl. No. 11/402,682, filed Apr. 11, 2006.
U.S. Appl. No. 11/402,986, filed Apr. 11, 2006.
U.S. Appl. No. 11/549,083, filed Oct. 12, 2006.
U.S. Appl. No. 11/662,339, filed Sep. 24, 2007.
U.S. Appl. No. 11/925,421, filed Oct. 26, 2007.
U.S. Appl. No. 12/052,337, filed Mar. 20, 2008.
U.S. Appl. No. 12/543,541, filed Aug. 19, 2009.
U.S. Appl. No. 12/609,473, filed Oct. 30, 2009.
U.S. Appl. No. 13/071,264, filed Mar. 24, 2011.
U.S. Appl. No. 13/071,276, filed Mar. 24, 2011.
U.S. Appl. No. 13/165,545, filed Jun. 21, 2011.
U.S. Appl. No. 13/180,316, filed Jul. 11, 2011.
U.S. Appl. No. 13/180,327, filed Jul. 11, 2011.
U.S. Appl. No. 13/253,848, filed Oct. 5, 2011.
U.S. Appl. No. 13/253,867, filed Oct. 5, 2011.
U.S. Appl. No. 13/275,232, filed Oct. 17, 2011.
U.S. Appl. No. 13/275,254, filed Oct. 17, 2011.
U.S. Appl. No. 09/651,777, Jan. 16, 2002 Supplemental Amendment.
U.S. Appl. No. 09/651,777, Feb. 6, 2002 Declaration of Robert E. Dudley dated (submitted with the Supplemental Amendment II dated Feb. 8, 2002), 9 pages.
U.S. Appl. No. 09/651,777, Feb. 8, 2002 Supplemental Amendment II, 46 pages.
U.S. Appl. No. 09/651,777, Mar. 27, 2007 Decision Granting Petition to Correct Inventorship under 37 CFR §1.324.
U.S. Appl. No. 09/651,777, Apr. 1, 2002 Letter in response to Mar. 28, 2002 Examiner Interview, 4 pages.
U.S. Appl. No. 09/651,777, Apr. 30, 2007 Certificate of Correction.
U.S. Appl. No. 09/651,777, May 7, 2002 Non-Final Rejection, 6 pages.
U.S. Appl. No. 09/651,777, May 20, 2002 Response after Non-Final Action, 12 pages.
U.S. Appl. No. 09/651,777, May 22, 2007 Certificate of Correction—Correction of Inventors.
U.S. Appl. No. 09/651,777, Jun. 12, 2003 Request for Certificate of Correction under 37 CFR §1.322 (2 pages of corrections).
U.S. Appl. No. 09/651,777, Jun. 12, 2003 Request for Certificate of Correction under 37 CFR §1.323 (1 page of corrections).
U.S. Appl. No. 09/651,777, Jun. 19, 2001 Non-Final Rejection, 10 pages.
U.S. Appl. No. 09/651,777, Jul. 23, 2002 Supplemental Response After Interview, 2 pages.
U.S. Appl. No. 09/651,777, Jul. 23, 2002 Declaration of Michele Alm, 5 pages.
U.S. Appl. No. 09/651,777, Jul. 23, 2002 Declaration of Sandy Faulkner, 7 pages.
U.S. Appl. No. 09/651,777, Jul. 24, 2002 Supplemental Amendment, 7 pages.
U.S. Appl. No. 09/651,777, Aug. 1, 2002 Supplemental Amendment, 5 pages.
U.S. Appl. No. 09/651,777, Aug. 13, 2002 Notice of Allowance, 6 pages.
U.S. Appl. No. 09/651,777, Aug. 20, 2002 Protest under 37 CFR §1.291(a).
U.S. Appl. No. 09/651,777, Oct. 17, 2003 Certificate of Correction.
U.S. Appl. No. 09/651,777, Oct. 29, 2001 Declaration of Jean-Louis Anspach, 4 pages.
U.S. Appl. No. 09/651,777, Oct. 29, 2001 Response after Non-Final Action, 23 pages.
U.S. Appl. No. 09/651,777, Nov. 29, 2004 Petition to correct inventorship under 35 USC §256, 37 CFR §1.324, and M.P.E.P. §1481 (a certificate of correction is submitted).
U.S. Appl. No. 09/651,777, Dec. 21, 2001 Supplemental Amendment, 15 pages.
U.S. Appl. No. 09/703,753, Jan. 15, 2003 Non-Final Rejection, 10 pages.
U.S. Appl. No. 09/703,753, Feb. 22, 2002 Notice of Appeal and Amendment/Argument after Notice of Appeal, 7 pages.
U.S. Appl. No. 09/703,753, Mar. 22, 2002 Advisory Action, 4 pages.
U.S. Appl. No. 09/703,753, Apr. 9, 2003 Response after Non-Final Action, 33 pages.
U.S. Appl. No. 09/703,753, Apr. 24, 2001 Non-Final Rejection, 12 pages.
U.S. Appl. No. 09/703,753, Jun. 5, 2002 Non-Final Rejection, 9 pages.
U.S. Appl. No. 09/703,753, Jun. 19, 2003 Response after Non-Final Action, 16 pages.
U.S. Appl. No. 09/703,753, Aug. 24, 2001 Response after Non-Final Action, 8 pages.
U.S. Appl. No. 09/703,753, Aug. 26, 2003 Final Rejection, 15 pages.
U.S. Appl. No. 09/703,753, Oct. 21, 2002 Response after Non-Final Action, 7 pages.
U.S. Appl. No. 09/703,753, Nov. 23, 2001 Final Rejection, 11 pages.
U.S. Appl. No. 09/892,981, Feb. 8, 2002 Non-Final Office Action, 8 pages.
U.S. Appl. No. 09/892,981, Feb. 9, 2004 Advisory Action, 3 pages.
U.S. Appl. No. 09/892,981, Feb. 24, 2005 Response to Non-Final Office Action, 5 pages.
U.S. Appl. No. 09/892,981, Feb. 26, 2003 Non-Final Office Action, 12 pages.

(56) References Cited

OTHER PUBLICATIONS

U.S. Appl. No. 09/892,981, Mar. 28, 2006 Non-Final Office Action, 6 pages.
U.S. Appl. No. 09/892,981, Apr. 8, 2005 Response to Non-Final Office Action, 2 pages.
U.S. Appl. No. 09/892,981, Apr. 16, 2004 RCE and Response to Final Office Action.
U.S. Appl. No. 09/892,981, Jun. 7, 2002 Response to Non-Final Office Action, 11 pages.
U.S. Appl. No. 09/892,981, Jun. 21, 2005 Final Office Action, 7 pages.
U.S. Appl. No. 09/892,981, Jul. 25, 2003 Response to Non-Final Office Action, 14 pages.
U.S. Appl. No. 09/892,981, Aug. 25, 2004 Non-Final Office Action, 7 pages.
U.S. Appl. No. 09/892,981, Aug. 27, 2002 Final Office Action, 11 pages.
U.S. Appl. No. 09/892,981, Sep. 28, 2006 Response to Non-Final Office Action, 6 pages.
U.S. Appl. No. 09/892,981, Oct. 16, 2003 Final Office Action, 11 pages.
U.S. Appl. No. 09/892,981, Nov. 26, 2002 RCE and Response to Final Office Action, 17 pages.
U.S. Appl. No. 09/892,981, Dec. 11, 2006 Final Office Action, 7 pages.
U.S. Appl. No. 09/892,981, Dec. 16, 2003 Response to Final Office Action, 8 pages.
U.S. Appl. No. 09/892,981, Dec. 16, 2005 RCE and Response to Final Office Action, 3 pages.
U.S. Appl. No. 10/033,101, Jan. 10, 2003 Non-Final Rejection, 12 pages.
U.S. Appl. No. 10/033,101, May 12, 2003 Response after Non-Final Action, 16 pages.
U.S. Appl. No. 10/033,101, Jun. 3, 2003 Supplemental Amendment and Request for Interview, 16 pages.
U.S. Appl. No. 10/033,101, Jun. 30, 2003 Supplemental Amendment B, 18 pages.
U.S. Appl. No. 10/033,101, Oct. 21, 2003 Final Rejection, 13 pages.
U.S. Appl. No. 10/046,454, Jan. 27, 2003 Notice of Allowance, 5 pages.
U.S. Appl. No. 10/046,454, Jun. 13, 2003 Request for Continued Examination (RCE), Petition to Withdraw, and Supplemental amendment, 9 pages.
U.S. Appl. No. 10/046,454, Jun. 18, 2003 Petition Decision of Granted to Withdraw from Issue, 1 page.
U.S. Appl. No. 10/046,454, Jul. 11, 2003 Supplemental Amendment B, 16 pages.
U.S. Appl. No. 10/046,454, Sep. 10, 2002 Non-Final Rejection, 8 pages.
U.S. Appl. No. 10/046,454, Sep. 20, 2002 Response after Non-Final Action, 8 pages.
U.S. Appl. No. 10/046,454, Oct. 16, 2003 Non-Final Rejection, 7 pages.
U.S. Appl. No. 10/046,454, Dec. 9, 2002 Supplemental amendment, 5 pages.
U.S. Appl. No. 10/098,232, Jul. 31, 2003 Preliminary Amendment, 8 pages.
U.S. Appl. No. 10/098,232, Oct. 20, 2003 Non-Final Rejection, 8 pages.
U.S. Appl. No. 10/098,232, Nov. 14, 2007 Request under Rule 48 correcting inventorship, 7 pages.
U.S. Appl. No. 10/099,725, Jan. 29, 2003 Non-Final Office Action.
U.S. Appl. No. 10/099,725, Oct. 1, 2002 Office Action.
U.S. Appl. No. 10/153,468, Feb. 24, 2004 Non-Final Rejection, 17 pages.
U.S. Appl. No. 10/153,468, Aug. 24, 2004 Response after Non-Final Action, 2 pages.
U.S. Appl. No. 10/153,468, Nov. 17, 2004 Final Rejection, 17 pages.
U.S. Appl. No. 10/248,267, Dec. 15, 2003 Non-Final Rejection, 17 pages.
U.S. Appl. No. 10/273,484, Dec. 15, 2003 Non-Final Rejection.
U.S. Appl. No. 10/436,380, Jan. 2, 2008 Final Office Action, 12 pages.
U.S. Appl. No. 10/436,380, Jan. 3, 2007 Amendment and Reply to Office Action, 11 pages.
U.S. Appl. No. 10/436,380, Jan. 23, 2009 Final Office Action, 18 pages.
U.S. Appl. No. 10/436,380, Apr. 22, 2009 Response to Final Office Action, 13 pages.
U.S. Appl. No. 10/436,380, May 2, 2008 RCE and Response to final Office Action, 18 pages.
U.S. Appl. No. 10/436,380, May 13, 2009 Notice of Allowance, 5 pages.
U.S. Appl. No. 10/436,380, May 28, 2008 Non-Final Office Action, 17 pages.
U.S. Appl. No. 10/436,380, Jun. 8, 2010 Certificate of Correction—Post Issue Communication, 1 page.
U.S. Appl. No. 10/436,380, Jul. 3, 2006 Non-Final Office Action, 13 pages.
U.S. Appl. No. 10/436,380, Jul. 17, 2007 Non-Final Office Action, 11 pages.
U.S. Appl. No. 10/436,380, Jul. 23, 2009 Amendment After Notice of Allowance, 5 pages.
U.S. Appl. No. 10/436,380, Aug. 5, 2009 Response to Amendment under Rule 312, 2 pages.
U.S. Appl. No. 10/436,380, Oct. 28, 2008 Declaration of Olivier Raux, 4 pages.
U.S. Appl. No. 10/436,380, Oct. 28, 2008 Declaration of Russel Potts, 30 pages.
U.S. Appl. No. 10/436,380, Oct. 28, 2008 Response to Non-Final Office Action, 16 pages.
U.S. Appl. No. 10/436,380, Nov. 19, 2007 Response to Non-Final Office Action, 10 pages.
U.S. Appl. No. 10/456,868, Jan. 12, 2006 Non-final Office Action, 13 pages.
U.S. Appl. No. 10/456,868, Jan. 26, 2011 Response to Non-final Office Action, 13 pages.
U.S. Appl. No. 10/456,868, Feb. 4, 2010 Declaration under 37 CFR 1.131, 23 pages.
U.S. Appl. No. 10/456,868, Feb. 4, 2010 Response to Non-Final Office Action, 8 pages.
U.S. Appl. No. 10/456,868, Apr. 12, 2011 Final Rejection, 14 pages.
U.S. Appl. No. 10/456,868, Apr. 25, 2006 Response to Non-FinalOffice Action, 7 pages.
U.S. Appl. No. 10/456,868, Apr. 25, 2007 Declaration of Valerie Masini-Eteve, 3 pages.
U.S. Appl. No. 10/456,868, Apr. 25, 2007 RCE and Response to Final Office Action, 7 pages.
U.S. Appl. No. 10/456,868, May 11, 2010 Non-Final Office Action, 11 pages.
U.S. Appl. No. 10/456,868, Jun. 28, 2006 Final Office Action, 10 pages.
U.S. Appl. No. 10/456,868, Aug. 5, 2009 Non-Final Office Action, 8 pages.
U.S. Appl. No. 10/456,868, Aug. 11, 2010 Response to Non-final Office Action, 9 pages.
U.S. Appl. No. 10/456,868, Oct. 27, 2010 Non-Final Office Action, 12 pages.
U.S. Appl. No. 10/456,868, Nov. 28, 2006 Declaration of Valerie Masini-Eteve.
U.S. Appl. No. 10/456,868, Nov. 28, 2006 Response to Final Office Action, 5 pages.
U.S. Appl. No. 10/531,526, Feb. 2, 2011 Non-Final Rejection, 9 pages.
U.S. Appl. No. 10/531,526, Feb. 22, 2010 Final Rejection, 9 pages.
U.S. Appl. No. 10/531,526, Mar. 18, 2008 Non-Final Rejection, 8 pages.
U.S. Appl. No. 10/531,526, May 12, 2009 Request for Continued Examination (RCE) and Amendment, 13 pages.
U.S. Appl. No. 10/531,526, Jul. 9, 2009 Non-Final Rejection, 10 pages.
U.S. Appl. No. 10/531,526, Jul. 17, 2008 Response after Non-Final Action, 16 pages.

(56) References Cited

OTHER PUBLICATIONS

U.S. Appl. No. 10/531,526, Jul. 28, 2011 Response to Non-Final Rejection, 17 pages.
U.S. Appl. No. 10/531,526, Aug. 20, 2010 Request for Continued Examination (RCE) and Amendment, 8 pages.
U.S. Appl. No. 10/531,526, Sep. 12, 2011 Final Office Action, 24 pages.
U.S. Appl. No. 10/531,526, Nov. 17, 2008 Final Rejection, 8 pages.
U.S. Appl. No. 10/531,526, Dec. 8, 2009 Response after Non-Final Action, 17 pages.
U.S. Appl. No. 10/787,071, Feb. 1, 2008 Response after Non-Final Action, 15 pages.
U.S. Appl. No. 10/787,071, May 29, 2008 Final Rejection, 31 pages.
U.S. Appl. No. 10/787,071, Oct. 2, 2007 Non-Final Rejection, 23 pages.
U.S. Appl. No. 10/825,540, Jun. 20, 2008 Non-Final Rejection, 22 pages.
U.S. Appl. No. 10/828,678, Jun. 25, 2008 Non-Final Rejection, 23 pages.
U.S. Appl. No. 10/829,618, Jan. 17, 2012 Interview Summary, 3 pages.
U.S. Appl. No. 10/829,618, Feb. 5, 2009 Non-Final Rejection, 11 pages.
U.S. Appl. No. 10/829,618, May 14, 2008 Non-Final Rejection, 20 pages.
U.S. Appl. No. 10/829,618, Jun. 1, 2010 Response after Non-Final Action, 13 pages.
U.S. Appl. No. 10/829,618, Aug. 5, 2009 Response after Non-Final Action, 10 pages.
U.S. Appl. No. 10/829,618, Aug. 11, 2010 Notice of Allowance, 8 pages.
U.S. Appl. No. 10/829,618, Oct. 5, 2011 Non-Final Office Action, 16 pages.
U.S. Appl. No. 10/829,618, Nov. 12, 2010 RCE and Preliminary Amendment, 8 pages.
U.S. Appl. No. 10/829,618, Nov. 13, 2008 Response after Non-Final Action, 10 pages.
U.S. Appl. No. 10/829,618, Nov. 30, 2009 Non-Final Rejection, 10 pages.
U.S. Appl. No. 10/829,618, Dec. 28, 2010 Interview Summary, 4 pages.
U.S. Appl. No. 10/867,435, Mar. 11, 2009 Final Rejection, 11 pages.
U.S. Appl. No. 10/867,435, Jun. 4, 2010 Response after Non-Final Action, 15 pages.
U.S. Appl. No. 10/867,435, Jun. 9, 2008 Non-Final Rejection, 18 pages.
U.S. Appl. No. 10/867,435, Aug. 13, 2010 Final Rejection, 10 pages.
U.S. Appl. No. 10/867,435, Sep. 11, 2009 Request for Continued Examination and Amendment, 13 pages.
U.S. Appl. No. 10/867,435, Oct. 11, 2011 Non-Final Office Action, 19 pages.
U.S. Appl. No. 10/867,435, Dec. 4, 2009 Non-Final Rejection, 10 pages.
U.S. Appl. No. 10/867,435, Dec. 9, 2008 Response after Non-Final Action, 19 pages.
U.S. Appl. No. 10/867,435, Feb. 14, 2011 Request for Continued Examination (RCE) and Amendment, 17 pages.
U.S. Appl. No. 10/867,445, Jan. 19, 2010 Non-Final Rejection, 11 pages.
U.S. Appl. No. 10/867,445, Mar. 11, 2008 Non-Final Rejection, 18 pages.
U.S. Appl. No. 10/867,445, Mar. 24, 2011 Request for Continued Examination and Amendment, 16 pages.
U.S. Appl. No. 10/867,445, Apr. 2, 2012 Response to Office Action, 15 pages.
U.S. Appl. No. 10/867,445, Apr. 10, 2009 Response after Non-Final Action, 99 pages.
U.S. Appl. No. 10/867,445, Jun. 24, 2008 Response after Non-Final Action, 20 pages.
U.S. Appl. No. 10/867,445, Jun. 28, 2012 Final Rejection, 22 pages.
U.S. Appl. No. 10/867,445, Jul. 15, 2009 Final Rejection, 11 pages.
U.S. Appl. No. 10/867,445, Jul. 19, 2010 Response after Non-Final Action, 17 pages.
U.S. Appl. No. 10/867,445, Sep. 24, 2010 Final Rejection, 10 pages.
U.S. Appl. No. 10/867,445, Oct. 10, 2008 Non-Final Rejection, 12 pages.
U.S. Appl. No. 10/867,445, Oct. 13, 2011 Office Action, 21 pages.
U.S. Appl. No. 10/867,445, Dec. 14, 2009 Request for Continued Examination and Amendment, 28 pages.
U.S. Appl. No. 10/925,421, Mar. 29, 2010 Response after Final Action and RCE, 13 pages.
U.S. Appl. No. 10/925,421, Apr. 12, 2011 Response after Non-Final Action, 14 pages.
U.S. Appl. No. 10/925,421, May 26, 2009 Response after Non-Final Action, 15 pages.
U.S. Appl. No. 10/925,421, Jun. 22, 2011 Final Rejection, 15 pages.
U.S. Appl. No. 10/925,421, Sep. 8, 2011 Response to Final Office Action, 10 pages.
U.S. Appl. No. 10/925,421, Sep. 29, 2009 Final Rejection, 17 pages.
U.S. Appl. No. 10/925,421, Oct. 12, 2010 Non-Final Rejection, 18 pages.
U.S. Appl. No. 10/925,421, Nov. 24, 2008 Non-Final Rejection, 16 pages.
U.S. Appl. No. 11/399,642, Feb. 8, 2010 Non-Final Office Action, 14 pages.
U.S. Appl. No. 11/399,642, Feb. 15, 2011 Request for Continued Examination (RCE) and Amendment, 13 pages.
U.S. Appl. No. 11/399,642, May 14, 2009 Final Office Action, 12 pages.
U.S. Appl. No. 11/399,642, Aug. 9, 2010 Response to Non-Final Office Action, 24 pages.
U.S. Appl. No. 11/399,642, Oct. 15, 2010 Final Office Action, 14 pages.
U.S. Appl. No. 11/399,642, Oct. 18, 2011 Office Action, 26 pages.
U.S. Appl. No. 11/399,642, Nov. 16, 2009 Response to Non-Final Office Action, 21 pages.
U.S. Appl. No. 11/402,682, Mar. 17, 2010 RCE and Response to Final Office Action, 11 pages.
U.S. Appl. No. 11/402,682, Jun. 2, 2009 Response to Non-Final Office Action, 13 pages.
U.S. Appl. No. 11/402,682, Sep. 17, 2009 Final Office Action, 13 pages.
U.S. Appl. No. 11/402,682, Dec. 2, 2008 Non-Final Office Action, 16 pages.
U.S. Appl. No. 11/402,986, Feb. 22, 2010 Response to Non-Final Office Action, 20 pages.
U.S. Appl. No. 11/402,986, May 14, 2010 Final Office Action, 25 pages.
U.S. Appl. No. 11/402,986, May 15, 2009 Response to Non-Final Office Action, 18 pages.
U.S. Appl. No. 11/402,986, Aug. 20, 2009 Non-Final Office Action, 30 pages.
U.S. Appl. No. 11/402,986, Nov. 15, 2010 RCE and Response to Final Office Action, 13 pages.
U.S. Appl. No. 11/402,986, Nov. 17, 2008 Non-Final Office Action, 21 pages.
U.S. Appl. No. 11/549,083, Jan. 8, 2010 Response to Notice of Non-Compliant Amendment, 6 pages.
U.S. Appl. No. 11/549,083, Jan. 14, 2009 Final Office Action, 10 pages.
U.S. Appl. No. 11/549,083, Mar. 25, 2010 Final Office Action, 7 pages.
U.S. Appl. No. 11/549,083, Apr. 1, 2009 RCE and Response to Final Office Action, 12 pages.
U.S. Appl. No. 11/549,083, Apr. 8, 2011 Non-Final Rejection, 7 pages.
U.S. Appl. No. 11/549,083, Apr. 24, 2008 Non-Final Office Action, 11 pages.
U.S. Appl. No. 11/549,083, Jun. 22, 2009 Non-Final Office Action, 9 pages.
U.S. Appl. No. 11/549,083, Sep. 27, 2010 RCE and Response to Final Office Action, 18 pages.

(56) References Cited

OTHER PUBLICATIONS

U.S. Appl. No. 11/549,083, Oct. 13, 2009 Declaration of Norman Weiner, 52 pages.
U.S. Appl. No. 11/549,083, Oct. 13, 2009 Response to Non-Final Office Action, 7 pages.
U.S. Appl. No. 11/549,083, Oct. 23, 2008 Declaration of Drs. Ramana Malladi and Jodi Miller (37 CFR 1.131), 9 pages.
U.S. Appl. No. 11/549,083, Oct. 23, 2008 Declaration of Norman Weiner, 62 pages.
U.S. Appl. No. 11/549,083, Oct. 23, 2008 Petition to Correct Inventorship, 5 pages.
U.S. Appl. No. 11/549,083, Oct. 23, 2008 Response to Non-Final Office Action, 12 pages.
U.S. Appl. No. 11/662,339, Jan. 19, 2011 Final Office Action, 18 pages.
U.S. Appl. No. 11/662,339, Feb. 3, 2009 Non-Final Office Action, 19 pages.
U.S. Appl. No. 11/662,339, Feb. 22, 2010 Response to Non-Final Office Action, 13 pages.
U.S. Appl. No. 11/662,339, May 29, 2009 Response to Non-Final Office Action, 9 pages.
U.S. Appl. No. 11/662,339, Jun. 14, 2010 Non-Final Office Action, 15 pages.
U.S. Appl. No. 11/662,339, Sep. 22, 2009 Non-Final Office Action, 16 pages.
U.S. Appl. No. 11/662,339, Oct. 4, 2010 Response to Non-Final Office Action, 13 pages.
U.S. Appl. No. 12/052,337, Mar. 29, 2010 Final Office Action, 12 pages.
U.S. Appl. No. 12/052,337, May 15, 2009 Non-Final Office Action, 17 pages.
U.S. Appl. No. 12/052,337, Sep. 29, 2010 RCE and Response to Final Office Action, 7 pages.
U.S. Appl. No. 12/052,337, Nov. 16, 2009 Response to Non-Final Office Action, 12 pages.
U.S. Appl. No. 12/543,541, Jan. 28, 2010 Examiner Interview Summary Record, 2 pages.
U.S. Appl. No. 12/543,541, Feb. 2, 2010 Applicants' comments to Examiner-initiated interview summary, 2 pages.
U.S. Appl. No. 12/543,541, Feb. 5, 2010 Non-Final Rejection, 24 pages.
U.S. Appl. No. 12/543,541, Mar. 5, 2010 Response after Non-Final Action, 12 pages.
U.S. Appl. No. 12/543,541, Apr. 5, 2010 Final Rejection, 21 pages.
U.S. Appl. No. 12/543,541, Aug. 19, 2009 Petition for 12-month Accelerated Exam, Pre-examination search document; accelerated examination support document, 56 pages.
U.S. Appl. No. 12/543,541, Oct. 5, 2010 Request for Continued Examination (RCE) and Amendment, 11 pages.
U.S. Appl. No. 12/543,541, Nov. 9, 2010 Non-Final Rejection 24 pages.
U.S. Appl. No. 12/543,541, Dec. 7, 2009 Petition for 12-month Accelerated Exam Decision—Granted, 4 pages.
U.S. Appl. No. 12/543,541, Dec. 9, 2010 Response after Non-Final Action, 6 pages.
U.S. Appl. No. 12/543,541, Dec. 30, 2010 Final Rejection, 20 pages.
U.S. Appl. No. 12/609,473, Apr. 29, 2011 Response after Non-Final Action, 11 pages.
U.S. Appl. No. 12/609,473, Jul. 20, 2011 Final Rejection, 15 pages.
U.S. Appl. No. 12/609,473, Dec. 7, 2010 Non-Final Rejection, 18 pages.
U.S. Appl. No. 13/071,264, Dec. 21, 2011 Non-Final Rejection, 23 pages.
U.S. Appl. No. 13/071,276, Jan. 6, 2012 Non-Final Rejection, 48 pages.
U.S. Appl. No. 13/165,545, Apr. 11, 2012 Non-Final Rejection, 22 pages.
U.S. Appl. No. 13/180,316, May 25, 2012 Non-Final Rejection, 24 pages.
U.S. Appl. No. 13/180,327, Jun. 15, 2012 Response After Non-final Rejection, 21 pages.
U.S. Appl. No. 13/180,327, Dec. 21, 2011 Non-Final Rejection.
U.S. Appl. No. 13/253,848, Mar. 29, 2012 Final Rejection, 52 pages.
U.S. Appl. No. 13/253,848, May 30, 2012 RCE, Response to Final Rejection, 22 pages.
U.S. Appl. No. 13/253,848, Dec. 22, 2011 Non-Final Rejection, 47 pages.
U.S. Appl. No. 13/253,867, Mar. 20, 2012 Response After Non-Final Rejection, 10 pages.
U.S. Appl. No. 13/253,867, Dec. 20, 2011 Non-Final Rejection, 22 pages.
U.S. Appl. No. 13/275,232, Mar. 2, 2012 Non-Final Rejection, 40 pages.
U.S. Appl. No. 13/275,232, Jun. 4, 2012 Response After Non-final Action, 15 pages.
U.S. Appl. No. 13/275,254, Mar. 22, 2012 Response After Non-final Action, 10 pages.
U.S. Appl. No. 13/275,254, Jul. 16, 2012 Final Rejection, 25 pages.
International Preliminary Examination Report—Application No. PCT/US2003/007910 (May 27, 2004).
International Search Report—Application No. PCT/US2003/032597 (May 19, 2004).
International Preliminary Examination Report—Application No. PCT/US2003/032597 (Jul. 8, 2004).
International Preliminary Report on Patentability I—Application No. PCT/US2006/013551 (May 29, 2007).
International Search Report—Application No. PCT/US2001/27202 (Jan. 29, 2002).
International Search Report—Application No. PCT/US2003/007910 (Oct. 17, 2003).
International Search Report and Written Opinion—Application No. PCT/EP2006/003974 (Sep. 4, 2006).
International Search Report and Written Opinion—Application No. PCT/US2006/013551 (Aug. 7, 2006).
International Preliminary Report on Patentability I—Application No. PCT/EP2006/003974 (Oct. 9, 2007).
International Preliminary Report on Patentability I—Application No. PCT/US2006/040481 (Apr. 16, 2008).
International Search Report—Application No. PCT/US01/27199, Reference No. 01902267 (International Filing Date: Aug. 29, 2001).
International Search Report—Application No. PCT/US01/27205, Reference No. 01736544 (International Filing Date: Aug. 29, 2001).
International Search Report of PCT/US2006/040481 mailed Jul. 13, 2007.
Singapore Patent Application No. 200802644-5, Search Report and Written Opinion, Dec. 2, 2009.
International Search Report dated Dec. 12, 2002 and International Preliminary Report on Patentability I dated Apr. 2, 2004—Application No. PCT/US2002/020141.
International Search Report and Written Opinion dated Apr. 23, 2008 and International Preliminary Report on Patentability I dated Mar. 17, 2009—Application No. PCT/US2006/013550.
International Search Report and Written Opinion dated Feb. 29, 2008 and International Preliminary Report on Patentability I dated Feb. 29, 2009—Application No. PCT/EP2008/053372.
European Search Report mailed May 28, 2002 in application No. EP01403166 (corresponding to US 2003/0087885).
Search report for EP0672422, published Jul. 28, 1994.
USPTO Word Mark Search on "CPE-215", (searched Oct. 21, 2002).
Written Opinion of the International Searching Authority of PCT/US2006/040481, Jul. 13, 2007.
Opposition in Venezuela VE000537/03 dated Apr. 3, 2003.
Opposition to CL1026-2007 dated Sep. 5, 2008.
Opposition to CO08036312 dated Feb. 10, 2010.
Opposition to ECSP088363 dated Apr. 11, 2008.
Response to Opposition to ECSP088363 dated Apr. 7, 2009.
"Isopropyl myristate," Martindale (2011) 4 pages.
"Propylene glycol," Martindale (2011) 7 pages).
"Alza introduces TESTODERM TTS for testosterone deficiency—survey finds key role of testosterone unknown to most men." Alza. Mar. 11, 1998. http://www.alza.com/print/pr_957321395 (accessed Nov. 15, 2004).

(56) References Cited

OTHER PUBLICATIONS

"Androderm Watson Pharmaceuticals reacquires U.S. and Canadian marketing rights to A(R) testosterone transdermal system." Watson Pharmaceuticals Inc. May 17, 1999.
"AndroGel Offers New Option for Testosterone Replacement," The Body (Mar. 31, 2000), available at http://www.thebody.com/content/art2023.html.
"Besins Grants Schering Distribution Rights for Testogel in Europe," Espicom Business Intelligence (Jul. 8, 2002).
"Cellegy Pharmaceuticals Initiates Phase III Clinical Trial Using Transdermal Testosterone Gel." PR Newswire. Mar. 29, 2000.
"Cellegy Pharmaceuticals Market Opportunities." Cellegy Pharmaceuticals. http://www.cellegy.com/products/market.html (accessed Nov. 19, 1998).
"Delatestryl (testosterone enanthate): Prescribing Information." Revised Oct. 1995. http://www.delatestryl.com/prescribing.body.htm (accessed Dec. 16, 2004).
"Erratum." The Lancet. (1999);354:602.
"Hypogonadism: Schering acquires distribution rights for Testogel in Europe," Pain & Central Nervous System Week: 14 (Aug. 19, 2002).
"New Testosterone Replacement Gel, AndroGel®, Available Nationwide to Treat Men with Low Testosterone." Androgel.com. http://www.androgel.com/media/press_release000614.htm (Jun. 14, 2000).
"Sandrena, a new estrogen gel, for the improvement of acceptability in menopause therapy", Organon press release, Copenhagen, Aug. 7, 1997.
"Schering Acquires Distribution Rights for Testogel(R) in Europe," PR Newswire (Jul. 2, 2002).
"Schering AG gets Euro Testogel Rights; Brief Article," Marketletter (Jul. 10, 2002).
"Schering Buys European Rights to Male HRT Product," Handelsblatt (English Version)(Jul. 3, 2002).
"Schering Buys European Rts for Hormone Therapy Testogel," Dow Jones International News (Jul. 2, 2002).
"Unimed forecasts steep rise in revenues," SCRIP No. 2338/39: 14 (May 27/29, 1998).
"Unimed Pharmaceuticals Completes Clinical Trial Enrollment for First Topical Testosterone Replacement Gel." Press Release. May 28, 1998.
"Unimed Pharmaceuticals files for FDA Approval of Androgel to Treat Low Testosterone Levels; Over 1 Mil Men in US Suffer from Hypogonadism," PharmaBusiness Issue 29 (Jul. 1999).
"Unimed Pharmaceuticals Licenses Testosterone Products." PR Newswire. Aug. 14, 1995.
"Unimed Pharmaceuticals Licenses Two Testosterone Products." Pharma Market letter. Aug. 21, 1995.
Abbasi A. Mattson DE, Cuisinier M, Schultz S, Rudman I, Drinka P, Rudman D: Hyposomatomedinemia and hypogonadism in hemiplegic men who live in nursing homes. Arch Phys Med Rehabil 75:594-9, 1994.
Abbasi AA, Drinka PJ, Mattson DE, Rudman D: Low circulating levels of insulin-like growth factors and testosterone in chronically institutionalized elderly men. J Amer Geri Soc 41:975-82, 1993.
ABCNews.com: Testosterone Patch Increases Women's Sex Drive, http://abcnews.go.com/sections/living/DailyNews/testosterone990615.html. Sep. 8, 2000.
Abdu, et al., Coronary Risk in Growth Hormone Deficient Hypopituitary Adults: Increased Predicted Risk is Due Largely to Lipid Profile Abnormalities, Clinical Endocrinology, vol. 55, pp. 209-216 (2001).
Abitbol, et al., Sex Hormones and the Female Voice, J Voice, Sep. 1999; 13(3): 424-46.
Abraham G. E., Ovarian and adrenal contribution to peripheral androgens during the menstrual cycle, J. Clin. Endocrinol. Metab. 1974; 39:340-346.
Adami, et al., Effect of Hyperandrogenism and Menstrual Cycle Abnormalities Bone Mass and Bone Turnover in Young Women, Clinical Endocrinology (OXF), vol. 48, No. 2, 169-173 (Feb. 1998).

Adesuyi, et al., Coronary Heart Disease/Myocardial Infarction: Testosterone Increases Human Platelet Thromboxane A sub 2 Receptor Density and Aggregation Responses, Circulation, vol. 91, No. 11, pp. 2742-2747 (Jun. 1, 1995).
Adult female postmenopausal subject. Stedman's Medial Dictionary, 25th Edition.
Adult female premenopausal subject. Stedman's Medial Dictionary, 25th Edition.
Advance Collaborative Group, Intensive blood glucose control and vascular outcomes in patients with type 2 diabetes. N Engl J Med. Jun. 12, 2008;358(24):2560-72. (Epub Date Jun. 6, 2008).
Agarwal, et al., Differential Response of Prostate Specific Antigen to Testosterone Surge after Luteinizing Hormone-Releasing Hormone Analogue in Prostate Cancer and Benign Prostatic Hyperplasia, BJU Intl., vol. 85, pp. 690-695 (2000).
Aguiar, A.J. et al., "Percutaneous absorption studies of chloramphenicol solutions," J. Pharm. Sci. (1969) 58(2):210-216.
Ahmed, et al., Transdermal Testosterone Therapy in the Treatment of Male Hypogonadism, J Clin Endocrinol Metab, Mar. 1988; 66(3): 546-51.
Akimoto, et al., Relationship Between Diurnal Rhythm of Serum Testosterone and Prostatic Markers (PSA and PAP) in Untreated Prostate Cancer, Urology, Mar. 1994; 43(3): 337-41.
Alberti, I. et al., "Effect of ethanol and isopropyl myristate on the availability of topical terbinafine in human stratum corneum, in vivo," Int. J. Pharm. (2001) 219:11-19.
Albertson's, Inc. Enters Agreement with Men's Health Network to Support National Men's Health Awareness Campaign: 'Time Out for Men's Health' Encourages Men to be Checked by a Doctor More Regularly, Yahoo!Finance.com (Aug. 29, 2002).
Alexander, et al., Testosterone and Sexual Behavior in Oral Contraceptive Users and Nonusers: A Prospective Study, Hormones and Behavior, vol. 24, No. 3, pp. 388-402 (Sep. 1990).
Alexander, et al., Androgen-Behavior Correlations in Hypogonadal Men and Eugonadal Men, Hormones and Behavior, vol. 33, pp. 85-94 (1998).
Alexander, et al., Sex Steroids, Sexual Behavior, and Selection Attention for Erotic Stimuli in Women Using Oral Contraceptives, Psychoneuroendocrinology, 1993; 18(2): 91-102.
Alivizatos, et al., Update of Hormonal Treatment in Cancer of the Prostate, Anticancer Drugs, Jun. 1993; 4(3):301-9.
Allen, Methyltestosterone 6-mg/g Gel, Int'l J. Pharm. Compounding, vol. 2(1), p. 52 (1998).
Allen, Testosterone Topical Vaginal Cream, U.S. Pharmacist, pp. 54, 56, 58, (Jan. 22, 2000).
Almeida, Sex Playing with the Mind. Effects of Oestrogen and Testosterone Mood and Cognition, Arq Neuropsiquiatr, Sep. 1999; 57(3A): 701-6. [Abstract only].
Alternative to Viagra for Women!, www.mdhealthline.com (Downloaded Aug. 7, 2000).
American association of Clinical Endocrinologies (AACE) medical guidelines for clinical practices for the evaluation and treatment of hypogonadism in adult male patients—2002 update. Endocr Pract 2002; 8(6):439-456.
Anabolic Steroid Boosts Weight, GMHC Treatment Issues, vol. 10, No. 9 (Sep. 1996) (no authors listed).
Anabolic Steroids, Project Inform Hotline Handout, www.projinf.org. (Downloaded Oct. 8, 1998).
Anabolic Steroids, Project Inform, Anabolic Steroids Quick Sheet (Dec. 1997).
Anabolic Steroids—A Simple Facts Sheet From the Network, www.network/simple/steroids (Downloaded Oct. 27, 1998).
Anawalt, Potential Expanded Indications for Androgen Treatment, The Endocrine Society, No. 166 (ENDO 2000).
Anderson et al., The effects of exogenous testosterone on sexuality and mood of normal men, J. Clin. Endocrinol. Metab., 1992, 75(6):1503-7.
Anderson, et al., Haemostatic Effects of Supraphysiological Levels of Testosterone in Normal Men, pp. 693-697 (1995).
Andro Gel, Netrition, http://www.netrition.com/andro_gel_page.html (1997-1998).
Androderm®, Physician Desk Reference, pp. 2796-2798 (1998).

(56) References Cited

OTHER PUBLICATIONS

Androgel (testosterone gel 1%), A Double-Blind, Randomized, Placebo-controlled, Parallel Study to Evaluate the Efficacy and Safety of AndroGel, as and Adjunct to Hypoglycemic Therapy, in the Treatment of Hypogonadal and Low Testosterone Men with Type 2 Diabetes. Solvay Pharmaceuticals. Jun. 20, 2008.
Androgel 1% (testosterone gel) CIII, available at http://www.rxabbott.com/pdf/androgel_PI.pdf, pp. 1-2. (Sep. 2009).
Androgel and Andractim, General Information (1997).
Androgel, The Medical Letter on Drugs and Therapeutics, vol. 42 (Issue 1080), pp. 49-52 (Jun. 12, 2000).
AndroGel® (Testosterone Gel). CIII Physicians Desk Reference, Issued Dec. 2000.
Androgel® 1% (Testosterone Gel). Physicians Desk Reference, pp. 3239-3241 (2004).
Androgel® 1% (Testosterone Gel). Physician's Package Insert, pp. 1 and 11 (2004).
Androgel® 1% Package Insert, Dec. 2000.
Androgen Deficiency in Aging Men Questionnaire, Saint Louis University, available at www.slu.edu/adam (retrieved May 23, 2005).
Andropausal, Los Gatos Longevity Institute, http://www.antiaging.com/andropause.html (1998).
Andropause Added to Men's Health Risk Assessment Tool, America's Pharmacist (Alexandria, VA), Jan. 2002.
Andropause, National Public Radio, The Connection Online (Jul. 29, 2003).
AndrosteDERM, http://www.gethuge.net/androderm1.htm (Jun. 22, 2000).
Angold, et al., Pubertal Changes in Hormone Levels and Depression in Girls, Psychol Med Sep. 1999; 29(5): 1043-53.
Annual Report pursuant to Section 13 or 15(d) of the Securities Exchange Act of 1934 for the Fiscal Year Ended Dec. 31, 1998, by Unimed Pharmaceuticals, Inc.
Ansel et al., Transdermal Drug Delivery Systems, Pharmaceutical Dosage Forms and Drug Delivery Systems, pp. 263-278 (1999).
Ansel, H. Introduction to Pharmaceutical Dosage Forms.Psychiatry. 43(12):279-308 (1981) (Jun. 15, 1998).
Approved Products: From Pipeline to Market, R&D Directions (West Trenton, NJ), Jun. 2002.
Arellano, A. et al., "Influence of propylene glycol and isopropyl myristate on the in vitro percutaneous penetration of diclofenac sodium from carbopol gels," Eur. J. Pharm. Sci. (1998) 7:129-135.
Arisaka et al., Systemic effects of transdermal testosterone for the treatment of microphallus in children. Pediatrics International: Official Journal of the Japan Pediatric Society APR, 43(2):134-136 (2001).
Arsenieva. "Androgen therapy of patients suffering from climacteric neurosis." Soviet Medicine (1964). [in Russian with English Abstract].
Arver et al., Long-Term Efficacy and Safety of a Permeation-Enhanced Testosterone Transdermal System in Hypogonadal Men, Clinical Endocrinology, vol. 47, pp. 727-737 (1997).
Arver, et al., Improvement of Sexual Function in Testosterone Deficient Men Treated for 1 Year with a Permeation Enhanced Testosterone Transdermal System, J Urol, May 1996; 155(5): 1604-8.
Asbill CS, et al., "Enhancement of transdermal drug delivery: chemical and physical approaches," Crit Rev Ther Drug Carrier Syst. (2000);17(6):621-58.
Asscheman H. Scrotal testosterone patches: a good addition to therapeutic options for hypogonadal men. Ned Tijdschr Geneeskd. Apr. 29, 2000;144(18):847-50.
Aungst, "Structure/effect studies of fatty acid isomers as skin penetration enhancers and skin irritants," Pharmaceutical Research (1989); 6(3):244-247.
Aungst, B.J., "Fatty acids as skin permeation enhancers," Chapter 9.1 of Percutaneous Penetration Enhancers, E.W. Smith, Editor, CRC Press (1995) 277-287.
Auxilium Pharmaceutical, Inc. Citizen's Petition Decision, Aug. 26, 2009, Docket No. FDA-2009-P-0123.

Aversa, et al., Androgens and Penile Erection: Evidence for a Direct Relationship Between Free Testosterone and Cavernous Vasodilation in Men with Erectile Dysfunction, Clinical Endocrinology, vol. 53, pp. 517-522 (2000).
Baarends, E. M., A. M. W. J. Schols, W. D. van Marken Lichtenbelt, and E. F. M. Wouters. Analysis of body water compartments in relation to tissue depletion in clinically stable patients with chronic obstructive pulmonary disease. Am. J. Clin. Nutr. 65: 88-94 (1997).
Baba, et al., Delayed Testosterone Replacement Restores Nitric Oxide Synthase-Containing Nerve Fibres and the Erectile Response in Rat Penis, BJU Intl., vol. 85, pp. 953-958 (2000).
Bachmann et al., Female androgen insufficiency: the Princeton consensus statement on definition, classification, and assessment, Fertility and Sterility, vol. 77, No. 4, Apr. 2002, pp. 660-665.
Bagatel et al., Metabolic & Behavioral Effects of High-Dose, Exogenous Testosterone in Healthy Men, J. Clinical Metabolism & Endocrinology 79:561-567 (1996).
Bagatell et al., Androgens in Men—Uses and Abuses. New England Journal of Medicine. 334(11):707-714 (1996).
Bagatell et al., Effects of Endogenous Testosterone and Estradiol on Sexual Behavior in Normal Young Men, Journal of Clinical Endocrinology and Metabolism, vol. 78, No. 3, pp. 711-716 (1994).
Baillie et al., Pathogenesis of vertebral crush fractures in men. Age and Aging 21:139 (1992).
Bain, "Andropause-Testosterone Replacement Therapy for Aging Men," Can Fam Physician 47:91-97 (Jan. 2001), Abstract.
Baker et al., Changes in the pituitary-testicular system with age. Clin. Endocrinol. 5:349 (1976).
Balagopal P, Rooyackers OE, Adey DB, Ades PA, Nair KS: Effects of aging on in vivo synthesis of skeletal muscle myosin heavy-chain and sarcoplasmic protein in humans. Am J Physiol 273 :E790-800, 1997.
Bals-Pratsch et al., Substitution Therapy of Hypogonadal Men with Transdermal Testosterone Over One Year, ACTA Endocrinologica (COPENH), vol. 118, pp. 7-13 (1988).
Bals-Pratsch, et al., Transdermal Testosterone Substitution Therapy for Male Hypogonadism, Lancet, Oct. 25, 1986; 2(8513): 943-6.
Bancroft, Endocrinology of Sexual Function, Clinics in Obstetrics and Gynecology, vol. 7, No. 2, pp. 253-281 (Aug. 1980).
Bancroft, et al., Androgens and the Menopause; a Study of 40-60-Year-Old Women, Clin Endocrinol (Oxf), Nov. 1996; 45(5): 577-87.
Bancroft, et al., Mood, Sexuality, Hormones, and the Menstrual Cycle. III. Sexuality and the Role of Androgens, Psychosom Med, Dec. 1983; 45(6): 509-16.
Bardin et al., Androgens: Risks and benefits. J. Clin. Endocrinol. Metab. 73:4 (1991).
Barlow et al., In Vivo Observations on Testosterone and Estradiol-17beta Protein Binding in Women, Journal of Clinical Endocrinology and Metabolism, vol. 29 (No. 6), p. 767-776, (Jan. 22, 1969).
Barrett, C.W. et al., "The effect of particle size and vehicle on the percutaneous absoption of fluocinole acetonide," Br. J. Dermatol. (1965) 77:576-578.
Barrett, C.W. et al., "The influence of vehicles on skin penetration," J. Pharm. Pharmacol. (1964) 16 Supp.: 104T-107T.
Barrett-Connor E. Lower endogenous androgen levels and dyslipidemia in men with non-insulin dependent diabetes mellitus. Ann. Int. Med. Dec. 1992 (1992).
Barrett-Connor, E., et al., Endogenous sex hormone levels in older adult men with diabetes mellitus. Am. J. Epidemiol., 132(5):895-901 (1990).
Barrett-Connor, Elizabeth et al. Bioavailable Testosterone and Depressed Mood in Older Men: The Rancho Bernardo Study. J. Clinical Endocrinology and Metabolism (1999); 84(2):573-577.
Barrett-Connor, et al., Cognitive Function and Endogenous Sex Hormones in Older Women, J. Am. Geriatr. Soc., vol. 47, No. 11, pp. 1289-1293 (Nov. 1999).
Barrett-Connor, et al., A Two-Year, Double-Blind Comparison of Estrogen-Androgen and Conjugated Estrogens in Surgically Menopausal Women. Effects Bone Mineral Density, Symptoms and Lipid Profiles, J Reprod Med, Dec. 1999; 44(12): 1012-20.
Barry, Dermatological Formulations, Percutaneous Absorption, Marcel Dekker (1983).
Barry, Low Testosterone Can Trigger Male Depression, Atlanta Business Chronicle, Feb. 14, 2002.

(56) References Cited

OTHER PUBLICATIONS

Barry, Prostate-Specific-Antigen Testing for Early Diagnosis of Prostate Cancer, N. Engl. J. Med., vol. 344, No. 18 , pp. 1373-1377 (May 23, 2001).
Barry, B.W. et al., "Effect of penetration enhancers on the permeation of mannitol, hydrocortisone and progesterone through human skin," J. Pharm. Pharmacol. (1987) 39:535-546.
Barry, B.W., "Mode of action of penetration enhancers in human skin," J. Contr. Rel. (1987) 6:85-97.
Bartnof, Testosterone Therapy Causes Menstruation to Return in Women with AIDS-Related Wasting, www.hivandhepatitis.com (Oct. 12, 1999).
Bartsch, et al., Sex Hormone Binding Globulin Binding Capacity, Testosterone, 5alpha-Dihydrotestosterone, Oestradiol and Prolactin in Plasma of Patients with Prostatic Carcinoma Under Various Types of Hormonal Treatment, ACTA Endocrinologica (COPENH), vol. 85, No. 3, pp. 650-664 (Jul. 1977).
Bartsch, et al., Interrelationships Between Sex Hormone-Binding Globulin and 17 beta-Estradiol, Testosterone, 5 alpha-Dihydrotestosterone, Thyroxine, and Triiodothyronine in Prepubertal and Pubertal Girls, J Clin Endocrinol Metab, Jun. 1980; 50(6): 1053-1056 (Jun. 1980).
Bartsch, Interrelationships Between Sex Hormone-Binding Globulin and Testosterone, 5 alpha-dihydrotestosterone and Oestradiol-17 beta in Blood of Normal Men, Maturitas, Jul. 1980; 2(2): 109-118.
Barzel, Recommended Testing Patients with Low Bone Density. J Clin Endocrinol Metab 88(3): 1403-1404(2003).
Basaria et al., "New Modalities of Transdermal Testosterone Replacement," Treat Endocrinol, 2(1): 1-9 (2003); Abstract.
Basson, et al., Androgen Replacement for Women, Canadian Family Physician, vol. 45, pp. 2100-2107 (Sep. 1999).
Baum, et., Effects of Testosterone, Dihydrotestosterone, or Estradiol Administered Neonatally on Sexual Behavior of Female Ferrets, Endocrinology, vol. II I (No. 3), pp. 773-780, (Jan. 22, 1982).
Baumgartner, et al., Predictors of Skeletal Muscle Mass in Elderly Men and Women, Mech Ageing Dev, Mar. 1, 1999; 107(2): 123-36.
Bazell, Male Hormone Gel May Pose Risks: Testosterone Therapy Promises Renewed Vigor, but Some Experts are Skeptical, NBC-TV NBC Nightly News Online (Jul. 31, 2002).
Beasley, Hormone Replacement Therapy for Men Gains Ground, Reuters, Jun. 21, 2002.
Behre HM, et al., Rationale, design and methods of the ESPRIT study: Energy, Sexual desire and body Proportions with AndroGel, Testosterone 1% gel therapy, in hypogonadal men, Aging Male. Jun. 2008;11(2):101-6.
Behre, et al., Testosterone Buciclate (20 Aet-1) in Hypogonadal Men: Pharmacokinetics and Pharmacodynamics of the New Long-Acting Androgen Ester, Journal of Endocrinology and Metabolism, vol. 75, No. 5, pp. 1204-1210 (1992).
Behre, et al., Long-Term Effect of Testosterone Therapy on Bone Mineral Density in Hypogonadal Men, Journal of Clinical Endocrinology and Metabolism, vol. 82, No. 8, pp. 2386-2390 (1997).
Behre, et al., Long-Term Substitution Therapy of Hypogonadal Men with Transscrotal Testosterone Over 7-10 Years, Clinical Endocrinology (1999) vol. 50, 629-635.
Behre, et al., Prostate Volume in Testosterone-Treated and Untreated Hypogonadal Men in Comparison to Age-Matched Normal Controls, Clin Endocrinol (OXF), Mar. 1994; 40(3): 341-9.
Behre,et al., Intramuscular Injection of Testosterone Undecanoate for the Treatment of Male Hypogonadism: Phase I Studies, European Journal of Endocrinology (1999);140:414-419.
Belgorosky, et al., Changes in Serum Sex Hormone-Binding Globulin and in Serum Non-Sex Hormone-Binding Globulin-Bound Testosterone During Prepuberty in Boys, J Steroid Biochem, 1987; 27(1-3): 291-295.
Belgorosky, et al., Dynamics of SHBG Response to Testosterone. Implications Upon the Immediate Biological Effect of Sex Hormones, J. Steroid Biochem., vol. 18, No. 6, pp. 783-787 (Jun. 1983).
Belgorosky, et al., Progressive Decrease in Serum Sex Hormone-Binding Globulin from Infancy to Late Prepuberty in Boys, J Clin Endocrinol Metab, Aug. 1986; 63(2): 510-512.
Belgorosky, Sex Hormone Binding Globulin Response to Testosterone. An Androgen Sensitivity Test, Acta Endocrinol (Copenh), May 1985; 109(1): 130-138.
Bennett, S.L. et al., "Optimization of bioavailability of topical steroids: non-occluded penetration enhancers under thermodynamic control," J. Pharm. Pharmacol (1985) 37:298-304.
Bentley Pharmaceuticals Announces License Agreement for Its Topical Testosterone Gel Formulation; Li, www.UVentures.com (Dec. 18, 2000).
Bentley Pharmaceuticals Announces Research and Licensing Agreements for Intranasal Pain Management and Topical Hormone Replacement Therapy, www.bentleypharm.com (downloaded Nov. 17, 2001).
Benzoyl peroxide. Wikipedia. http://en.wikipedia.org/wiki/Benzoyl_peroxide. pp. 1-3. Downloaded on Oct. 13, 2009.
Berger, RS et al., A reappraisal of the 21-day cumulative irritation test in man. J. Toxicol. Cut. and Ocular Toxicol. (1982) 1:109-115.
Berndt et al., "Consumption Externalities and Diffusion in Pharmaceutical Markets: Antiulcer Drugs," National Bureau of Economic Research Working Paper 7772 (2000).
Berndt et al., "Information, Marketing, and Pricing in the U.S. Antiulcer Drug Market," The American Economic Review 85(2): 100-105 (May 1995).
Berner, et al., Pharmacokinetic Characterisation of Transdermal Delivery System, Clin Pharmacokinet, Feb. 1994; 26(2): 121-34.
Bernini, et al., Endogenous Androgens and Carotid Intimal-Medical Thickness in Women, J Clin Endocrinol Metab, Jun. 1999; 84(6): 2008-12.
Berrie, "Testosterone Gel Addition Benefits Men With Erectile Dysfunction Who Do Not Respond to PDE5s Alone if Testosterone Levels Are Low," Presented at European Society for Sexual Medicine (ESSM/ISSM) 2008, Belgium.
Besins International Licenses Testogel to Schering, In Vivo: The Business & Medicine Report (Norwalk, CT), Sep. 2002.
Betamethasone dipropionate (Disprosone, Diprolene) MedicineNet.com. http:www.medicinenet.com/betamethasone_dipropionate/article.htm. pp. 1-3. Downloaded Oct. 13, 2009.
Bevier W et al., Aerobic capacity, muscle strength and bone density in elderly men and women. J. Bon. Miner. Res. 4:421 (1989).
Bhasin et al., The effects of supraphysiologic doses of testosterone on muscle size and strength. N. Eng. J. Med. 335: 1-7 (1996).
Bhasin S, et al., Testosterone replacement increases fat-free mass and muscle size in hypogonadal men J Clin Endocrinol Metab 82(2):407-13, 1997.
Bhasin S. et al., Editorial Commentary: Testosterone Supplementation for Cognitive Loss. J. Androl.: 45-46 (Jan./Feb. 2002).
Bhasin, Clinical Review 34—Androgen Treatment of Hypogonadal Men, Journal of Clinical Endocrinology and Metabolism, vol. 74, No. 6, pp. 1221-1225 (1992).
Bhasin, et al., Can Androgen Therapy Replete Lean Body Mass and Improve Muscle Function in Wasting Associated with Human Immunodeficiency Virus Infection?, J. of Parental and Enteral Nutrition, vol. 23, pp. S195-S201 (1999).
Bhasin, et al., Effects of Testosterone Replacement with a Nongenital, Transdermal System, Androderm, in Human Immunodeficiency Virus-Infected Men with Low Testosterone Levels, J. or Clinical Endocrinology and Metabolism, vol. 83, No. 9, pp. 3155-3162 (1998).
Bhasin, et al., Testosterone Supplementation in Older Men: A Rational Idea Whose Time Has Not Yet Come, J. of Andrology, vol. 22, No. 5, pp. 718-731 (2001).
Bhasin, et al., A Biodegradable Testosterone Microcapsule Formulation Providing Uniform Eugonadal Levels of Testosterone for 10-11 Weeks in Hypogonadal Men, J Clin Endocrinol Metab, Jan. 1992; 74(1): 75-83.
Bhasin, et al., Therapeutic Perspective—Issues in Testosterone Replacement in Older Men, Journal of Clinical Endocrinology and Metabolism, vol. 83, No. 10, pp. 3435-3448 (1998).

(56) References Cited

OTHER PUBLICATIONS

Bhowmick et al., Sexual Precocity in a 16-Month-Old Boy Induced by Indirect Topical Exposure to Testosterone, Clinical Pediatric, vol. 46(6), pp. 540-543 (2007).
Biopharmaceutical Firm Launched in Northbrook, Northbrook Star (Northbrook, IL), Aug. 29, 2002.
Biotech Business, "Testosterone Gel Restores Male Hormone Blood Levels" (Apr. 1999).
Biotech Business, "Unimed Submits NDA to Market "Androgel" Testosterone Gel" (Jun. 1999).
Bisschop, et al., Effects of Nandrolone Decanoate on Respiratory and Peripheral Muscles in Male and Female Rats, www.uth.tms.edu. (1996, Downloaded Oct. 8, 1998).
Bloch, et al., Pituitary-Adrenal Hormones and Testosterone Across the Menstrual Cycle in Women with Premenstrual Syndrome and Controls, Biol Psychiatry, Jun. 15, 1998; 43(12): 897-903.
Bocchinfuso, et al., Expression and Differential Glycosylation of Human Sex Hormone-Binding Globulin by Mammalian Cell Lines, Mol Endocrinol, Nov. 1991; 5(11): 1723-1729.
Bockserman, Med. Plastics and Biomaterials Mag., pp. 26-33 (Jul. 1996).
Bond, et al., Sex Hormone Binding Globulin in Clinical Perspective, Acta Obstet. Gynecol. Scand., vol. 66, pp. 255-262 (1987).
Bonithon-Kopp, et al., Relationship Between Sex Hormones and Haemostatic Factors in Healthy Middle-Aged Men, Atherosclerosis, vol. 71, pp. 71-76 (1988).
Bonney, Hormone Replacement Therapy for Men, American Clinical Laboratory, http://iscpubs.com/pubs/acl1197.html (Nov./Dec. 1997).
Booji, et al., Androgens as Adjuvant Treatment in Postmenopausal Female Patients with Rheumatoid Arthritis, Ann Rheum Dis, Nov. 1996; 55(11): 811-5.
Boots, et al., Measurement of Total Serum Testosterone Levels Using Commercially Available Kits: High Degree of Between-Kit Variability, Fertil Steril, Feb. 1988; 69(2): 286-292.
Borah et al., Risedronate preserves bone architecture in postmenopausal women with osteoporosis as measured by three-dimensional microcomputed tomography. Bone, 34:736-46 (2004).
Boyle, et al., Serum Testosterone Measurements, Am J Clin Pathol, Jun. 1984; 81(6): 754-761.
Brachet et al., Children's virilization and the use of a testosterone gel by their fathers, Eur J Pediatr, vol. 164, pp. 646-647 (2005).
Braunsteiner, et al., Essential Role of Post-Heparin Lipoprotein Lipase Activity and of Plasma Testosterone in Coronary Artery Disease, The Lancet, pp. 1242-1244 (Jun. 1, 1985).
Brawer MK. et al., Screening for prostatic carcinoma with prostate-specific antigen. J. Urol 147:841 (1992).
Brill, et al., Single and Joint Impact on One-Month of Transdermal Testosterone (T) and/or Recombinant Human Growth Hormone (rhGH) Supplementation on Body Composition, Strength, Balance, Function and Muscle IGF-1 and Androgen Gene Expression in Healthy Older Men: A Prospective Randomized Double-Blind Crossover, The Endocrine Society, No. 1647 (ENDO 2000).
Brinkmann, I. et al., "An attempt to clarify the influence of glycerol, propylene glycol, isopropyl myristate and a combination of propylene glycol and isopropyl myristate on human stratum corneum," Pharmazie (2005) 60:215-220.
Brinkmann, I. et al., "Role of isopropyl myristate, isopropyl alcohol and a combination of both in hydrocortisone permeation across the human stratum corneum," Skin Pharmacol. Appl. Skin Physiol. (2003) 16:393-404.
Brocks, et al., Pharmacokinetics of Testosterone in Hypogonadal Men After Transdermal Delivery: Influence of Dose, Journal of Clinical Pharmacology, vol. 36, pp. 732-739 (1996).
Brodsky IG, Balagopal P, Nair KS. Effects of testosterone replacement on muscle mass and muscle protein synthesis in hypogonadal men. J Clin Endocrinol Metab 1996;81(10) 3469-3475.
Brokaw, T, NBC-TV NBC Nightly News, LIFETIME Transcript on NBC's Don Lemon Interview (Nov. 7, 2002).

Bronaugh et al., Vehicle effects on percutaneous absorption: in vivo and in vitro comparison with human skin, Br. J. Dermatol., vol. 11, pp. 1-11 (1986).
Broniarczyk-Dyla, et al., Aging of the Skin During Menopause, Medical Science Monitor vol. 5 (No. 5) 1024-1029. (Jan. 22, 1999).
Bross, et al., Androgen effects on body composition and muscle function: implications for the use of androgens as anabolic agents in sarcopenic states. Baillieres Clin. Endocrinol. Metab 12: 365-378 (1998).
Bruun, et al., Dihydrotestosterone Measured in Core Biopsies from Prostatic Tissues, Am J Clin Oncol, 1988; 11 Suppl 2:S27-9.
Buckler, et al., Pharmacokinetics of a Novel Transdermal Delivery System for Testosterone in Women Journal of Endocrinology, vol. 144 p. P329 (1995).
Buckler, et al., The Effects of Low-Dose Testosterone Treatment on Lipid Metabolism, Clotting Factors and U/trasonographic Ovarian Morphology in Women, Clinical Endocrinology, vol. 49, pp. 173-178 (1997).
Buckler, et al., Which Androgen Replacement Therapy for Women?, J Clin Endocrinol Metab, Nov. 1998; 83(11):3920-4.
Buhling et al., AIPPI Summary Report on Selection Inventions—The Inventive Step Requirement, Other Patentability and Scope of Protection (2009).
Bunch, et al., Pituitary Radiographic Abnormalities and Clinical Correlates of Hypogonadism in Elderly Males Presenting with Erectile Dysfunction, The Aging Male, vol. 5, pp. 38-46 (2002).
Burdet, et al., Administration of growth hormone to underweight patients with chronic obstructive pulmonary disease. A prospective, randomized, controlled study. Am. J. Respir. Crit Care Med. 156: 1800-1806 (1997).
Burge et al., "Idiopathic hypogonadotropic hypogonadism in a male runner is reversed by clomiphene citrate." Fertil. Steril. 67(4): 783-85 (1997).
Burger H. G. et al., The management of persistent menopausal symptoms with oestradiol-testosterone implants: clinical, lipid and hormonal results, Maturitas 1984; 6:351-358.
Burger, et al., Effect of Combined Implants of Oestradiol and Testosterone on Libido in Postmenopausal Women, British Medical Journal (Clin. Res. Ed.), vol. 294, No. 6577, pp. 936-937 (Apr. 11, 1987).
Business Wire, "Preliminary Data Show Topical Testosterone Replacement Gel May Effectively Restore Blood Levels of Male Hormone" (Feb. 11, 1999).
Business Wire, "Unimed Pharmaceuticals Submits NDA to Market Androgel—Testosterone Gel—for Men with Low Testosterone" (Apr. 29, 1999).
Buvat et al., Endocrine Screening in 1,022 Men with Erectile Dysfunction: Clinical Significance and Cost-Effective Strategy, The J. of Urology, vol. 158, pp. 1764-1767 (Nov. 1997).
Cable, C.G., "Oleic acid," Pharmaceutical Excipients (2009) 3 pages.
Calendar—It's a Guy Thing, Houston Chronicle, Sep. 11, 2002.
Calendar—Men's Health, Atlanta Journal-Constitution, Oct. 29, 2002.
Capaldini L. Fatigue and HIV Part II. Interview Interview with Lisa Capaldini, M.D. by John S. James. AIDS Treat News. Apr. 3, 1998, downloaded at http://www.thebody.com/content/art31526.html (Nov. 11, 2010).
Carey, et al., A Study to Evaluate Serum and Urinary Hormone Levels Following Short and Long Term Administration of Two Regimens of Progesterone Cream in Postmenopausal Women, British Journal of Obstetrics and Gynaecology, p. 722-726, (Jun. 22, 2000).
Carey, et al., Transdermal Testosterone Treatment of Hypogonadal Men, The Journal of Urology, vol. 140, pp. 76-79, (Jul. 1988).
Carlstrom, et al., Relationship Between Serum Testosterone and Sex Hormone-Binding Globulin in Adult Men with Intact or Absent Gonadal Function, International Journal of Andrology, vol. 13, pp. 67-73 (1990).
Carter, et al., Longitudinal evaluation of prostate-specific antigen levels in men with and without prostate disease. JAMA 267:2215 (1992).
Casaburi, et al., Anabolic therapies in chronic obstructive pulmonary disease. Monaldi Arch. Chest Dis. 53: 454-459 (1998).

(56) References Cited

OTHER PUBLICATIONS

Cascione, Evaluation of the use of a unique testosterone topical gel formulation and a transdermal testosterone patch (Androderm), Department of Veterans Affairs, Abstract, Jun. 5, 2001.

Cashdan, Hormones, Sex and Status in Women, Hormones and Behavior, vol. 29, pp. 354-366 (Sep. 1995).

Casson, et al., Testosterone Delivery Systems for Women: Present Status and Future Promise, Seminars in Reproductive Endocrinology, vol. 16 (No. 2). p. 153-159 (Jan. 22, 1998).

Casson, et al., Androgen Replacement Therapy in Women: Myths and Realities, Int J Fertil Menopausal Stud; Jul.-Aug. 1996; 41(4):412-22.

Castelo-Branco, et al., Circulating Hormone Levels in Menopausal Women Receiving Different Hormone Replacement Therapy Regimens, Journal of Reproductive Medicine, vol. 40 (No. 8), pp. 556-560, (Aug. 22, 1995).

Catalona W. et al., Measurement of prostate-specific antigen in serum as a screening test for prostate cancer. N Engl J. Med 324:1156 (1991).

CBS Evening News, "More Men Take Testosterone," Transcript of CBS television broadcast (Aug. 25, 2002).

Cellegy Pharmaceuticals Market Opportunities, Cellegy Pharmaceuticals, Inc., http://www.cellegy.com/corp/market.html (1997).

Cellegy Pharmaceuticals, Inc. Annual Report (Form 10-K) pursuant to The Securities Exchange Act of 1934 for the Fiscal Year Ended Dec. 31, 1998, filed on Mar. 22, 1999.

Cellegy Pharmaceuticals, Inc. Annual Report (Form 10-K) pursuant to The Securities Exchange Act of 1934 for the Fiscal Year Ended Dec. 31, 1999, filed on Mar. 14, 2000.

Cellegy Pharmaceuticals, Inc. Annual Report (Form 10-KSB) pursuant to The Securities Exchange Act of 1934 for the Fiscal Year Ended Dec. 31, 1997, filed on Mar. 31, 1998.

Cellegy Pharmaceuticals, Inc. Annual Report (Form 10-KSB) pursuant to The Securities Exchange Act of 1934 for the Fiscal Year Ended Dec. 31, 1996, filed on Mar. 28, 1997.

Cellegy Pharmaceuticals, Inc. Investors: Press Releases, Cellegy Pharmaceuticals Receives FDA Nonapproval Letter for Fortigel, Jul. 7, 2003, www.cellegy.com.

Center, et al., Mortality After All Major Types of Osteoporotic Fracture in Men and Women: An Observational Study, The Lancet, vol. 353, pp. 878-882 (Mar. 13, 1999).

Chakravarti, et al., Endocrine Changes and Symptomatology After Oophorectomy in Premenopausal Women, Br J Obstet Gynaecol, Oct. 1977; 84(10): 769-75.

Chan, TC. Percutaneous penetration enhancers: An update. Prcdgs of 9th Biennial Intl Conf of Perspectives in Percutaneous Penetration, La Grand Motte, France, Apr. 13, 2004; published Jan. 2005.

Chemana et al., Percutaneous absorption of 5-alpha-dihydrotestosterone in Man II. Percutaneous administration of 5-alpha-dihydrotestosterone in hypogonadal men with idiopathic haemochromatosis; clinical, metabolic and hormonal effectiveness. International Journal of Andrology 5:595-606 (1982).

Chemistry: The Central Science, 2d Edition, pp. 75-76, 84-86, 348-349 (1981).

Chen, et al., The Correlation Between Pretreatment Serum Hormone Levels and Treatment Outcome for Patients with Prostatic Cancer and Bony Metastasis, BJU Intl., vol. 89, pp. 710-713 (2002).

Chen, et al., Therapeutic Patents for Topical and Transdermal Drug Delivery Systems, Expert Opinion on Therapeutic Patents, vol. 10 (No. 7, pp. 1035-1043 (2000).

Cheng, R. Columbia Labs Reports Data on Testosterone Buccal Pdt, Dow Jones News Service, Jun. 20, 2002.

Cherrier, et al., Testosterone Supplementation Improves Spatial and Verbal Memory in Healthy Older Men, Neurology, vol. 57, pp. 80-88 (2001).

Cherrier, et al., T-Gel Study: Cognitive Effects of Exogenous Testosterone Manipulation in Hypogonadal Men, (Jun. 7, 1999), University of Washington.

Chevallier, et al., A double-blind, placebo-controlled study on the effects of transdermal testosterone replacement in hypogonadal men with type 2 diabetes or metabolic syndrome: the TIMES2 study, European Association of Urology, PosterSesseionOnline.com (2008).

Chiang HS, et al., Testosterone gel monotherapy improves sexual function of hypogonadal men mainly through restoring erection: evaluation by IIEF score.Urology. Apr. 2009;73(4):762-6. (Epub Date: Jan 1, 2009).

Chik Z, et al., Correcting endogenous concentrations of testosterone influences bioequivalence and shows the superiority of TDS(R)-testosterone versus Androgel(R), Int J Clin Pharmacol Ther. Apr. 2009;47(4):262-8.

Chilcott et al., Transepidermal Water Loss Does not Correlate with Skin Barrier Function In Vitro, The Journal of Investigative Dermatology, vol. 118, No. 5, pp. 871-875, May 2002.

Choi, et al., Transdermal Dihydrotestosterone Therapy and its Effects on Patients with Microphallus, J Urol, Aug. 1993; 150(2 Pt 2): 657-660.

Christiansen, Behavioral Correlates of Testosterone, Testosterone: Action, Deficiency, Substitution, 109-111 (1998).

Chudakov B, et al., Transdermal testosterone gel prn application for hypoactive sexual desire disorder in premenopausal women: a controlled pilot study of the effects on the Arizona sexual experiences scale for females and sexual function questionnaire, J Sex Med. Jan. 2007;4(1):204-8.

Citron, et al., Prevalence of Hypothalmic-Pituitary Imaging Abnormalities in Impotent Men with Secondary Hypogonadism, The J. of Urol., vol. 155, pp. 529-533 (Feb. 1996).

Clarys, P. et al., "In vitro percutaneous penetration through hairless rat skin: influence of temperature, vehicle and penetration enhancers," Eur. J. Pharma. Biopharm. (1998) 46:279-283.

Cleary et al., The effect of intensive glycemic treatment on coronary artery calcification in type 1 diabetic participants of the Diabetes Control and Complications Trial/Epidemiology of Diabetes Interventions and Complications (DCCT/EDIC) Study. Diabetes. Dec. 2006;55(12):3556-65.

Clift, Let Us Pause, Brattleboro Reformer (Brattleboro, VT), Aug. 17, 2002.

Clift, Medicalizing Middle Age: Now Drug Companies Go After Men, The Keene Sentinel (Keene, NH), Aug. 18, 2002.

Cofrancesco, Jr., et al., Transdermal Testosterone Delivery Systems, The Endocrinologist, vol. 6, No. 3, pp. 207-213 (1996).

Cohan GR, et al., A prospective study of the safety and efficacy of a topical transdermal testosterone gel versus intramuscular injections of testosterone for the treatment of testosterone deficiency in male HIV-infected patients. Poster presentation #H-1912 at the Interscience Conference on Antimicrobial Agents and Chemotherapy Annual Meeting, Oct. 2002, Chicago, IL.

Colao, et al., Effect of GH and/or Testosterone Deficiency on the Prostate: An Ultrasonographic and Endocrine Study in GH-deficient Adult Patients, Euro. J. of Endocrinology, vol. 143, pp. 61-69 (2000).

Colker, Q and A: Ask Dr. Colker, Muscular Development (Setauket, NY), Aug. 2002.

Columbia Laboratories Announces European Marketing Partnership With Ardana Bioscience for Testosterone Buccal Bioadhesive Product, www.bioexchange.com (Oct. 17, 2002).

Colvard DS et al., Identification of androgen receptors in normal human osteoblast-like cells. Proc Natn Acad Sci 86:854 (1989).

Company Interview: MacroChem Corporation (MCHM), The Wall Street Transcript (New York, NY), Jul. 8, 2002 at 201-205.

Conan, N. Men's Health Series, Part II: Male Menopause, National Public Radio Talk of the Nation Online (Oct. 15, 2002).

Confranceso Jr., et al., Testosterone Replacement Treatment Options for HIV-Infected Men, J. of Aids and Human Retrovirology, vol. 16, pp. 254-265 (1997).

Conway, et al., Randomized Clinical trial of Testosterone Replacement Therapy in Hypogonadal Men, Int J Androl, Aug. 1988; 11(4): 247-64.

Cooper, E.R., "Increased skin permeability for lipophilic molecules," J. Pharma. Sci. (1984) 73(8):1153-1156.

Cooper, et al., Epidemiology of Osteoporosis, Trends Endocrinol. Metab., vol. 3, pp. 224-229 (1992).

(56) References Cited

OTHER PUBLICATIONS

Cooper, et al., Effect of Fatty Acids and Alcohols on the Penetration of Acyclovir Across Human Skin in Vitro, Journal of Pharmaceutical Sciences, vol. 74, No. 6, pp. 688-689 (Jun. 1985).
Cornwell, P.A. et al., Modes of action of terpene penetration enhancers in human skin; differential scanning calorimetry, small-angle x-ray diffraction and enhancer uptake studies, Int. J. Pharmaceu. (1996) 127:9-26.
Corona G, et al., Six-month administration of 1% testosterone gel is able to restore erectile function in hypogonadal patients with erectile dysfunction, Arch Ital Urol Androl. Sep. 2008;80(3):103-8.
Corrales, et al., Partial Androgen Deficiency in Aging Type 2 Diabetic Men and Its relationship to Glycemic Control, Metabolism 53(5):666-72 (May 2004).
Correspondence to FDA from Testocreme® and Citizen Petition (Jul. 3, 2001).
Correspondence to Testocreme® from FDA regarding response to Citizen's Petition (Apr. 12, 2002).
Cortaid. RxList.com. http://www.rxlist.com/cortaid-drug.htm. pp. 1-2. Downloaded on Oct. 13, 2009.
Crols, Solvay Sees 2 Bln Euros in Drug Sales in 2002, Reuters, Jul. 5, 2002.
Cunningham, et al, Plasma Sex Hormone-Binding Globulin Levels Decrease During the Second Decade of Life Irresponsive of Pubertal Status, Journal of Clinical Endocrinology and Metabolism, vol. 58, No. 5, pp. 915-918 (1984).
Cunningham, et al, Testosterone Replacement Therapy and Sleep-Related Erections in Hypogonadal Men, Journal of Clinical Endocrinology and Metabolism, vol. 70, No. 3, 792-797 (1990).
Cunningham, et al., Testosterone Replacement with Transdermal Therapeutic System, Physiological Serum Testosterone and Elevated Dihydrotestosterone Levels, JAMA, May 5, 1989; 261(17): 2525-30.
Cunningham, et al., Testosterone Transdermal Delivery System, Pharmacology. Biology and Clinical Applications of Androgens. vol. 42, pp. 437-447 (1996 Wiley-Liss, Inc).
Cutolo, et al., Androgen Replacement Therapy in Male Patients with Rheumatoid Arthritis, Arthritis and Rheumatism, vol. 34, No. 1, pp. 1-5 (Jan. 1991).
Cutolo, et al., Hypothalamic-Pituitary-Adrenocortical Axis Function in Premenopausal Women with Rheumatoid Arthritis Not Treated with Glucocorticoids, J Rheumatol, Feb. 1999; 26(2): 282-8.
Cutter, Christopher, Compounded Percutaneous Testosterone Gel: Use and Effects in Hypogondal Men, JABFP, col. 14(1), pp. 22-32 (2001).
d'A Semple, P., W. S. Watson, R. Hume, and G. R Sutherland. Potassium studies in chronic obstructive airways disease. Thorax 33: 734-739 (1978).
Daly, R.C. et al., Testosterone's Effects Not Limited to Mood. Arch Gen Psychiatry 57: 403-404(Apr. 2001).
Damassa, et al., Sex Hormone-Binding Globulin and Male Sexual Development, Neuroscience and Biobehavioral Reviews, vol. 19, No. 2, pp. 165-175 (1995).
Data Supports Safety of Estratest for Men, Doctor's Guide, www.pslgroup.com (Mar. 9, 1998).
Davidson JM. et al., Effects of androgens on sexual behavior in hypogonadal men. J. Clin. Endocrinol. Metab. 48:955 (1979).
Davidson, et al., Hormonal Changes and Sexual Function in Aging Men, Journal of Clinical Endocrinology and Metabolism, vol. 57, No. 1, pp. 71-77 (1983).
Davidson, et al., Hormonal Replacement and Sexuality in Men, Clinics in Endocrinology and Metabolism, vol. 11, No. 3, pp. 599-623 (Nov. 1982).
Davis et al., Testosterone Enhances Estradiol's Effects on Postmenopausal Bone Density and Sexuality, Maturitas, vol. 21, No. 3, pp. 227-236 (Apr. 1995).
Davis, Androgen Treatment in Women, Medical Journal of Australia, vol. 170 (No. 11), p. 545-549. (Jun. 7, 1999).
Davis, The Clinical Use of Androgens in Female Sexual Disorders, Journal of Sex & Marital Therapy, vol. 24, pp. 153-163 (1998).
Davis, Androgen Replacement in Women: A Commentary, J Clin Endocrinol Metab, Jun. 1999; 84(6): 1886-91.
Davis, et al., Clinical Review 82: Androgens and the Postmenopausal Woman, J. Clin Endocrinol Metab, Aug. 1996; 81(8): 2759-63.
Davis, et al., Use of Androgens in Postmenopausal Women, Curr Opin Obstet Gynecol, Jun. 1997; 9(3): 177-80.
De Boer et al., Insulin therapy, hyperglycemia, and hypertension in type 1 diabetes mellitus. Arch Intern Med. Sep. 22, 2008;168(17):1867-73.
De Lignieres et al., Treatment of Male Hypogonadism by Topical Administration of Androgens. In: Mauvais-Jarvis et al. Eds. Percutaneous Absorption of Steroids, pp. 273-283 (1980).
De Lignieres, Transdermal Dihydrotestosterone Treatment of Andropause, Annals of Medicine 25: 235-241, (1993).
De Lunardo, et al., Determination of Acceptability of 2 Cutaneous Estradiol Gels, In a Dose of 1.5 mg Daily, J. Gynecol. Obstet. Bio. Reprod. (Paris), vol. 29, No. pp. 509-516, (Sep. 2000). (Abstract only).
De Ronde, Hyperandrogenism after transfer of topical testosterone gel: case report and review of published and unpublished studies, Human Reproduction, vol. 24(2), pp. 425-428 (2008).
De Ronde, Willem, Testosterone Gel for the Treatment of Male Hypogonadism, Expert Opin. Biol. Ther., vol. 9(2), pp. 249-253 (2009).
De Rose, et al., Combined Oral Therapy with Sildenafil and Doxazosin for the Treatment of Non-Organic Erectile Dysfunction Refractory to Sildenafil Monotherapy, Intl. J. of Impotence Research, vol. 14, pp. 50-53 (2002).
Definition of Isopropyl Myristate (5103), The Merck Index—An Encyclopedia of Chemicals, Drugs, and Biologicals, 11th edition, p. 821 (1989).
Delanoe et al., Androgenisation of Female Partners of Men on Medroxyprogesterone Acetate/Percutaneous Testosterone Contraception, The Lancet (Feb. 1984), p. 276.
Delatestryl BTG (testosterone cypionate), USP, Revised Dec. 2005.
Demery, A. Contraception Masculine Soins Gyn.-Obs.-Puer,-Ped No. 72 (May 1987) pp. 33-38.
Denis, Future Implications for the Management of Benign Prostatic Hyperplasia, Eur Urol, 1994; 25 Suppl 1:29-34.
Depo-Testosterone (testosterone cypionate), USP, Revised Aug. 2002.
Derogatis, The Derogatis Interview for Sexual Functioning (DISF/DISF-SR): an introductory report, J Sex Marital Ther. 1997 Winter;23(4):291-304.
Deslypere JP et al., Influence of age on pulsatile luteinizing hormone release and responsiveness of the gonadotrophs to sex hormone feedback in men. J. Clin. Endocrinol. Metab. 64:68 (1987).
Deslypere JP. et al., Leydig cell function in normal men: effect of age, life-style, residence, diet and activity. J. Clin. Endocrinol. Metab. 59:955-962 (1984).
Devogelaer et al., Low bone mass in hypogonadal males. Effect of testosterone substitution therapy, a densitometric study. Maturitas. Aug. 1992;15(1):17-23.
Diamond T. et al., Effects of testosterone and venesection on spinal and peripheral bone mineral in six hypogonadal men with hemochromatosis. J. Bone Min Res 6:39 (1991).
Ding, et al., Sex Hormone-Binding Globulin Mediates Prostate Androgen Receptor Action via a Novel Signaling Pathway, Endocrinology, vol. 139, No. 1, pp. 213-218 (Jan. 1998).
Dissemond, et al., Venous Leg Ulcers in a Patient with Klinefelter's Syndrome and Increased Activity of Plaminogen Activator Inhibitor-1, Acta. Derm. Venerol., vol. 83, pp. 149-150 (2002).
Dobs A, Clinical Trial of Testosterone Gel HRT in Hypogonal Men, Computer Retrieval of Information on Scientific Projects, downloaded at http://commons.ciLnih.gov/crisp3/CRISP_UB.getdoc?textkey=6457885&p_grant_num=5MO1RR000052-400738 (Feb. 19, 2002).
Dobs et al., Short-term pharmacokinetic comparison of a novel testosterone buccal system and a testosterone gel in testosterone deficient men. Current Med. Res. and Opns. 20(5):729-738 (2004).
Dobs et al., Pharmacokinetic Characteristics, Efficacy and Safety of Buccal Testosterone in Hypogonadal Males: A Pilot Study, J. Clinical Endocrinology & Metabolism 83:33-39 (1998).

(56) References Cited

OTHER PUBLICATIONS

Dobs, Androgen Therapy in AIDS Wasting, Bailliere's Clinical Endocrinology and Metabolism, vol. 12, No. 3, pp. 379-390 (Oct. 1998).
Dobs, A.S. Endocrine Disorders in Men Infected with Human Immunodeficiency Virus. Am. J. of Med. 84: 611-616 (Mar. 1988).
Dobs, et al., An Open Label Phase III Study of Fortigel (Testosterone) 2% Gels in Hypogondal Makes, ASA Poster (2009).
Dobs, et al., Pharmacokinetics, Efficacy and Safety of a Permeation-Enhanced Testosterone Transdermal System in Comparison with Bi-Weekly Injections of Testosterone Enanthate for the Treatment of Hypogonadal Men, J Clin Endocrinol Metab. Oct. 1999;84(10):3469-78.
Donahoe, et al., The effect of an aggressive nutritional support regimen on body composition in patients with severe COPD and weight loss. Am. J. Respir. Crit Care Med. 149(4):A3-A13 (1994).
Doren, Basic Principles of Hormone Replacement Therapy in the Postmenopause, Ther. Umsch Vo. 57 (No. 10). pp. 628-634 (Oct. 2000): (Abstract only).
Dosik et al., Tolerability comparison of adapalene gel, 0.3% versus tazarotene cream, 0.05% in subjects with healthy skin. (Clinical report). Journal of drugs in Dermatology. Jun. 1, 2007.
Douchi, et al., Serum Androgen Levels and Muscle Mass in Women with Polycystic Ovary Syndrome, Obstetrics & Gynecology, vol. 94, No. 3, pp. 337-340 (1999).
Douglas, et al., Effect of Exogenous Testosterone Replacement on Prostate-Specific Antigen and Prostate-Specific Membrane Antigen Levels in Hypogonadal Men, J. of Surg. Oncology, vol. 59, pp. 246-250 (1995).
Dr. N's Menopause & Hysterectomy Resource Page, http://www.menopausehysterectomy.com/methods.htm (accessed Jun. 22, 2000).
Drafta, et al., The Effects of Endocrine Therapy on Plasma Steroids in Prostatic Carcinoma Patients, Endocrinolgie, Jul.-Sep. 1984; 22(3): 191-7.
Drake, et al., Associations Between Circulating Sex Steroid Hormones and Cognition in Normal Elderly Women, Neurology, Feb. 2000; 54(3): 599-603.
Drobac et al., A workshop on pubertal hormone replacement options in the United States, Journal of Pediatric Endocrinology and Metabolism, 19(1):55-64 (2006).
Ducharme, Male Menopause: The Real Thing?, PN/Paraplegia News, Nov. 2002.
Duncan PW, et al., Functional reach: a new clinical measure of balance. J Geron 45:M192-7, 1990.
Earthman, CP, et al., A comparison of bioimpedance methods for detection of body cell mass change in HIV infection. J. Appl, Physiol 88: 944-956 (2000).
Echikson, Solvay CEO's Positive Outlook Breaks with Usual Caution, Dow Jones News Service, Jun. 6, 2002.
Edelstein, et al., The Latest Option and Future Agents for Treating Male Hypogonadism, Expert Opin. Pharmcaother., vol. 8(17), pp. 2991-3008 (2007).
Ehrenfeld, T. Health: A Loving Feeling, Newsweek (Nov. 11, 2002).
El Tribunal De Justicia De La Comunidad Andina, Oct. 27, 2000 (available at http://intranet.comunidadandina.org/Documentos/Procesos/21-ip-2000.doc).
ENDO 99: Testosterone Patch Effective for Diminished Sexual Function in Surgically Menopausal Women, Doctor's Guide to the Internet, www.docguide.com (Jun. 15, 1999).
Engelen, et al., Nutritional depletion in relation to respiratory and peripheral skeletal muscle function in out-patients with COPD. Eur. Respir. J. 7: 1793-1797 (1994).
English, et al., Low-Dose Transdermal Testosterone Therapy Improves Angina Threshold in Men with Chronic Stable Angina: A Randomized, Double-Blind, Placebo-Controlled Study, Circulation, vol. 102, pp. 1906-1911 (2000).
English, et al., Men with Coronary Artery Disease Have Lower Levels of Androgens than Men with Normal Coronary Angiograms, European Heart J., vol. 21, pp. 890-894 (2000).

English, et al., Testosterone Acts as Coronary Vasodilator by a Calcium Antagonistic Action, J. of Endocrinological Investigation, vol. 25, pp. 455-458 (2002).
Eriksson, et al., Serum Levels of Androgens are Higher in Women with Premenstrual Irritability and Dysphoria Than in Controls, Psychoneuroendocrinology, vol. 17, Nos. 2-3, pp. 195-204 (May-Jul. 1992).
Ernesti, et al., Absorption and Metabolism of Topically Applied Testosterone in an Organotypic Skin Culture, Skin Pharmacol, 1992; 5(3): 146-153.
Escoffier et al., Age-related mechanical properties of human skin: an in vivo study, the Society for Dermatology, Inc. 353 (1989).
Esposito, J, Rights to Market: Marketing Presence in Oncology, Med Ad News (West Trenton, NJ), Oct. 2002.
EstroGel® 0.06% (estradiol gel), 500123, 3E Rev Mar. 2004, pp. 1-16.
Estrogel, www.netdoktor.dk/medicin/Fakta/Estrogel (Downloaded Jun. 26, 2001).
Events Calendar: Events for the week of Dec. 13-19—Sportmart: Time Out for Men's Health, St. Paul Pioneer Press, Dec. 13, 2002.
Ewing, et al., Dihydrotestosterone Concentration of Beagle Prostatic Tissue: Effect of Age and Hyperplasia, Endocrinology, Dec. 1983; 113(6): 2004-9.
Experimental Abbott drug halts spread of prostate cancer. Chicago Tribune, Jun. 5, 2001.
Exton, et al., Cardiovascular and Endocrine Alternations after Masturbation-Induced Orgasm in Women, Psychosom Med, May-Jun. 1999; 61(3): 280-9.
Fabbri, et al., Testosterone Treatmet to Mimic Hormone Physiology in Androgen Replacement Therapy: A View on Testosterone Gel and Other Preparation Available, Expert Opin. Biol. Ther., vol. 7(7), pp. 1093-1106 (2007).
Fahmy, et al., Is the Measurement of Serum Testosterone Routinely Indicated in Men with Erectile Dysfunction?, BJU Intl., vol. 84, pp. 482-484 (1999).
Fahrner et al., Effects of Endurance Exercise on Free Testosterone Concentration and the Binding Affinity of Sex Hormone Binding Globulin (SHBG), International Journal of Sports Medicine, vol. 19, No. 1, pp. 12-15 (Jan. 1998). (Abstract only).
Farmer et al., Race and sex differences in hip fracture incidence. Am J. Public Health 74:1374 (1984).
FDA Guidance for Industry, Bioavailability and Bioequivalence Studies for Orally Administered Drug Products—General Considerations, Mar. 2003.
FDA Guidance for Industry, Developing Products for Weight Management (Draft Guidance), Feb. 2007.
FDA Guidance for Industry, Statistical Approaches to Establishing Bioequivalence, Jan. 2001.
FDA press release, Testosterone Gel Safety Concerns Prompt FDA to Require Label Changes, Medication Guide, May 7, 2009.
Fedorak et al., A novel colon-specific steroid prodrug enhances sodium chloride absorption in rat colitis, Am. J. Physiol, 269:G210-218 (1995).
Feigl, et al., Design of the Prostate Cancer Prevention Trial (PCPT), Controlled Clinical Trials, vol. 16, pp. 150-163 (1995).
Feldman, et al., Impotence and Its Medical and Psychosocial Correlates: Results of the Massachusetts Male Aging Study, The J. of Urology, vol. 151, pp. 54-61 (Jan. 1994).
Feldmann et al., Percutaneous Penetration of 14C Hydrocortisone in Man. Archives of Dermatology. 94:649-651 (1966).
Female Sexual Dysfunction and Andropause Could be Advisory Cmte. Topics, The Pink Sheet (Chevy Chase, MD), Mar. 18, 2002.
Female Testosterone in Phase II, Pharmaceutical Business News, vol. 12 (No. 279), p. 17 (Nov. 8, 1996).
Ferenchick, Are Androgenic Steroids Thrombogenic?, The New England Journal of Medicine, p. 476 (Feb. 15, 1990).
Ferreira, I. et al., The influence of 6 months of oral anabolic steroids on body mass and respiratory muscles in undernourished COPD patients. Chest 114: 19-28 (1998).
Fertility Industry News; Unimed Pharmaceuticals' Androgel Shows Solid Promise for Men. Aug. 19, 1998. http://staging.inciid.org/fertinews/androgel.html (Androgel Press Release Aug. 19, 1998).

(56) References Cited

OTHER PUBLICATIONS

Fiet J et al., Percutaneous absorption of 5a-dihydrotestosterone in man. I. Plasma androgen and gonadotropin levels in normal adult men after percutaneous administration of 5a-dihydrotestosterone. Int J. Androl 5:586 (1982).
Findlay et al., Journal of Clinical Endocrinology & Metabolishm, 64(2):266-68 (1987).
Findlay, et al., Treatment of Primary Hypogonadism in Men by the Transdermal Administration of Testosterone, J Clin Endocrinol Metab, Feb. 1989; 68(2): 369-373.
Finkelstein JK et al., Osteoporosis in men with idiopathic hypogonadotrophic hypogonadism. Ann Intern Med. 106:354 (1987).
Finkelstein JS, et al., Increases in bone density during treatment of men with idiopathic hypogonadotropic hypogonadism. J Clin Endocrinol Metab 1989; 69 ; 69:776-783.
First Phase of Testosterone TDS Trial Successful. Press release. Mar. 5, 2004.
Floter, et al., Administration of Testosterone Undecanoate in Postmenopausal Women: Effects on Androgens, Estradiol, and Gonadotrophins , Menopause, Jul.-Aug. 2000; 7(4): 251-6.
Flynn MA et al., Total body potassium in aging humans: longitudinal study. Am J. Clin. Nutr. 50:713 (1989).
Folstein MF, et al., Mini-mental state. A practical method for grading the cognitive state of patients for the clinician. J Psychiatr Res. 1975; 12: 189-198.
Forbes GB. et al., Age and sex trends in lean body mass calculated from 40K measurements: with a note on theoretical basis for the procedure Ann NY Acad Sci 110:225 (1963).
Fournier et al., Value of a Percutaneous Estrogen Solution in Stopping Lactation, Rev. Fr. Gynecol. Obstet., vol. 85, No. 12, pp. 715-719 (Dec. 1990). (Abstract only).
Fowler, et al., The Response of Metastatic Adenocarcinoma of the Prostate to Exogenous Testosterone, The J. of Urology, vol. 126, pp. 372-375 (Sep. 1981).
Francis RM et al., Osteoporosis in hypogonadal men: role of decreased plasma 1.21-dihydroxy vitamin D, calcium malabsorption and low bone formation. Bone 7:261 (1986).
Francoeur, M. et al., "The protein-lipid structure of stratum corneum in relation to its phase and permeability properties," Biophys. J. (1990) 57:188a.
Francoeur, M.L. et al., "Oleic acid: its effects on stratum corneum in relation to (trans)dermal drug delivery," Pharm. Res. (1990) 7(6):621-627.
Franklin, et al., Precocious Puberty Secondary to Topical Testosterone Exposure, Journal of Pediatric Endocrinology &Metabolism, vol. 16(1), pp. 107-110 (2003).
Fransen, et al., Excess Mortality or Institutionalization After Hip Fracture: Men Are at Greater Risk than Women, JAGS, vol. 50, pp. 685-690 (2002).
Free Health Screenings Offered Saturday for Men, The Tampa Tribune, Nov. 8, 2002.
Freidl KE et al., High density lipoprotein cholesterol is not decreased if an aromatizable androgen is administered. Metabolism 39:69-74 (1990).
Friday, Jul. 5—Men's Health, Arizona Republic (Phoenix, AZ), Jul. 5, 2002.
Friedl KE et al., The administration of pharmacological doses of testosterone or 19-nortestosterone to normal men is not associated with increased insulin secretion or impaired glucose tolerance. J. Clin. Endocrinol. Metab. 68:971 (1989).
Fugl-Myer, et al., On Life Satisfaction in Male Erectile Dysfunction, Intl. J. of Impotence Research, vol. 9, pp. 141-148 (1997).
Fukayama S. et al., Direct modulation by androgens of the response of human bone cells (SaOS-2) to human parathyroid hormone (PTH) and PTH related protein. Endocrinology 125:1789 (1989).
Furuyama et al., Radioimmunoassay for Plasma Testosterone, Steroids, vol. 16, No. 4, pp. 415-428 (1970).

Gabiga, H. et al., "Effect of penetration enhancers on isosorbide dinitrate penetration through rat skin from a transdermal therapeutic system," Int. J. Pharma. (2000) 199:1-6.
Gaidano et al., Dynamics of the Binding Capacity of Plasma Sex Hormone Binding Globulin (SHBG) for Testosterone and Dihydrotestosterone During Puberty, Clinical Chimica Acta, vol. 100, No. 2, pp. 91-97 (Jan. 15, 1980).
Gallagher JC. et al., Epidemiology of fractures of the proximal femur in Rochester, Minnesota. Clen. Orth. Rel.Res. 150:163 (1980).
Gallagher, et al., Androgens Contribute to the Stimulation of Cancellous Bone Formation by Ovarian Hormones in Female Rats, The American Physiological Society, pp. E407-E412 (1996).
Gann et al., Prospective Study of Sex Hormone Levels and Risk of Prostate Cancer, Journal of National Cancer Institute, vol. 88, No. 16, pp. 1118-1126 (Aug. 21, 1996).
Garban et al., Restoration of Normal Adult Penile Erectile Response in Aged Rats by Long-Term Treatment with Androgens, Biology of Reproduction, vol. 53, pp. 1365-1372 (1995).
Garnett et al., A Cross-Sectional Study of the Effects of Long-Term Percutaneous Hormone Replacement Therapy on Bone Density, Obstetrics & Gynecology, vol. 78, No. 6, pp. 1002-1007 (Dec. 1991).
Garnett et al., The Effects of Plasma Estradiol Levels on Increases in Vertebral and Femoral Bone Density Following Therapy with Estradiol and Estradiol with Testosterone Implants, Obstetrics and Gynecology. vol. 79, No. 6, pp. 968-972 (Jun. 1992).
Gearon, Dealing with Male Menopause, DiscoveryHealth.com (Jan. 2, 2002).
Gefael, Graeme's Testosterone Page, www.voyager.co.nz (May 12, 2000).
Geist S. H., Androgen therapy in the human female, J. Clin. Endocrinol. 1941; 1:154-161.
Gelfand et al., Androgen and estrogen-androgen hormone replacement therapy: a review of the safety literature, 1941-1996. Clinical Therapeutics, Excerpta Medica, Princeton, NJ, US vol. 19, No. 3, 1997, pp. 383-404.
Geller, Basis for Hormonal Management of Advanced Prostate Cancer, Cancer, Feb. 1, 1993; 71(3 Suppl): 1039-45.
Geller, et al., DHT in Prostate Cancer Tissue—a Guide to Management and Therapy, Prostate, 1985; 6(1):19-25.
Geller, Nonsurgical Treatment of Prostatic Hyperplasia, Cancer, Jul. 1, 1992; 70(1 Suppl): 339-45.
Geller, Pathogenesis and Medical Treatment of Benign Prostatic Hyperplasia, Prostate Suppl, 1989; 2:95-104.
Gennaro, Remington: The Science and Practice of Pharmacy, 20th Edition, "gels": pp. 745-747 (2000).
Gennaro, Remington: The Science and Practice of Pharmacy, 20th Edition, "sodium hydroxide": p. 1047 (2000).
Gennaro, Remington: The Science and Practice of Pharmacy, 20th Edition, Chapter 44, penetration enhancers,: pp. 842-843 (2000).
Gennaro, Remington: The Science and Practice of Pharmacy, 20th Edition, Chapter 57, Drug Absorption, Action, and Disposition, (2003).
Gennaro, et al., Remington's Pharmaceutical Sciences, Eighteenth Edition, pp. 1305, 1314-1315 (1990).
Genuth et al., Glycation and carboxymethyllysine levels in skin collagen predict the risk of future 10-year progression of diabetic retinopathy and nephropathy in the diabetes control and complications trial and epidemiology of diabetes interventions and complications participants with type 1 diabetes. Diabetes. Nov. 2005;54(11):3103-11.
Gerrity MS, Gaylord S. Williams ME. Short version of the timed manual performance test. Development, reliability and validity. Med Care 1993;31(7):617-628.
Gerstenbluth, Prostate-Specific Antigen Changes in Hypogonadal Men Treated with Testosterone Replacement, J. of Andrology, vol. 23, No. 6, pp. 922-926 (Nov./Dec. 2002).
Gertner, J.M., I-70, Hypogonadism is Uncommon in Men with Aids-Associated Wasting. 38th Annual ICAAC, Abstracts: 384.
Get it Checked! Radio: Audio News Release. Mens Health Network: Jun. 10-16, 2002?
Ghosh et al., Methods of Enhancement of Transdermal Drug Delivery: Part I, Physical and Biochemical Approaches, Pharmaceutical Technology, pp. 73-90 (Mar. 1993).

(56) References Cited

OTHER PUBLICATIONS

Ghosh et al., Methods of Enhancement of Transdermal Drug Delivery: Part IIA, Chemical Permeation Enhancers, Pharmaceutical Technology, pp. 62-90 (Apr. 1993).
Ghosh et al., Methods of Enhancement of Transdermal Drug Delivery: Part IIB, Chemical Permeation Enhancers, Pharmaceutical Technology, pp. 68-76 (May 1993).
Ghusn et al., Evaluation and Treatment of Androgen Deficiency in Males. The Endocrinologist 1(6):399-408 (1991).
Goggin, et al., The Relationship of Mood, Endocrine, and Sexual Disorders in Human Immunodeficiency Virus Positive (HIV+) Women: an Exploratory Study, Psychosom Med, Jan.-Feb. 1998; 60(1): 11-6.
Goldberg-Cettina et al., Enhanced transdermal delivery of estradiol in vitro using binary vehicles of isopropyl myristate and short-chain alkanols, Int'l J. Pharmaceutics (1995);114:237-245.
Golden GM, et al., "Role of stratum corneum lipid fluidity in transdermal drug flux," J Pharm Sci. Jan. 1987;76(1):25-8.
Gonzalez-Sagrado, et al., Reference Values and Methods Comparison of a New Testosterone Assay on the AxSYM System, Clin Biochem, Apr. 2000; 33(3): 175-9.
Gonzalo IT et al., Levonorgestrel implants (Norplant II) for male contraception clinical trials: combination with transdermal and injectable testosterone. J Clin Endocrinol Metab. Aug. 2002;87(8):3562-72.
Good, et al., Bone Mineral Density and Body Composition in Lean Women with Polycystic Ovary Syndrome, Fertil Steril, Jul. 1999; 72(1): 21-5.
Goodman & Gilman, Pharmacological Basis of Therapeutics, Ninth Edition (McGraw-Hill, New York, 1996), p. 8.
Goodman, et al., Action of Skin Permeation Enhancers Azone, Oleic Acid and Decylmethyl Sulphoxide: Permeation and DSC Studies. J Pharm Pharmacol 38(Supply): 71P, 1986.
Goodman, M. et al., "Action of penetration enhancers on human skin as assessed by the permeation of model drugs 5-fluorouracil and estradiol. I. Infinite dose technique," J. Invest. Dermatol. (1988) 91:323-327.
Goodman, M. et al., "Lipid-protein-partitioning (LPP) theory of skin enhancer activity: finitie dose technique," Int. J. Pharma. (1989) 57:29-40.
Gooren L J. G. and Polderman K. H., Safety aspects of androgens. In Testosterone: Action, Deficiency, Substitution. E. Nieschlag and H M. Behre, editors, Springer-Verlag, Heidelberg, p. 136 (1990).
Gooren, Androgen levels and sex function in testosterone-treated hypogonadal men, Archives of Sexual Behavior 16(6):463-473 (1987).
Gooren, Human male sexual functions do not require aromatization of testosterone: a study using tamoxifen, testolactone, and dihydrotestosterone, Arch. Sex. Behav. 14(6):539-48 (1985).
Gooren, A Ten-Year Safety Study of the Oral Androgen Testosterone Undecanoate, J Androl. May-Jun. 1994;15(3):212-5.
Gordon C L, et al., Relation between image-based assessment of distal radius trabecular structure and compressive strength, Canad. Assoc. Radiol. J., 49:390-7 (1998).
Gosker, et al., Skeletal muscle dysfunction in chronic obstructive pulmonary disease and chronic heart failure: underlying mechanisms and therapy perspectives. Am. J. Clin. Nutr. 71: 1033-1047 (2000).
Gouchie, et al., The Relationship Between Testosterone Levels and Cognitive Ability Patterns, Psychoneuroendocrinology, vol. 16, No. 4, pp. 323-334 (1991).
Gould, Duncan, A Novel Metered-Dose 2% Testosterone Gel Treatment for Male Hypogonadism, JMHG, vol. 4(4), pp. 419-427 (2007).
Graeme's Testosterone Page, http://www.voyager.co.nz/~gtuck/graeme/ (May 12, 2000).
Granger CV, et al., Functional assessment scales: a study of persons with multiple sclerosis. Arch Phys Med Rehab 71:870-5, 1990.
Gravholt, et al., Reduced Androgen Levels in Adult Turner Syndrome: Influence of Female Sex Steroids and Growth Hormone Status, Clinical Endocrinology, vol. 50(6), p. 791-800. (Jan. 22, 1999).
Gray A, et al., Age, disease, and changing sex hormone levels in middle-aged men: results of the Massachusetts Male Aging Study. J Clin Endocrinol Metab 73:1016-25, 1991.
Gray A. et al., An examination of research design effects on the association of testosterone and male aging: results of a meta-analysis. J. Clin Epidemiol 44:671 (1991).
Greendale, et al., Endogenous Sex Steroids and Bone Mineral Density in Older Women and Men: the Rancho Bernardo Study, J Bone Miner Res, Nov. 1997; 12(11): 1833-43.
Greenspan SL. et al., Osteoporosis in men with hyperprolactinemic hypogonadism. Ann Intern Med 104:777-82 (1986).
Gregory, et al., A Mechanism for Androgen Receptor-mediated Prostate Cancer Recurrence After Androgen Deprivation Therapy, Cancer Research, vol. 61, pp. 4315-4319 (Jun. 1, 2001).
Gregory, et al., Androgen Receptor Expression in Androgen-independent Prostate Cancer Is Associated with Increased Expression of Androgen-regulated Genes, Cancer Research, vol. 58, pp. 5718-5724 (Dec. 15, 1998).
Greider, "Experts Divided on Value of Testosterone Therapy for Men," AARP Bulletin Online (Jul.-Aug. 2003).
Griffin, J.E. "Hormonal Replacement Therapy at the Time of Expected Puberty in Patients With Gonadal Failure." The Endocrinologist (2003);13(3):211-213.
Griggs RC et al., Effect of testosterone on muscle mass and muscle protein synthesis. J. Appl Physiol 66:498 (1989).
Grignon, et al., College of American Pathologists Conference XXVI on Clinical Relevance of Prognostic Markers in Solid Tumors: Report of the Prostate Cancer Working Group, Arch. Pathol. Lab. Med., vol. 119, pp. 1122-1126 (Dec. 1995).
Grinspoon, et al., Body Composition and Endocrine Function in Women with Acquired Immunodeficiency Syndrome Wasting, J. Clin Endocrinol Metab, May 1997; 82(5): 1332-7.
Grinspoon, et al., Effects of Androgen Administration in Men with the AIDS Wasting Syndrome: A Randomized, Double-Blind, Placebo-Controlled Trial, Ann. Intern. Med., vol. 129, pp. 18-26 (1998).
Grinspoon, Scientific Project: AIDS Wasting in Women—Anabolic Effects of Testosterone, http://commons.cit.nih.gov/crisp3/CRISP_LIB.getdoc?textkey=6381169&p_grant_num=5R01DK054167-04 (downloaded at Feb. 19, 2002).
Grober ED, et al., Efficacy of changing testosterone gel preparations (Androgel or Testim) among suboptimally responsive hypogonadal men, Int J Impot Res. Mar.-Apr. 2008;20(2):213-7. (Epub Date: Sep. 27, 2007).
Gruber, et al., Effect of Percutaneous Androgen Replacement Therapy on Body Composition and Body Weight in Postmenopausal Women, Maturitas, vol. 29, pp. 253-259 (Jun. 1998).
Guay, et al., Testosterone Treatment in Hypogonadal Men: Prostate-Specific Antigen Level and Risk of Prostate Cancer, Endocrine Practice, vol. 6, No. 2, pp. 132-138 (Mar.-Apr. 2000).
Guideline on Clinical Evaluation of Medical Products Used in Weight Control-Addendum on weight control in children. European Medicines Agency. Nov. 15, 2007.
Gunawardena, et al., Testosterone Is a Potential Augmentor of Antioxidant-induced Apoptosis in Human Prostate Cancer Cells, Cancer Detection and Prevention, vol. 26, pp. 105-113 (2002).
Guralnik JM, et al., A short physical performance battery assessing lower extremity function: Association with self-regulated disability and predictors of mortality and nursing home admission. J Gerontol Med Sci 1994;49:M85-M94.
Guzick, et al., Sex, Hormones, and Hysterectomies, The New England Journal of Medicine, vol. 343, No. 10, pp. 730-731 (Sep. 7, 2000).
Gwin et al., The effect of topical pilocarpine on intraocular pressure and pupil size in the normotensive and glaucomatous beagle. Investigative Ophthalmology and Visual Science 16:1143-1148 (1977).
Hadgraft et al., eds. "Transdermal Drug Delivery: Developmental Issues and Research Initiatives." Marcel Dekker: New York (1990). Ch. 10.
Hadigan, Scientific Project: AIDS Wasting in Women: Anabolic Effects of Testosterone Treatment Only, http://commons.cit.nih.gov/crisp3/CRISP_LIB.getdoc?textkey=6439601&p_grant_num=3M01RR000088-37S10365 (downloaded Feb. 19, 2001).

(56) References Cited

OTHER PUBLICATIONS

Hagenfeldt Y, Linde K, Sjoberg HE, Zumkeller W, Arver S: Testosterone increases serum 1,25-dihydroxy vitamin D and insulin-like growth factor-1 in hypogonadal men. Int J Androl 15:93-102, 1992.
Hajjar, et al., Outcomes of Long-Term Testosterone Replacement in Older Hypogonadal Males: A Retrospective Analysis, J. of Clinical Endocrinology and Metabolism, vol. 82, No. 11, pp. 3793-3796 (1997).
Hak, Elisabeth A., Authors Response: Low Levels of Endogenous Androgens Increase the Risk of Atherosclerosis in Elderly Men-Further Supportive data. J Clin Endocrinol Metab 88(3): 1404(2003).
Hak, et al., Low Levels of Endogenous Androgens Increase the Risk of Atherosclerosis in Elderly Men: The Rotterdam Study, The J. of Endocrinology & Metabolism, vol. 87, No. 8, pp. 3632-3639 (2002).
Hall, et al., A Randomized Trial of Testosterone Therapy in Males with Rheumatoid Arthritis, Brit. J. of Rheumatology, vol. 35, pp. 568-573 (1996).
Hameed, A. et al. Delivery of testosterone replacement therapy. Curr Opin in Invest Drugs 2003. 4(1):1213-1219.
Handbook of Pharmaceutical Excipients, Third Edition, pp. 71-73, 85-90, 244-255, 263-266, 336-339, 465-467, 568-569, 599-601 (2000).
Handbook of Pharmaceuticals Excipients, Fourth Edition, pp. 89-92, 95-100, 289-296, 309-313, 543-545, 566-567, 654-656, 691-693 (2003).
Handelsman, et al., Pharmacokinetics and Pharmacodynamics of Testosterone Pellets in Man, Journal of Clinical Endocrinology and Metabolism, vol. 70, No. 1., pp. 216-222 (1990).
Hanke, et al., Effect of Testosterone on Plaque Development and Androgen Receptor Expression in the Arterial Vessel Wall, Circulation, vol. 103, No. 10, pp. 1382-1385 (Mar. 13, 2001).
Hansen, Nanette et al., Transcript of Early Today, (NBC television broadcast Jul. 31, 2002).
Hansen, R.P. et al., "The branched-chain fatty acids of mutton fat. 3. The isolation of 16 methylheptadecanoic acid," Methylheptadecanoic Acid in Mutton Fat, 16 (1956) 64:214-216.
Hanson DA et al., A specific immunoassay for monitoring human bone resorption: quantitation of type I collagen crosslinked n-telopeptides in urine. J. Bone Min Res 7:1251 (1992).
Hardy, et al., Endocrine Assessment of Impotence—Pitfalls of Measuring Serum Testosterone Without Sex-Hormone-Binding Globulin, Postgrad Med J (1994) 70, 836-837.
Harman SM. et al., Reproductive hormones in aging men. I. Measurement of sex steroids, basal luteinizing hormone, and Leydig cell response to human chorionic gonadotropin. J. Clin Endocrinol. Metab. 51:35 (1980).
Harman SM. et al., Reproductive hormones in aging men. II. Basal pituitary gonadotropins and gonadotropin responses to luteinizing hormone releasing hormone. J. Clin. Endocrinol. Metab. 54:547 (1982).
Hatch et al., Hirsutism: implications, etiology and management. Am. J. Obstet. Gynec. 140: 815-830 (1981).
Hecht, Ask Dr. Hecht, New York Daily News, Apr. 22, 2002.
Heikkila, et al., Serum Androgen-Anabolic Hormones and the Risk of Rheumatoid Arthritis, Ann Rheum Dis, May 1998; 57(5): 281-5.
Heiss, et al., Associations of Body Fat Distribution, Circulating Sex Hormones Bone Density in Postmenopausal Women, J Clin Endocrinol Metab, May 1995; 80(5): 1591-6.
Hendrick, Bill, Over the Hill? Atlanta Journal-Constitution, Healthy Living, Sep. 17, 2002.
Hengge, U. R., M. Baumann, R Maleba, N. H. Brockmeyer, and M. Goos. Oxymetholone promotes weight gain in patients with advanced human immunodeficiency virus (HIV-1) infection. Br. J. Nutr. 75: 129-138 (1996).
Herkenne, C. et al., "Effect of propylene glycol on ibuprofin absorption into human skin in vivo," J. Pharma. Sci. (2008) 97(1):185-197.
Hermens, WA. Delivery of hormones: some new concepts. Pharm. Weekbl Sci. 14(4A):253-7. 1992.

Herschberg AD., A new treatment of climacteric disorders, Gynecol Prat. 1965;16:433-42. (Article in French with English Summary).
Heymsfield SB et al., Dual photon absorptiometry: comparison of bone mineral and soft tissue mass measurements in vivo with established methods. Ann J Clin. Nutr 49:1283 (1989).
Hill, et al., Analysis of Relations Between Serum Levels of Epitestosterone, Estradiol, Testosterone, IGF-1 and Prostatic Specific Antigen in Men with Benign Prostatic Hyperplasia in Carcinoma of the Prostate, Physiol. Res., vol. 49 (Suppl. 1), pp. S113-S118 (2000).
HIV Wasting Syndrome, www.thebody.com (May 1997).
HIV Wasting Treatment: Nandrolone Decanoate, www.hivinsite.ucsf.edu (Aug. 1, 1995).
HIV/AIDS Clinical Trials in the New Orleans Area, ACTG 329, www.tmc.tulane.edu (Downloaded Oct. 8, 1998).
Hobbs CJ, Plymate SR, Rosen CJ, Adler RA: Testosterone administration increases insulin-like growth factor-1 levels in normal men. J Clin Endocrinol Metab 77:776-9, 1993.
Hochhaus, et al., A Selective HPLC/RIA for dexamethasone and its prodrug dexamethasone-21-sulphobenzoate sodium in biological fluids, Biomed. Chrom., 6:283-286 (1992).
Hoelgaard, A. et al., "Dermal drug delivery—improvement by choice of vehicle or drug derivative," J. Control. Release (1985) 2:111-120.
Hoffman, et al., Is Low Serum Free Testosterone a Marker for High Grade Prostate Cancer?, J. Urology, vol. 163, pp. 824-827 (Mar. 2000).
Holman et al., 10-year follow-up of intensive glucose control in type 2 diabetes. New England Journal of Medicine (2008);359(15):1577-1589.
Holownia, et al., A Clinical Evaluation of a Direct Radioimmunoassay of Testosterone; Clin Chim Acta, Jan. 31, 1993; 214(1): 31-43.
Hormone Therapy, BioSante Pharmaceuticals. Available at http://web.archive.org/web/20020607191414/biosantepharma.com/products/hrt.html (Downloaded in Oct. 2002).
Howell et al., "Testosterone Deficiency and Replacement," Horm Res, 56 Suppl 1: 86-92 (2001); Abstract.
Howland, The Other Hormone Replacement Therapy: Testosterone in Menopausal Women, HealthGate, www.bewell.com (Aug. 7, 2000).
Hsieh, et al., Risk Factors for Prostate Cancer: A Case-Control Study in Greece, Int. J. Cancer, vol. 80, pp. 699-703 (1999).
Humberstone et al., Comparison of pharmacokinetics and tolerability following application of an Estraderm 50® patch or a novel Estradiol Metered-Dose Transdermal Spray (MTDS®). Poster. Presented at the North American Menopause Society (NAMS) 13th Annual Meeting, Chicago, Oct. 2002.
Humberstone et al., Elevation of serum testosterone levels in oophorectomized women following application of a novel Metered-Dose Transdermal Spray (MTDS(RM)). Poster. Presented at the North American Menopause Society (NAMS) 13th Annual Meeting, Chicago, Oct. 2002.
Humberstone et al., Pharmacokinetics of estradiol after application of an Estradiol Metered-Dose Transdermal System (MDTS(RM)): Linearity and effect of washing the application site. Poster, Acrux Drug Delivery Solutions. Presented at American Association of Pharmaceutical Scientists (AAPS) (2002), Abstract published at AAPS PharmSci. 2002; 4(S1).
Husband Crabby, Sluggish, WebMD.com (May 6, 2002).
Hwang S N, et al., Probability-based structural parameters from three-dimensional nuclear magnetic resonance images as predictors of trabecular bone strength., Med. Phys., 24:1255-61 (1997).
Hydrocortisone (hydrocortisone cream 2.5%, and hydrocortisone ointment 2.5%). RxList.com. http://www.rxlist.com/hydrocortisone-drug.htm. pp. 1-2. Downloaded on Oct. 13, 2009.
Idson, et al., Percutaneous Absorption Enhancers, D&CI, pp. 30-33 (Jul. 1985).
Impotence Treatments, Impotence World Association, http://www.imootenceworld.org/treatment.htm (2000).
Industry News: Mens Health Effort, M M R/MASS Market Retailers (New York, NY), Sep. 23, 2002.
Information on TestoCreme® from www.testocreme.com. Downloaded on Oct. 21, 2002.

(56) References Cited

OTHER PUBLICATIONS

International Cosmetic Ingredient Dictionary and Handbook (2004) p. 912 Monographs—from "Isosteareth-25" to "Isostearic Acid".
Internet information on Bentley Pharmaceuticals, research. businessweek.com (Oct. 21, 2002).
Iqbal, et al., Binding of Testosterone and Oestradiol to Sex Hormone Binding Globulin, Human Serum Albumin and Other Plasma Proteins: Evidence for Non-Specific Binding of Oestradiol to Sex Hormone Binding Globulin, Clinical Science, vol. 64, No. 3, pp. 307-314 (Mar. 1983).
Isaacs, et al., Etiology and Disease Process of Benign Prostatic Hyperplasia, Prostate. Suppl 2:33-50 (1989).
Isaacs, Etiology of Benign Prostatic Hyperplasia, Eur Urol, 1994; 25 Suppl 1:6-9.
Isaia, et al., Effect of Testosterone on Bone in Hypogonadal Males, Maturitas, vol. 15, pp. 47-51 (1992).
Isidori et al.,Erectil dysfunction. Recent Prog. Med., Jul.-Aug. 1999; 90(7-8):396-402.
Itoh et al., The Assessment of Bioavailable Androgen Levels from the Serum Free Testosterone Level, Nippon Naibunpi Gakkai Zasshi, vol. 67, No. 1, pp. 23-32 (Jan. 20, 1991). (Abstract only).
Jackson JA et al., Bone histomorphometry in hypogonadal and engonadal men with spinal osteoporosis. J. Clin Endocrinol. Metab. 65:53 (1987).
Jackson JA, Riggs MW, Spiekerman AM: Testosterone deficiency as a risk factor for hip fractures in men: a case-control study. Am J Med Sci 304:4-8, 1992.
Jackson S A, et al., Vertebral fracture definition from population-based data: preliminary results from the Canadian Multicenter Osteoporosis Study (CaMos), Osteoporosis Int., 11:680-7 (2000).
Jaffa et al., Connective tissue growth factor and susceptibility to renal and vascular disease risk in type 1 diabetes. J Clin Endocrinol Metab. May 2008;93(5):1893-900. (Epub Date: Mar. 4, 2008).
Jaffe, et al., Effect of 5-Alpha-Reductase Inhibition on Sex-Hormone-Binding Globulin in Elderly Men, Horm. Res., vol. 41, pp. 215-217 (1994).
Jain, et al., Testosterone Supplementation for Erectile Dysfunction: Results of a Meta-Analysis, The J. or Urology, vol. 164, pp. 371-375 (Aug. 2000).
James JS. San Francisco area: testosterone replacement study, injection vs. patch. AIDS Treat News. Oct. 20, 1995(233):7-8.
Janowsky JS et al., Testosterone administration enhances spatial cognition in older men. Soc for Neurosci Ann Meeting, New Orleans, LA (1991).
Janowsky, et al., Sex Steroids Modify Working Memory, J. of Cognitive Neuroscience, vol. 12, No. 3, pp. 407-414 (2000).
Janowsky, et al., Testosterone Influences Spatial Cognition in Older Men, Behavioral Neuroscience, vol. 108, No. 2, pp. 325-332 (1994).
Jarkander-Rolff, et al., Transdermal Application of a Testosterone Gel—A Pharmacokinetic Study. Menopause (1997), vol. 4(4): 251.
Jarvinen et al., "Steady-state pharmacokinetics of oestraradiol gel in post-menopausal women: effects of application area and washing," British Journal of Obstetrics and Gynaecology 104(16): 14-18 (1997).
Javanbakht, et al., Pharmacokinetics of a Novel Testosterone Matrix Transdermal System in Healthy, Premenopausal Women and Women Infected with the Human Immunodeficiency Virus, Journal of Clinical Endocrinology and Metabolism, vol. 85, No. 7, pp. 2395-2401 (Jul. 2000).
Jenkins et al., Serum lipoproteins in the diabetes control and complications trial/epidemiology of diabetes intervention and complications cohort: associations with gender and glycemia. Diabetes Care. Mar. 2003;26(3):810-8.
Jiang Y, et al., Recombinant human parathyroid hormone (1-34) [teriparatide] improves both cortical and cancellous bone structure., J. Bone Miner. Res., 18:1932-41 (2003).
Jin, et al., Effects of Androgen Deficiency and Replacement on Prostate Zonal Volumes, Clinical Endocrinology, vol. 54, pp. 437-445 (2001).
Jockenhovel, at al., Pharmacokinetics and Pharmacodynamics of Subcutaneous Testosterone Implants in Hypogonadal Men, Clinical Endocrinology, vol. 45, pp. 61-71 (1996).
Johnson L. Spermatogenesis and aging in the human. J. Andro 7:331 (1986).
Jones, et al., Placebo Controlled Study on the Effects of Transdermal Testosterone Gel in Hypogonadal Men with Type II Diabetes (T2D) or Metabolic Syndrome(MS) in Diabetic Control and Insulin Sensitivity: The TIMES 2 Study, p. 3-422, Endo Society 2008.
Jones, et al., Pulmonary Vasodilatory Action of Testosterone: Evidence of Calcium Antagonistic Action, J. Cardiovasc. Pharmacol., vol. 39, No. 6, pp. 814-823 (Jun. 2002).
Jones, R. et al., Low Levels of Endogenous Androgens Increase the Risk of Atherosclerosis in Elderly Men: Further Supportive Data. J Clin Endocrinol Metab 88(3): 1403-1404(2003).
Jordan, Allergy and Topical Irritation Associated With Transdermal Testosterone Administration: A Comparison of Scrotal and Nonscrotal Transdermal Systems, American Journal o Contact Dermatitis. vol. 8 (No. 2).pp. 108-113 (Jun. 1997).
Joseph, et al., Relationship of Serum Sex-Steroid Hormones and Prostate Volume in African American Men, The Prostate, vol. 53, pp. 322-329 (2002).
Juenemann, et al., Androgen Deficiency in Prostate Carcinoma- and BPH-Patients?, American Urological Association, Abstract No. 193.
Kalantaridou, et al., Transdermal Testosterone Replacement for Young Women with Spontaneous Premature Ovarian Failure: A Pilot Study, No. 2322, www.abstracts-on-1 (Downloaded Aug. 7, 2000).
Kalman, Future Pharmacy: What's the T Team Up to?, Muscular Development (Setauken, NY), Sep. 2002.
Kang, et al., Effect of Oral Administration of Testosterone on Brachial Arterial Vasoreactivity in Men with Coronary Artery Disease, The Amer. J. of Cardiology, vol. 89, pp. 862-864 (Apr. 1, 2002).
Kanikkannan N, et al., "Structure-activity relationship of chemical penetration enhancers in transdermal drug delivery," Curr Med Chem. Jun. 2000;7(6):593-608.
Kanis J A, et al., The components of excess mortality after hip fracture, Bone, 32:468-73 (2003).
Kao, et al., Skin Absorption and Cutaneous First Pass Metabolism of Topical Steroids: in vitro Studies with Mouse Skin in Organ Culture, J Pharmacol Exp Ther, May 1987; 241(2): 482-487.
Karr, et al., Induction of Benign Prostatic Hypertrophy in Baboons, Urology, Mar. 1984; 23(3): 276-89.
Kasper, et al., Development, Progression, and Androgen-Dependence of Prostate Tumors in Probasin-Large T Antigen Transgenic Mice: a Model for Prostate Cancer, Lab Invest, Mar. 1998; 78(3): 319-333.
Kasperk CH et al., Androgens directly stimulate proliferation of bone cells in vitro. Endocrinology 124:1576 (1989).
Kasting, G.B. et al., "Skin penetration enhancement of triprolidine base by propylene glycol," J. Pharma. Sci. (1993) 82(5):551-552.
Katz, M. et al., "Absorption of drugs through the skin," Reprint from Handbook of Experimental Pharmacology, edited by O. Eichler et al., Chapter 7 (1971) 103-174.
Katznelson L, et al., Increase in bone density and lean body mass during testosterone administration in men with acquired hypogonadism, J. Clin. Endocrinol. Metab., 4358-4365 (1996).
Katznelson, Therapeutic Role of Androgens in the Treatment of Osteoporosis in Men, Bailliere's Clinical Endocrinology and Metabolism, vol. 12, No. 3:453-470 (Oct. 1998).
Kaufman JM, et al., Safety and efficacy of a testosterone (T) gel in a geriatric population. Abstract #1104 at the 97th Annual Meeting of the American Urological Association, May 25-30, 2002, Orlando, FL.
Kaufman, Efficacy and Safety of a New, Topical Testosterone Gel (T-gel) for Male Hormonal Supplementation, International Journal of Impotence Research, vol. 12, Supplement 3, p. S75 (B9) (Sep. 2000).
Kaufman, "Hormone Gel Stirs Debate," The Washington Post, p. A01 (May 27, 2000).
Kaufman, et al., Background for Studies on the Treatment of Male Osteoporosis: State of the Art, Ann. Rheum. Dis., vol. 59, pp. 765-772 (2000).

(56) References Cited

OTHER PUBLICATIONS

Kaufman, et al., Declining Gonadal Function in Elderly Men, Bailliere's Clinical Endocrinology and Metabolism, vol. 11, No. 2, pp. 289-307 (Jul. 1997).
Kellie S E, et al., Sex-specific and race-specific hip fracture rates, Am J. Public Health, 80:326-8 (1990).
Kelly PJ et al., Dietary calcium, sex hormones, and bone mineral density in men. Br. Med. J. 300:1361-4 (1990).
Kenny, et al., Determinants of Bone Density in Healthy Older Men With Low Testosterone Levels, J. of Gerontology, vol. 55A, No. 9, pp. M492-M497 (2000).
Kerr, Hormone Therapy a Risk for Men, Too: Testosterone Perils May Go Up With Age, Newsday (Melville, NY), Dec. 17, 2002.
Khan, et al., Radioimmunoassay for Human Testosterone-Estradiol Binding Globulin, J. Clinical Endocrinology and Metabolism, vol. 54, pp. 705-710 (1982).
Khosla S. et al., Relationship of serum sex steroid levels and bone turnover markers with bone mineral density in men and women: A key role for bioavailable estrogen, J Clin Endocrinol Metab. 1998;83(7): 2266-74.
Khosla, Oestrogen, Bones, and Men: When Testosterone Just Isn't Enough, Clinical Endocrinology, vol. 56, pp. 291-293 (2002).
Kim et al., "Preparation and evaluation of Eudragit gels. v. rectal gel preparations for sustained release and avoidance of first-pass metabolism of lidocaine." Chem. Pharm. Bull. 50(10): 2800-2804 (1992).
Kim et al., Formulation of a reservoir-type testosterone transdermal delivery system. International Journal of Pharmaceutics. 219:51-9 (2001).
Kim et al., Skin permeation of testosterone and its easier derivatives in rats. Journal of Pharmacy and Pharmacology. Apr. 2000; 52 (4) 369-75.
Kim, DD et al., Mutual hairless rat skin permeation-enhancing effect of ethanol/water system and oleic acid. J. Pharm. Sci. 85(11): 1191-1195 (1996).
Kim, Testosterone Gel Promising in Hypoglandal Men (Benefits Seen at 29 Months), Family Practice News, Nov. 1, 2002.
Kirn, Testosterone Gel's Benefits Sustained at 29 Months, Internal Medicine News (Rockville, MD), Sep. 15, 2002.
Kirschner, et al., Androgen Production and Metabolism in Normal and Virilized Women, Metabolism, vol. 21 (7), pp. 667-688, (Jul. 22, 1972).
Kirschner, et al., Androgen-Estrogen Metabolism in Women with Upper Body Versus Lower Body Obesity, Journal of Clinical Endocrinology and Metabolism, vol. 70, No. 2, pp. 473-479 (Feb. 1990).
Klein et al., Fibrinogen is a marker for nephropathy and peripheral vascular disease in type 1 diabetes: studies of plasma fibrinogen and fibrinogen gene polymorphism in the DCCT/EDIC cohort. Diabetes Care. May 2003;26(5):1439-48.
Klinicheskaya endokrinologiya pod. Red. Prof. N.T. Starkovoy, M. Medicina, 1991, p. 426. [Russian; English machine translation included.].
Klose et al., Enhanced Percutaneous Penetration of Ethinyl Estradiol using Across(RM) Enhancers in Spray Formulations. Poster, Acrux Drug Delivery Solutions. Presented at American Association of Pharmaceutical Scientists (AAPS) (2002), Abstract published at AAPS PharmSci. 2002; 4(S1).
Klugo et al., Response of micropenis to topical testosterone and gonadotropin. J. Urol. 119(5):667-8 (May 1978).
Knussmann, et al., Relations Between Sex Hormone Levels and Sexual Behavior in Men, Archives of Sexual Behavior, vol. 15, No. 5, p. 429-445 (1986).
Koenig HG, et al., Self-rated depression scales and screening for major depression in the older hospitalized patient with medical illness. J Am Geriatr Soc 36:699-706, 1988.
Kolata, Male Hormone Therapy Popular but Untested, N.Y. Times, Aug. 19, 2002.
Kong, et al., Testosterone Therapy in HIV Wasting Syndrome: Systematic Review and Meta-Analysis, The Lancet Infectious Diseases, vol. 2, pp. 692-699 (Nov. 2002).
Korbonits et al., A comparison of a novel testosterone bioadhesive buccal system, striant, with a testosterone adhesive patch in hypogonadal males. J. Clinical Endocrinology and Metabolism 89(5): 2039-2043 (2004).
Korenman SG et al., Secondary hypogonadism in older men: its relation to impotence. J. Clin Endocrinol Metab. 71:963 (1990).
Korenman, et al., Androgen Therapy of Hypogonadal Men with Transscrotal Testosterone Systems, Am J Med, Sep. 1987; 83(3): 471-478.
Kraemer, et al., Orgasmic Frequency and Plasma Testosterone Levels in Normal Human Males, Archives of Sexual Behavior, vol. 5, No. 2, p. 125 (1976).
Krahe, et al., Risk Factors for Decreased Bone Density in Premenopausal Women, Braz J Med Biol Res, Sep. 1997; 30(9): 1061-6.
Krotkieweski M et al., Impact of obesity on metabolism in men and women. Importance of regional adipose tissue distribution. J. Clin. Invest 72:1150 (1983).
Krumholtz, et al., Prostate-Specific Antigen Cutoff of 2.6 ng/mL for Prostate Cancer Screening is Associated with Favorable Pathologic Tumor Features, Urology, vol. 60, pp. 469-474 (2002).
Kuhn, et al., Gynecomastia: Effect of Prolonged Treatment with Dihydrotestosterone by the Percutaneous Route, Presse Medicine, vol. 12, No. 1, pp. 21-25 (Jan. 8, 1983). (Abstract only).
Kuhn, et al., Effects of 10 Days Administration of Percutaneous Dihydrotestosterone on the Pituitary-Testicular Axis in Normal Men, J Clin Endocrinol Metab, Feb. 1984; 58(2): 231-5.
Kuhn, et al., Traitement Androgenique Percutane des Hypogonadismes Masculins. Efficacite Comparee de la Testosterone et d la Dihydrotestosterone: Etude de 40 Observations, Contraception-Fertilite-Sexualite, vol. 14, No. 11, pp. 1031-1036 (1986).
Kuhnert, et al., Testosterone substitution with a new transdermal, hydroalcoholic gel applied to scrotal or non-scrotal skin: a multicentre trial, European Journal of Endocrinology, vol. 153, pp. 317-326 (2005).
Kunz, et al., Virilization of Young Children After Topical Androgen Use by Their Parents, Pediatrics, vol. 114(1), pp. 282-284 (2004).
Kwan et al., "The nature of androgen action on male sexuality: a combined laboratory-self-report study on hypogonadal men." J. Clin. Endocrinol Metab. 57(3): 557-562 (1983).
Kydonieus et al., Transdermal Delivery of Drugs vol. II. Drug and Cosmetic Industry, pp. 57-62 (1987).
Kyprianou, et al., Quantal Relationship Between Prostatic Dihydrotestosterone and Prostatic Cell Content: Critical Threshold Concept, The Prostate, vol. 11, pp. 41-50 (1987).
La Sexualite, L'Androgel, Le Gel Miracle, www.aci-multimedia.net/feminin/androgel (Downloaded May 9, 2001). [French; English machine translation included].
Labrie, et al., Physiological Changes in Dehydroepiandrosterone are not Reflected by Serum Levels of Active Androgens and Estrogens but of their Metabolites: Intracrinology, J Clin Endocrinol Metab, Aug. 1997; 82(8): 2403-2409.
Lacayo, Are You Man Enough?, Time Europe, www.Time.com, vol. 155, No. 16 (Apr. 24, 2000).
Lachin et al., Effect of glycemic exposure on the risk of microvascular complications in the diabetes control and complications trial—revisited. Diabetes. Apr. 2008; 57(4):995-1001. (Epub Date: Jan. 25, 2008).
Lagiou, et al., Serum Steroids in Relation to Benign Prostatic Hyperplasia, Oncology, vol. 54, No. 6, pp. 497-501 (Nov.-Dec. 1997).
Lammers, et al., Combination Therapy for Erectile Dysfunction: A Randomized, Double Blind, Unblended Active-Controlled, Cross-Over Study of the Pharmacodynamics and Safety of Combined Oral Formulations of Apomorphine Hydrochloride, Phentolamine Mesylate and Papaverine Hydrochloride in Men with Moderate to Severe Erectile Dysfunction, Intl. J. of Impotence Research, vol. 14, pp. 54-60 (2002).
Langtry, et al., Sildenafil: A Review of its Use in Erectile Dysfunction, Drugs, vol. 57, No. 6, pp. 967-989 (Jun. 1999).
Lanman BM et al., The role of human patch testing in a product development program. Joint Conference on Cosmetic Sciences, The

(56) References Cited

OTHER PUBLICATIONS

Toilets Goods Association (currently the Cosmetic, Toiletry and Fragrance Association), Washington D.C., Apr. 21-23, 1968.
Larsen and H. Bundgaard, Prodrug forms for the sulfonamide group. I. Evaluation of N-acyl derivatives, N-sulfonylamidines, N-sulfonylsulfilimines and sulfonylureas as possible prodrug derivatives, Int. J. Pharmaceutics, 37:87-95 (1987).
Larsen et al., Int. J. Pharmaceutics, 47, 103 (1988).
Lawrence, J. Husband Crabby, Sluggish? MSN.com (May 6, 2002).
Lee KK, et al., A simple self-report diary for assessing psychosexual function in hypogonadal men, J Androl. Sep.-Oct. 2003;24(5):688-98.
Lee, Men's Health: Testosterone Gel Study Demonstrates Safety and Efficacy up to 42 Months in Men with Low Testosterone, Health & Medicine Week (Atlanta, GA), Aug. 5, 2002.
Lee, New Gel Treatment Proven and FDA Approved for Effective Treatment of Low Testosterone, 50+ Senior News (Bellport, NY), Dec. 2002.
Legro, et al., Role of Androgens in the Growth of Endometrial Carcinoma: An in Vivo Animal Model, American Journal of Obstetrics and Gynecology, vol. 184 (No. 3), p. 303-308, (2001).
Leiblum, et al., Vaginal Atrophy in the Postmenopausal Woman. The Important Sexual Activity and Hormones, JAMA, Apr. 22-29, 1983;249(16): 2195-8.
Leichtnam et al., "Identification of penetration enhancers for testosterone transdermal delivery from spray formulations," Journal of Controlled Relesae (2006);113:57-62.
Leifke, et al., Age-Related Changes of Serum Sex Hormones, Insulin-like Growth Factor-1 and Sex-hormone Binding Globulin Levels in Men: Cross-sectional Data from a Healthy Male Cohort, Clinical Endocrinology, vol. 53, pp. 689-695 (2000).
Leifke, et al., Effects of Testosterone Replacement Therapy on Cortical and Trabecular Bone Mineral Density, Verbetral Body Area and Paraspinal Muscle Area in Hypogonadal Men, European Journal of Endocrinology (1998);138:51-58.
Leigh, Antidote for Middle Age Met with Joy, Skepticism, San Mateo County Times, Nov. 25, 2002.
Leigh, Doctors Wary of Testosterone Drug Despite FDA's Approval, The Argus (Fremont, CA), Nov. 25, 2002.
Leigh, Some Doctors Question Use of Testosterone Gel: Despite FDA's Approval, Ointment for Men Might Increase Risk of Prostate Cancer, Alameda Times-Star (Oakland, CA), Nov. 25, 2002.
Leinonen, et al., Serum Sex Hormone Binding Globulin and Testosterone Binding After Estradiol Administration, Castration, and Their Combination in Men with Prostatic Carcinoma, Invest Urol, Jul. 1979; 17(1): 24-27.
Lemon, Testosterone Promises Renewed Vigor: Hormone Replacement Credited with Boosting Energy in Aging Men, MSNBC.com (Nov. 7, 2002).
Leopold, C.S. et al., "An attempt to clarify the mechanism of the penetration enhancing effects of lipophilic vehicles with differential scanning calorimetry (DSC)," J. Pharm. Pharmacol. (1995) 47:276-281.
Lesher EL, Berryhill J: Validation of the geriatric depression scale-short form among inpatients. J Clin Psycho140:256-60, 1994.
Letters to the Editor, J. Clin. Endocrinol. Metab., vol. 88, No. 3, pp. 1402-1405 (Mar. 2003).
Leucuta et al., Abstract of Clujul Medical, 1983 ;56(4) :371-376.
Leuprorelin/testosterone—First Report of Heart Transplant Rejection: 3 Case Reports, Reactions, vol. 27, No. 912 (Jul. 2002).
Levy, Manopause: Experts Discuss Treatments for Testosterone Deficiencies in Older Men, Journal Inquirer (Manchester, CT), Aug. 26, 2002.
Lewis, et al, Serum 5.alpha.-Dihydrotestosterone and Testosterone Changes with Age in Man, Acta Endocrinologica, 82 (1976) 444-448.
Lewis, et al., Proceedings: Age-Related Changes in Serum 5aplhadihydrotestosterone and Testosterone in Normal Men, Journal of Endocrinology, vol. 67, No. 2, PQ. 15P (Nov. 1975).

Liao, J., Androgen Action: Molecular Mechanism and Medical Application, Formos Med. Assoc., vol. 93, No. 9, pp. 741-751 (Sep. 1994).
Lieberherr, et al., Androgens Increase Intracellular Calcium Concentration and Inositol 1,4,5-Triphosphate and Diacylglycerol Formation via a Pertussis Toxin-sensitive G-protein, The J. of Biological Chemistry, vol. 269, No. 10, pp. 7217-7223 (Mar. 11, 1994).
Lieberman et al., eds. "Pharmaceutical Dosage Forms—Disperse Systems." vol. 2. Marcel Dekker: New York (1989). Ch. 13.
Lignieres, Effect of High Dihydrotestosterone Plasma Levels on Prostate of Aged Men. Second International Androgen Workshop, Long Beach, CA, USA (1995).
Lin, S. et al., Transdermal testosterone delivery: comparison between scrotal and nonscrotal delivery systems. Pharm Dev and Tech. 4(3): 405-414 (1999).
Linet, et al., Efficacy and Safety of Intracavernosal Alprostadil in Men with Erectile Dysfunction, The New England J. of Medicine, vol. 334, No. 14, pp. 873-877 (Apr. 4, 1996).
Ling, et al., Testosterone (T) Enhances Apoptosis-Related Damage in Human Vascular Endothelial Cells, Endocrinology, vol. 143, No. 3, pp. 1119-1125 (2002).
Liu, et al., Impact of Assay Parameters on the Accuracy of Free PSA Test: Source and Stability of Calibrator, Calibration Curve Fitting, and Level of Total PSA in the Serum. J Clinical Laboratory Analysis 12:304-309 (1998).
Lo, et al., Reproductive Function in Human Immunodeficiency virus Infection, The J. of Clinical Endocrinology & Metabolism, vol. 86, No. 6, pp. 2338-2343 (2001).
Lobo R. A., Chapter 20: Androgen excess in Infertility, Contraception and Reproductive Endocrinology, Third Edition. D R Mishell, V. Davajan and R. Lobo, Editors. Blackwell Scientific Publications, Boston. pp. 422-446, 1991.
Loftsson T. et al., Cyclodextrins as Co-Enhancers in Dermal and Transdermal Drug Delivery, Pharmazie, vol. 2, pp. 137-139 (1998).
London Rubber Industries Ltd's Patent, Reports of Patent, Design, and Trade Mark Cases, No. 2, p. 31 (1968).
Longcope, et al., Androgens, Estrogens, and Sex Hormone-Binding Globulin in Middle-Aged Men, Journal of Clinical Endocrinology and Metabolism, vol. 71, No. 6, pp. 1442-1446 (Dec. 1990).
Longstreth, et al., Transdermal Testosterone Pharmacokinetics Remain Unchanged With Prolonged Treatment, Unimed Pharmaceuticals (Oct. 31, 2000).
Lopes-Virella et al., Risk factors related to inflammation and endothelial dysfunction in the DCCT/EDIC cohort and their relationship with nephropathy and macrovascular complications. Diabetes Care. Oct. 2008;31(10):2006-12. (Epub Date: Jul. 15, 2008).
Louie, Transdermal Testosterone Replacement to Improve Women's Sexual 120 Functioning, Canadian Family Physician pp. 1571-1573 ( Aug. 22, 2001).
Loyd. "Benzocaine 2% Anesthetic Gel." Int'l J. Pharm. Compounding. 2(4): 296 (1998).
Lucas, Finasteride Cream in Hirsutism, Endocrine Practice, 7(1):5-10 (2001).
Lugg et al., The Role of Nitric Oxide in Erectile Function, J. Andrology, vol. 16, pp. 2-4, (1995).
Luster, B. Sex Sells: But Buyers Should Beware of Natural Supplements that Haven't Been Tested and May Have Dangerous Side Effects, The Courier-Journal (Louisville, KY), Mar. 4, 2002.
Ly et al., A Double-Blind, Placebo-Controlled, Randomized Clinical Trial of Transdermal Dihydrotestosterone Gel on Muscular Strength, Mobility, and Quality of Life in Older Men with Partial Androgen Deficiency, The Journal of Clinical Endocrinology & Metabolism, vol. 86, No. 9, pp. 4078-4088 (2001).
Maclennan, et al., Hormone Replacement Therapies in Women at Risk of Cardiovascular Disease and Osteoporosis in South Australia in 1997, Medical Journal of Australia, vol. 170 (No. 11), p. 524-527, (Jun. 7, 1999).
MacroChem Accelerates Development of Top for Impotence, www.pslgroup.com (Apr. 10, 1997).
Macrochem announces initiation of next clinical trial of Opterone, first testosterone cream for male hypogonadism. Macrochem Press Release. Dec. 8, 2004.

(56) References Cited

OTHER PUBLICATIONS

MacroChem Awarded U.S. Patent Covering Transdermal Hormone Replacement Incorporating Proprietary SEPA® Technology and Hormonally Active Drugs Such as Testosterone, Estradiol and Progesterone, http://www.mchm.com/press/pr24.asp (Oct. 21, 1999).
Macrochem. Macrochem announces initiation of clinical trial of Opterone, first absorption-enhanced topical cream to treat testosterone deficiency. Press release. Dec. 16, 2003.
Macrochem. MCHM begins dose study for testosterone cream. Press Release. Dec. 16, 2003.
Macrochem. SEPA enhanced testosterone for topical applications: Macrochem investigational topical treatment for testosterone deficiency. Press Release. Dec. 8, 2004.
Magoha, East Afr. Med. J. (1997) vol. 74(10) pp. 642-644, East Afr. Med. J. (1997) vol. 74(10) pp. 642-644.
Mahabadi V, et al., Combined transdermal testosterone gel and the progestin nestorone suppresses serum gonadotropins in men, J Clin Endocrinol Metab. Jul. 2009;94(7):2313-20. (Epub Date: Apr. 14, 2009).
Maibach, et al., The Effect of DMSO on Percutaneous Penetration of Hydrocortisone and Testosterone in Man, Annals New York Academy of Sciences (Mar. 1967), pp. 423-427.
Majumdar S, et al., Correlation of trabecular bone structure with age, bone mineral density, and osteoporotic status: in vivo studies in the distal radius using high resolution magnetic resonance imaging, J. Bone Miner. Res., 12:111-8 (1997).
Mak, V.H.W. et al., "Oleic acid concentration and effect in human stratus corneum: non-invasive determination by attenuated total reflectance infrared spectroscopy in vivo," J. Control. Rel. (1990) 12:67-75.
Mak, V.H.W. et al., "Percutaneous penetration enhancement in vivo measured by attenuated total reflectance infrared spectroscopy," Pharm. Res. (1990) 835-841.
Male Hormone Patch Approved, Nuphann, http://www.nuoharm.com/malehorm.htm. (Jun. 16, 2000).
Male hypogonadism, Merck Index, pp. 1-6 (Jun. 2007).
Man, et al., Optimization of Physiological Lipid Mixtures for Barrier Repair, J Invest Dermatol, May 1996; 106(5): 1096-1101.
Manopause: Experts Seeking Treatments for Middle-Age Male Testosterone Deficiency, The Patriot Ledger (Quincy, MA), Jul. 9, 2002.
Manos, FDA Approves Gel to Treat Low Testosterone Levels, www.testocreme.com. Downloaded on May 9, 2001.
Mantzoros et al., Insulin-like Growth Factor 1 in Relation to Prostate Cancer and Benign Prostatic Hyperplasia, Brit. J. of Cancer, vol. 76, No. 9, pp. 1115-1118 (1997).
Mantzoros, et al, Contribution of Dihydrotestosterone to Male Sexual Behaviour, British Medical Journal, No. 6990, vol. 310, pp. 1289-1291 (May 20, 1995).
Mantzoros, et al., Leptin Concentrations in the Polycystic Ovary Syndrome, J Clin Endocrinol Metab, Jun. 1997; 82(6): 1687-91.
Mantzoros, et al., Serum Steroids in Relation to Benign Prostatic Hyperplasia, Oncology, Nov.-Dec. 1997; 54(6):497-501.
Marbury et al., Evaluation of the Pharmacokinetic Profiles of the New Testosterone Topical Gel Formulation, Testim(TM), Compared to AndroGel(R), Biopharm. Drug Dispos., 24:115-120 (2003).
Marin, et al., Androgen Treatment of Abdominally Obese Men, Obesity Research, vol. 1(4), pp. 245-251 (1993).
Marin, et al., Androgen Treatment of Middle-Aged, Obese Men: Effects on Metabolism, Muscle and Adipose Tissues, European Journal of Medicine, vol. 1, No. 6, pp. 329-336 (Oct. 1992).
Marin, et al., Androgen-dependent Nitric Oxide Release in Rat Penis Correlates with Levels of Constitutive Nitric Oxide Synthase Isoenzymes, Biology of Reproduction, vol. 61, pp. 1012-1016 (1999).
Marin, et al., The Effects of Testosterone Treatment on Body Composition and Metabolism in Middle-Aged Obese Men, Intl. J. of Obesity, vol. 16, pp. 991-997 (1992).
Marks, et al., Effect of Testosterone Replacement Therapy on Prostate Tissue in Men With Late-Onset Hypogonadism—A Randomized Controlled Trial, JAMA, vol. 296(19), pp. 2351-2361 (2006).
Marzulli FN. Photoirritation (Phototoxicity, Phototoxic Dermatitis) in Dermatotoxicology, 5th Ed., Eds. Marzulli et al., Washington D.C. 231-237 (1996).
Masi, Sex Hormones and Rheumatoid Arthritis: Cause or Effect Relationships in a Complex Pathophysiology?, Clin Exp Rheumatol, Mar.-Apr. 1995; 13(2): 227-40.
Masters, et al., Investigation of Sex-Hormone Binding Globulin Interference in Direct Radioimmunoassays for Testosterone and Estradiol, Clinical Chemistry, vol. 35, No. 6, pp. 979-984 (Jun. 1989).
Mather, et al., Free Plasma Testosterone Levels During the Normal Menstrual Cycle, Journal of Endocrinol. Invest., vol. 8, No. 5, pp. 437-441 (Oct. 1985).
Matsumoto A.M., Hormonal therapy of male hypogonadism. Endocrinology and Metabolism Clinics of North America, 23(4):857-875 (1994).
Mayorga, P. et al., "Formulation study of a transdermal delivery system of primaquine," Int. J. Pharm. (1996) 132:71-79.
Mazer N. et al., Comparison of the steady-state pharmacokinetics, metabolism, and variability of a transdermal testosterone patch versus a transdermal testosterone gel in hypogonadal men, J Sex Med. Mar. 2005;2(2):213-26.
Mazer, et al., Enhanced Transdermal Delivery of Testosterone: A New Physiological Approach for Androgen Replacement in Hypogonadal Men, Journal of Controlled Release, vol. 19, pp. 347-361 (1992).
Mazer, New Clinical Applications of Transdermal Testosterone Delivery in Men and Women, J Controlled Release, Mar. 1, 2000; 65(1-2): 303-15.
Mazess, et al., Influence of Age and Body Weight on Spine and Femur Bone Density in U.S. White Men, J. of Bone and Mineral Research, vol. 5, No. 6; pp. 645-652 (1990).
Mccarthy, et al., Ventricular Thrombosis and Systemic Embolism in Bodybuilders: Etiology and Management, Ann. Thorac. Surg., vol. 70, pp. 658-660 (2000).
McClellan, et al., Transdermal Testosterone. ADIS New Drug Profile—Drugs, Feb. 1998 55(2): 253-258.
McClure et al., Hypogonadal impotence treated by transdermal testosterone. Urology 37(3):224-228 (1991).
Mccook, Testosterone Boost May Help Some with Parkinson's, ReutersHealth.com (Nov. 26, 2002).
McCoy, et al., A Longitudinal Study of the Effects of Menopause on Sexuality, Maturitas, Sep. 1985; 7(3): 203-10.
Mcdonnell, et al., A Survey of 2851 Patients with Hemochromatosis: Symptoms and Response to Treatment, The Am. J. Med., vol. 106, No. 6, pp. 619-624 (Jun. 1999).
McGraw-Hill Dictionary of Scientific and Technical Terms, 5th Edition, pp. 26, 1541 (1994).
McGuire M. Instant History: The Week, Chicago Tribune, Dec. 1, 2002.
McHorney CA, et al., The MOS 36-Item Short-Form Health Survey (SF-36): II. Psychometric and clinical tests of validity in measuring physical and mental health constructs, Med Care. Mar. 1993;31(3):247-63.
McLoed, et al., A glucocorticoid prodrug facilitates normal mucosal function in rat colitis without adrenal suppression. Gastroenterol., 106:405-413 (1994).
McMahon, et al., Treatment of Intracorporeal Injection Nonresponse with Sildenafil Alone or in Combination with Triple Agent Intracorporeal Injection Therapy, The J. of Urology, vol. 162, pp. 1992-1998 (Dec. 1999).
Mean, et al., Study on the Binding of Dihydrotestosterone, Testosterone and Oestradiol Sex Hormone Binding Globulin, Clin Chim Acta, Oct. 1, 1977; 80(1): 171-180.
Medline Plus, Drug Information: Testosterone Topical, available at www.nlm.nih.gov/medlineplus/druginfo/medmaster/a605020.html (retrieved Jun. 3, 2005).
Meier DE et al., Marked decline in male vertebral bone mineral content with age: association with free testosterone level. Clin. Res 32:705A (1984) [Abstract].

(56) References Cited

OTHER PUBLICATIONS

Meier DE et al., Marked disparity between trabecular and cortical bone Joss with age in healthy men. Ann. Int. Med. 101:605 (1984).
Meikle, Prostate size in hypogonadal men treated with a nonscrotal permeation-enhanced testosterone transdermal system. Urology 49(2):191 (1997).
Meikle, et al., Androderm: A Permeation Enhanced Non-Scrotal Testosterone Transdermal System for the Treatment of Male Hypogonadism, Pharmacology Biology and Clinical Applications of Androgens, vol. 43, pp. 449-457 (1996 Wiley-Liss, Inc.).
Meikle, et al., Enhanced Transdermal Delivery of Testosterone Across Nonscrotal Skin Produces Concentrations of Testosterone and Its Metabolites in Hypogonadal Men, J Clin Endocrinol Metab, Mar. 1992; 74(3): 623-628.
Meikle, et al., Familial Effects on Plasma Sex-Steroid Content in Man: Testosterone, Estradiol and Sex-Hormone-Binding Globulin, Metabolism, Jan. 1982; 31(1): 6-9.
Meikle, et al., Familial Prostatic Cancer Risk and Low Testosterone, J Clin Endocrinol Metab, Jun. 1982; 54(6): 1104-8.
Meikle, et al., Pharmacokinetics and Metabolism of a Permeation-Enhanced Testosterone Transdermal System in Hypogonadal Men: Influence of Application Site—A Clinical Research Center Study, Journal of Clinical Endocrinology and Metabolism, (1996);81(5):1832-40.
Meilahn, et al., Association of Sex hormones and adiposity with plasma levels of fibrinogen and PAI-1 in Postmenopausal Women, American Journal of Epidemiology, vol. 143 (2) p. 159-166 (1996).
Men's Health Screenings, The Washington Post, Jun. 11, 2002.
Mendel, Rates of Dissociation of Sex Steroid Hormones from Human Sex Hormone-Binding Globulin: a Reassessment, J Steroid Biochem Mol Biol, Oct. 1990; 37(2): 251-255.
Mendenhall, Custom Fit: Compounding Pharmacies Tailor Hormone Replacement Therapies to Individual Women, Pittsburgh Post-Gazette, May 28, 2002.
Meneely GR. et al., Analysis of factors affecting body composition determined from potassium content in 915 normal Subjects. Ann NY Acad Sci 110:271 (1963).
Menopause and Testosterone, www.womenshealth.com (Downloaded Aug. 7, 2000).
Merhi, et al., Postmenopausal virilization after spousal use of topical androgens, Fertility and Sterility, vol. 87(4), pp. 976.e13-976.e15 (2007).
Mermall, et al., Temporal (Circadian) and Functional Relationship between Pro Specific Antigen and Testosterone in Healthy Men, Urology, Jul. 1995; 46(1): 45-53.
Merriam Webster's Collegiate Dictionary, 10th Edition, pp. 3, 9, 27, 39, 246, 291, 340, 398, 567, 622, 663, 702, 722, 870, 871, 1095, 1174, 1177, 1359 (1994).
Messing, et al., Immediate Hormonal Therapy Compared with Observation After Radical Prostatectomy and Pelvic Lymphadenectomy in Men with Node-Positive Prostate Cancer, N. Engl. J. Med., vol. 34, No. 1, pp. 1781-1788 (Dec. 9, 1999).
Methyltestosterone 1-2MG, Question No. 1151236.012. "Medi-Hut Clarifies Syntest Formula." Business Wire (accessed Apr. 16, 2002).
Methyltestosterone, http://www.mesomorphosis.com/steroid-profiles/methyltestosterone.htm, Apr. 15, 2002.
Methyltestosterone, http://www.rxlist.com/cgi/generic3/methyltes_ids.htm, Apr. 15, 2002, 2 pages.
Mettlin, et al., Characteristics of Prostate Cancer Detected in the American Cancer Society—National Prostate Cancer Detection Project, The J. of Urol., vol. 152, pp. 1737-1740 (Nov. 1994).
Miekle AW et al., Transdermal testosterone gel: pharmacokinetics, efficacy of dosing and application site in hypogonadal men. BJU Int. Apr. 2004 93(6): 789-95.
Miller, Benign Prostatic Hyperplasia: Nutritional and Botanical Therapeutic.
Miller, et al., Transdermal Testosterone Administration in Women with Acquired Immunodeficiency Syndrome Wasting: A Pilot Study, Journal of Clinical Endocrinology and Metabolism, vol. 83, No. 8, pp. 2717-2725 (1998).
Miller, et al., Androgen Deficiency in Women with Hypopituitarism, The Journal of Clinical Endocrinology & Metabolism, vol. 86, No. 2, pp. 561-567 (2001).
Miller, M et al., Contemporary Use of Complexed PSA and Calculated Percent Free PSA for Early Detection of Prostate Cancer: Impact of Changing Disease Demographics. Urology 57:1105-1111 (2001).
Minoxidil. Wikipedia. http://en.wikipedia.org/wiki/Minoxidil. pp. 1-3. Downloaded on Oct. 13, 2009.
Misra, et al., Biphasic Testosterone Delivery Profile Observed With Two Different Transdermal Formulations. Pharmaceutical Research, vol. 14, No. 9, pp. 1264-1268 (1997).
Mitchell, et al., Longitudinal Effects of Aging on Serum Total and Free Testosterone Levels in Healthy Men, The J. of Clinical Endocrinology and Metabolism, vol. 86, No. 2, pp. 724-731 (2001).
Mitchell, et al., Age Related Changes in the Pituitary-Testicular Axis in Normal Men; Lower Serum Testosterone Results from Decreased Bioactive LH Drive, Clin Endocrinol (Oxf), May 1995; 42(5): 501-507.
Moffat, et al., Longitudinal Assessment of Serum Free Testosterone Concentration Predicts Memory Performance and Cognitive Status in Elderly Men, The J. of Clin. Endocrinology & Metabolism, vol. 87, No. 11, pp. 5001-5007 (2002).
Moller, et al., Sex Hormone-Binding Globulin Mediates Prostate Androgen Receptor Action via a Novel Signaling Pathway, Endocrinology, Jan. 1998; 139(1):213-8.
Mollgaard, et al., Permeation of Estradiol Through the Skin—Effect of Vehicles, International Journal of Pharmaceutics, vol. 15, pp. 185-197 (1983).
Mollgaard, et al., Vehicle Effect on Topical Drug Delivery, Acta Pharm. Suec., vol. 20, pp. 433-442 (1983).
Monath, et al., Physiologic Variations of Serum Testosterone Within the Normal Range Do Not Affect Serum Prostate-Specific Antigen, Urology 46(1): 58-61 (1995).
Monga, et al., Patient Satisfaction with Testosterone Supplementation for the Treatment of Erectile Dysfunction, Arch. of Andrology, vol. 48, pp. 433-442 (2002).
Monnier et al., Skin collagen glycation, glycoxidation, and crosslinking are lower in subjects with long-term intensive versus conventional therapy of type 1 diabetes: relevance of glycated collagen products versus HbA1c as markers of diabetic complications. DCCT Skin Collagen Ancillary Study Group. Diabetes Control and Complications Trial. Diabetes. Apr. 1999;48(4):870-80.
Monterey, http://www.wellnessmd.com/testo.html (Jul. 10, 2000).
Mooney, Anabolic Steroids for AIDS Therapy: Differences Between Analogs, No. 1, www.digiweb.com. (Jul. 1998).
Mooney, Frequency of Administration—Testosterone & Nandrolone, vol. 1, No. 4, www.medibolics.com (Downloaded Oct. 8, 1998).
Mooradian, et al., Biological Actions of Androgens, Endocrine Reviews, vol. 8, No. 1, pp. 1-28 (1987).
Moreland, et al., "Sildenafil, A Novel Inhibitor of Phosphodiesterase Type 5 in Human Corpus Cavernosum Smooth Muscle Cells," Life Sciences (1998);62(20):PL309-318.
Morgan et al., An Ergonomic and Performance Evaluation of a Metered-Dose Transdermal Spray (MDTS(RM)) in Women of Postmenopausal Age. Poster, Acrux Drug Delivery Solutions. Presented at American Association of Pharmaceutical Scientists (AAPS) (2002), Abstract published at AAPS PharmSci. 2002; 4(S1).
Morgan et al., Enhanced Skin Permeation of Sex Hormones with Novel Topical Spray Vehicles, J. Pharm. Science (1998) vol. 87 No. 10, pp. 1213-1218.
Morgan et al., Enhanced Transdermal Delivery of Sex Hormones in Swine with a Novel Topical Aerosol, J. Pharm. Science (1998) vol. 87 No. 10, pp. 1219-1225.
Morgan et al., Photostabilization of Estradiol by Padimate O or Octyl Salicylate When Added to a Transdermal S[ray as Dermal Penetration Enhancing Excipients. Poster, Acrux Drug Delivery Solutions. Presented at American Association of Pharmaceutical Scientists (AAPS) (2002), Abstract published at AAPS PharmSci. 2002; 4(S1).

(56) References Cited

OTHER PUBLICATIONS

Morgentaler A, Response to: Efficacy of changing testosterone gel preparations (Androgel or Testim) among suboptimally responsive hypogonadal men, Int J Impot Res. May-Jun. 2008;20(3):331; author reply 332.
Morgentaler, A. Transcript of CBS-TV Interview with the Early Show, (CBS television broadcast Aug. 30, 2002).
Morgentaler, et al., Occult Prostate Cancer in Men with Low Serum Testosterone Levels, vol. 276, No. 23, pp. 1904-1906 (Dec. 18, 1996).
Morgentaler, et al., Letters to the Editor, Testosterone's Uses The New Yorker, Aug. 19 & 26, 2002.
Morley JE. et al., Validation of a screening questionnaire for androgen deficiency in aging males. Metabolism, 2000;49(9):1239-1242.
Morley, Testosterone Treatment in Older Men: Effects on the Prostate, Endocr. Pract., vol. 6, No. 2, pp. 218-221 (2000).
Morley, "Testosterone Replacement in Older Men and Women," J Gend Specif Med, 4(2): 49-53 (2001); Abstract.
Morley, et al., Androgen Deficiency in Aging Men: Role of Testosterone Replacement Therapy, J. Lab. Clin. Med., vol. 135, No. 5, pp. 370-378 (May 2000).
Morley, et al., Longitudinal Changes in Testosterone, Luteinizing Hormone, and Follicle-Stimulating Hormone in Healthy Older Men, Metabolism, vol. 46, No. 4 (Apr. 1997), pp. 410-413.
Morley, J. E., et al., Effects of testosterone replacement therapy in old hypogonadal males: a preliminary study. J. Am. Geriatr. 41: 149-152 (1993).
Morris, et al., Marital Sex Frequency and Midcycle Female Testosterone, Arch Sex Behav, Feb. 1987; 16(1):27-37.
Morrison and Boyd Organic Chemistry, 3rd Edition, Boston, US (1973), pp. 36-37.
Morrison, Androgens in the Elderly: Will Androgen Replacement Therapy Improve Mood, Cognition, and Quality of Life in Aging Men and Women, Psychopharmacology Bulletin, vol. 33, No. 2, pp. 293-296 (1997).
Mother Molly's Guide for Living: Daddy, Too. Post-Messenger (New Glarus, WI), Aug. 7, 2002.
Mukherjee, et al., Testosterone Attenuates Expression of Vascular Cell Adhesion Molecule-1 by Conversion to Estradiol by Aromatase in Endothelial Cells: Implications in Atherosclerosis, PNAS, vol. 99, No. 6, pp. 4055-4060 (Mar. 19, 2002).
Mulhall, et al., Effect of testosterone supplementation on sexual function in hypogonadal men with erectile dysfunction. Urology; 63:348-353, 2004.
Müller et al., Testosterontherapie des Hypogonadismus , Schweizerische Arztezeitung, vol. 81, No. 46, pp. 2589-2593 (2000) [German; English Summary Machine Translated].
Mulligan, K., et al., Use of growth hormone and other anabolic agents in AIDS wasting. JPEN J. Parenter. Enteral Nutr. 23: S202-S209 (1999).
Mussoline M E, et al., Risk factors for hip fracture in white men: the NHANES I Epidemiologic Follow-up Study. J. Bone Miner. Res. 13: 918-24 (1998).
Mydlo, et al., Initial Results Utilizing Combination Therapy for Patients with a Suboptimal Response to Either Alprostadil or Sildenafil Monotherapy, Eur. Urol., vol. 38, pp. 30-34 (2000).
Mydlo, et al., Results from Different Patient Populations Using Combined Therapy with Alprostadil and Sildenafil: Predictors of Satisfaction, BJU Intl., vol. 86, pp. 469-473 (2000).
Myers, et al., Effects of Estrogen, Androgen, and Progestin on Sexual Psychophysiology and Behavior in Postmenopausal Women, Journal of Clinical Endocrinology and Metabolism, vol. 70, No. 4, pp. 1124-1131 (Apr. 1990).
Mylonakis, et al., Clin. Infect. Dis., 2001, 33, p. 857-864.
N.N. AIDS Alert, American health consultants, Jun. 1999.
Nagelberg, et al., Cerebrovascular Accident Associated with Testosterone Therapy in a 21-year-old Hypogonadal Man, N. Engl. J. Med., vol. 314, No. 10, pp. 649-650 (Mar. 6, 1986).
Naik, A. et al., "Mechanism of oleic acid-induced skin penetration enhancement in vivo in humans," J. Control Rel. (1995) 37:299-306.

Nakhla, et al, Stimulation of Prostate Cancer Growth by Androgens and Estrogens Through the Intermediacy of Sex Hormone-Binding Globulin, Endocrinology, vol. 137, No. 10, pp. 4126-4129 (Oct. 1996).
Nankin HR et al., The aging Leydig cell III. Gonadotropin stimulation in men. J. Androl 2:181 (1981).
Nankin, et al., Daytime Titers of Testosterone, LH, Estrone, Estradiol, and Testosterone-Binding Protein: Acute Effects of LH and LH-Releasing Hormone in Men, Journal of Clinical Endocrinology Metabolism, vol. 41, pp. 271-281 (1975).
Nankin, et al., Decreased Bioavailable Testosterone in Aging Normal and Impotent Men, J Clin Endocrinol Metab, Dec. 1986; 63(6):1418-1420.
NAPS, Hey Men, It's Time for a Health Tune-Up. Available at http://www.wscare.com/viewArticle?ID=374714, Date published: Jul. 10, 2002.
Nathorst-Boos, J, et al., Treatment with percutaneous testosterone gel in postmenopausal women with decreased libido—effects on sexuality and psychological general well-being, Maturitas (2006);53(1):11-8 (Abstract only).
Navarro, et al., Salivary Testosterone in Postmenopausal Women with Rheumatoid Arthritis, J Rheumatol, Jun. 1998; 25(6): 1059-62.
Need, et al., Double-Blind Placebo-Controlled Trial of Treatment of Osteoporosis with the Anabolic Nandrolone Decanoate, Osteoporosis Int. Supplement 1: S218-222 (1993).
Need, et al., Effects of Nandrolone Therapy on Forearm Bone, www.medmedia.com (Downloaded Oct. 8, 1998).
Nehra, et al., Rationale for Combination Therapy of Intraurethral Prostaglandin $E_1$ and Sildenafil in the Salvage of Erectile Dysfunction Patients Desiring Noninvasive Therapy, Intl. J. of Impotence Research, vol. 14, Suppl. 1, pp. S38-S42 (2002).
Neugarten BL, Havigurst RJ, Tobin SS. The measurement of life satisfaction. J Gerontol 16:134-43, 1961.
Nevalainen, et al., Hormone Regulation of Human Prostate in Organ Culture, Cancer Res, Nov. 1, 1993; 53(21):5199-207.
Never Too Buff, Time Europe, www.time.com, vol. 155, No. 16 (Apr. 24, 2000).
New Drug Application for Testosterone Gel Accepted for Review by FDA Represents First NDA with Bentley's Proprietary CPE-215 Technology, Business Wire (Mar. 6, 2002).
New Treatment Approved for Low Testosterone, Not Born Yesterday (La Canada Flintridge, CA), Dec. 2002.
Ng. Martin et al., Prospective Study of Effect of Androgens on Serum Inflammatory Markers in Men, Arterioscler. Thromb. Vasc. Biol., vol. 22, pp. 1136-1141 (2002).
Nicolazzo, J.A. et al., "Synergistic enhancement of testosterone transdermal delivery," J. Contr. Rel. (2005) 103:577-585.
Nicoli, S. et al., "Dermatopharmacokinetics: factor influencing drug clearance from the stratum corneaum," Pharm. Res. (2009) 26(4):865-871.
Nieschlag E. et al., Reproductive functions in young fathers and grandfathers. J. Clin. Endocrinol. Metab. 55:876 (1982).
Nieschlag et al., Testosterone: Action, Deficiency, Substitution, Chapters 1, 6-16 (1999).
Nieschlag, Eberhard, Testosterone Treatment Comes of Age: New Options for Hypogonadal Men, Clinical Endocrinology, vol. 65, pp. 275-281 (2006).
Nieschlag, et al., eds., Testosterone: Action—Deficiency—Substitution (2d ed.), pp. 335-337.
Nilas, et al., Bone Mass and its Relationship to Age and the Menopause, J Clin Endocrinol Metab, Oct. 1987; 65(4): 697-702.
Nishimura, Y., M. Tsutsumi, H. T. Tsunenari, H. Maeda, and M. Yokoyama. Relationship between respiratory muscle strength and lean body mass in men with COPD. Chest 107: 1232-1236 (1995).
Notice of NDA No. 202763 Concerning Testosterone Gel, 1% with Paragraph IV Certification Concerning U.S. Pat. No. 6,503,894 dated Mar. 16, 2011 (Teva).
Notification of Certification of Invalidity, Unenforceability and/or Non-Infringement for U.S. Pat. No. 6,503,894 B1 Pursuant to Section 505(b)(3) of the Federal Food, Drug and Cosmetic Act dated Sep. 20, 2011 (Perrigo).
Novelli, et al., Pharmacogenetics of Human Androgens and Prostatic Diseases, Pharmacogenomics, vol. 2, No. 1, pp. 65-72 (2001).

(56) References Cited

OTHER PUBLICATIONS

Noveon Bulletin 10: Neutralization Procedures (Jan. 2002).
Noveon Bulletin 11: Thickening Properties (Jan. 2002).
Noveon Bulletin 14: Formulating Topical Properties (Jan. 2002).
Noveon Product Specification: Carbopol 1342 NF (Jan. 2003).
Noveon Product Specification: Carbopol 674 Polymer (Nov. 2001).
Noveon Product Specification: Carbopol 676 Polymer (Nov. 2001).
Noveon Product Specification: Carbopol 934 NF Polymer (Jan. 2003).
Noveon Product Specification: Carbopol 940 NF Polymer (Jan. 2003).
Noveon Product Specification: Carbopol 941 NF Polymer (Jan. 2003).
Noveon Product Specification: Carbopol 971P NF Polymer (Jan. 2003).
Noveon Product Specification: Carbopol 974P NF Polymer (Jan. 2003).
Noveon Product Specification: Carbopol 980 NF Polymer (Jan. 2003).
Noveon Product Specification: Carbopol Aqua 30 Polymer (Nov. 2002).
Noveon Product Specification: Carbopol ETD 2020 Polymer (Nov. 2001).
Noveon Product Specification: Carbopol ETD 2623 Polymer (Nov. 2001).
Noveon Product Specification: Carbopol ETD 2691 Polymer (Nov. 2001).
Noveon Product Specification: Carbopol EZ-2 Polymer (Aug. 2003).
Noveon Product Specification: Carbopol EZ-3 Polymer (Aug. 2003).
Noveon Product Specification: Carbopol Ultrez 10 NF Polymer (May 2003).
Noveon Product Specification: Carbopol Ultrez 21 Polymer (Sep. 2003).
Noveon Standard Test Procedure SA-051A: Determination of Waiting Time & Brookfield Viscosity of Carbopol Ultrez and EZ Polymers (Aug. 2002).
Noveon TDS-207: Carbopol ETD Polymers: Formulation Tips (Jan. 2002).
Noveon TDS-297: Carbopol Ultrez 21 Polymer, Technical Data Sheet (Feb. 2003).
Noveon TDS-60: Applications Technology for Carbopol Resins and Cosmetic Formulations (2001).
Noveon TDS-64: Typical Properties of Carbopol Polymers (Jan. 2002).
Noveon, Formulating Hydroalcoholic Gels with Carbopol Polymers, Noveon TDS-255, Dec. 1999.
Noveon, Neutralizing Carbopol and Pemulen Polymers in Aqueous and Hydroalcoholic Systems, Commercial Brochure TDS-237 (Oct. 1998) by Noveon Inc. of Cleveland, Ohio.
O'Carrol & Bancroft, Testosterone Therapy for Low Sexual Interest and Erectile Dysfunction in Men: A Controlled Study, Brit. J. Psychiatry 145:146-151 (1984).
O'Carroll et al., "Androgens, behaviour and nocturnal erection in hypogonadal men: the effects of varying the replacement dose." Clin. Endocrinol. 23: 527-538 (1985).
O'Connor, Managing Menopause—Part 2: What Are the Choices in Treatment? Medicine Today, vol. 2 (No. 2), p. 30-39, (Feb. 22, 2001).
Oden Z M, et al., The effect of trabecular structure on DXA-based predictions of bovine bone failure. Calcif. Tissue Int., 63:67-73 (1998).
Okun, et al., Beneficial Effects of Testosterone Replacement for the Nonmotor Symptoms of Parkinson Disease, Arch. Neurol., vol. 59, pp. 1750-1753 (Nov. 2002).
Okun, et al., Refractory Nonmotor Symptoms in Male Patients with Parkinson Disease Due to Testosterone Deficiency: A Common Unrecognized Comorbidity, Arch. Neurol., vol. 59, pp. 807-811 (May 2002).
O'Neill T W, et al., The prevalence of vertebral deformity in European men and women: the European Vertebral Osteoporosis Study. J. Bone Miner. Res., 11:1010-8 (1996).
Ongpipattanakul, B. et al., "Evidence that oleic acid exists in a separate phase within stratum corneum lipids," Pharm. Res. (1991) 8(3):350-354.
Openbrier, D. R., M. M. Irwin, R. M. Rogers, G. P. Gottlieb, J. H. Daubner, D. H. Van Theil and B. E. Pennock. Nutritional status and lung function in patients with emphysema and chronic bronchitis. Chest 83: 11-22 (1983).
Oppermann, Testosterone Replacement Carries Definite Risks for Men, Chicago Daily Herald, Jun. 3, 2002.
Options, Alt Med. Rev., (vol. 1, pp. 18-25 (1996). (Abstract only).
Orwell ES et al., The impact of osteophytic and vascular calcifications on vertebral mineral density measurements in men. J. Clin. Endocrinol. Metab. 70:1202 (1990).
Orwoll ES et al., The rate of bone mineral loss in normal men and the effects of calcium and cholecalciferol supplementation. Ann. Int. Med. 112:29 (1990).
Orwoll, E. S., Oviatt, S., Biddle, J., and Janowsky, J. Transdermal testosterone supplementation in normal older men. Proc. 74th Endocr. Soc. Meetings, San Antonio, TX. Jun. 24, 1992 (1992).
Osborne et al., Skin Penetration Enhancers Cited in Technical Literature, Pharmaceutical Technology. pp. 58, 60, 62, 64 and 66, Nov. 1997.
Ostrenga, et al., Significance of Vehicle Composition I: Relationship Between Topical Vehicle Composition, Skin Penetrability, and Clinical Efficacy, Journal of Pharmaceutical Sciences, vol. 60, No. 8, pp. 1175-1179 (Aug. 1971).
Ostrenga, et al., Significance of Vehicle Composition II: Prediction of Optimal Vehicle Composition, Journal of Pharmaceutical Sciences, vol. 60, No. 8, pp. 1180-1183 (Aug. 1971).
Oxford Dictionary of Biochemistry and Molecular Biology, "ethanol": p. 218 (1997).
Pabla D, Zia H, A comparative permeation/release study of different testosterone gel formulations, Drug Deliv. Aug. 2007;14(6):389-96.
Package insert for Estrogel, (Mar. 2004).
Padova, et al., Pubarche Induction with Testosterone Treatment in Women with Panhypopituitarism, Fertil Steril, Feb. 1996; 65(2): 437-9.
Page ST et al., Testosterone gel combined with depomedroxyprogesterone acetate is an effective male hormonal contraceptive regimen and is not enhanced by the addition of a GnRH antagonist, J Clin Endocrinol Metab. Nov. 2006;91(11):4374-80. (Epub Date: Aug. 29, 2006).
Pannek, et al., The Role of PSA and Percent Free PSA for Staging and Prognosis Prediction in Clinically Localized Prostate Cancer, Seminars in Urologic Oncology, vol. 16, No. 3, pp. 100-105 (Aug. 1998).
Parfitt A M, Implications of architecture for the pathogenesis and prevention of vertebral fracture. Bone, 13:S41-7 (1992).
Parfitt A M, et al., Relationships between surface, volume, and thickness of iliac trabecular bone in aging and in osteoporosis. Implications for the microanatomic and cellular mechanisms of bone loss. J. Clin. Invest., 72:1396-409 (1983).
Park, et al., Effects of Androgens on the Expression of Nitric Oxide Synthase mRNAs in Rat Corpus Cavernosum, BJU Int'l vol. 83, pp. 327-333 (1999).
Parker, et al., Experience with Transdermal Testosterone Replacement in Hypogonadal Men, Clinical Endocrinology (OXF), vol. 50, pp. 57-62 (1999).
Patch Ups Women's Sex Drive. ABCNEWS.com: http://abcnews.go.com/sections/living/DailyNews/testosterone990615.html (Sep. 8, 2000).
Pavlov. "Indications and technique of intra-articular administration of hydrocortisone to patients with infectious nonspecific polyarthritis." Soviet Medicine (1964). [in Russian with English Abstract].
Pedersen, et al., Relationship Between Sex Hormones, Body Composition and Metabolic Risk Parameters in Premenopausal Women, Eur J Endocrinol, Aug. 1995; 133(2): 200-6.
Pena, Topical Drug Delivery Formulations, ed. Osborne and Amann, vol. 42, pp. 381-388 (1990).
Penson, et al., Androgen and Pituitary Control of Penile Nitric Oxide Synthase and Erectile Function in the Rat, Biology of Reproduction, vol. 55, pp. 567-574 (1996).

(56) References Cited

OTHER PUBLICATIONS

Percutacrine Strong Androgenic Testosterone Percutacrine Androgenique Forte from VIDAL dictionary (1985).
Peres, Clinical Trials to Test Efficacy of Testosterone-Replacement Therapy for Men, Knight-Ridder Tribune Business News, Nov. 29, 2002.
Peres, Hormones Now a Men's Issue, Chicago Tribune, Nov. 29, 2002.
Peres, Replacement Hormones New Issue for Men, Pittsburgh Post-Gazette, Jan. 5, 2003.
Peres, Researchers Consider Benefits of Male Hormone Replacement, Houston Chronicle, Jan. 3, 2002.
Perez CA, I love my Androgel, Posit Aware. Nov.-Dec. 2003;14(6):42-3.
Perry, et al., Osteoporosis in Men: Are We Ready to Diagnose and Treat?, Curr. Rheumatol. Res., vol. 3, No. 3, pp. 240-244 (Jun. 2001).
Pershing, L.K. et al., "Disparity of in vitro and in vivo oleic acid-enhanced beta-estradiol percutaneous absorption across human skin," Pharm. Res. (1993) 10(12):1745-1750.
Persky, et al., The Relation of Plasma Androgen Levels to Sexual Behaviors and Attitudes of Women, Psychosomatic Medicine, vol. 44, No. 4, pp. 305-319 (Sep. 1982).
Persky, et al., Plasma Testosterone Level and Sexual Behavior of Couples. Arch Sex Behav, May 1978; 7(3): 157-73.
Petra, The Plasma Sex Steroid Binding Protein (SBP or SHBG): A Critical Review of Recent Developments of the Structure, Molecular Biology, and Function, J. Steroid Biochem. Mol. Biol. vol. 40, pp. 735-753 (1991).
Petrangeli, et al., Effects of Two Different Medical Treatments on Dihydrotestosterone Content and Androgen Receptors in Human Benign Prostatic Hyperplasia. J Steroid Biochem, 1988; 30(1-6): 395-9.
Petrow, The Dihydrotestosterone (DHT) Hypothesis of Prostate Cancer and its Therapeutic Implications. Prostate, 1986; 9(4): 343-61.
Pfeilschifter, et al., Osteoporosis Due to Cancer Treatment: Pathogenesis and Management, J. of Clin. Oncology, vol. 18, No. 7, pp. 1570-1593 (Apr. 2000).
Phillips GB, Pinkernell BH, Jinh TY: The association of hypotestosteronemia with coronary artery disease in men. Arteriosclerosis & Thrombosis 14:701-6, 1994.
Phillips L et al., A comparison of rabbit and human skin response to certain irritants. Toxicol. Appl. Pharmacol. 21, 369-82 (1972).
Pilepich, et al., Androgen Deprivation with Radiation Therapy Compared with Radiation Therapy Alone for Locally Advanced Prostatic Carcinoma: A Randomized Comparative Trial of the Radiation Therapy Oncology Group, Urology, vol. 45, No. 4, pp. 616-623 (Apr. 1995).
Pirke KM et al., Age related changes in free plasma testosterone, dihydrotestosterone and oestradiol. Acta Endocrinol. 80: 171 (1975).
Pirke, et al., Age Related Changes and Interrelationships Between Plasma Testosterone, Oestradiol and Testosterone-Binding Globulin in Normal Adult Males, Acta Endocrinologica (COPENH), vol. 74, No. 4, pp. 792-800 (Dec. 1973).
Place, et al., Transdermal Delivery of Testosterone with Testoderm to Provide Normal Circadian Pattern of Testosterone. Ann NY Acad Sci, 1991; 618:441-9.
Plymate, et al., Androgens, Lipids, and Cardiovascular Risk, Annals of Internal Medicine, vol. 117, No. 10, pp. 871-872 (Nov. 15, 1992).
Plymate, et al., Circadian Variation in Testosterone, Sex Hormone-Binding Globulin and Calculated Non-Sex Hormone-Binding Globulin Bound Testosterone in Healthy Young and Elderly Men. J Androl, Sep.-Oct. 1989; 10(5): 366-71.
Plymate, et al., Effects of Sex Hormone Binding Globulin (SHBG) on Human Prostatic Carcinoma. J Steroid Biochem Mol Biol, 1991; 40(4-6): 833-839.
Pollard et al., Dihydrotestosterone does not induce prostate adenocarcinoma in L-W rats, Prostate 10:325-331 (1987).
Polsy, et al., HIV-Associated Wasting in the HAART Era: Guidelines for Assessment, Diagnosis, and Treatment, AIDS Patient Care and STDs, vol. 15, No. 8, pp. 411-423 (2001).

Poor, et al., Determinants of Reduced Survival Following Hip Fractures in Men, Clinical Orthopaedics and Related Research, No. 319, pp. 260-265 (Oct. 1995).
Pope Jr., et al., Testosterone Gel Supplementation for Men with Refractory Depression: A Randomized, Placebo-Controlled Trial. Am. J. Psychiatry, 160(1): 105-111 (2003).
Porche DJ. Treatment review. Testosterone (Testoderm). J Assoc Nurses AIDS Care. Jul.-Aug. 1995;6(4):43-5.
Porter, et al., Humoral Mechanisms in Prostate Cancer: A Role for FSH, Urologic Oncology, vol. 6, pp. 131-138 (2001).
Postma, et al., Effects of Testosterone Administration on Selective Aspects of Object-Location Memory in Healthy Young Women, Psychoneuroendocrinology, vol. 25, pp. 563-575 (2000).
Poteat, et al., Appropriateness of Prostate-Specific Antigen Testing, Am. J. Clin. Pathol., vol. 113, pp. 421-428 (2000).
Poulsen, B.J. et al., "Effect of topical vehicle composition on the in vitro release of fluocinolone acetonide and its acetate ester," J. Pharm. Sci. (1968) 57(6):928-933.
Preidt, Testosterone: Shot in the Arm for What Ails Aging Males, HealthScoutNews.com (Aug. 5, 2002).
Press Release, "Schering AG—Male Hormone Therapy" (Jul. 2, 2002).
Press Release, "The Endocrine Society Responds to the Institute of Medicine Report on Testosterone Therapy for Older Men" (Nov. 17, 2003).
Press Release, Cellegy Announces Settlement of PDI Litigation (Apr. 12, 2005).
Press Release, FDA Approves Androgel, First Gel to Treat Male Testosterone Deficiency (Feb. 29, 2000) from www.androgel.com/media/press_release000229.htm.
Prince RL et al., Prevention of postmenopausal osteoporosis: A comparative study of exercise, calcium supplementation and hormone-replacement therapy. N Engl J. Med 325:1189 (1991).
Procter & Gamble, TheraTech Plan Testosterone Patch for Use by Women. The Wall Street Journal, p. B6 (Dec. 4, 1997).
Product information—Testoderm TTS, Physicians' Desk Reference, Alza pp. 517-520 (1999).
Prospectus—Cellegy Pharmaceuticals, Inc., Oppenheimer & Co., pp. 1-4, 20821-20828 (it is 21-28 on U.S. Appl. No. 10/153,468) (1997).
Quincey et al., The metabolism of [1,2-3H]17 {alpha}-methyltestosterone in human subjects, J. Endocrinol. 37(1):37-35 (1967).
R&D Directions, "Products Filed for Approval: Androgel—Unimed Applies for FDA Approval for Androgel Gel for the Treatment of Low Testosterone Levels in Hypogonadal Men," 5(7) (Jul. 1999).
Rabkin, et al., Testosterone Therapy for Human Immunodeficiency Virus-Positive Men With and Without Hypogonadism, J. Clin. Psychopharmacol., vol. 19, No. 1, pp. 19-27 (Feb. 1999).
Rabkin, et al., Treatment of Depression in HIV+ Men: Literature Review and Report of an Ongoing Study of Testosterone Replacement Therapy, Ann. Behav. Med., vol. 18, No. 1, pp. 24-29 (1996).
Rabkin, J et al., A double-blind, Placebo-Controlled Trial of Testosterone Therapy for HIV-Positive Men With Hypogonadal Symptoms. Arch Gen Psychiatry 57: 141-147 (Feb. 2000).
Radio: Public Service Announcement: Transcripts for Advertisements: Low Testosterone in Men, an Easily Diagnosed and Treated Condition. PSA. :15, :30, :60 Versions.
Raisz, et al., Comparison of the Effects of Estrogen Alone and Estrogen Plus Androgen on Biochemical Markers of Bone Formation and Resorption in Postmenopausal Women, Journal of Clinical Endocrinology and Metabolism, vol. 81, No. 1, pp. 37-43 (Jan. 1996).
Rako, Testosterone Deficiency: a Key Factor in the Increased Cardiovascular Risk to Women Following Hysterectomy or with Natural Aging? J Womens Health, Sep. 1998; 7(7): 825-9.
Ramzy, P. I., S. E. Wolf, and D. N. Herndon. Current status of anabolic hormone administration in human burn injury. JPEN J. Parenter. Enteral Nutr. 23: S190-S194 (1999).
Random House Webster's Unabridged Dictionary, 2d Edition, "ethanol": p. 665 and "alcohol": p. 49 (2005).
Random House Webster's Unabridged Dictionary, 2d Edition, "pharmaceutical": p. 1451 and "drug": p. 600 (2005).

(56) References Cited

OTHER PUBLICATIONS

Raudaskoski, et al., Sex-Hormone Binding Globulin as an Indicator of the Hepatic Impacts of Continuous Combined Hormone Replacement Regimens, Maturitas, vol. 29 ( No. 1), p. 87-92, ( Jan. 22, 1998).
Ray Fox et al., Medical Expenditures for the Treatment of Osteoporotic Fractures in the United States in 1995: Report from the National Osteoporosis Foundation, J. of Bone and Mineral Research, vol. 12, No. 1, pp. 24-35 (1997).
Ray, et al., ISATT Series 2007, Men's Health Information (Presentation).
Rebora, Baldness and Coronary Artery Disease: The Dermatologic Point of View of a Controversial Issue, Arch Dermatol. 137:943-947 (2001).
Reed RL et al., The relationship, between muscle mass and muscle strength in the elderly. J. Am Ger Soc 39:555 (1991).
Rehm, Testosterone and Andropause, National Public Radio, The Diane Rehm Show Summary Introduction (Aug. 14, 2002).
Reichardt, J. Prostatic Steroid 5α—Reductase, an Androgen Metabolic Gene. Mayo Clin Proc. 75(suppl):S36-S39 (2000).
Reilly et al., Androgenic Regulation of NO Availability in Rat Penile Erection, 18 J. Andrology 110 (1997): 110-115.
Research & Education Institute at Harbor-UCLA Medical Center, Testosterone Gel (AndroGel(R)) Study Demonstrates Safety and Efficacy Persists Up to 42 Months in Men with Low Testosterone, Yahoo!Finance.com (Jun. 20, 2002).
Retin-A (tretinoin) Cream; Retin-A (tretinoin) Gel; Retin-A (tretinoin) Liquid. Daily Med. http://dailymed.nlm.nih.gov/dailymed/drugInfo.cfm?id=3734. pp. 1-13. Downloaded on Oct. 13, 2009.
Retinopathy and nephropathy in patients with type 1 diabetes four years after a trial of intensive therapy. Am J Ophthalmol. May 2000;129(5):704-5.
Retinopathy and nephropathy in patients with type 1 diabetes four years after a trial of intensive therapy. NEJM. 2000. 342:381-9.
Retnakaran et al., Risk factors for renal dysfunction in type 2 diabetes: U.K. Prospective Diabetes Study 74. Diabetes. Jun. 2006;55(6):1832-9.
Reuters News, "Unimed Files to Market Gel to Treat Impotence" (Apr. 29, 1999).
Reynolds, Do women with impaired sexual function following oophorectomy benefit from transdermal testosterone at a physiologic dose? The Journal of Family Practice, vol. 49 (No. 12n), p. 1075 (Dec. 2000).
Rheology Modifiers Handbook, 2000, p. 81-88, published by William Andrew Publishing.
Rhoden et al., "Risks of Testosterone-Replacement Therapy and Recommendations for Monitoring," N Engl J Med 350:5, 482-492 (2004).
Rhoden, et al., The Relationship of Serum Testosterone to Erectile Function in Normal Aging Men, The J. of Urol., vol. 167, pp. 1745-1748 (Apr. 2002).
Rich JB, Brandt J. Lesh K, Dobs AS. The effect of testosterone on cognition in hypogonadal men. ICE the endocrine society p. 734 #OR58-6 (1996).
Richmond et al., Male pubertal development and the role of androgen therapy, Nature Clinical Practice Endocrinology and Metabolism, 3(4):338-344 (2007).
Rietschel, et al., Prevalence of Hypogonadism among Men with Weight Loss Related to Human Immunodeficiency Virus Infection Who Were Receiving Highly Active Antiretroviral Therapy, Clinical Infectious Diseases, vol. 31, pp. 1240-1244 (2000).
Riggs, et al., A Unitary Model for Involutional Osteoporosis: Estrogen Deficiency Causes Both Type I and Type II Osteoporosis in Postmenopausal Women and Contributes to Bone Loss in Aging Men, J. of Bone and Mineral Research, vol. 13, No. 5, pp. 763-773 (1998).
Riggs, Unimed Begins Pivotal Clinical Trial for Innovative Testosterone Gel, Unimed News Release, pp. 1-2 (Mar. 31, 1997).
Ringham, et al., Dose Proportionality and Systemic Bioavailability of a Testosterone Topical Gel in Hypogonadal Men, Unimed Pharmaceuticals (Oct. 31, 2000).
Rizzo, "Advertising and Competition in the Ethical Pharmaceutical Industry: The Case of Antihypertensive Drugs," J Law & Econ 42(1): 89-116 (Apr. 1999).
Roberts, et al., PSA Doubling Time as a Predictor of Clinical Progression After Biochemical Failure Following Radical Prostatectomy for Prostate Cancer, Mayo Clin. Proc., vol. 76, pp. 576-581 (2001).
Roberts, More Men Take Testosterone, CBS-TV CBS Morning News Online (Aug. 25, 2002).
Robinson, M.K. et al., "Evaluation of the primary skin irritation and allergic contact sensitization potential of transdermal triprolidine," Fund. Appl. Toxico. (1991) 17:103-119.
Rodriguez, Study of Drug to Preserve Lean Muscle Mass Recruiting Patients, ALPA 9701: Study Recruiting Patients, www.apla.org (Downloaded Oct. 8, 1998).
Rogol A.D., New facets of androgen replacement therapy during childhood and adolescence. Expert Opinion on Pharmacotherapy, 6(8):1319-1336 (2005).
Rogol, Nature clinical practice endocrinology and metabolism vol. 3, No. 4, Apr. 2007, pp. 338-344.
Rogol, Pubertal androgen therapy in boys. Pediatr. Endocrinol. Rev., Mar. 2005; 2(3):383-90.
Rolf, et al., Interpersonal testosterone transfer after topical application of a newly developed testosterone gel preparation, Clinical Endocrinology, vol. 56, pp. 637-641 (2002).
Rolf, et al., Pharmacokinetics of a new transdermal testosterone gel in gonadotrophin-suppressed normal men, European Journal of Endocrinology, vol. 146, pp. 673-679 (2002).
Rosano et al., Acute Anti-Ischemic Effect of Testosterone in Men with Coronary Artery Disease, Circulation, vol. 99, No. 13, pp. 1666-1670 (Apr. 6, 1999).
Rosano, et al., Antianginal and Lipid Lowering Effect of Chronic Oral Androgen Supplementation in Elderly Male Patients with Coronary Heart Disease. JACC, Abstract No. 835-4 (Feb. 2001).
Rosen, et al., The International Index of Erectile Function (IIEF): A Multidimensional Scale for Assessment of Erectile Dysfunction, Urology, vol. 49, pp. 822-830 (1997).
Rosenthal BD, et al., Adjunctive use of AndroGel (testosterone gel) with sildenafil to treat erectile dysfunction in men with acquired androgen deficiency syndrome after failure using sildenafil alone, Urology. Mar. 2006;67(3):571-4.
Rosner et al., Sex Hormone-Binding Globulin Mediates Steroid Hormone Signal Transduction at the Plasma Membrane, J. Steroid Biochem. Mol. Biol. vol. 69:481-5 (1999).
Roubenoff, et al., Role of Cytokines and Testosterone in Regulating Lean Body Mass and Resting Energy Expenditure in HIV-infected Men, Am. J. Physiol. Endocrinol. Metab., vol. 283, pp. E138-E145 (2002).
Rouru, et al., Serum Leptin Concentrations in Women with Polycystic Ovary Syndrome. J Clin Endocrinol Metab, Jun. 1997; 82(6): 1697-700.
Rousseau, et al, Inhibition of Steroid-Protein Interactions by Dicyclohexane Derivatives. J Steroid Biochem, vol. 31, No. 4B, pp. 691-697 (1988).
Rowe et al., Handbook of Pharmaceutical Excipients, 2d ed. (1994).
Rubens RM et al., Further studies on Leydig cell function in old age. J. Clin. Endocrinol. Metab. 39:40 (1974).
Rudman D, Drinka PJ, Wilson CR, Mattson DE, Scherrnan F, Cuisinier MC, Schults S: Relations of endogenous anabolic hormones and physical activity to bone mineral density and lean body mass in elderly men. Clin Endocrinol 40:653-61, 1994.
Saad F, et al., A dose-response study of testosterone on sexual dysfunction and features of the metabolic syndrome using testosterone gel and parenteral testosterone undecanoate, J Androl. Jan.-Feb. 2008;29(1):102-5. (Epub Date: Oct. 3, 2007).
Saad F, et al., Effects of testosterone gel followed by parenteral testosterone undecanoate on sexual dysfunction and on features of the metabolic syndrome, Andrologia. Feb. 2008;40(1):44-8.
Saar, B.G. et al., "Imaging drug delivery to skin with stimulated raman scattering microscopy," Mol. Pharm. (2011) 8:969-975.

(56) References Cited

OTHER PUBLICATIONS

Saeedi M et al., A randomized, double-blind, controlled trial of testosterone gel treatment versus vehicle control on the facial hair of young men with beta-thalassemia major, J Dermatolog Treat. 2007;18(5):271-4.

Salehian et al., Pharmacokinetics, bioefficacy and safety of sublingual testosterone cyclodextrin in hypogonadal men: comparison to testosterone enanthate—a clinical research center study. J. Clin. Endocrinol. Metab. 80: 3567-75 (1995).

Sanctis et al., Clinical experience using the Androderm testosterone transdermal system in hypogonadal adolescents and young men with beta-thalassemia major. J. Ped. Endocrinol. Metab. 11, Supp. 3, 891-900 (1998) (abstract only).

Sands, et al., Exogenous Androgens in Postmenopausal Women, Am J Med, Jan. 16, 1995; 98(1A): 76S-79S.

Santavirta S et al., Determinants of osteoporotic thoracic vertebral fracture. Screening of 57,000 Finnish women and men. Acta Orthop Scand 63:198 (1992).

Santos, P. et al., "Oxybutinin permeation in skin: the influence of drug and solvent activity," Int. J. Pharma. (2010) 384:67-72.

Santus G. C. et al., Transdermal enhancer patent literature, Journal of Controlled release, Elsevier Science Publishers, (1993);25:1-20.

Sarrel P. et al., Estrogen and estrogen-androgen replacement in postmenopausal women dissatisfied with estrogen-only therapy, sexual behavior and neuroendocrine responses, Journal of Reproductive Medicine, Oct. 1998;43(10):847-856.

Sasagawa I, et al., Serum levels of total and free testosterone in men undergoing hemodialysis. Arch Androl 1998;40(20):153-158.

Sato, K. et al., "Effect and mode of action of aliphatic esters on the in vitro skin permeation of nicorandil," Int. J. Pharma. (1988) 43:31-40.

Sattler FR, et al., Effects of pharmacological doses of nandrolone decanoate and progressive resistance training in immunodeficient patients infected with Human Immunodeficiency Virus. J Clin Endocrinol Metab 84:1268-76, 1999.

Sauvez et al., "Cutaneously applied 4-hydroxytamoxifen is not carcinogenic in female rats." Carcinogenesis. 20(5): 843-850 (1999).

Savvas, et al., Increase in Bone Mass after One Year of Percutaneous Oestradiol and Testosterone Implants in Post-Menopausal Women Who Have Previously Received Long-Term Oral Oestrogens, British Journal of Obstetrics Gynecology, vol. 99, No. 9, pp. 757-760 (Sep. 1992).

Schaefer et al., Skin Barrier, Principles of Percutaneous Absorption, ed. Kager, pp. 164-171 (1996).

Schaison et al., Testosterone,: Percutaneous dihydrotestosterone treatment, Ch. 15, pp. 423-435 (1999).

Schaison G, Nahoul K, Couz B) Percutaneous dihydrotestosterone (DHT) treatment. Testosterone: Action. Deficiency and Substitution E. Nieschlag, H.M. Behre (Eds.). Springer-Verlag, New York, pp. 155-164 (1990.

Schaison, et al., On the Role of Dihydrotestosterone in Regulating Luteinizing Hormone Secretion in Man, J Clin Endocrinol Metab, Nov. 1980; 51(5): 1133-1137.

Schatzl, et al., Endocrine Patterns in Patients with Benign and Malignant Prostatic Diseases, The Prostate, vol. 44, pp. 219-224 (2000).

Schatzl, et al., High-Grade Prostate Cancer is Associated With Low Serum Testosterone Levels, The Prostate, vol. 47, pp. 52-58 (2001).

Schering AG Business: Reproductive, Metabolic. Biocentury Part II, Belmont, CA (Jul. 8, 2002).

Schiavi RC, et al., Effect of Testosterone Administration on Sexual Behavior and Mood in Men with Erectile Dysfunction. Arch. Sex Behav., Jun. 1997 26(3):231-41.

Schols, A. M., P. B. Soeters, R. Mostert, R. J. Pluymers, and E. F. Wouters. Physiologic effects of nutritional support and anabolic steroids in patients with chronic obstructive pulmonary disease. A placebo-controlled randomized trial. Am. J. Respir. Crit Care Med. 152: 1268-1214 (1995).

Schoor, M., Livening Up Libidos: Testosterone Patches Can Help Revive Women's Sex Drive, www.abcnews.com, Sep. 6, 2000.

Schottner, et al., Lignans Intefering with 5 alph-Dihydrotestosterone Binding to Human Sex Hormone-Binding Globulin, J Natl Prod, Jan. 1988; 61(1): 119-121.

Schreiner-Engel, et al., Low Sexual Desire in Women: the Role of Reproductive Hormones, Hormones and Behavior, vol. 23, No. 2, pp. 221-234 (Jun. 1989).

Schreiner-Engel, et al., Sexual Arousability and the Menstrual Cycle, Psychosom Med Jun. 1981; 43(3): 199-214.

Schulthesis, D et al., Pilot study of the transdermal application of testosterone gel to the penile skin for the treatment of hypogonadotropic men with erectile dysfunction Abstract. World J Urol 18: 431-435 (2000).

Schurmeyer, et al., Comparative Pharmacokinetics of Testosterone Enanthate and Testosterone Cyclohexanecarboxylate as Assessed by Serum and Salivary Testosterone Levels in Normal Men, International Journal of Andrology, (1984);vol. 7, pp. 181-187.

Schustack A, Meshiaj D, Waiss Z, Gottloib L. L. Intramuscular iron replenishment and replacement combined with testosterone enanthoate in maintenance hemodialysis anemia: a follow up of up to 8 years in 16 patients. Clin Nephrol 1985; 23(6):303-306.

Schwartz RS et al., "Body Fat Distribution in Healthy Young and Older Men" Journal of Gerontology: Medical Sciences, 1990. vol. 45. No. 6. M18I-I85.

Scott JD et al., Prospective study of topical testosterone gel (AndroGel) versus intramuscular testosterone in testosterone-deficient HIV-infected men, HIV Clin Trials. Nov.-Dec. 2007;8(6):412-20.

Seeman E, et al., Risk factors for spinal osteoporosis in men. Am J. Med 75:977 (1983).

Seidenfeld, M.A. et al., "The general properties, actions and toxicity of propyvene glycol," J. Pharm. Exp. Ther. (1932) 109-121.

Seidman SN, Rabkin JG. Testosterone replacement therapy for hypogonadal men with SSRI-refractory depression . Journal of Affective Disorder 4H: 157-161 (1998).

Seidman, et al., J Clin Psychiatry 2001 ;62:406-412.

SEPA Testosterone Transdermal Gel Receives Application by FDA, Doctor's Guide Global Edition, http://pslgroup.com/dg/123aa.htm (Jan. 15, 1997).

Sexual Dysfunction in the Male—Sexual Arousal Disorder, The Merck Manual, Sixteenth Edition, Ch. 139, pp. 1575-1576 (1992).

Shabsigh R, et al., Randomized study of testosterone gel as adjunctive therapy to sildenafil in hypogonadal men with erectile dysfunction who do not respond to sildenafil alone, J Urol. May 2008;179(5 Suppl):S97-S102.

Shabsigh R, et al., Testosterone replacement therapy with testosterone gel 1% converts sildenafil non-responders to responders in men with hypogonadism and erectile dysfunction who failed prior sildenafil therapy. Abstract #954 at the 98th Annual Meeting of the American Urological Association, Apr. 26-May 1, 2003, Chicago, IL.

Shabsigh, Recent Developments in Male Sexual Dysfunction, Curr Psychiatry Rep. Jun. 2000;2(3):196-200.

Shabsigh, The Effects of Testosterone on the Cavernous Tissue and Erectile Dysfunction, World J. of Urol., vol. 15, pp. 21-26 (1997).

Shabsigh, et al., Intracavernous Alprostadil Alfadex (Edex/Viridal) is Effective and Safe in Patients with Erectile Dysfunction After Failing Sildenafil (Viagra), Urology, vol. 55, pp. 477-480 (2000).

Shanbhag, et al., The Temperature Dependence of the Binding of 5 Alpha-Dihydrotestosterone and Estradiol to the Sex Hormone Globulin (SHBG) of Human Plasma, J Steroid Biochem, Feb. 1986; 24(2): 549-555.

Shaneyfelt et al., Hormonal Predictors of Prostate Cancer: A Meta-Analysis, Journal of Clinical Oncology, vol. 18, No. 4, pp. 847-853, 2000.

Shapiro et al., Testosterone and Other Anabolic Steroids as Cardiovascular Drugs, Am. J. of Therapeutics, vol. 6, No. 3 May 1999, pp. 167-174.

Sheffield-Moore M, Urban RJ, Wolf SE, Jiang J, Catlin DH, Herndon DN, Wolfe RR, Ferrando AA: Short-term oxandrolone administration stimulates net muscle protein synthesis in young men. J Clin Endocrinol Metab 84:2705-11, 1999.

(56) References Cited

OTHER PUBLICATIONS

Sheikh VI, Yesavage VA: Geriatric Depression scale (GDS): recent evidence and development of a shorter version. Clinical Gerontology: A Guide to Assessment and intervention. New York: Haworth Press, 1986, 165-74.
Sherwin B. B. and Gelfand M. M., Differential symptom response to parenteral estrogen and/or androgen administration in the surgical menopause, Am. J. Obstet. Gynecol. 1985; 151:153-160.
Sherwin, Affective Changes with Estrogen and Androgen Replacement Therapy in Surgically Menopausal Women, Journal of Affective Disorders, vol. 14, pp. 177-187 (1988).
Sherwin, Estrogen and/or Androgen Replacement Therapy and Cognitive Functioning in Surgically Menopausal Women, Psychoneuroendocrinology, vol. 13, No. 4, pp. 345-357 (Mar. 1988).
Sherwin, Sex Hormones and Psychological Functioning in Postmenopausal Women, Experimental Gerontology, vol. 29, Nos. 3&4, pp. 423-430 (May-Aug. 1994).
Sherwin, et al., Androgen Enhances Sexual Motivation in Females: a Prospective Crossover Study of Sex Steroid Administration in the Surgical Menopause, Psychosom Med, Jul.-Aug. 1985; 47(4): 339-51.
Sherwin, et al., Postmenopausal Estrogen and Androgen Replacement and Lipoprotein Lipid Concentrations, Am J Obstet Gynecol, Feb. 1987; 156(2): 414-9.
Sherwin, et al., The Role of Androgen in the Maintenance of Sexual Functioning in Oophorectomized Women, Psycosomatic Medicine, 49: 397-409 (1987).
Shibasaka, Effect of Testosterone Replacement Therapy on Serum PSA in Patients with Klinefelter Syndrome, Archives of Andrology, vol. 47, pp. 173-176 (2001).
Shifren, et al, Transdermal Testosterone Treatment in Women with Impaired Sexual Function After Oophorectomy, The New England Journal of Medicine, vol. 343, No. 10, pp. 682-688 (Sep. 7, 2000). (Abstract only).
Shifren, et al., Do women with impaired sexual function following oophorectomy benefit from transdermal testosterone at a physiologic dose? The Journal of Family Practice, vol. 49 (No. 12), pp. 1148 (Dec. 2000).
Shimizu, et al., Androgen-Induced Production of Colony-Stimulating Factor (CSF) and Colony-Inhibitory Factor (CIF) in the Submandibular Gland in Femal Mice, Journal of Pharrnacobio-Dyn., vol. 12 (6), pp. 352-356, (Jan. 22, 1989).
Shin, S-C. et al., "Enhancing effects of fatty acids on piroxicam permeation through rat skins," Drug Dev. Ind. Pharma. (2000) 26(5):563-566.
Shirai, et al., Effects of Testosterone, Dihydrotestosterone and Estrogen on 3,2'-Dimethy1-4-Aminobiphenyl-Induced Rat Prostate Carcinogenesis, Int J Cancer, Apr. 15, 1994; 57(2):224-8.
Shouls, et al., Contact Allergy to Testosterone in an Androgen Patch: Control of Symptoms by Pre-Application of Topical Corticosteroid, Contact Dermatitis, p. 124-125, (Aug. 22, 2001).
Shuster et al., The influence of age and sex on skin thickness, skin collagen and density. British Journal of Dermatology 93:639 (1975).
Sidh, et al., Adenocarcinoma of Prostate: Role of 17beta-Estradiol and 5alpha-Dihydrotestosterone Binding Proteins, Urology, Jun. 1979; 13(6): 597-603.
Signorello, et al., Serum Steroids in Relation to Prostate Cancer Risk in a Case-Control Study (Greece), Cancer Causes Control, Jul. 1997; 8(4): 632-636.
Simms, Use of Male Sex Hormone is Growing, Wisconsin State Journal (Jul. 29, 2002).
Simon et al., Androgen Therapy Improves Insulin Sensitivity and Decreases Leptin Level in Healthy Adult Men with Low Plasma Total Testosterone, Diabetes Care, vol. 24, No. 12, pp. 2149-2151 (Dec. 2001).
Simon HB, On call. My wife and I are both 62 and healthy. She started taking Prempro during her menopause eight years ago but has now decided to stop the hormones. I began taking DHEA five years ago, but I switched to AndroGel when my doctor gave me a prescription last year. Should I stay on AndroGel, go back to DHEA, or stop hormones? Harv Mens Health Watch. Jan. 2003;7(6):8.
Simon, et al., Association Between Plasma Total Testosterone and Cardiovascular Risk Factors in Healthy Adult Men: The Telecom Study, J. of Clin. Endocrinology and Metabolism, vol. 82, No. 2, pp. 682-685 (1997).
Simon, et al., Safety Profile: Transdermal Testosterone Treatment of Women After Oophorectomy, Obstetrics & Gynecology, vol. 97 (Suppl. 4), DD. 10S-11S (Apr. 2001).
Simon, et al., Percutaneous Absorption of 17 Beta-Estradiol in Ovariectomized Rhesus Monkeys: Skin and Serum Pharmacokinetics. Fertility and Sterility, vol. 53, No. 3, pp. 561-565 (Mar. 1990).
Simon, et al., The Absorption of Oral Micronized Progesterone: The Effect of Food, Dose Proportionality, and Comparison With Intramuscular Progesterone. Fertility and Sterility, vol. 60, No. 1, pp. 26-33 (Jul. 1993).
Sinaki M et al., Relationship between bone mineral density of spine and strength of back extensors in healthy postmenopausal women. Mayo Clint Proc 61:116 (1986).
Sinaki M. Exercise and osteoporosis. Arch Phy Med Rehab 70:220 (1989).
Singh, et al., Pharmacokinetics of a Transdermal Testosterone System in Men with End Stage Renal Disease Receiving Maintenance Hemodialysis and Healthy Hypogonadal Men, The J. of Clinical Endocrinology & Metabolism, vol. 86, No. 6, pp. 2437-2445 (2001).
Singh, et al., The Effects of Varying Doses of T on Insulin Sensitivity, Plasma Lipids, Apolipoproteins, and C-Reactive Protein in Healthy Young Men, The J. of Clin. Endocrinology & Metabolism, vol. 87, No. 1, pp. 136-143 (2002).
Sinha-Hikim et al., The Use of a Sensitive Equilibrium Dialysis Method for the Measurement of Free Testosterone Levels in Healthy, Cycling Women and in HIV-Infected Women, J. Clinical Endocrinology & Metabolism 83:1312-18. (1998).
Sinkula et al., Rationale for design of biologically reversible drug derivatives: prodrugs. J. Pharm. Sci., 64:181-210 (1975).
Sitruk-Ware, Percutaneous and Transdermal Oestrogen Replacement Therapy, Annals of Medicine, vol. 25, pp. 77-82 (1993).
Skakkebaek, et al., Androgen Replacement with Oral Testosterone Undecanoate in Hypogonadal Men: A Double Blind Controlled Study, Clinical Endocrinology (1981) 14, 49-61.
Slater, et al., Pharmacokinetics of Testosterone After Percutaneous Gel or Buccal Administration Fertility and Sterility, vol. 76 (No. 1), D. 32-37 (Jul. 22, 2001).
Slayden SM., Risks of menopausal androgen supplementation, Semin Reprod Endocrinol. 1998;16(2): 145-52.
Smerdely, et al., Predictors of Bone Mass in Healthy Older Men in the Community, MJA, vol. 173, pp. 183-186 (Aug. 21, 2000).
Smith et al., Percutaneous Penetration Enhancers, pp. 21-28 (1995).
Smith, et al., The Nature of Prostate Cancer Detected Through Prostate Specific Antigen Based Screening, The J. of Urol., vol. 152, pp. 1732-1736 (Nov. 1994).
SmithKline Beecham's New 5 mg Androderm Testosterone Transdermal System Now Available, International Association of Physicians in AIDS Care, .http://www.iapac.org/clinmgt/compnews/sb061297.html(Jun. 12, 1997).
Snitker T. The Nation Takes a 'Time Out for Men's Health'—Free Health Screenings for Men Across the U.S., WCNC-TV (NBC) Online (Jun. 11, 2002).
Snow-Harter C et al., Muscle strength as a predictor of bone mineral density in young women. J. Bone Miner Res 5:589 (1990).
Snyder et al., Effect of testosterone treatment on body composition and muscle strength in, men over 65 years of age. J Clin Endocrinol Metab 84:2647-53 (1999).
Snyder et al., Effects of Testosterone Replacement in Hypogonadal Men, J. Clin. Endocrinol. Metab., 85:2670-7 (2000).
Snyder et al., Treatment of Male Hypogonadism with Testosterone Enanthate. J. Clinical Endocrinology and Metabolism 51(5): 1335-9 (1980).
Snyder, Effects of Age on Testicular Function and Consequences of Testosterone Treatment, The J. of Clinical Endocrinology & Metabolism, vol. 86, No. 6, pp. 2369-2372 (2001).

(56) References Cited

OTHER PUBLICATIONS

Snyder, et al., Effect of Testosterone Treatment of Bone Mineral Density in Men Over 65 Years of Age, The Journal of Clinical Endocrinology and Metabolism, vol. 84, No. 6, pp. 1966-1972 (1999).
Sobel, S. Clinical Considerations of Transdermal Drugs. Chapter 24, pp. 431-436. Topical Drug Bioavailability, Bioequivalence, and Penetration (eds. Shah, VP and Maibach, HI).1993.
Solvay Eyes Acquisitions, Confirms FY Double-Digit Growth, Dow Jones News Service, Jul. 31, 2002.
Solvay Pharmacueticals, Estratest Prescribing and Safety Information and Patient Information (2005).
Solvay Pharmacueticals; AndroGel 1%, Dec. 2000, pp. 1-2.
Southren A. L., et al., Further study of factors-affecting the metabolic clearance rate of testosterone in man, J. Clin. Endocrinol. Metab. 1968; 28:1105-1112.
Spark et al., Dihydrotestosterone gel: a novel androgen for AIDS wasting syndrome. 79th Annual Meeting of the Endocrine Society (Abstract) 1997.
Sparrow D et al., The influence of age, alcohol consumption, and body build on gonadal function in men. J. Clin. Endocrinol. Metab. 51: 508 (1980).
Spector, et al., Free and Serum Testosterone Levels in 276 Males: A Comparative Study of Rheumatoid Arthritis, Ankylosing Spondylitis and Healthy Controls, Clinical Rheumatology, vol. 8, No. 1, pp. 37-41 (1989).
Spector, et al., Low Free Testosterone Levels in Rheumatoid Arthritis, Annals of the Rheumatic Diseases, vol. 47, pp. 65-68 (1988).
Stafford, et al., Androgen Deficiency and Bone Mineral Density in Men with Rheumatoid Arthritis, The J. of Rheumatology, vol. 27, No. 12, pp. 2786-2790 (2000).
Stahl, et al., Effects of Tamoxifen on the Levels of Luteinizing Hormone (LH), Follicle Stimulating Hormone (FSH), Prolactin (PRL), 17 beta-oestradiol (E2), Total and Free Testosterone (T) and Total and Free Dihydrotestosterone (DHT) in blood of Patients with benign prostatic hyperplasia, Exp Clin Endocrinol Jul. 1983;82(1):21-8, (Abstract only).
Stanley HL et al., Does hypogonadism contribute to the occurrence of a minimal trauma hip fracture in elderly men. J. Am Ger Soc 39:766 (1991).
Steams El et al., Declining testicular function with age, hormonal and clinical correlates. Am J. Med 57:761 (1974).
Stedman's Concise Medical Dictionary, 4th Edition, "formula": p. 376 (2001).
Stehli, et al., Info—Androgel, www.mageos.ifrance.com/nade38/androgel (Downloaded May 9, 2001). [French; English machine translation included].
Steidle et al., AA2500 Testosterone Gel Normalizes Androgen Levels in Aging Males with Improvements in Body Composition and Sexual Function. J. Clinical Endocrinology & Metabolism 88(6):2673-2681 (2003).
Stepan JJ et al., Castrated men exhibit bone loss: effect of calcitonin treatment on biochemical indices of bone remodeling. J. Clin Endocrinol. Metab. 69:528 (1989).
Stephan, et al., Prostate-Specific Antigen, Its Molecular Forms, and Other Kallikrein Markers for Detection of Prostate Cancer, Urology, vol. 59, pp. 2-8 (2002).
Stephenson, As Genes Differ, So Should Interventions for Cancer, JAMA, vol. 285, No. 14, pp. 1829-1830 (Apr. 11, 2001).
Sternbach, Age-Associated Testosterone Decline in Men: Clinical Issues for Psychiatry. Am. J. Psychiatry (1998) vol. 155(10), pp. 1310-1318.
Stineman MG, Shea JA, Jette A, Tassoni CJ, Ottenbacher KJ, Fiedler R, Granger CV: The functional independence measure: tests of scaling assumptions, structure, and reliability across 20 diverse; impairment categories. Arch Phys Med Rehab 77:1101-8, 1996.
Stomati, et al., Effects of Hormonal Replacement Therapy on Plasma Sex Hormone-Binding Globulin, Androgen and Insulin-Like Growth Factor-1 Levels in Postmenopausal Women, Journal of Endocrinological Investigation, vol. 19 (No. 8), p. 535-541, (Jan. 22, 1996).
Stomati, et al., Endocrine, Neuroendocrine and Behavioral Effects of Oral Dehydroepiandrosterone Sulfate Supplementation in Postmenopausal Women, Gynecological Endocrinology, vol. 13 (No. 1), p. 134 15-24, (Jan. 22, 1999).
Strategy for Change: Pharmaceuticals Represent a Major Direction of Solvay's Growth Strategy and the Objective is to Have the Pharmaceutical Business Grow More Rapidly, Med Ad News (West Trenton, NJ), Sep. 2002.
Straub, et al., Involvement of the Hypothalmic-Pituitary-Adrenal/Gonadal Axis and the Peripheral Nervous System in Rheumatoid Arthritis: Viewpoint Based on a Systemic Pathogenetic Role, Arthritis & Rheumatism, vol. 44, No. 3, pp. 493-507 (Mar. 2001).
Strawford, et al., Effects of Nandrolone Decanoate Therapy in Borderline Hypogonadal Men with HIV-Associated Weight Loss, J. of AIDS and Human Retrovirology, vol. 20, pp. 137-146 (1999).
Studd, et al., The Relationship Between Plasma Estradiol and the Increase in Bone Density in Postmenopausal Women After Treatment with Subcutaneous Hormone Implants, American Journal of Obstetrics and Gynecology, vol. 163, No. 5 (Part 1), pp. 1474-1479 (Nov. 1990).
Stuenkel, et al, Sublingual Administration of Testosterone-Hydroxypropyl-.beta.-Cyclodextrin Inclusion Complex Simulates Episodic Androgen Release in Hypogonadal Men, Journal of Clinical Endocrinology and Metabolism, vol. 72, No. 5, pp. 1054-1059 (1991).
Sturdee, D. W., et al., Br. J. Obstet. Gynecol. (1997) 104:109-115.
Styne, D., Puberty, Basic and Clinical Endocrinology, 6th Edition, Greenspan F S and Gardner D G, ed. McGraw-Hill, New York, 2001.
Suchner, U., M. M. Rothkopf, G. Stanislaus, D. H. Elwyn, V. Kvetan, and J. Askanazi. Growth hormone and pulmonary disease—Metabolic effects in patients receiving parenteral nutrition. Arch. Intern. Med. 150: 1225-1230 (1990).
Suenderhauf et al., Therapy of menopausal syndrome with a combination of ovocyclin and perandren. Schweizerische Medizinische Wochenschrift, vol. 32, No. 22, May 31, 1952, pp. 589-590. [German; English machine translation included.].
Suh, H. et al., "Effectiveness and mode of action of isopropyl myristate as a permeation enhancer for naproxin through shed snake skin," J. Pharm. Pharma. (1996) 48:812-816.
Supac-ss, Guidance for Industry: Nonsterile Semisolid Dosage Forms—Scale-Up and Postapproval Changes: Chemistry, Manufacturing, and Controls; In Vitro Release Testing and In Vivo Bioequivalence Documentation (May 1997).
Surber et al., Optimization of Topical Therapy: Partitioning of Drugs into Stratum Corneum, Pharmaceutical Res., vol. 7(12), pp. 1320-1324 (1990).
Susman, 'Male Menopause' Therapy Hotly Debated, The Palm Beach Post, Aug. 28, 2002.
Svetec, et al., The Effect of Parenteral Testosterone Replacement on Prostate Specific Antigen in Hypogonadal Men with Erectile Dysfunction, The J. of Urol., vol. 158, pp. 1775-1777 (Nov. 1997).
Swerdloff RS et al., Androgen replacement therapy. In Current Therapy in Endocrinology and Metabolism (4th edition), Bardin C.W. (Ed) Decker, Philadelphia pp. 255 (1991).
Swerdloff RS, et al., Transdermal testosterone (T) gel is efficacious and safe in older compared to young men. Poster presentation #P2-648 at the 84th Annual Meeting of the Endocrine Society, Jun. 19-22, 2002, San Francisco, CA.
Swerdloff RS, et al., "Long-term pharmacokinetics of transdermal testosterone gel in hypogonadal men," J Clin Endocrinol Metab. Dec. 2000;85(12):4500-10.
Szadurski. "The application of a galvanic penetration test for the rapid determination of skin resistance to bases." Przeglad dermatologiczny [Dermatological Review]. 55(1):20-3 (1968).
Sznitowska, M. et al., "The effect of sorption promoters on percutaneous permeation of a model switterion—baclofen," Int. J. Pharm. (1996) 137:125-132.
Tan KC et al., Alterations in hepatic lipase and lipoprotein subfractions with transdermal testosterone replacement therapy. Clin Endocrinol (Oxf). 51(6):765-9 (1999).
Tangredi, et al., Hypertension as a Complication of Topical Testosterone Therapy. The Annals of Pharmacotherapy, vol. 35 (No. 10), p. 1205-1207 (Oct. 22, 2001).

(56) References Cited

OTHER PUBLICATIONS

Tanojo, H. et al., "In vivo human skin permeability enhancement by oleic acid: a laser Doppler velocimetry study," J. Cont. Rel. (1999) 58:97-104.
Taylor, A.K., "Isopropyl myristate," Pharmaceutical Excipients (2009) 348-349.
TDS Delivers Testosterone safely and effectively. Press release. Oct. 1, 2004.
Teichert, A Man's Pain: Age-Related Testosterone Loss in Men, Coined by One Doctor as Mano-Pause, Fuels Medical Debate, The Montgomery Journal (Rockville, MD), Jul. 9, 2002.
Tennant, PSA Levels, IPPS Scores Normal: Transdermal Testosterone Gel Safe Over Long Term, Urology Times (Cleveland, OH), Oct. 2002.
Tenover JL: Testosterone and the aging male. J Androl 18:103-106, 1997.
Tenover JS et al., Serum bioactive and immunoreactive follicle-stimulating hormone levels and the response to clomiphene in healthy young and elderly men. J. Clin. Endocrinol. Metab. 64:1103 (1987).
Tenover JS. Effects of testosterone supplementation in the aging male. J. Clin Endocrinol. Metab. 75:1092-1098 (1992).
Tenover, et al., Age-Related Alterations in the Circadian Rhythms of Pulsatile Luteinizing Hormone and Testosterone Secretion in Healthy Men. J Gerontol, Nov. 1988; 43(6): M163-9.
Tenover, et al., The Effects of Aging in Normal Men on Bioavailable Testosterone and Luteinizing Hormone Secretion: Response to Clomiphene Citrate, J Clin Endocrinol Metab, Dec. 1987; 65(6): 1118-1126.
Tenover. "Male Hormone Replacement Therapy Including 'Andropause.'" Endocrinol. Metab. Clin. North. Am. 27(4): 969-987 (1998).
Testim 1% (Testosterone Gel) CIII Medication Guide, Sep. 2009, available at http://www.auxilium.com/PDFs/20090918%20Testim%20PI%20DPT%20FDA%20approved.pdf.
Testim 1% (Testosterone Gel), Physician Desk Reference, pp. 711-713 (2004).
TestoCreme—A Natural Transdermal Testosterone Replacement Therapy, www.testocreme.com.
Testocreme—No Shots, No Pills, No Patches, www.testocreme.com (Downloaded Jul. 10, 2000).
Testocreme Transdermal Testosterone Is New, Preventive Medicine Clinic of.
Testosterone Aids Post-Menopausal Women, BBC News Online: Health, www.bbc.co.uk. (Jun. 14, 1999).
Testosterone and Aging: Clinical Research Directions, Institute of Medicine of the National Academies (Liverman and Blazer, eds.)(2004).
Testosterone Gel May Help Men with Low Sex Drive, WRAL Online, http://www.wral-tv.com/features/healthteam/1997/0814-tgel/ (Aug. 14, 1997).
Testosterone Patch Treats Sexual Dysfunction in Women, Biomedical Technology Information Service vol. 23 (No. 21), pp. 244 (Dec. 1996).
Testosterone Patch Trial for Women with AIDS, Pharmaceutical Business News. vol. 12 (No. 275), p. 19 (Sep. 14, 1996).
Testosterone Replacement Therapy: Effective Treatments Are Available, MayoClinic.com (Feb. 26, 2002).
Testosterone Therapy—for Women?, Health News, www.onhealth.com (May 7, 1996).
Testosterone Undecanoate—Schering AG. Drugs RD. 2004; 5(6):368-9.
Testosterone's Role in the Female Sex Drive, USA Today News, www.usatoday.com (Apr. 8, 1996).
Testosterone-Topical Fortigel—Cellegy: Fortigel Tostrex, BioDrugs, vol. 17(4), pp. 299-300 (2003) (No authors listed).
Textbook of Dermatology, 6th Edition, vol. 4, p. 3524 (Chapman et al., eds.)(1998).
The Endocrine Society, Summary from the Second Annual Andropause Consensus Meeting (2001).
The Male Body: A Physician's Guide to What Every Man Should Know About His Sexual Health. CBS-TV The Early Show Online:Eye on Health (Aug. 30, 2002).
The Merck Index, 13th Edition, "Testosterone": p. 1638 and "Stanolone": p. 1566 (2001).
The Nation Takes a 'Time Out for Men's Health'—Free Health Screenings for Men Across the U.S., Yahoo!Finance.com (Jun. 11, 2002).
The Testosterone Source, http://www.testosteronesource.com (1998).
The United States Pharmacopeia, "alcohol": pp. 42-43 (1995).
The United States Pharmacopeia, "viscosity" (2002).
The United States Pharmacopeia, pp. 958, 2213-2225, 2568, 2619 (2002).
Thompson, ed. "The Concise Oxford Dictionary." 9th ed. Oxford: Oxford University Press, 1995, pp. 1014.
Thompson, et al., Effect of Intravenous Testosterone on Myocardial Ischemia in Men with Coronary Artery Disease, Am. Heart J., vol. 143, pp. 249-256 (2002).
Thompson, Hey Guys, If You Have Your Health . . . , HealthScoutNews, http://www.healthscoutnews.com/view.cfm?id=507614 (Jun. 12, 2002).
Time Out for Men's Health, The Weekly Planet (Tampa, FL), Nov. 4, 2004.
Tirassa, et al., High-Dose Anabolic Androgenic Steroids Modulate Concentrations of Nerve Growth Factor and Expression of its Low Affinity Receptor (p75-NGFr) in Male Rat Brain, Journal of Neuroscience Research, vol. 47, No. 2, pp. 198-207 (Jan. 15, 1997).
Tostran 2% Gel Medicinal Guide, available at http://emc.medicines.org.uk/printfriendlydocument.aspx?documentid=19702&companyid (Jul. 13, 2009).
Toutiou E. et al., Enhanced Delivery of Drugs Into and Across the Skin by Ethosomal Carriers, Drug Development Research, vol. 50 pp. 406-415 (2000).
Toutiou E. et al., Ethosomes—Novel Vesicular Carriers for Enhanced Delivery: Characterization and Skin Penetration Properties, Journal of Controlled Release, vol. 65 pp. 403-418 (2000).
Traish et al., Effects of Castration and Androgen Replacement on Erectile Function in a Rabbit Model, Endocrinology 140:1861 (1999).
Transdermal Technologies Profile. Available at pharmalicensing.com/company/dc/2252. (Dec. 16, 2004).
Transdermal Testosterone, Cellegy Pharmaceuticals, www.Cellegy.com. Downloaded on Oct. 21, 2002.
Transpharma Medical, Product Applications: Testosterone, www.transpharma-medical.com/product_apps_testosterone.html (downloaded Dec. 16, 2004).
Trbovich, Drug Development & Biotechnology Companies, The Wall Street Transcript (New York, NY), Feb. 4, 2002, at 18-24.
Tremblay et al., "Plasma concentrations of free and non-TeBG bound testosterone in women on oral contraceptives." Contraception. 10(6): 599-605 (1974). (Abstract only).
Trials for the Treatment of Wasting, AIDS Treatment Data Network, www.aidsinfonyc.org (Downloaded Oct. 8, 1998).
Trottet, L. et al., "Effect of finite doses of propylene glycol on enhancement of in vitro percutanous permeation of loperamide hydrochloride," Int. J. Pharma. (2004) 274:213-219.
Truelove, "Widening Range of Hormone Drugs; Rights to Market; Schering AG Reacquired Sales, Distribution Rights for Testogel; Brief Article," Med Ad News 10(21): 5 (2002).
Tsai et al., Effect of Barrier Disruption by Acetone Treatment on the Permeability of Compounds with Various Lipophilicities: Implications for the Permeability of Compromised Skin, Journal of Pharmaceutical Sciences, vol. 90, pp. 1242-1254, 2001.
Tsai, et al., Metabolic Approaches to Enhance Transdermal Drug Delivery. 1. Effect of Lipid Synthesis Inhibitors, J Pharm Sci, Jun. 1996; 85(6): 643-648.
Tsitouras, Effects of Age on Testicular Function, Endocrinology and Metabolism Clinics, vol. 16, No. 4, p. 1045-1059 (Dec. 1987).
Tuiten, et al., Time Course of Effects of Testosterone Administration on Sexual Arousal in Women, Arch Gen Psychiatry, Feb. 2000; 57(2): 149-53.

(56) References Cited

OTHER PUBLICATIONS

Tuller, Competitors to Viagra Get Ready to Rumble, N.Y. Times, Sep. 23, 2002.
Tutten, et al., Discrepancies Between Genital Responses and Subjective Sexual Function during Testosterone Substitution in Women with Hypothalamic Amenorrhea, Psychosom Med, May-Jun. 1996; 58(3): 234-41.
Tymchuk, et al., Role of Testosterone, Estradiol, and Insulin in Diet- and Exercise-Induced Reductions in Serum-Stimulated Prostate Cancel Cell Growth in Vitro, Nutrition and Cancer, vol. 42, No. 1, pp. 112-116 (2002).
UK Prospective diabetes study group, Effect of intensive blood-glucose control with metformin on complications in overweight patients with type 2 diabetes (UKPDS 34) The Lancet, vol. 352, Sep. 12, 1998, pp. 854-865.
UK Prospective diabetes study group, Intensive blood-glucose control with sulphylureas or insulin compared with conventional treatment and risk complications in patients with type 2 diabetes (UKPDS 33) The Lancet, vol. 352, Sep. 12, 1998, pp. 837-853.
Ulrich D, et al., The ability of three-dimensional structural indices to reflect mechanical aspects of trabecular bone, Bone, 25:55-60 (1999).
Unimed Pharmaceuticals' Androgel Shows Solid Promise for Men, Fertility Industry News, www.INCIID.com (Aug. 19, 1998).
Unimed pharmaceuticals initiates phase III geriatric hypogonadism study in elderly men: Broad US patent covering DHT delivery for androgen therapy is issued. Unimed News Release, Sep. 10, 1997.
Unimed Products, "Androgel™ (testosterone gel) 1% CIII," internet article May 11, 2000 [Retrieved from internet: http://web.archieve.org/web/20000511171938/http://www.unimed.com/proddisc2.html, retrieved on Jun. 14, 2012].
Urban RJ, et al., Testosterone administration to elderly men increases skeletal muscle strength and protein synthesis. Am J Physiol 269:E820-6, 1995.
Urman B., et al., Elevated serum testosterone, hirsutism and virilism associated with combined androgen-estrogen hormone replacement therapy, Obstet. Gynecol., 1991; 77:595-598.
USP Drug Information—Anabolic Steroids (Systemic), Mayo Clinic, www.mayohealth.org (Downloaded Oct. 8, 1998).
Valero-Politi, et al., Annual Rhythmic Variations of Follitropin, Lutropin, Testosterone and Sex-Hormone-Binding Globulin in Men, Clinica Chimica Acta, vol. 271, No. 1, pp. 57-71 (Mar. 9, 1998).
Valero-Politi, et al., Daily Rhythmic and Non-Rhythmic Variations of Follitropin, Lutropin, Testosterone, and Sex-Hormone-Binding Globulin in Men, Eur J Clin Chem Clin Biochem, Jun. 1996; 34(6): 455-462.
Van Den Beld AW, Huhtaniemi IT, Pettersson KSL, Pols HAP, Grobbee DE, De Jong FH, Lamberts SWJ: Luteinizing hormone and different genetic variants, as indicators of frailty in healthy elderly men. J Clin Endocrinol Metab 84:1334-9, 1999.
Van Gaal, et al., Sex Hormones, Body Fat Distribution, Resting Metabolic Rate and Glucose-Induced Thermogenesis in Premenopausal Obese Women, Int J Obes Relat Metab Disord, May 1994; 18(5): 333-8.
van Honk, et al., Correlations Among Salivary Testosterone, Mood, and Selective Attention to Threat in Humans. Horm Behav. Aug. 1999; 36(1): 17-24.
Van Scott et al., Hyperkeratinization, Corneocyte Cohesion, and Alpha Hydroxy Acids, J. Am Acad Dermatol11:867-879 (1984).
Vaubourdolle, et al., Effect of Dihydrotestosterone on the Rate of Ethanol Elimination in Healthy Men. Alcohol Clin. Exp. Res., vol. 15, No. 2, pp. 238-240 (Mar. 1991).
Vedi S, et al., Effects of hormone replacement therapy on cancellous bone microstructure in postmenopausal women. Bone, 19:69-72 (1996).
Velazquez et al., "Testosterone Replacement Therapy," Arch Androl 41(2): 79-90 (Sep.-Oct. 1998); Abstract.
Veldhuis JD et al., Attenuation of luteinizing hormone secretory burst amplitude as a proximate basis for the hypoandrogenism of healthy aging in men. J. Clin. Endocrinol. Metab. 75:707-713 (1992).
Veldhuis, et al., Muting of Androgen Negative Feedback Unveils Impoverished Gonadotropin-Releasing Hormone/Luteinizing Hormone Secretory Reactivity in Healthy Older Men, the Journal of Clinical Endocrinology & Metabolism, vol. 86, No. 2, pp. 529-535. (2001).
Vergel, Anabolic Steroids: A Practical Guide, CRIA Update, vol. 7, No. 3 (Summer 1998).
Vermeulen A et al., Testosterone secretion and metabolism in male senescence. J. Clin. Endocrinol. Metab. 34:730 (1972).
Vermeulen A. Androgens in aging male. J. Clin. Endocrinol. Metab. 73:221 (1991).
Vermeulen A. Nyctohemeral growth hormone profiles in young and aged men: correlation with somatomedin-C levels. J. Clin. Endocrinol. Metab. 64:884 (1987).
Vermeulen, et al., Long-Term Transdermal Dihydrotestosterone Therapy: Effects on Pituitary Gonadal Axis and Plasma Lipoproteins, Maturitas, vol. 7, pp. 281-287 (1985).
Vetter et al., Quantitative Determination of Isostearic Acid Isomers in Skin Creams by GC-MS-SIM, Chromatographia 2009, 70, Jul. (No. 1/2). pp. 157-164.
Viagra and Testocreme Together, www.testocreme.com (downloaded Feb. 28, 2002).
Vijayakumar, et al., Results of a Study to Correlate Serum Prostate Specific antigen Reproductive Hormone Levels in Patients with Localized Prostate Cancer. J Natl Med Assoc, Nov. 1995; 87(11): 813-9.
Vogel W, Klaiber EL, Broverman DM. Roles of gonadal steroid hormones in psychiatric depression in men and women. Prog. Neuro-Psychopharrnocol 2: 487-503 (1978).
Voigt, et al., The Role of Tissue Steroids in Benign Hyperplasia and Prostate Cancer, Urologe [A], Nov. 1987; 26(6):349-57.
Wagner, et al., Testosterone as a Treatment for Fatigue in HIV+ Men, Gen. Hospital Psychiatry, vol. 20, pp. 209-213 (1998).
Wagner, et al., A Comparative Analysis of Standard and Alternative Antidepressants in the Treatments of Human Immunodeficiency Virus Patients, Comprehensive Psychiatry, vol. 37, No. 6, pp. 402-408 (Nov./Dec. 1996).
Wagner, et al., Exercise as a Mediator of Psychological and Nutritional Effects of Testosterone Therapy in HIV+ Men, Official Journal of the American College of Sports Medicine, pp. 811-817 (1998).
Walters, Penetration Enhancers and Their Use in Transdermal Therapeutic Systems, pp. 202-227 (1990).
Wandell, et al., Assessing Sexual Functioning in Patients with Chronic Disorders by Using a Generic Health-Related Quality of Life Questionnaire, Quality of Life Research, vol. 9, pp. 1081-1092 (2001).
Wang & Swerdloff, "Androgen Replacement Therapy," The Finnish Medical Society DUODECIM, Ann. Med. 29: 365-370 (1997).
Wang C, et al., Does pretreatment testosterone affect responsiveness to long term transdermal testosterone gel (Androgel) in hypogonadal men. Poster presentation #P2-166 at the 85th Annual Meeting of the Endocrine Society, Jun. 19-22, 2003, Philadelphia, PA.
Wang C, et al., Long term efficacy and safety of transdermal testosterone gel (Androgel) in hypogonadal men. Poster presentation #P2-646 at the 84th Annual Meeting of the Endocrine Society, Jun. 19-22, 2002, San Francisco, CA.
Wang et al. "Transdermal Testosterone Gel Improves Sexual Function, Mood, Muscle Strength, and Body Composition Parameters in Hypogonadal Men." J. Clin. Endocrin. Metab. (2000);85(8):2839-53.
Wang et al., Long-Term Testosterone Gel (Androgel) Treatment Maintains Beneficial Effects on Sexual Function and Mood, Lean, and Fat Mass, and Bone Mineral Density in Hypogonadal Men , J. Clin. Endocrinol. Metab., vol. 85, No. 5, pp. 2085-2098 (May 2004).
Wang et al., Male Reproductive Function, Kluwer Acad. Publ. (May 1999). Table of Contents.
Wang J. et al., Body fat from body density: underwater weighing vs dual-photon absorptiometry. Am J. Physiol 256:E829 (1989).
Wang, et al., Effects of Transdermal Testosterone Gel on Bone Turnover Markers and Bone Mineral Density in Hypogonadal Men, Clinical Endocrinology, vol. 54, No. 6, pp. 739-750 (2001). (Abstract only).

(56) References Cited

OTHER PUBLICATIONS

Wang, et al., Effects of Transdermal Testosterone Gel on Bone Turnover Markers and Bone Mineral Density in Hypogonadal Men, Clinical Science: Reproduction (Male)-Prostate, Male Reproduction Poster Session, No. 2348, Board 579 (Jun. 22, 2000).
Wang, et al., Pharmacokinetics of Transdermal Testosterone Gel in Hypogonadal Men, Abstract P2-51, 80th Annual Meeting of the Endocrine Society, New Orleans, Louisiana, Jun. 1998 (ENDO '98).
Wang, et al., Salivary Testosterone in Men: Further Evidence of a Direct Correlation with Free Serum Testosterone, Journal of Clinical Endocrinology and Metabolism, vol. 53, No. 5, pp. 1021-1024 (Nov. 1981).
Wang, et al., Transdermal Testosterone Gel Improves Sexual Function, Mood, Muscle Strength, and Body Composition Parameters in Hypogonadal Men, Basic Science: Reproduction-Gonadal Control (Male), Male Reproduction Oral Session, The Endo Society No. 1360 ENDO 2000) (Jun. 24, 2000).
Wang, et al., "Comparative Pharmacokinetics of Three Doses of Percutaneous Dihydrotestosterone Gel in Healthy Elderly Men—A Clinical Research Center Study," Journal of Clinical Endocrinology and Metabolism Aug. 1998;83(8):2749-2757.
Wang, et al., "Pharmacokinetics of Transdermal Testosterone Gel in Hypogonadal Men: Application of Gel at One Site Versus Four Sites: A General Clinical Research Center Study," The Journal of Endocrinology and Metabolism, Mar. 2000;85(3):964-969.
Wang, et al., New Androgen Formulations, The Endocrine Society, No. 167 (ENDO 2000).
Wang, et al., Sublingual Testosterone Replacement Improves Muscle Mass and Strength, Decreases Bone Resorption, and Increases Bone Formation Markers in Hypogonadal Men—A Clinical Research Center Study, J Clin Endocrinol Metab. Oct. 1996;81(10):3654-62.
Wang, et al., Testosterone Replacement Therapy Improves Mood in Hypogonadal Men—A Clinical Research Center Study, Journal of Clinical Endocrinology and Metabolism, vol. 81, No. 10, pp. 3578-3583 (1996).
Ware et al., "The MOS 36-Item Short-Form Health Survey." Med. Care. 30(6): 473-83 (1992).
Warner BA et al., Effects of aging and illness on the pituitary testicular axis in men: qualitative as well as quantitative changes in luteinizing hormone. J. Clin. Endocrinol. Metab. 60:263-268 (1985).
Warnock et al., "Female Hypoactive sexual disorder: Case studies of physiologic androgen replacement," J. Sex and Marital Therapy (1999);25:175-182.
Warnock Jk, et al., Female hypoactive sexual desire disorder due to androgen deficiency: clinical and psychometric issues, Psychopharmacol Bull. 1997;33(4):761-6.
Watts, et al., Comparison of Oral Estrogens and Estrogens Plus Androgen on Mineral Density, Menopausal Symptoms, and Lipid-Lipoprotein Profiles in Surgical Menopause, Obstet Gynecol, Apr. 1995; 85(4):529-37.
Webb et. al., "Sildenafil citrate and blood-pressure-lowering drugs: results of drug interaction studies with an organic nitrate and a calcium antagonist." American Journal of Cardiology (1999);83(5A):21C-28C.
Webb, et al., Effect of Acute Testosterone on Myocardial Ischemia in Men with Coronary Artery Disease, Am. J. of Cardiol., vol. 83, No. 3, pp. 437-439, A9 (Feb. 1, 1999).
Webb, et al., Effects of Testosterone on Coronary Vasomotor Regulation in Men with Coronary Heart Disease, Circulation, vol. 100, pp. 1690-1696 (1999).
Webster's New Collegiate Dictionary. 2000. Definition of Prevention. p. 933.
Weekend datebook: Nov. 14-17—Time Out for Men's Health, The Seattle Times, Nov. 14, 2002.
Weinbauer et al., Pharmacokinetics and Pharmacodymanics of testosterone enanthate and dihydrotestosterone enanthate in non-human primates. ACTA Endocrinologica (COPENH) 122(4):432-444 (1990).
Weiner DK, et al., Does functional reach improve with rehabilitation? Arch Phys Med Rehabil 74:796-800, 1993.
Weiner DK, et al., Functional reach: a marker of physical frailty. J Amer Geriatr Soc 40:203-7, 1991.
Weinstein et al., Topical methotrexate therapy for psoriasis. Arch Dermatol. 1989; 125(2):227-230.
Weissberger AJ and Ho KKY: Activation of the somatotropic axis by testosterone in adult males: evidence for the role of aromatization. J Clin Endocrinol Metab 76:1407-1412, 1993.
Weller, P.J., "Propylene glycol," Pharmaceutical Excipients (2009) 592-594.
Wellner et al., "Systemic therapy with dermal application: Transdermal therapeutic systems (TTS)," Dermatologie in Beruf und Umwelt (Dermatol. Beruf Umwelt) (Germany) Mar. 1, 2006, 54/1 (13-18) [Article in German, English Abstract submitted only].
Westaby et al., Liver damage from long-term methyltestosterone, The Lancet, vol. 310, Issue 8032, pp. 261-263.
Wheeler, M D, Endocrinol and Metab Clin N. Am., 20(1):1-14 (1991).
Whittaker, J. S., C. F. Ryan, P.A. Buckley, and J. D. Road. The effects of refeeding on peripheral and respiratory muscle function in malnourished chronic obstructive pulmonary disease patients. Am. Rev. Respir. Dis. 142: 283-288 (1990).
Willemse, et al., No Change in Plasma Free Testosterone Ratio and Plasma Sex Hormone-Binding Globulin Concentration During hCG Stimulation, Journal of Clinical Endocrinology and Metabolism, vol. 58, No. 6, pp. 1193-1196 (Jun. 1984).
Williams AC and Barry BW, "Penetration enhancers," Adv Drug Deliv Rev. Mar. 27, 2004;56(5):603-18.
Williams Textbook of Endocrinology, 10th Ed., pp. 720-725 (Larsen et al., eds)(2002).
Wilson JD, Androgen abuse by athletes. Endocr Rev 9:181 (1988).
Wilson, et al., Nutrition and chronic lung disease. Am. Rev. Respir. Dis. 132: 1347-1365 (1999).
Wilson, et al., Use of Topical Corticosteroid Pretreatment to Reduce the Incidence and Severity of Skin Reactions Associated with Testosterone Transdermal Therapy, Clinical Therapeutics vol. 20 (No. 2), p. 299-306, (Jan. 22, 1998).
Wilson, The Pathogenesis of Benign Prostatic Hyperplasia, Am J Med, May 1980; 68(5): 745-56.
Winter et al., Serum LH Concentrations in Hypogonadal Men During Transdermal Testosterone Replacement Through Scrotal Skin: Further Evidence That Ageing Enhances Testosterone Negative Feedback. The Testoderm Study Group, Clinical Endocrinology (OXF), vol. 47, No. 3, pp. 317-322 (Sep. 1997).
Winters et al., LH, Non-SHBC Testosterone and Estradiol Levels During Testosterone Replacement of Hypogonadal Men: Further Evidence that Steroid Negative Feedback Increases as Men Grow Older, Journal of Andrology, Dec. 3, 2009 (Published-Ahead-of-Print).
Winters et al., Pituitary-Testicular Function in Men with Testicular Failure Treated with a 2% Testosterone Gel: Further Evidence that Increased Testosterone Negative Feedback Contributes to the Gonadotropin Disturbances as Men Grow Older, P3-639, Endo Society 2008.
Winters SJ et al., Episodic luteinizing hormone (LH) secretion and the response of LH and follicle-stimulating hormone to LH-releasing hormone in aged men: evidence for coexistent primary testicular insufficiency and an impairment in gonadotropin secretion. J. Clin Endocrinol. Metab. 55:560 (1982).
Winters, Current Status of Testosterone Replacement Therapy in Men, Arch. Fam. Med., vol. 8, pp. 257-263 (1999).
Winters, The Gonadotropin-Suppressive Activity of Androgen is Increased in Elderly Men; Metabolism, Nov. 1984; 33(11): 1052-1059.
Wittert et al., Androgen Deficiency in Aging Men, The Endocrine Society, No. 126 (ENDO 2000).
Wolf et al., Testosterone and Cognition in Elderly Men: A Single Testosterone Injection Blocks the Practice Effect in Verbal Fluency, But Has No Effect on Spatial or Verbal Memory, Biol. Psychiatry, vol. 47, pp. 650-654 (2000).
Wolk et al., Insulin-like Growth Factor 1 and Prostate Cancer Risk: A Population-Based, Case-Control Study, J. of the Natl. Cancer Inst., vol. 90, No. 12, pp. 911-915 (Jun. 17, 1998).

(56) References Cited

OTHER PUBLICATIONS

Women and HIV, Women and HIV Discussion Paper, pp. 1-12 (Jan. 1998).
Women's Hormones: Testosterone, the Other Female Hormone, Harvard Women's Health Watch, Sep. 2002, at 4-5.
Wong TK et al., Bone mass response to testosterone replacement in hypogonadal men. J. Bone and Min Res Suppl 1., p. 5390, Abstract 1092 (Sep. 4, 1989).
Woodford, et al., Optimization of Bioavailability of Topical Steroids: Thermodynamic Control, The Journal of Investigative Dermatology, vol. 79, No. 6, pp. 388-391 (Dec. 1982).
Worboys, et al., Testosterone Therapy improves endothelium-dependent and endothelium-independent vasodilation in postmenopausal women on established hormone replacement therapy, The Endocrine Society (ENDO 2000).
World Health Organization. Guidelines for the use of androgens in men. World Health Organization: Geneva (1992).
Woznicki, Feature: Doctors Debate Hormones for Men, United Press International, Aug. 8, 2002.
Wu SZ & Weng XZ: Therapeutic effects of an androgenic preparation on myocardial ischemia and cardiac function in 62 elderly male coronary heart disease patients. Chinese Med J 106:415-8, 1993.
Xie et. al., "Induction of high incidence of mammary tumour in female Noble rats with a combination of 17β-oestradiol and testosterone," Carcinogenesis (1999); 20(6):1069-1078.
Yaffe et al., Sex Hormones and Cognitive Function in Older Men, JAGS, vol. 50, pp. 707-712 (2002).
Yesavage JA, Brink TL, Rose TL, Lum O, Huang V. Adey M, Leirer VO: Development and validation of a geriatric depression screening scale: a preliminary report. J Psychiatr Res 17:37-49, 1983.
Yesavage JA, Davidson J. Widrow L, Berger PA. Plasma testosterone levels, depression. sexuality and age. Biological Psychiatry 20: 199-225 (1985).
Your health and Well-Being, SF-36v2™ survey, 2000 by Quality Metric Incorporated and Medical Outcomes Trust. 6 pages.
Yu et al., Sexual Development in a Two-Year-Old-Boy Induced by Topical Exposure to Testosterone, Pediatrics, vol. 104(2), e23 (1999).
Yu et al., Testosterone Pharmacokinetics after Application of an Investigational Transdermal System in Hypogonadal Men, Journal of Clinical Pharmacology, vol. 37, pp. 1139-1145 (1997).
Yu et al., Transdermal Testosterone Administration in Hypogonadal Men:Comparison of Pharmacokinetics at Different Sites of Application and at the First and Fifth Days of Application, Journal of Clinical Pharmacology, vol. 37, pp. 1129-1138 (1997).
Yu Z et al., DeMonS—a new deconvolution method for estimating drug absorbed at different time intervals and/or drug disposition model parameters using a monotonic cubic spline. Biopharm Drug Dispos. Aug. 1997;18(6):475-87.
Zagars, et al., Serum Testosterone—A Significant Determinant of Metastatic Relapse for Irradiated Localized Prostate Cancer, Urology, vol. 49, No. 3, pp. 327-334 (1997).
Zartarian, et al., Comparative Evaluation of the Acceptability of a New Estradiol Gel TX11323(A) and a Reference Gel, J. Gyencol. Obstet. Biol. Reprod. (Paris), Vo. 25, No. 5, pp. 451-456 (1996). (Abstract only).
Zatz JL et al., Topical Protective and Cosmetic Products. Transdermal and Topical Drug Delivery Systems. Eds. Ghosh et al., Interpharm Press Inc., Illinois 1997.
Zatz, J.L. et al., "Evaluation of solvent-skin interaction in percutanous absorption," J. Soc. Cos. Chem. (1983) 34:327-334.
Zeginiadou, et al., NonLinear Binding of Sex Steroids to Albumin and Sex Hormone Binding Globulin, Eur J Drug Metab Pharmacokinet, Jul. 1997; 22(3): 229-235.
Zetterberg C et al., Epidemiology of hip fractures in Goteborg, Sweden, 1940-1983. Clen Orth Rel Res 191:43 (1984).
Zhang et al., Association Between Prostate Cancer and Serum Testosterone Levels, The Prostate, vol. 53, pp. 179-182 (2002).
Zhao H et al., The effects of pressure-sensitive adhesives and solubilizers on the skin permeation of testosterone from a matrix-type transdermal delivery system. Drug Dev Ind Pharm. Oct. 2002;28(9):1125-31.
Ziegler et al., Interactions between nutrients and peptide growth factors in intestinal growth, repair, and function. JPEN J. Parenter. Enteral Nutr. 23: S174-S183 (1999).
Zimulti (rimonabant), NDA 21-888, Briefing Information for FDA Advisory Committee Meeting. May 10, 2007, available at http://www.fda.gov/ohrms/dockets/ac/07/briefing/2007-4306b1-01-sponsor-backgrounder.htm (Feb. 9, 2011).
Zmuda, et al., Exercise Increases Serum Testosterone and Sex Hormone-Binding Globulin Levels in Older Men, Metabolism, vol. 45, No. 8, pp. 935-939 (Aug. 1996).
Zonagen Product Pipeline, www.zonagen.com/html/product_pipeline.htm (downloaded Dec. 17, 2004).
Zonagen reports initial findings comparing Androxal to Androgel form from US Phase I/II safety and efficacy study in men with low testosterone. Press release. Jul. 15, 2004.
Zumoff B. et al., Age variation of the 24-hour mean plasma concentrations of androgens, estrogens and gonadotropins in normal adult men. J. Clin. Endocrinol. Metab. 54:534 (1982).
Docket Report for *Unimed Pharmaceuticals, Inc. v. Watson Pharmaceuticals, Inc.* (retrieved from PACER Jan. 4, 2011).
Complaint by Unimed Pharmaceuticals filed Aug. 21, 2003.
Plaintiff Unimed Pharmaceutical, Inc.'s Rule 7.1 Corporate Ownership Disclosure Statement filed Aug. 21, 2003.
First Amended Complaint by Unimed Pharmaceuticals filed Aug. 22, 2003.
Answer and Counterclaim by Watson Pharmaceuticals filed Oct. 27, 2003.
Answer to Counterclaim by Unimed Pharmaceuticals filed Nov. 17, 2003.
Joint Preliminary Report and Discovery Plan filed Nov. 26, 2003.
Certificate of Interested Persons filed Nov. 26, 2003.
Letter by Watson Pharmaceuticals directed to Judge Thrash as a Response to the Letter Motion to Compel filed Oct. 21, 2004.
Watson Pharmaceutical's Motion to Issue Letter of Request for International Judicial Assistance dated Dec. 2, 2004.
Request for International Judicial Assistance by Judge Thrash dated Dec. 22, 2004.
Unimed Pharmaceuticals, Inc.'s Objections to Watson Pharmaceuticals, Inc.'s Notice of Depositions filed Mar. 17, 2005.
Watson's Principal Claim Construction Brief filed Jul. 25, 2005.
Plaintiff's Memorandum on Claim Construction (Redacted Version) filed Jul. 25, 2005.
Watson's Reply to Plaintiff's Principal Claim-Construction Brief dated Aug. 12, 2005.
Plaintiff's Opposition Brief on Claim Construction (Redacted Version) dated Aug. 12, 2005.
Watson's Motion to Strike Section VI of Plaintiffs' Memorandum on Claim Construction filed Aug. 12, 2005.
Plaintiff's Response to Watson's Motion to Strike Section VI of Plaintiff's Claim Construction Memorandum filed Aug. 26, 2005.
Watson's Reply in Support of Its Motion to Strike Section VI of Plaintiffs' Claim-Construction Memorandum filed Sep. 9, 2005.
Defendant Watson Pharmaceuticals. Inc.'s Motion for Partial Summary Judgment filed Sep. 9, 2005.
Plaintiffs' Consolidated Memorandum of Law in Opposition to Defendants' Motions for Partial Summary Judgment filed Oct. 17, 2005.
Unimed Pharmaceuticals, Inc.'s Statement of Additional Facts which are Material and Present a Genuine Issue for Trial filed Oct. 17, 2005.
Plaintiffs' Consolidated Response to Defendants Watson's and Paddock's Statement of Material Facts as to Which There are No Genuine Issues to be Tried filed Oct. 17, 2005.
Watson's Response to Plaintiffs' Statement of Additional Facts which are Material and Present a Genuine Issue for Trial filed Nov. 11, 2005.
Watson's Reply to Plaintiffs' Consolidated Opposition to Defendants' Motions for Partial Summary Judgment filed Nov. 11, 2005.

(56) References Cited

OTHER PUBLICATIONS

Defendant Watson Pharmaceuticals, Inc.'s Motion for Partial Summary Judgment of Invalidity of Claims 1-30 for Failure to Comply with the Written Description Requirement filed Nov. 23, 2005.
Plaintiffs' Consolidated Memorandum of Law in Opposition to Defendants' Motions for Partial Summary Judgment of Invalidity of Claims 1-30 filed Dec. 19, 2005.
Unimed Pharmaceuticals, Inc.'s Statement of Additional Facts which are Material and Present a Genuine Issue for Trial filed Dec. 19, 2005.
Plaintiffs' Consolidated Response to Defendants Watson's and Paddock's Statements of Material Facts as to Which There are No Genuine Issues to be Tried Regarding Invalidity of Claims 1-30 of the '894 Patent Lacking a Written Description under 35 U.S.C. § 112 filed Dec. 19, 2005.
Watson's Reply Memorandum of Law in Support of its Motion for Partial Summary Judgment of Invalidity of Claims 1-30 for Failure to Comply with the Written Description Requirement filed Jan. 19, 2006.
Watson's Response to Plaintiff's Statement of Additional Facts which are Material and Present a Genuine Issue for Trial filed Jan. 19, 2006.
Docket Report for *Unimed Pharmaceuticals, Inc.* v. *Paddock Laboratories, Inc.* (retrieved from PACER Jan. 4, 2011).
Complaint by Unimed Pharmaceuticals dated Aug. 21, 2003.
Plaintiff Unimed Pharmaceuticals, Inc.'s Rule 7.1 Corporate Ownership Disclosure Statement filed Aug. 21, 2003.
Answer and Counterclaim by Paddock Laboratories filed Oct. 22, 2003.
Answer to Counterclaims by Unimed Pharmaceuticals filed Nov. 12, 2003.
Certificate of Interested Persons filed Nov. 21, 2003.
Joint Preliminary Report and Discovery Plan filed Nov. 21, 2003.
Defendant's Rule 26 Disclosures filed Dec. 12, 2003.
Paddock's Motion to Issue Letters of Request for International Judicial Assistance filed Dec. 1, 2004.
Request for International Judicial Assistance by Judge Thrash dated Dec. 9, 2004.
Unimed Pharmaceuticals, Inc.'s Objections to Paddock Laboratories, Inc.'s Notices of Depositions Under Rule 30(b)(6) dated Mar. 17, 2005.
Paddock's Opening Claim Construction Brief (Redacted Version) filed Jul. 25, 2005.
Paddock's Opposition Claim Construction Brief filed Aug. 12, 2005.
Defendant Paddock Laboratories, Inc.'s Motion for Partial Summary Judgment filed Sep. 27, 2005.
Memorandum in Support of Paddock's Motion for Partial Summary Judgment of Invalidity of Claims 1-30 of the '894 Patent as Lacking a Written Description as Required by 35 U.S.C. § 112, First Paragraph with Respect to the Claimed Ranges of Sodium Hydroxide filed Oct. 18, 2005.
Paddock's Reply Memorandum in Further Support of its Motion for Partial Summary Judgment as to the Inapplicability and Invalidity of the Certificate of Correction filed Nov. 11, 2005.
Paddock's Response to Plaintiffs' Statement of Additional Facts which are Material and Present a Genuine Issue for Trial filed Nov. 11, 2005.
Defendant Paddock Laboratories, Inc.'s Motion in Limine to Exclude Unimed's Argument and Expert Testimony on the Basis of, and Support in the Specification for, the Sodium Hydroxide Ranges Recited in Certain Claims of the '894 Patent filed Nov. 28, 2005.
Plaintiffs' Memorandum of Law in Opposition to Paddock's Motion in Limine to Exclude Plaintiffs' Argument and Expert Testimony on the Sodium Hydroxide Ranges filed Jan. 13, 2006.
Paddock's Reply memorandum in Further Support of its Motion for Partial Summary Judgment as to the Invalidity of Claims 1-30 under 35 U.S.C. § 112 filed Jan. 19, 2006.
Paddock's Response to Unimed's Statement of Additional Facts which are Material and Present a Genuine Issue for Trial with Respect to Paddock's motion of Summary Judgment that Claims 1-30 of the '894 Patent are Invalid under 35 U.S.C. § 112 filed Jan. 19, 2006.
Paddock's Reply Brief in Further Support of its Motion In Limine to Exclude Unimed's Argument and Expert Testimony on the Basis of, and Support in the Specification for, the Sodium Hydroxide Ranges Recited in Certain Claims of the '894 Patent filed Jan. 31, 2006.
Consent Judgment and Order of Permanent Injunction dated Sep. 15, 2006.
Docket Report for In re Androgel Antitrust Litigation (No. II) (retrieved from PACER Jan. 5, 2011).
Complaint, *Meijer, Inc.* v. *Unimed Pharmaceuticals, Inc.* (originally filed in C.D. Cal. on Feb. 2, 2009).
Complaint, *Louisiana Wholesale Drug Co.* v. *Unimed Pharmaceuticals, Inc.* (originally filed in C.D. Cal. on Feb. 3, 2009).
Complaint, *Rochester Drug Co-operative, Inc.* v. *Unimed Pharmaceuticals, Inc.* (originally filed in C.D. Cal. on Feb. 3, 2009).
First Amended Complaint, *Federal Trade Commission* v. *Watson Pharmaceuticals, Inc.*, Case No. CV 09-598 MRP (originally filed in C.D. Cal. on Feb. 12, 2009).
Complaint, *Stephen L. LaFrance Pharmacy, Inc.* v. *Unimed Pharmaceuticals, Inc.* (originally filed in D.N.J. on Mar. 31, 2009).
Complaint, *Fraternal Order of Police* v. *Unimed Pharmaceuticals, Inc.* (originally filed in D.N.J. on Apr. 17, 2009).
Complaint, *Scurto* v. *Unimed Pharmaceuticals, Inc.* (originally filed in D.N.J. on Apr. 21, 2009).
Complaint, *United Food and Commercial Workers Unions and Employers Midwest Health Benefits Fund* v. *Unimed Pharmaceuticals, Inc.* (originally filed in D. Minn. 2009).
Complaint, *Rite Aid Corp.* v. *Unimed Pharmaceuticals, Inc.* (originally filed in M.D. Penn. on Jun. 17, 2009).
Complaint, *Walgreen Co.* v. *Unimed Pharmaceuticals, Inc.* (originally filed in M.D. Penn. on Jun. 29, 2009).
Complaint, *Jabo's Pharmacy, Inc.* v. *Solvay Pharmaceuticals, Inc.* (originally filed in Circuit Court for Cocke County, Tennessee on Oct. 30, 2009).
Complaint, *Supervalu Inc.* v. *Unimed Pharmaceuticals, Inc.* (originally filed in N.D. Ga. on Apr. 7, 2010).
Complaint, *LeGrand* v. *Unimed Pharmaceuticals, Inc.* (originally filed in N.D. Ga. on Sep. 10, 2010).
Order Granting in Part and Denying in Part Defendant's Motions to Dismiss dated Feb. 22, 2010.
Amended Class Action Complaint and Jury Demand, *Fraternal Order of Police* v. *Unimed Pharmaceuticals, Inc.*, Case No. 09-md-2084-TWT (filed Mar. 5, 2010).
Plaintiff's Answer to Teva's Counterclaims (Redacted) dated Jun. 27, 2011.
United States Patent Office Action for U.S. Appl. No. 13/965,499 dated Nov. 21, 2013 (23 pages).
United States Patent Office Action for U.S. Appl. No. 13/831,217 dated Dec. 13, 2013 (32 pages).
United States Patent Office Action for U.S. Appl. No. 13/831,231 dated Dec. 16, 2013 (9 pages).
United States Patent Office Action for U.S. Appl. No. 13/831,189 dated Dec. 11, 2013 (11 pages).
United States Patent Office Action for U.S. Appl. No. 13/831,207 dated Dec. 11, 2013 (10 pages).
U.S. Patent Office Notice of Allowance for U.S. Appl. No. 13/831,207 dated Mar. 25, 2014 (12 pages).
U.S. Patent Office Notice of Allowance for U.S. Appl. No. 13/831,217 dated Mar. 26, 2014 (13 pages).
U.S. Patent Office Notice of Allowance for U.S. Appl. No. 13/831,231 dated Mar. 31, 2014 (14 pages).
U.S. Patent Office Notice of Allowance for U.S. Appl. No. 13/831,189 dated Mar. 31, 2014 (17 pages).
United States Patent Office Action for U.S. Appl. No. 13/965,499 dated Jun. 2, 2014 (28 pages).
United States Patent Office Action for U.S. Appl. No. 13/781,849 dated Sep. 26, 2014 (26 pages).
Androgel 1.62% Label Information, Medication Guide, Abbvie Inc. (Jun. 2014).
"Access Pharmaceuticals Signs Merger Agreement to Acquire MacroChem Corp," Drugs.com (Jul. 10, 2008) 3 pages.
"Cellegy Pharmaceuticals and Prostrakan Group announce approval of Tostrex ® gel in first European Country," Press Release (Oct. 19, 2005) 2 pages, www.biospace.com/new_printaspn.

(56) References Cited

OTHER PUBLICATIONS

AIDS Treatment News, Issue 339 (Mar. 17, 2000).
AIDS Treatment News, Issue No. 307 (Nov. 20, 1998).
American Association of Clinical Endocrinologists Medical Guidelines for Clinical Practice for the Evaluation and Treatment of Hypogonadism in Adult Male Patients—2002 Update, Endocrine Practice (2002) 8(6):440-456.
Ashland Carbomers brochure, "Essential rheology modifers for personal care formulating," Ashland, Inc.
ATSDR, Agency for Toxic Substances & Disease Registry—"Sodium hydroxide" 20 pages.
ATSDR, Agency for Toxic Substances & Disease Registry—"Sodium Hydroxide" Cas # 1310-73-2, 2 pages, Division of Toxicology Tox FAQs (Apr. 2002).
Bach, M. et al., "Percutaneous penetration enhancement and its qualification," Eur. J. Pharm. Biopharm. (1998) 46:1-13.
Barry, B.W., "Modern methods of promoting drug absorption through the skin," Molec. Aspects med. (1991) 12:195-241.
Ben-Galim, E. et al., "Topically applied testosterone and phallic growth," Am. J. Dis. Child (1980) 134:296-298.
Berti, J.J. et al., "Transcutaneous drug delivery: a practical review," Mayo Clin. Proc. (1995) 70:581-586.
Bhasin, S. et al., "Testosterone therapy in adult men with Androgen deficiency syndromes: an Endocrine Society clinical practice guideline," J. Clin. Endocrin. Metab. (2006) 91(6):1995-2010.
Bucks, D.A.W., "Bioavailability of topically administered steroids: a 'mass balance' technique," J. Invest. Derm (1988) 90:29-33.
Carson, C.C., III, "Prevalance, diagnosis and treatment of hypogonadism in primary care practice," http://www.bumc.bu.edu/sexualmedicine/publications/prevalence-diagnosis . . . (Dec. 22, 2014).
Casiraghi, A. et al., "Occlusive properties of monolayer patches: in vitro and in vivo evaluation," Pharm. Res. (2002) 19(4):423-426.
Chien, Y.W., "Developmental concepts and practice in transdermal therapeutic systems," Chapter 2, Transdermal Controlled Systemic Medications, marcel Dekker, New York (1987) 25-81.
Chien, Y.W., "Transdermal controlled-release drug administration," Chapter 5, Novel Drug Delivery Systems, Marcel Dekker, New York (1982) 149-217.
Chilcott, R.D. et al., "Inter- and intralaboratory variation of in vitro diffusion cell measurements: an international multicenter study using quasi-standardized methods and materials," J. Pharm. Sci. (2005) 94(3):632-638.
Cutter, C.B., "Compounded testosterone gels: a guide for clinicians and pahrmacists," Int. J. of Pharm. Comp. (2000) 4(6):432-437.
Dempski, R.E. et al., "An in vitro study of the relative moisture occlusion properties of severally topical vehicles and saran wrap," J. Invest. Derm. (1965) 44(5):361-363.
Drug Bank: Dihydrotestosterone, Acc. No. DB02901, www.drugbank.ca/drugs/DB02901, pp. 1-9.
Drug Bank: Testosterone, DB00624, www.drugbank.ca/drugs/DB00624, pp. 1-17.
European Medicines Agency, "Guideline on quality of transdermal patches," (Aug. 23, 2012) 28 pages.
Fang, J.Y. et al., "Percutaneous absorption of capsaicin, nonivamide and sodium nonivamide acetate from gel and ointment bases: in vitro formulation evaluations in pigs and in vivo bioengineering methods in humans," Int. J. Pharma. (1996) 30:121-135.
FDA Drug Safety Communication: "FDA adding general warning to testosterone products about potential for venous blood clots," (Jun. 19, 2014) 2 pages.
FDA Drug Safety Communication: "FDA evaluating risk of stroke, heart attach and death with FDA-approved testosterone products," (Jan. 31, 2014) 2 pages.
FDA Guidance for Industry, "Bioavailability and bioequivalence studies for orally administered drug products—general considerations," (Oct. 2000) 28 pages.
FDA Guidance for Industry, "Nonsterile semisolid dosage forms scale-up and post approval changes: chemistry, manufacturing and controls; in vitro release testing and in vivo bioequivalence documentation," (May 1997).
FDA Response to Abbott Laboratories Citizen Petition to Philip Katz re: FDA-2010-P-0196 (Oct. 4, 2010).
FDA Response to Auxilium Pharmaceuticals, Inc.'s Citizen Petition to Anthony DelConte Re: FDA-2009-P-0123 (Aug. 26, 2009).
Finkelstein, J.S. et al., "Gonadal steroids and body composition, strength and sexual function in men," N. Eng. J. Med. (2013) 369(11):1011-1022.
Finkle, W.D. et al., "Increased risk of non-fatal myocardial infarction following testosterone therapy prescription in men," PLOS One (2014) 9(1):e85805.
Flynn, G.L., "Cutaneous and transdermal delivery: processes and systems of delivery," Mod. Pharmaceutics (1996) 3rd Edition, Chapter 8, p. 239-298.
Flynn, G.L., "II. Topical and transdermal delivery—provinces of realism," in Dermal and Transdermal Drug Delivery (Band 31) 33-65.
Foresta (testosterone) gel—NDA approval letter to Endo Pharmaceuticals from Department of Health and Human Services (Dec. 29, 2010).
Formulations, Int. J. of Pharm. Compounding (1998) 2(1) various.
Fortesta label (Jun. 2014).
Fortesta NDA 21-463 Summary Review from Center for Drug Evaluation and Research (Dec. 29, 2010).
Freedom Cepapro Gel Fact Sheet, Freedom Inc., 2 pages.
Gennaro, A.R., "Medicated topicals," Remington: The Science and Practice of Pharmacy, 20th Edition, Chapter 44 (2000) p. 836-857.
Gennaro, A.R., 19th Edition, Remington: Practice of the Science & Pharmacy, mack Publishing Co., Pennsylvania (1995) p. 1104, 1396, 1411, 1414.
GMHC Treatment Issues, "Testosterone for Wasting," (1996) 10(1).
Gosh, T.K. et al., Transdermal and Topical Drug Delivery Systems, Interpharm Press, Inc. (1997) p. 3-6, 21, 357-364.
Hadgraft, J., "Passive enhancement strategies in topical and transdermal drug delivery," Int. J. Pharma. (1999) 184:1-6.
Hameed, A. et al., "Delivery of testosterone replacement therapy," Curr. Opin. Invest. Drugs (2003) 4(10):1213-1219.
Handbook of Pharmaceutical Excipients, 2nd Edition, A. Wade & P.J. Weller, American Pharm. Assoc. Washington (1994) "Alcohol" definition.
Hori, M. et al., "Classification of percutaneous penetration enhancers: a conceptual diagram," Chapter 13 in Percutaneous Absorption, Mechanisms-Methodology-DrugDelivery, 2nd Edition (1989) Marcel Dekker 197-211.
Inactive Ingredient Guide, FDA (Jan. 1996).
Lin, J. et al., "Study on formation of testosterone gel," China Pharmacist (2005) 8(9) with translation.
Lund, W., editor, The Pharmaceutical Codex, 12th Edition, principles & Practice of Pharmaceutics, London (1994) 192-197.
Lunenfeld, B. et al., "ISA, ISSAM and EAU recommendations for the investigation, treatment and monitoring of late-onset hypogonadism in males: scientific background and rationale," the Aging Male (2005) 8(2):59-74.
McCullough, A.R. et al., "A multi-institutional observational study of testosterone levels after testosterone pellet (TestopelÒ) insertion," J. Sex Med. (2012) 9:594-601.
Menczel, E. et al., "In vitro human percutaneous penetration of benzyl alcohol and testosterone: epidermal-dermal retention," J. Invest. Derm. (1970) 54(5):386-394.
Miselnicky, S.R. et al., "The influence of solubility, protein binding and percutaneous absorption on reservoir formation in skin," J. Soc. Cosmet. Chem. (1988) 39:169-177.
Morales, A. et al., "Investigation, treatment and monitoring of late-onset hypogonadism in males," The Aging Male (2002) 5:74-86.
Mulhall, J.P. et al., Clinical Care Pathways in Andrology (2014) Chapter 12, Hypogonadism: Treatment.
Mulligan, T. et al., "Prevalence of hypogonadism in males aged at least 45 years: the HIM study," Int. J. Clin. Pract. (2006) 60(7):762-769.

(56) References Cited

OTHER PUBLICATIONS

Nieschlag, E. et al., "Testosterone replacement therapy: current trends and future directions," Human Reproduction Update (2004) 10(5):409-419.
Orange Book Query, "Orange Book: Approved drug products with therapeutic equivalence evaluations," (Feb. 10, 2015).
Orange Book Query, "Orange book: Approved drug products with therapeutic equivalence evaluations," (Feb. 23, 2009).
Orange Book, "Approved drug products with therapeutic equivalence evaluations" (1998) 18th Edition.
Percutaneous Absorption: Drugs, Cosmetics, mechanisms, Methodology, Edited by Robert L. Bronaugh et al., Fourth edition, vol. 155 (2005) Taylor & Francis Group, p. 3-5, 65-83, 213-234.
Pfister, W.R., "Transdermal and dermal therapeutic systems: current status," Transdermal and topical drug delivery systems, Chapter 2, 33-112, Interpharm Press, Illinois 91997).
Pfister, W.R., Chapter 2, "Transderma-dermal therapeutic systems: current status," in Transdermal and Topical Drug Delivery Systems, Interpharm Press (1997) p. 33-112.
Physician's Desk Reference (1990) 44th Edition, p. 1570, 2244-2247.
Physician's Desk Reference (1991) 45th Edition, p. 890-891, 1982-1983, 2291-2293.
Physician's Desk Reference (1993) 47th Edition, p. 415, 1245-1250, 1268-1270.
Physician's Desk Reference (2004) 58th Edition, p. 711-713, 1332-1333, 3239-3241.
Physician's Desk Reference for Ophthalmic Medicines (2001) 29th Edition, p. 103, 207-208, 219-222, 253-255, 266-267, 281.
Prausnitz, M.R. et al., "Transdermal drug delivery," Nat. Biotechnol. (2008) 26(11):1261-1268.
Ranade, V.V. et al., In Drug Delivery Ssytems, Chapter 6, "Transdermal drug delivery," p. 177-208, CRC Press (1996).
Remington the Science and Practice of Pharmacy, 21st Edition, Lippincott, Williams & Wilkins, Philadelphia, (2006) Part 5: Pharmaceutical Manufacturing, p. 770-772.
SBA Clinical Pharmacology and Biopharmaceutics Reviews, Center for Drug Evaluation and Research for "Fortesa" (Dec. 9, 2010 and Dec. 27, 2010), App. No. 021463Orig1s000.
Schacht, W.H. et al., "Pharmaceutical patent term extensions: a brief explanation," CRS Report for Congress (Jan. 31, 2002).
Schering Press Releases (2002).
Seftel, A., "Male hypogonadism. Part II: etiology, pathophysiology, and diagnosis," Int. J. Impotence Res. (2006) 18:223-228.
Seidenari, S. et al., "Sodium hydroxide—induced irritant dermatitis as asssessed by computerized elaboration of 20 MHz B-scan images and by TEWL measurement: a method for investigating skin barrier function," Acta Derm Venereol. (1995) 75:97-101.
Sigma-Aldrich, "5Alpha-Androstan-17beta-o1-3-one" Technical Information (2015) 3 pages.
T1500 Sigma, "Testosterone " Sigma-Aldrich, www.sigmaaldrich.com/catalog/products/sigma/t1500?lang, 3 p.
Testim Approval letter by Department of Health and Human Services to Auxilium Pharmaceuticals, Inc. (Oct. 31, 2002).
Walker, R.B. et al., "The role of percutaneous penetration enhancers," Adv. Drug Del. Rev. (1996) 18:295-301.
Walters, K.A. et al., "The structure and function of skin" from Dermatological and Transdermal Formulations, Informa Healthcare USA, New York (2007) 1-14, 94-95, 100-101, 168-169, 325-326.
Williams Textbook of Endocrinology, 10th Edition, Saunders, p. 720-725.
Wilson, J.D. et al., "The conversion of testosterone to 5alpha-Androstan-17beta-o1-3-one (dihydrotestosterone) by skin slices of man," J. Clin. Invest. (1969) 48:371-379.
Zhang, J. et al., "In vitro enhancement of lactate esters on the percutaneous penetration of drugs with different lipophilicity," AAPS PharmSciTech (2010) 11(2), 10 pages.
Docket Report for In re Androgel Antitrust Litigation (No. II) (update as of Nov. 19, 2014).

Memorandum of Law in Support of Defendants' Motion to Dismiss the Second Amended Complaint dated Nov. 23, 2009.
Memorandum of Law in Support of Defendants Par Pharmaceutical Companies, Inc. and Paddock Laboratories, Inc.'s Motion to Dismiss the Private Plaintiffs' Second Amended Complaints dated Nov. 23, 2009.
Defendants' Solvay Pharmaceuticals, Inc. and Unimed Pharmaceuticals, LLC Answer to Plaintiffs' Second Amended Complaint, in Case No. 09-CV-956, dated Mar. 9, 2010.
Defendants' Solvay Pharmaceuticals, Inc. and Unimed Pharmaceuticals, LLC Answer to Plaintiffs' Second Amended Complaint, in Case No. 09-CV-957, dated Mar. 9, 2010.
Defendants' Solvay Pharmaceuticals, Inc. and Unimed Pharmaceuticals, LLC Answer to Plaintiffs' Second Amended Complaint in Case No. 09-CV-958, dated Mar. 9, 2010.
Second Amended Complaint—Class Action, dated May 29, 2009 in Case No. 09-CV-00956.
Second Amended Complaint—Class Action, dated May 28, 2009 in Case No. 09-CV-00957.
Second Amended Complaint—Class Action, dated May 29, 2009 in Case No. 09-CV-00958.
Complaint dated Jun. 29, 2009 in Case No. 1:09-CV-3019.
Complaint dated Apr. 7, 2010 in Case No. 1:10-CV-1024.
Complaint dated Jun. 17, 2009 in Case No. 1:09-CV-02776.
Consolidated Amended End-Payor Class Action Complaint and Demand for Jury Trial dated Aug. 5, 2014.
Unimed's Reply to Plaintiffs' Response re: Notice of Supplemental Authority for Cross-Motions for Summary Judgment Regarding Objective Merit dated Aug. 6, 2012.
Transcript of the Motions Hearing Before the Honorable Thomas W. Thrash, Jr., U.S. District Court Judge, held on Sep. 14, 2012 (summary judgment hearing).
Corrected Opinion and Order Re: Motions for Summary Judgment and Motion to Exclude the Expert Report of Dr. Norman Weiner dated Oct. 30, 2012.
Order on Defendants' Motion to Dismiss dated Feb. 22, 2010.
Order Clarification on Direct Purchasers claims dated Sep. 16, 2010.
Plaintiffs' Memorandum of Law in Opposition of Defendants' Motions to Dismiss the Second Amended Complaint, dated Oct. 28, 2009.
Reply Memorandum in Further Support of Defendants' Motion to Dismiss the Second Amended Complaint dated Dec. 4, 2009.
Defendants' Solvay Pharmaceuticals, Inc. and Unimed Pharmaceuticals, LLC's Answer to Plaintiffs' Complaint in Case No. 09-cv-2776, dated Mar. 9, 2010.
Defendants' Solvay Pharmaceuticals, Inc. and Unimed Pharmaceuticals, LLC Answer to Plaintiffs' Complaint in Case No. 09-cv-3019 dated Mar. 9, 2010.
Defendants' Abbott Products, Inc. f/k/a Solvay Pharmaceuticals, Inc. and Unimed Pharmaceuticals, LLC Answer to Plaintiffs Complaint in Case No. 09-CV-1024, dated Jun. 7, 2010.
Memorandum of Law in Support of Defendants' Motion to Dismiss the Androgel Indirect Purchasers' Complaints, dated Oct. 30, 2009.
Memorandum of Law in Support of Defendants Par Pharmaceutical Companies, Inc. and Paddock Laboratories, Inc.'s Motion to Dismiss the Indirect Purchaser Plaintiffs' Complaints dated Oct. 30, 2009.
End-Payor Plaintiffs' Opposition to Defendants' Motions to Dismiss, dated Dec. 2, 2009.
Reply Memorandum in Support of Defendants' Motion to Dismiss the Androgel Indirect Purchasers Complaints dated Dec. 21, 2009.
Reply Memorandum in Support of Defendants Par Pharmaceutical Companies, Inc. and Paddock Laboratories, Inc.'s Motion to Dismiss the End Payor Class Action Complaints, dated Dec. 16, 2009.
Answer of Defendants Abbvie Products LLC F/K/A Solvay Pharmaceuticals, Inc. and Unimed Pharmaceuticals, LLC to Consolidated Amended End-Payor Class Action Complaint in Case No. 1:09-CV-02914, dated Oct. 23, 2014.
Docket Report as of Nov. 19, 2014.
Complaint for Patent Infringement dated Apr. 29, 2011.
Proposed Order for Motion for Summary Judgment of No Infringement dated Aug. 1, 2011.
Proposed Order for Motion for Summary Judgment of No Infringement dated Sep. 1, 2011.

(56) References Cited

OTHER PUBLICATIONS

Joint Stipulation of Dismissal dated Dec. 28, 2011.
Exhibit 17 (Excerpt from Schwarz file history)—Amendment in U.S. Appl. No. 07/017,962 dated Nov. 11, 1987.
Letter from Mary B. Graham to Judge Bartle dated Oct. 20, 2011.
Complaint dated Oct. 31, 2011.
Notice of Voluntary Dismissal dated Dec. 22, 2011.
Memorandum Order dated Jul. 23, 2014.
Amended Joint Claim Chart filed Sep. 19, 2014.
Memorandum of Law in Support of Defendants Par Pharmaceutical Companies, Inc. and Paddock Laboratories, Inc.'s Motion to Dismiss the Second Amended Complaint, dated Nov. 23, 2009.
Plaintiff Federal Trade Commission's Consolidated Opposition to Defendants' Motions to Dismiss dated Aug. 21, 2009.
Reply Memorandum in Support of Defendants' Motion to Dismiss the Second Amended Complaint, dated Sep. 11, 2009.
Reply Memorandum of Law in Support of Defendants Par Pharmaceutical Companies, Inc. and Paddock Laboratories, Inc.'s Motion to Dismiss the Second Amended Complaint dated Sep. 11, 2009.
Answer of Defendant Abbvie Products LLC f/k/a Solvay Pharmaceuticals, Inc. to Plaintiff Federal Trade Commission's Second Amended Complaint for Injunctive and other Equitable Relief, dated Jan. 15, 2014.
Second Amended Complaint for Injunctive and other Equitable Relief dated May 28, 2009.
US 6,214,374, 04/2001, Schmirler et al. (withdrawn)

\* cited by examiner

PHARMACEUTICAL COMPOSITION AND METHOD FOR TREATING HYPOGONADISM

RELATED APPLICATIONS

This application is a continuation of U.S. patent application Ser. No. 10/248,267 filed on Jan. 3, 2003, which is a continuation of U.S. patent application Ser. No. 09/651,777 filed Aug. 30, 2000, now U.S. Pat. No. 6,503,894, the disclosures of which are incorporated herein by reference in their entirety to the extent permitted by law.

FIELD OF THE INVENTION

The present invention is directed to a pharmaceutical composition comprising testosterone in a gel formulation, and to methods of using the same.

BACKGROUND OF THE INVENTION

A. Testosterone Metabolism in Men.

Testosterone is the major circulating androgen in men. More than 95% of the 6-7 mg of testosterone produced per day is secreted by the approximately 500 million Leydig cells in the testes. Two hormones produced by the pituitary gland, luteinizing hormone ("LH") and follicle stimulating hormone ("FSH"), are required for the development and maintenance of testicular function.

The most important hormone for the regulation of Leydig cell number and function is LH. In eugonadal men, LH secretion from the pituitary is inhibited through a negative-feedback pathway by increased concentrations of testosterone through the inhibition of the release of gonadotropin-releasing hormone ("GRH") by the hypothalamus. FSH promotes spermatogenesis and is essential for the normal maturation of sperm. FSH secretion from the pituitary normally is inhibited through a negative-feedback pathway by increased testosterone concentrations.

Testosterone is responsible primarily for the development and maintenance of secondary sex characteristics in men. In the body, circulating testosterone is metabolized to various 17-keto steroids through two different pathways. Testosterone can be metabolized to dihydrotestosterone ("DHT") by the enzyme 5α-reductase. There are two forms of 5α-reductase in the body: one form is found predominately in the liver and non-genital skin while another form is found in the urogenital tract of the male and the genital skin of both sexes. Testosterone can also be metabolized to estradiol ("E2") by an aromatase enzyme complex found in the liver, fat, and the testes.

Testosterone circulates in the blood 98% bound to protein. In men, approximately 40% of the binding is to the high-affinity sex hormone binding globulin ("SHBG"). The remaining 60% is bound weakly to albumin. Thus, a number of measurements for testosterone are available from clinical laboratories. The term "free" testosterone as used herein refers to the fraction of testosterone in the blood that is not bound to protein. The term "total testosterone" or "testosterone" as used herein means the free testosterone plus protein-bound testosterone. The term "bioavailable testosterone" as used herein refers to the non-SHBG bound testosterone and includes testosterone weakly bound to albumin.

The conversion of testosterone to DHT is important in many respects. For example, DHT binds with greater affinity to SHBG than does testosterone. In addition, in many tissues, the activity of testosterone depends on the reduction to DHT, which binds to cytosol receptor proteins. The steroid-receptor complex is then transported to the nucleus where it initiates transcription and cellular changes related to androgen action. DHT is also thought to lower prostate volume and inhibit tumor development in the prostate. Thus, given the importance of DHT and testosterone in normal body functioning, researchers frequently assess and report androgen concentrations in patients as total androgen ("DHT+T") or as a ratio of DHT to testosterone ("DHT/T ratio").

The following table from the UCLA-Harbor Medical Center summarizes the hormone concentrations in normal adult men range:

TABLE 1

| Hormone Levels in Normal Men | |
|---|---|
| Hormone | Normal Range |
| Testosterone | 298 to 1043 ng/dL |
| Free testosterone | 3.5 to 17.9 ng/dL |
| DHT | 31 to 193 ng/dL |
| DHT/T Ratio | 0.052 to 0.33 |
| DHT + T | 372 to 1349 ng/dL |
| SHBG | 10.8 to 46.6 nmol/L |
| FSH | 1.0 to 6.9 mIU/mL |
| LH | 1.0 to 8.1 mIU/mL |
| $E_2$ | 17.1 to 46.1 pg/mL |

There is considerable variation in the half-life of testosterone reported in the literature, ranging from 10 to 100 minutes. Researchers do agree, however, that circulating testosterone has a diurnal variation in normal young men. Maximum levels occur at approximately 6:00 to 8:00 a.m. with levels declining throughout the day. Characteristic profiles have a maximum testosterone level of 720 ng/dL and a minimum level of 430 ng/dL. The physiological significance of this diurnal cycle, if any, however, is not clear.

B. Hypogonadal Men and Current Treatments for Hypogonadism.

Male hypogonadism results from a variety of patho-physiological conditions in which testosterone concentration is diminished below the normal range. The hypogonadic condition is sometimes linked with a number of physiological changes, such as diminished interest in sex, impotence, reduced lean body mass, decreased bone density, lowered mood, and energy levels.

Researchers generally classify hypogonadism into one of three types. Primary hypogonadism includes the testicular failure due to congenital or acquired anorchia, XYY Syndrome, XX males, Noonan's Syndrome, gonadal dysgenesis, Leydig cell tumors, maldescended testes, varicocele, Sertoli-Cell-Only Syndrome, cryptorchidism, bilateral torsion, vanishing testis syndrome, orchiectomy, Klinefelter's Syndrome, chemotherapy, toxic damage from alcohol or heavy metals, and general disease (renal failure, liver cirrhosis, diabetes, myotonia dystrophica). Patients with primary hypogonadism show an intact feedback mechanism in that the low serum testosterone concentrations are associated with high FSH and LH concentrations. However, because of testicular or other failures, the high LH concentrations are not effective at stimulating testosterone production.

Secondary hypogonadism involves an idiopathic gonadotropin or LH-releasing hormone deficiency. This type of hypogonadism includes Kallman's Syndrome, Prader-Labhart-Willi's Syndrome, Laurence-Moon-Biedl's Syndrome, pituitary insufficiency/adenomas, Pasqualini's Syndrome, hemochromatosis, hyperprolactinemia, or pituitary-hypothalamic injury from tumors, trauma, radiation, or obesity. Because patients with secondary hypogonadism do not demonstrate an intact feedback pathway, the lower testosterone concentrations are not associated with increased LH or FSH levels. Thus, these men have low testosterone serum levels but have gonadotropins in the normal to low range.

Third, hypogonadism may be age-related. Men experience a slow but continuous decline in average serum testosterone after approximately age 20 to 30 years. Researchers estimate that the decline is about 1-2% per year. Cross-sectional studies in men have found that the mean testosterone value at age 80 years is approximately 75% of that at age 30 years. Because the serum concentration of SHBG increases as men age, the fall in bioavailable and free testosterone is even greater than the fall in total testosterone. Researchers have estimated that approximately 50% of healthy men between the ages of 50 and 70 have levels of bioavailable testosterone that are below the lower normal limit. Moreover, as men age, the circadian rhythm of testosterone concentration is often muted, dampened, or completely lost. The major problem with aging appears to be within the hypothalamic-pituitary unit. For example, researchers have found that with aging, LH levels do not increase despite the low testosterone levels. Regardless of the cause, these untreated testosterone deficiencies in older men may lead to a variety of physiological changes, including sexual dysfunction, decreased libido, loss of muscle mass, decreased bone density, depressed mood, and decreased cognitive function. The net result is geriatric hypogonadism, or what is commonly referred to as "male menopause." Today, hypogonadism is the most common hormone deficiency in men, affecting 5 in every 1,000 men. At present, it is estimated that only five percent of the estimated four to five million American men of all ages with hypogonadism currently receive testosterone replacement therapy. Thus, for years, researchers have investigated methods of delivering testosterone to men. These methods include intramuscular injections (43%), oral replacement (24%), pellet implants (23%), and transdermal patches (10%). A summary of these methods is shown in Table 2.

TABLE 2

Mode of Application and Dosage of Various Testosterone Preparations

| Preparation | Route Of Application | Full Substitution Dose |
|---|---|---|
| In Clinical Use | | |
| Testosterone enanthate | Intramuscular injection | 200-25.0 g every 2-3 weeks |
| Testosterone cypionate | Intramuscular injection | 200 mg every 2 weeks |
| Testosterone undecanoate | Oral | 2-4 capsules at 40 mg per day |
| Transdermal testosterone patch | Scrotal skin | 1 membrane per day |
| Transdermal testosterone patch | Non-scrotal skin | 1 or 2 systems per day |
| Testosterone implants | Implantation under the abdominal skin | 3-6 implants of 200 mg every 6 months |
| Under Development | | |
| Testosterone cyclodextrin | Sublingual | 2.5-5.0 mg twice daily |
| Testosterone undecanoate | Intramuscular injection | 1000 mg every 8-10 weeks |
| Testosterone buciclate | Intramuscular injection | 1000 mg every 12-16 weeks |
| Testosterone microspheres | Intramuscular injection | 315 mg for 11 weeks |
| Obsolete | | |
| 17α-Methyltestosterone | Oral | 25-5.0 g per day |
| Fluoxymesterone | Sublingual | 10-25 mg per day |
| | Oral | 10-20 mg per day |

As discussed below, all of the testosterone replacement methods currently employed suffer from one or more drawbacks, such as undesirable pharmacokinetic profiles or skin irritation. Thus, although the need for an effective testosterone replacement methodology has existed for decades, an alternative replacement therapy that overcomes these problems has never been developed. The present invention is directed to a 1% testosterone hydroalcoholic gel that overcomes the problems associated with current testosterone replacement methods.

1. Subdermal Pellet Implants.

Subdermal implants have been used as a method of testosterone replacement since the 1940s. The implant is produced by melting crystalline testosterone into a cylindrical form. Today, pellet implants are manufactured to contain either 100 mg (length 6 mm, surface area 1172) or 200 mg of testosterone (length 12 mm, surface area 202 mm2) Patients receive dosages ranging from 100 to 1,200 mg, depending on the individual's requirements. The implants are inserted subcutaneously either by using a trocar and cannula or by open surgery into an area where there is relatively little movement. Frequently, the implant is placed in the lower abdominal wall or the buttock. Insertion is made under local anesthesia, and the wound is closed with an adhesive dressing or a fine suture.

Implants have several major drawbacks. First, implants require a surgical procedure which many hypogonadal men simply do not wish to endure. Second, implant therapy includes a risk of extrusion (8.5%), bleeding (2.3%), or infection (0.6%). Scarring is also a risk. Perhaps most important, the pharmacokinetic profile of testosterone pellet implant therapy fails to provide men with a suitable consistent testosterone level. In general, subdermal testosterone implants produce supra-physiologically high serum testosterone levels which slowly decline so that before the next injection subnormally low levels of testosterone are reached. For example, in one recent pharmacokinetic study, hypogonadal patients who received six implants (1,200-mg testosterone) showed an initial short-lived burst release of testosterone within the first two days after application. A stable plateau was then maintained over then next two months (day 2: 1,015 ng/dL; day 63: 990 ng/dL). Thereafter, the testosterone levels declined to baseline by day 300. DHT serum concentrations also rose significantly above the baseline, peaking at about 63 days after implementation and greatly exceeding the upper limit of the normal range. From day 21 to day 189, the DHT/T ratio was significantly increased. The pharmacokinetic profiles for testosterone, DHT, and DHT/T in this study are shown in FIG. 1. See "Jockenhovel et al., Pharmacokinetics and Pharmacodynamics of Subcutaneous Testosterone Implants in Hypogonadal Men," 45 *Clinical Endocrinology* 61-71 (1996). Other studies involving implants have reported similar undesirable pharmacokinetic profiles.

2. Injection of Testosterone Esters.

Since the 1950s, researchers have experimented with the intermuscular depot injection of testosterone esters (such as enanthate, cypionate) to increase testosterone serum levels in hypogonadal men. More recent studies have involved injection of testosterone buciclate or testosterone undecanoate in an oil-based vehicle. Other researchers have injected testosterone microcapsule formulations.

Testosterone ester injection treatments suffer from many problems. Patients receiving injection therapy often complain that the delivery mechanism is painful and causes local skin reactions. In addition, testosterone microcapsule treatment requires two simultaneous intramuscular injections of a relatively large volume, which may be difficult to administer due to the high viscosity of the solution and the tendency to block the needle. Other men generally find testosterone injection therapy inconvenient because injection usually requires the patient to visit his physician every two to three weeks.

Equally important, injection-based testosterone replacement treatments still create an undesirable pharmacokinetic profile. The profile generally shows a supra-physiologic testosterone concentration during the first 24 to 48 hours followed by a gradual fall often to sub-physiologic levels over the next few weeks. These high serum testosterone levels, paralleled by increases in E2, are also considered the reason for acne and gynecomastia occurring in some patients, and for polycythaemia, occasionally encountered especially in older patients using injectable testosterone esters. In the case of testosterone buciclate injections, the treatment barely provides normal androgen serum levels and the maximal increase of serum testosterone over baseline does not exceed 172 ng/dL (6 nmol/dL) on average. Because libido, potency, mood, and energy are thought to fluctuate with the serum testosterone level, testosterone injections have largely been unsuccessful in influencing these variables. Thus, testosterone injection remains an undesirable testosterone replacement treatment method.

3. Oral/Sublingual/Buccal Preparations of Androgens.

In the 1970s, researchers began using oral, sublingual, or buccal preparations of androgens (such as fluoxymesterone, 17α-methyl-testosterone, or testosterone undecanoate) as a means for testosterone replacement. More recently, researchers have experimented with the sublingual administration of testosterone-hydroxypropyl-beta-cyclodextrin inclusion complexes. Predictably, both fluoxymesterone and methyl testosterone are 17-alkylated and thus associated with liver toxicity. Because these substances must first pass through the liver, they also produce an unfavorable effect on serum lipid profile, increasing LDL and decreasing HDL, and carbohydrate metabolism. While testosterone undecanoate has preferential absorption through the intestinal lymphatics, it has not been approved in the United States.

The pharmacokinetic profiles for oral, sublingual, and buccal delivery mechanisms are also undesirable because patients are subjected to super-physiologic testosterone levels followed by a quick return to the baseline. For example, one recent testing of a buccal preparation showed that patients obtained a peak serum hormone levels within 30 minutes after administration, with a mean serum testosterone concentration of 2,688+/−147 ng/dL and a return to baseline in 4 to 6 hours. See Dobs et al., Pharmacokinetic Characteristics, Efficacy and Safety of Buccal Testosterone in Hypogonadal Males: A Pilot Study, 83 *J. Clinical Endocrinology & Metabolism* 33-39 (1998). To date, the ability of these testosterone delivery mechanisms to alter physiological parameters (such as muscle mass, muscle strength, bone resorption, urinary calcium excretion, or bone formation) is inconclusive. Likewise, researchers have postulated that super-physiologic testosterone levels may not have any extra beneficial impact on mood parameters such as anger, nervousness, and irritability.

4. Testosterone Transdermal Patches.

The most recent testosterone delivery systems have involved transdermal patches. Currently, there are three patches used in the market: TESTODERM® (testosterone transdermal), TESTODERM® TTS (testosterone transdermal), and ANDRODERM® (testosterone transdermal system).

a. TESTODERM® (Testosterone Transdermal).

TESTODERM® (testosterone transdermal, Alza Pharmaceuticals, Mountain View, Calif.) was the first testosterone-containing patch developed. The TESTODERM® (testosterone transdermal) patch is currently available in two sizes (40 or 60 cm2). The patch contains 10 or 15 mg of testosterone and delivers 4.0 mg or 6.0 mg of testosterone per day. TESTODERM® (testosterone transdermal) is placed on shaved scrotal skin, aided by application of heat for a few seconds from a hair dryer.

FIG. 2 shows a typical pharmacokinetic testosterone profile for both the 40 cm2 and 60 cm2 patch. Studies have also shown that after two to four weeks of continuous daily use, the average plasma concentration of DHT and DHT/T increased four to five times above normal. The high serum DHT levels are presumably caused by the increased metabolism of 5α-reductase in the scrotal skin.

Several problems are associated with the TESTODERM® (testosterone transdermal) patch. Not surprisingly, many men simply do not like the unpleasant experience of dry-shaving the scrotal hair for optimal contact. In addition, patients may not be able to wear close-fitting underwear when undergoing treatment. Men frequently experience dislodgment of the patch, usually with exercise or hot weather. In many instances, men experience itching and/or swelling in the scrotal area. Finally, in a number of patients, there is an inability to achieve adequate serum hormone levels.

b. TESTODERM® TTS (Testosterone Transdermal).

The most recently developed non-scrotal patch is TESTODERM® TTS (testosterone transdermal, Alza Pharmaceuticals, Mountain View, Calif.). It is an occlusive patch applied once daily to the arm, back, or upper buttocks. The system is comprised of a flexible backing of transparent polyester/ethylene-vinyl acetate copolymer film, a drug reservoir of testosterone, and an ethylene-vinyl acetate copolymer membrane coated with a layer of polyisobutylene adhesive formulation. A protective liner of silicone-coated polyester covers the adhesive surface.

Upon application, serum testosterone concentrations rise to a maximum at two to four hours and return toward baseline within two hours after system removal. Many men, however, are unable to obtain and/or sustain testosterone levels within the normal range. The pharmacokinetic parameters for testosterone concentrations are shown as follows:

TABLE 3

TESTODERM ® TTS (testosterone transdermal) Testosterone Parameters

| Parameters | Day 1 | Day 5 |
|---|---|---|
| Cmax (ng/dL) | 482 ± 149 | 473 ± 148 |
| Tmax (h) | 3.9 | 3.0 |
| Cmin (ng/dL) | 164 ± 104 | 189 ± 86 |
| Tmin (h) | 0 | 0 |

The typical 24-hour steady state testosterone concentration achieved with TESTODERM® TTS (testosterone transdermal) patch is shown in FIG. 3.

Because of TESTODERM® (testosterone transdermal) patch is applied to the scrotal skin while the TESTODERM® TTS (testosterone transdermal) patch is applied to non-scrotal skin, the two patches provide different steady-state concentrations of the two major testosterone metabolites, DTH and E2:

TABLE 4

Hormone Levels Using TESTODERM ® (testosterone transdermal) and TESTODERM ® TTS (testosterone transdermal)

| Hormone | Placebo | TESTODERM ® (testosterone transdermal) | TESTODERM ® TTS (testosterone transdermal) |
| --- | --- | --- | --- |
| DHT (ng/dL) | 11 | 134 | 38 |
| $E_2$ (pg/ml) | 3.8 | 10 | 21.4 |

Likewise, in contrast to the scrotal patch, TESTODERM® TTS (testosterone transdermal) treatment creates a DHT/T ratio that is not different from that of a placebo treatment. Both systems, however, suffer from similar problems. In clinical studies, TESTODERM® TTS (testosterone transdermal) is associated with transient itching in 12% of patients, erythema in 3% of patients, and puritus in 2% of patients. Moreover, in one 14-day study, 42% of patients reported three or more detachments, 33% of which occurred during exercise.

c. ANDRODERM® (Testosterone Transdermal System).

ANDRODERM® (testosterone transdermal system, Watson Laboratories, Inc., Corona, Calif.) is a testosterone-containing patch applied to non-scrotal skin. The circular patch has a total surface area of 37 cm.2 The patch consists of a liquid reservoir containing 12.2 mg of testosterone and a permeation-enhanced vehicle containing ethanol, water, monoglycerides, fatty acid esters, and gelling agents. The suggested dose of two patches, applied each night in a rotating manner on the back, abdomen, upper arm, or thigh, delivers 4.1 to 6.8 mg of testosterone.

The steady state pharmacokinetic profile of a clinical study involving ANDRODERM® (testosterone transdermal system) is shown in FIG. 4. In general, upon repeated application of the ANDRODERM® (testosterone transdermal system) patch, serum testosterone levels increase gradually for eight hours after each application and then remain at this plateau level for about another eight hours before declining.

In clinical trials, ANDRODERM® (testosterone transdermal system) is associated with skin irritation in about a third of the patients, and 10% to 15% of subjects have been reported to discontinue the treatment because of chronic skin irritation. Preapplication of corticosteroid cream at the site of application of ANDRODERM® (testosterone transdermal system) has been reported to decrease the incidence and severity of the skin irritation. A recent study, however, found that the incidence of skin reactions sufficiently noxious enough to interrupt therapy was as high as 52%. See Parker et al., Experience with Transdermal Testosterone Replacement in Hypogonadal Men, 50 *Clinical Endocrinology* (Oxf) 57-62 (1999). The study reported: Two-thirds of respondents found the ANDROPATCH® (testosterone transdermal) unsatisfactory. Patches were variously described as noisy, visually indiscrete, embarrassing, unpleasant to apply and remove, and generally to be socially unacceptable. They fell off in swimming pools and showers, attracted ribald comments from sporting partners, and left bald red marks over trunk and limbs. Dogs, wives, and children were distracted by noise of the patches with body movements. Those with poor mobility or manual dexterity (and several were over 70 years of age) found it difficult to remove packaging an apply patches dorsally.

d. Transdermal Patch Summary.

In sum, the transdermal patch generally offers an improved pharmacokinetic profile compared to other currently used testosterone delivery mechanisms. However, as discussed above, the clinical and survey data shows that all of these patches suffer from significant drawbacks, such as buritus, burn-like blisters, and erythema. Moreover, one recent study has concluded that the adverse effects associated with transdermal patch systems are "substantially higher" than reported in clinical trials. See Parker, supra. Thus, the transdermal patch still remains an inadequate testosterone replacement therapy alternative for most men.

5. DHT Gels.

Researchers have recently begun investigating the application of DHT to the skin in a transdermal gel. However, the pharmacokinetics of a DHT-gel is markedly different from that of a testosterone gel. Application of DHT-gel results in decreased serum testosterone, E2, LH, and FSH levels. Thus, DHT gels are not effective at increasing testosterone levels in hypogonadal men. Accordingly, there is a definite need for a testosterone formulation that safely and effectively provides an optimal and predictable pharmacokinetic profile.

SUMMARY OF INVENTION

The foregoing problems are solved and a technical advance is achieved with the present invention. The present invention generally comprises a testosterone gel. Daily transdermal application of the gel in hypogonadal men results in a unique pharmacokinetic steady-state profile for testosterone. Long-term treatment further results in, for example, increased bone mineral density, enhanced libido, enhanced erectile frequency and satisfaction, increased positive mood, increased muscle strength, and improved body composition without significant skin irritation. The present invention is also directed to a unique method of administering the testosterone gel employing a packet having a polyethylene liner compatible with the components of the gel.

BRIEF DESCRIPTION OF DRAWINGS

FIG. 17 is a graph showing the osteocalcin concentrations on days 0 through 180 for hypogonadal men receiving either 5.0 g/day of ANDROGEL® (testosterone gel), 10.0 g/day of ANDROGEL® (testosterone gel), or the testosterone patch (by initial treatment group).

DETAILED DESCRIPTION

Figure 1:
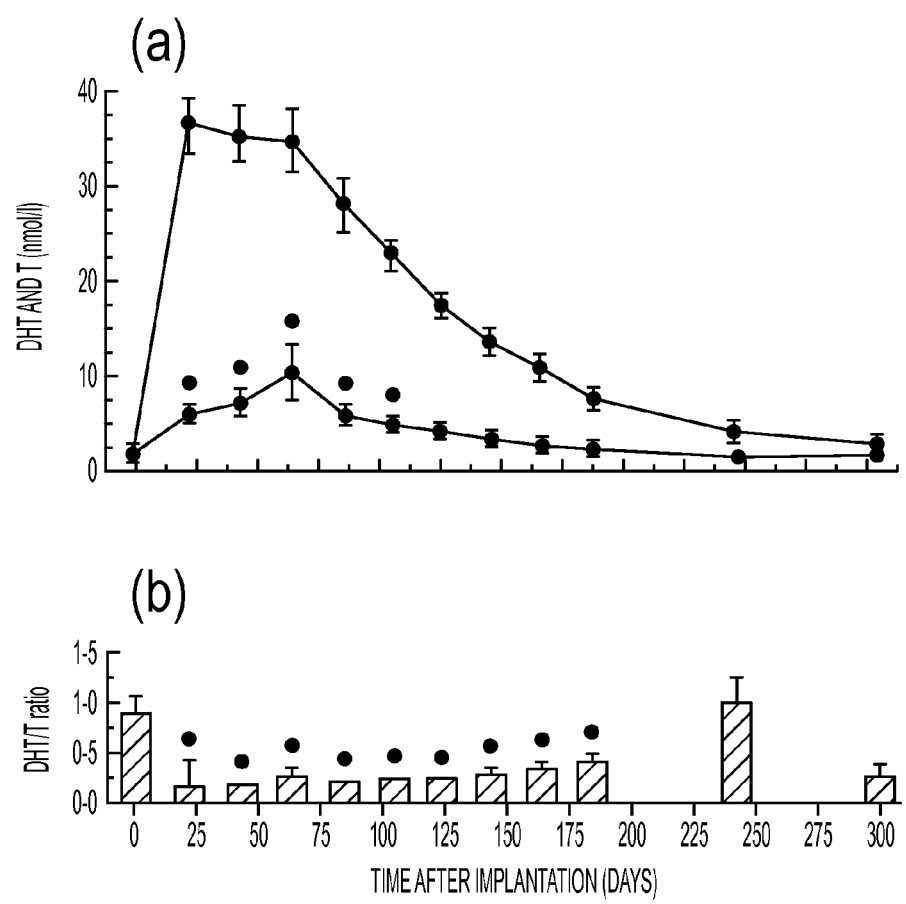
FIG. 1 is a graph of testosterone concentrations, DHT concentrations, and the DHT/T ratio for patients receiving a subdermal testosterone pellet implant over a period of 300 days after implantation.
Figure 2:
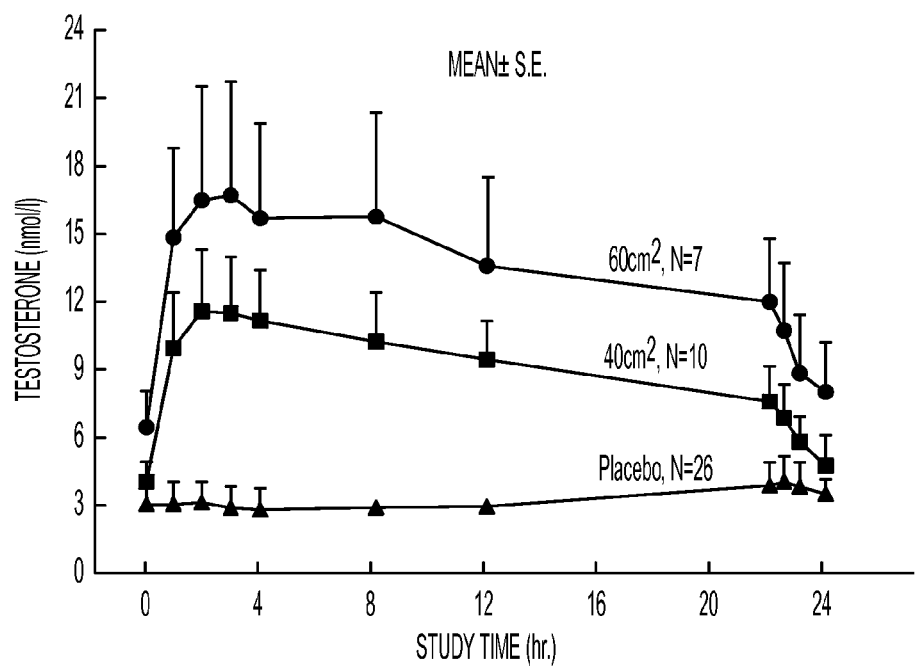
FIG. 2 shows a typical pharmacokinetic testosterone profile for both the 40 cm2 and 60 cm2 patch. Studies have also shown that after two to four weeks of continuous daily use, the average plasma concentration of DHT and DHT/T increased four to five times above normal. The high serum DHT levels are presumably caused by the increased metabolism of 5α-reductase in the scrotal skin.
Figure 3:
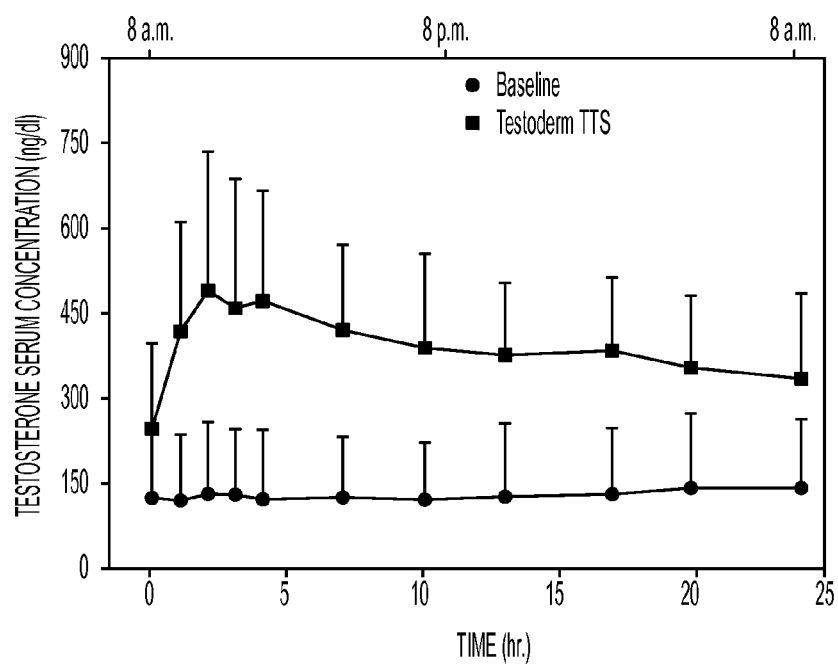
FIG. 3 is a 24-hour testosterone pharmacokinetic profile for patients receiving the TESTODERM® TTS (testosterone transdermal) patch.
Figure 4:
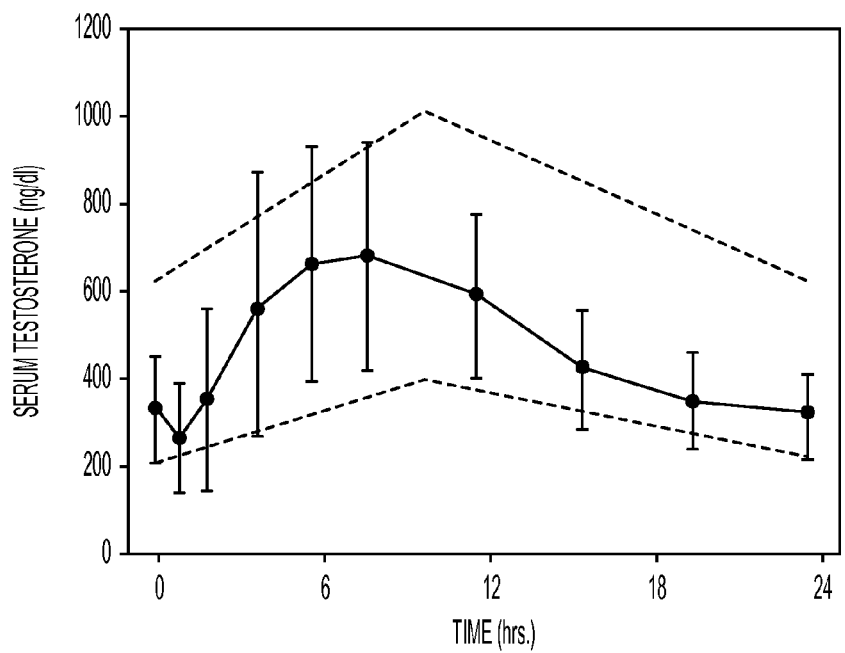
FIG. 4 is a 24-hour testosterone pharmacokinetic profile for patients receiving the ANDRODERM® (testosterone transdermal system) patch.

While the present invention may be embodied in many different forms, several specific embodiments are discussed herein with the understanding that the present disclosure is to be considered only as an exemplification of the principles of the invention, and it is not intended to limit the invention to the embodiments illustrated.

The present invention is directed to a pharmaceutical composition for percutaneous administration comprising at least one active pharmaceutical ingredient (e.g., testosterone) in a hydroalcoholic gel. In a broad aspect of the invention, the active ingredients employed in the composition may include anabolic steroids such as androisoxazole, bolasterone, clostebol, ethylestrenol, formyldienolone, 4-hydroxy-19-nortestosterone, methenolone, methyltrienolone, nandrolone, oxymesterone, quinbolone, stenbolone, trenbolone; androgenic steroids such as boldenone, fluoxymesterone, mestanolone, mesterolone, methandrostenolone, 17-methyltestosterone, 17-Alpha-methyl-testosterone 3-cyclopentyl enol ether, norethandrolone, normethandrone, oxandrolone, oxymetholone, prasterone, stanlolone, stanozolol, dihydrotestosterone, testosterone; and progestogens such as anagestone, chlormadinone acetate, delmadinone acetate, demegestone, dimethisterone, dihydrogesterone, ethinylestrenol, ethisterone, ethynodiol, ethynodiol diacetate, flurogestone acetate, gestodene, gestonorone caproate, haloprogesterone, 17-hydroxy-16-methylene-progesterone, 17 Beta-hydroxyprogesterone, 17 Alpha-hydroxyprogesterone caproate, medrogestone, medroxyprogesterone, megestrol acetate, melengestrol, norethindrone, norethindrone acetate, norethynodrel, norgesterone, norgestimate, norgestrel, norgestrienone, 19-norprogesterone, norvinisterone, pentagestrone, progesterone, promegestone, quingestrone, and trengestone; and all enantiomers, isomers and derivatives of these compounds. (Based upon the list provided in The Merck Index, Merck & Co. Rahway, N.J. (1998)).

In addition to the active ingredient, the gel comprises one or more lower alcohols, such as ethanol or isopropanol; a penetration enhancing agent; a thickener; and water. Additionally, the present invention may optionally include salts, emollients, stabilizers, antimicrobials, fragrances, and propellants.

A "penetration enhancer" is an agent known to accelerate the delivery of the drug through the skin. These agents also have been referred to as accelerants, adjuvants, and absorption promoters, and are collectively referred to herein as "enhancers." This class of agents includes those with diverse mechanisms of action including those which have the function of improving the solubility and diffusibility of the drug, and those which improve percutaneous absorption by changing the ability of the stratum corneum to retain moisture, softening the skin, improving the skin's permeability, acting as penetration assistants or hair-follicle openers or changing the state of the skin such as the boundary layer.

The penetration enhancer of the present invention is a functional derivative of a fatty acid, which includes isosteric modifications of fatty acids or non-acidic derivatives of the carboxylic functional group of a fatty acid or isosteric modifications thereof. In one embodiment, the functional derivative of a fatty acid is an unsaturated alkanoic acid in which the COOH group is substituted with a functional derivative thereof, such as alcohols, polyols, amides and substituted derivatives thereof. The term "fatty acid" means a fatty acid that has four (4) to twenty-four (24) carbon atoms. Non-limiting examples of penetration enhancers include C8-C22 fatty acids such as isostearic acid, octanoic acid, and oleic acid; C8-C22 fatty alcohols such as oleyl alcohol and lauryl alcohol; lower alkyl esters of C8-C22 fatty acids such as ethyl oleate, isopropyl myristate, butyl stearate, and methyllaurate; di(lower)alkyl esters of C6-C8 diacids such as diisopropyl adipate; monoglycerides of C8-C22 fatty acids such as glyceryl monolaurate; tetrahydrofurfuryl alcohol polyethylene glycol ether; polyethylene glycol, propylene glycol; 2-(2-ethoxyethoxy) ethanol; diethylene glycol monomethyl ether; alkylaryl ethers of polyethylene oxide; polyethylene oxide monomethyl ethers; polyethylene oxide, dimethyl ethers; dimethyl sulfoxide; glycerol; ethyl acetate; acetoacetic ester; N-alkylpyrrolidone; and terpenes.

The thickeners used herein may include anionic polymers such as polyacrylic acid (CARBOPOL® by B.F. Goodrich Specialty Polymers and Chemicals Division of Cleveland, Ohio), carboxymethylcellulose and the like. Additional thickeners, enhancers and adjuvants may generally be found in United States Pharmacopeia/National Formulary (2000); Remington's The Science and Practice of Pharmacy, Meade Publishing Co.

The amount of drug to be incorporated in the composition varies depending on the particular drug, the desired therapeutic effect, and the time span for which the gel is to provide a therapeutic effect. The composition is used in a "pharmacologically effective amount." This means that the concentration of the drug is such that in the composition it results in a therapeutic level of drug delivered over the term that the gel is to be used. Such delivery is dependent on a number of variables including the drug, the form of drug, the time period for which the individual dosage unit is to be used, the flux rate of the drug from the gel, surface area of application site, etc. The amount of drug necessary can be experimentally determined based on the flux rate of the drug through the gel, and through the skin when used with and without enhancers.

One such testosterone gel has only recently been made available in the United States under the trademark ANDROGEL® (testosterone gel) by Unimed Pharmaceuticals, Inc., Deerfield, Ill., one of the assignees of this application. In one embodiment, the gel is comprised of the following substances in approximate amounts:

TABLE 5

Composition of ANDROGEL ® (testosterone gel)

| SUBSTANCE | AMOUNT (w/w) PER 100 g OF GEL |
|---|---|
| Testosterone | 1.0 g |
| CARBOPOL ® 980 | 0.90 g |
| Isopropyl myristate | 0.50 g |
| 0.1N NaOH | 4.72 g |
| Ethanol (95% w/w) | 72.5 g* |
| Purified water (qsf) | 100 g |

*Corresponding to 67 g of ethanol.

One skilled in the art will appreciate that the constituents of this formulation may be varied in amounts yet continue to be within the spirit and scope of the present invention. For example, the composition may contain about 0.1 to about 10.0 g of testosterone, about 0.1 to about 5.0 g CARBOPOL® (polyacrylic acid), about 0.1 to about 5.0 g isopropyl myristate, and about 30.0 to about 98.0 g ethanol; or about 0.1% to about 10.0% of testosterone, about 0.1% to about 5.0% CARBOPOL® (polyacrylic acid), about 0.1% to about 5.0% isopropyl myristate, and about 30.0% to about 98.0% ethanol, on a weight to weight basis of the composition.

A therapeutically effective amount of the gel is rubbed onto a given area of skin by the user. The combination of the lipophilic testosterone with the hydroalcoholic gel helps drive the testosterone in to the outer layers of the skin where it is absorbed and then slowly released into the blood stream. As demonstrated by the data presented herein, the administration of the gel of the present invention has a sustained effect.

Toxicity and therapeutic efficacy of the active ingredients can be determined by standard pharmaceutical procedures, e.g., for determining LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The term "treatment" as used herein refers to any treatment of a human condition or disease and includes: (1) preventing the disease or condition from occurring in a subject which may be predisposed to the disease but has not yet been diagnosed as having it, (2) inhibiting the disease or condition, i.e., arresting its development, (3) relieving the disease or condition, i.e., causing regression of the condition, or (4) relieving the conditions caused by the disease, i.e., stopping the symptoms of the disease.

Although the examples of the present invention involve the treatment of disorders associated with hypogonadal men, the composition and method of the present invention may be used to treat these disorders in humans and animals of any kind, such as dogs, pigs, sheep, horses, cows, cats, zoo animals, and other commercially bred farm animals.

The present invention is further illustrated by the following examples, which should not be construed as limiting in any way. The contents of all cited references throughout this application are hereby expressly incorporated by reference. The practice of the present invention will employ, unless otherwise indicated, conventional techniques of pharmacology and pharmaceutics, which are within the skill of the art.

Example 1

Treatment of Hypogonadism in Male Subjects

One embodiment of the present invention involves the transdermal application of ANDROGEL® (testosterone gel) as a method of treating male hypogonadism. As demonstrated below, application of the gel results in a unique pharmacokinetic profile for testosterone, as well as concomitant modulation of several other sex hormones. Application of the testosterone gel to hypogonadal male subjects also results in (1) increased bone mineral density, (2) enhanced libido, (3) enhanced erectile capability and satisfaction, (4) increased positive mood, (5) increased muscle strength, and (6) better body composition, such increased total body lean mass and decreased total body fat mass. Moreover, the gel is not generally associated with significant skin irritation.

Methods.

In this example, hypogonadal men were recruited and studied in 16 centers in the United States. The patients were between 19 and 68 years and had single morning serum testosterone levels at screening of less than or equal to 300 ng/dL (10.4 nmol/L). A total of 227 patients were enrolled: 73, 78, and 76 were randomized to receive 5.0 g/day of ANDROGEL® (testosterone gel) (delivering 50 mg/day of testosterone to the skin of which about 10% or 5 mg is absorbed), 10.0 g/day of ANDROGEL® (testosterone gel) (delivering 100 mg/day of testosterone to the skin of which about 10% or 10 mg is absorbed), or the ANDRODERM® (testosterone transdermal system) testosterone patch ("T patch") (delivering 50 mg/day of testosterone), respectively.

As shown in the following table, there were no significant group-associated differences of the patients' characteristics at baseline.

TABLE 6

| Baseline Characteristics of the Hypogonadal Men | | | |
|---|---|---|---|
| | T patch | ANDROGEL ® (testosterone gel) (5.0 g/day) | ANDROGEL ® (testosterone gel) (10.0 g/day) |
| Treatment Group | | | |
| No of subjects enrolled | 76 | 73 | 78 |
| Age (years) | 51.1 | 51.3 | 51.0 |
| Range (years) | 28-67 | 23-67 | 19-68 |
| Height (cm) | 179.3 ± 0.9 | 175.8 ± 0.8 | 178.6 ± 0.8 |
| Weight (kg) | 92.7 ± 1.6 | 90.5 ± 1.8 | 91.6 ± 1.5 |
| Serum testosterone (nmol/L) | 6.40 ± 0.41 | 6.44 ± 0.39 | 6.49 ± 0.37 |
| Causes of hypogonadism | | | |
| Primary hypogonadism | 34 | 26 | 34 |
| Klinefelter's Syndrome | 9 | 5 | 8 |
| Post Orchidectomy/Anorchia | 2 | 1 | 3 |
| Primary Testicular Failure | 23 | 20 | 23 |
| Secondary hypogonadism | 15 | 17 | 12 |
| Kallman's Syndrome | 2 | 2 | 0 |
| Hypothalimic Pituitary Disorder | 6 | 6 | 3 |
| Pituitary Tumor | 7 | 9 | 9 |
| Aging | 6 | 13 | 6 |
| Not classified | 21 | 17 | 26 |
| Years diagnosed | 5.8 ± 1.1 | 4.4 ± 0.9 | 5.7 ± 1.24 |
| Number previously treated with testosterone | 50 (65.8%) | 38 (52.1%) | 46 (59.0%) |
| Type of Previous Hormonal Treatment | | | |
| Intramuscular injections | 26 | 20 | 28 |
| Transdermal patch | 12 | 7 | 8 |
| All others | 12 | 11 | 10 |
| Duration of treatment (years) | 5.8 ± 1.0 | 5.4 ± 0.8 | 4.6 ± 80.7 |

Forty-one percent (93/227) of the subjects had not received prior testosterone replacement therapy. Previously treated hypogonadal men were withdrawn from testosterone ester injection for at least six weeks and oral or transdermal androgens for four weeks before the screening visit. Aside from the hypogonadism, the subjects were in good health as evidenced by medical history, physical examination, complete blood count, urinalysis, and serum biochemistry. If the subjects were on lipid-lowering agents or tranquilizers, the doses were stabilized for at least three months prior to enrollment. Less than 5% of the subjects were taking supplemental calcium or vitamin D during the study. The subjects had no history of chronic medical illness, alcohol or drug abuse. They had a normal rectal examination, a PSA level of less than 4 ng/mL, and a urine flow rate of 12 mL/s or greater. Patients were excluded if they had a generalized skin disease that might affect the testosterone absorption or prior history of skin irritability with ANDRODERM® (testosterone transdermal system) patch. Subjects weighing less than 80% or over 140% of their ideal body weight were also excluded.

The randomized, multi-center, parallel study compared two doses of ANDROGEL® (testosterone gel) with the ANDRODERM® (testosterone transdermal system) testosterone patch. The study was double-blind with respect to the ANDROGEL® (testosterone gel) dose and open-labeled for the testosterone patch group. For the first three months of the study (days 1 to 90), the subjects were randomized to receive 5.0 g/day of ANDROGEL® (testosterone gel), 10.0 g/day of ANDROGEL® (testosterone gel), or two non-scrotal patches. In the following three months (days 91 to 180), the subjects were administered one of the following treatments: 5.0 g/day of ANDROGEL® (testosterone gel), 10.0 g/day of ANDROGEL® (testosterone gel), 7.5 g/day of ANDROGEL® (testosterone gel), or two non-scrotal patches. Patients who were applying ANDROGEL® (testosterone gel) had a single, pre-application serum testosterone measured on day 60 and, if the levels were within the normal range of 300 to 1,000 ng/dL (10.4 to 34.7 nmol/L), then they remained on their original dose. Patients with testosterone levels less than 300 ng/dL and who were originally assigned to apply 5.0 g/day of ANDROGEL® (testosterone gel) and those with testosterone levels more than 1,000 ng/dL who had received 10.0 g/day of ANDROGEL® (testosterone gel) were then reassigned to administer 7.5 of ANDROGEL® (testosterone gel) for days 91 to 180.

Accordingly, at 90 days, dose adjustments were made in the ANDROGEL® (testosterone gel) groups based on the pre-application serum testosterone levels on day 60. Twenty subjects in the 5.0 g/day ANDROGEL® (testosterone gel) group had the dose increased to 7.5 g/day. Twenty patients in the 10.0 g/day ANDROGEL® (testosterone gel) group had the ANDROGEL® (testosterone gel) dose reduced to 7.5 g/day. There were three patients in the testosterone patch group who were switched to 5.0 g/day ANDROGEL® (testosterone gel) because of patch intolerance. One 10.0 g/day ANDROGEL® (testosterone gel) subject was adjusted to receive 5.0 g/day and one 5.0 ANDROGEL® (testosterone gel) subject had the dose adjusted to 2.5 g/day. The number of subjects enrolled into day 91 to 180 of the study thus consisted of 51 receiving 5.0 g/day of ANDROGEL® (testosterone gel), 40 receiving 7.5 g/day of ANDROGEL® (testosterone gel), 52 receiving 10.0 g/day of ANDROGEL® (testosterone gel), and 52 continuing on the ANDRODERM® (testosterone transdermal system) patch. The treatment groups in this example may thus be characterized in two ways, either by "initial" or by the "final" treatment group.

Subjects returned to the study center on days 0, 30, 60, 90, 120, 150, and 180 for a clinical examination, skin irritation and adverse event assessments. Fasting blood samples for calcium, inorganic phosphorus, parathyroid hormone ("PTH"), osteocalcin, type I procollagen, and skeletal specific alkaline phosphatase ("SALP") were collected on days 0, 30, 90, 120, and 180. In addition, a fasting two-hour timed urine collection for urine creatinine, calcium, and typecollagen cross-linked N-telopeptides ("N-telopeptide") were collected on days 0, 30, 90, 120, and 180. Other tests performed were as follows: (1) Hematology: hemoglobin, hematocrit, red blood cell count, platelets, white blood cell counts with differential analysis (neutrophils, lymphocytes, monocytes, eosinophils, and basophils); (2) Chemistry: alkaline phosphatase, alanine aminotransferase, serwn glutamic pyruvic transaminase ("ALT/SGPT"), asparate aminotransferase/ serwn glutamin axaloacetic transaminase ("AST/SGOT"), total bilirubin, creatinine, glucose, and elecrolytes (sodium, potassium, choride, bicarbonate, calcium, and inorganic phosphorus); (3) Lipids: total cholesterol, high-density lipoprotein ("HDL"), low-density lipoprotein ("LDL"), and triglycerides; (4) Urinalysis: color, appearance, specific gravity, pH, protein, glucose, ketones, blood, bilirubin, and nitrites; and (5) Other: PSA (screening days 90-180), prolactin (screening), and testosterone (screening) including electrolytes, glucose, renal, and liver function tests and lipid profile, were performed at all clinic visits. Bone mineral density ("BMD") was analyzed at day 0 and day 180.

A. ANDROGEL® (Testosterone Gel) and ANDRODERM® Patch.

Approximately 250 g of ANDROGEL® (testosterone gel) was packaged in multidose glass bottles that delivered 2.25 g of the gel for each actuation of the pump. Patients assigned to apply 5.0 g/day of ANDROGEL® (testosterone gel) testosterone were given one bottle of ANDROGEL® (testosterone gel) and one bottle of placebo gel (containing vehicle but no testosterone), while those assigned to receive 10.0 g/day of ANDROGEL® (testosterone gel) were dispensed two bottles of the active ANDROGEL® (testosterone gel). The patients were then instructed to apply the bottle contents to the right and left upper arms/shoulders and to the right and left sides of the abdomen on an alternate basis. For example, on the first day of the study, patients applied two actuations from one bottle, one each to the left and right upper arm/shoulder, and two actuations from the second bottle, one each to the left and right abdomen. On the following day of treatment, the applications were reversed. Alternate application sites continued throughout the study. After application of the gel to the skin, the gel dried within a few minutes. Patients washed their hands thoroughly with soap and water immediately after gel application.

The 7.5 g/day ANDROGEL® (testosterone gel) group received their dose in an open-label fashion. After 90 days, for the subjects titrated to the ANDROGEL® (testosterone gel) 7.5 g/day dose, the patients were supplied with three bottles, one containing placebo and the other two ANDROGEL® (testosterone gel). The subjects were instructed to apply one actuation from the placebo bottle and three actuations from a ANDROGEL® (testosterone gel) bottle to four different sites of the body as above. The sites were rotated each day taking the same sequence as described above.

ANDRODERM® (testosterone transdermal system) testosterone patches each delivering 2.5 mg/day of testosterone were provided to about one-third of the patients in the study. These patients were instructed to apply two testosterone patches to a clean, dry area of skin on the back, abdomen, upper arms, or thighs once per day. Application sites were rotated with approximately seven days interval between applications to the same site.

On study days when the patients were evaluated, the gel/patches were applied following pre-dose evaluations. On the remaining days, the testosterone gel or patches were applied at approximately 8:00 a.m. for 180 days.

B. Study Method and Results:
Hormone Pharmacokinetics.

On days 0, 1, 30, 90, and 180, the patients had multiple blood samples for testosterone and free testosterone measurements at 30, 15 and 0 minutes before and 2, 4, 8, 12, 16, and 24 hours after ANDROGEL® (testosterone gel) or patch application. In addition, subjects returned on days 60, 120, and 150 for a single blood sampling prior to application of the gel or patch. Serum DHT, E2, FSH, LH and SHBG were measured on samples collected before gel application on days 0, 30, 60, 90, 120, 150, and 180. Sera for all hormones were stored frozen at 20° C. until assay. All samples for a patient for each hormone were measured in the same assay whenever possible. The hormone assays were then measured at the Endocrine Research Laboratory of the UCLA-Harbor Medical Center.

The following table summarizes the pharmacokinetic parameters were measured for each patient:

TABLE 7

Pharmacokinetic Parameters

| | |
|---|---|
| $AUC_{0-24}$ | area under the curve from 0 to 24 hours, determined using the linear trapezoidal rule. |
| $C_{base}$ or $C_o$ | Baseline concentration |
| $C_{avg}$ | time-averaged concentration over the 24-hour dosing interval determined by $AUC_{0-24}/24$ |
| $C_{max}$ | maximum concentration during the 24-hour dosing interval |
| $C_{min}$ | minimum concentration during the 24-hour dosing interval |
| $T_{max}$ | time at which $C_{max}$ occurred |
| $T_{min}$ | time at which $C_{min}$ occurred |
| Fluctuation Index | extent of variation in the serum concentration over the course of a single day, calculated as $(C_{max} - C_{min})/C_{avg}$ |
| Accumulation ratio | increase in the daily drug exposure with continued dosing, calculated as the ratio of the AUC at steady on a particular day over the AUC on day 1 (e.g., $AUC_{day\,30}/AUC_{day\,1}$) |
| Net $AUC_{0-24}$ | $AUC_{0-24}$ on days 30, 90, 180 − $AUC_{0-24}$ on day 0 | a. Testosterone Pharmacokinetics:
(1) Methods.
Serum testosterone levels were measured after extraction with ethylacetate and hexane by a specific radioimmunoassay ("RIA") using reagents from ICN (Costa Mesa, Calif.). The cross reactivities of the antiserum used in the testosterone RIA were 2.0% for DHT, 2.3% for androstenedione, 0.8% for 3-Beta-androstanediol, 0.6% for etiocholanolone and less than 0.01% for all other steroids tested. The lower limit of quantitation ("LLQ") for serum testosterone measured by this assay was 25 ng/dL (0.87 nmol/L). The mean accuracy of the testosterone assay, determined by spiking steroid free serum with varying amounts of testosterone (0.9 to 52 nmol/L), was 104% and ranged from 92% to 117%. The intra-assay and inter-assay coefficients of the testosterone assay were 7.3 and 11.1%, respectively, at the normal adult male range. In normal adult men, testosterone concentrations range from 298 to 1,043 ng/dL (10.33 to 36.17 nmol/L) as determined at the UCLA-Harbor Medical Center.

(2) Baseline Concentration.

Figure 5A:
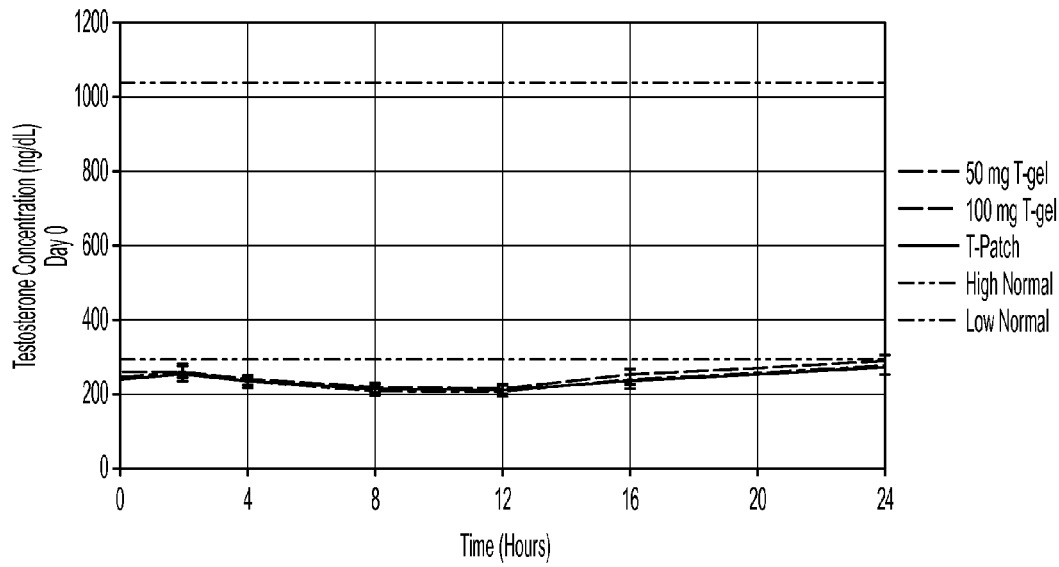
FIG. 5(*a*) is a graph showing the 24-hour testosterone pharmacokinetic profile for hypogonadal men prior to receiving 5.0 g/day of ANDROGEL® (testosterone gel), 10.0 g/day of ANDROGEL® (testosterone gel), or the testosterone patch (by initial treatment group).
FIG. 5(b) is a graph showing the 24-hour testosterone pharmacokinetic profile for hypogonadal men on the first day of treatment with either 5.0 g/day of ANDROGEL® (testosterone gel), 10.0 g/day of ANDROGEL® (testosterone gel), or the testosterone patch (by initial treatment group).
FIG. 5(c) is a graph showing the 24-hour testosterone pharmacokinetic profile for hypogonadal men on day 30 of treatment with either 5.0 g/day of ANDROGEL® (testosterone gel), 10.0 g/day of ANDROGEL® (testosterone gel), or the testosterone patch (by initial treatment group).
FIG. 5(d) is a graph showing the 24-hour testosterone pharmacokinetic profile for hypogonadal men on day 90 of treatment with either 5.0 g/day of ANDROGEL® (testosterone gel), 10.0 g/day of ANDROGEL® (testosterone gel), or the testosterone patch (by initial treatment group).
FIG. 5(e) is a graph showing the 24-hour testosterone pharmacokinetic profile for hypogonadal men on day 180 of treatment with either 5.0 g/day of ANDROGEL® (testosterone gel), 10.0 g/day of ANDROGEL® (testosterone gel), or the testosterone patch (by final treatment group).
FIG. 5(f) is a graph showing the 24-hour testosterone pharmacokinetic profile for hypogonadal men on day 0, 1, 30, 90, and 180 of treatment with 5.0 g/day of ANDROGEL® (testosterone gel).
FIG. 5(g) is a graph showing the 24-hour testosterone pharmacokinetic profile for hypogonadal men on day 0, 1, 30, 90, and 180 of treatment with 10.0 g/day of ANDROGEL® (testosterone gel).
FIG. 5(h) is a graph showing the 24-hour testosterone pharmacokinetic profile for hypogonadal men on day 0, 1, 30, 90, and 180 of treatment with the testosterone patch.

As shown in Table 8 and FIG. 5(a), at baseline, the average serum testosterone concentrations over 24 hours (Cavg) were similar in the groups and below the adult normal range. Moreover the variations of the serum concentration (based on maximum and minimum concentrations during the 24-hour period, Cmax and Cmin, respectively) during the day were also similar in the three groups. FIG. 5(a) shows that the mean testosterone levels had a maximum level between 8 to 10 a.m. (i.e., at 0 to 2 hours) and the minimum 8 to 12 hours later, demonstrating a mild diurnal variation of serum testosterone. About one-third of the patients in each group had Cavg within the lower normal adult male range on day 0 (24/73 for the 5.0 g/day ANDROGEL® (testosterone gel) group, 26/78 for the 10.0 g/day ANDROGEL® (testosterone gel) group, and 25/76 for testosterone patch group). All except three of the subjects met the enrollment criterion of serum testosterone less than 300 ng/dL (10.4 nmol/L) on admission.

TABLE 8(a)

Baseline Phamacokinetic Parameters by Initial Treatment Group (Mean ± SD)

| | 5.0 g/day T-Gel | 10.0 g/day T-gel | T-patch |
|---|---|---|---|
| N | 73 | 78 | 76 |
| $C_{avg}$ (ng/dL) | 237 ± 130 | 248 ± 140 | 237 ± 139 |
| $C_{max}$ (ng/dL) | 328 ± 178 | 333 ± 194 | 314 ± 179 |
| $T_{max}$* (hr) | 4.0 (0.0-24.5) | 7.9 (0.0-24.7) | 4.0 (0.0-24.3) |
| $C_{min}$ (ng/dL) | 175 ± 104 | 188 ± 112 | 181 ± 112 |
| $T_{min}$* (hr) | 8.01 (0.0-24.1) | 8.0 (0.0-24.0) | 8.0 (0.0-23.9) |
| Fluc Index (ratio) | 0.627 ± 0.479 | 0.556 ± 0.384 | 0.576 ± 0.341 |

*Median (Range*)

TABLE 8(b)

Baseline Testosterone Pharmacokinetic Parameters by Final Treatment Group (Mean ± SD)

| | Doses Received During Initial => Extended Treatment Phases | | | | |
|---|---|---|---|---|---|
| | 5.0 g/day T-gel | 5.0 => 7.5 g/day T-gel | 10.0 => 7.5 g/day T-gel | 10.0 g/day T-gel | T-patch |
| N | 53 | 20 | 20 | 58 | 76 |
| $C_{avg}$ (ng/dL) | 247 ± 137 | 212 ± 109 | 282 ± 157 | 236 ± 133 | 237 ± 140 |
| $C_{max}$ (ng/dL) | 333 ± 180 | 313 ± 174 | 408 ± 241 | 307 ± 170 | 314 ± 179 |
| $T_{max}$* (hr) | 4.0 (0.0-24.5) | 4.0 (0.0-24.0) | 19.7 (0.0-24.3) | 4.0 (0.0-24.7) | 4.0 (0.0-24.3) |
| $C_{min}$ (ng/dL) | 185 ± 111 | 150 ± 80 | 206 ± 130 | 182 ± 106 | 181 ± 112 |
| $T_{min}$* (hr) | 8.0 (0.0-24.1) | 11.9 (0.0-24.0) | 8.0 (0.0-23.3) | 8.0 (0.0-24.0) | 8.0 (0.0-23.9) |
| Fluc Index (ratio) | 0.600 ± 0.471 | 0.699 ± 0.503 | 0.678 ± 0.580 | 0.514 ± 0.284 | 0.576 ± 0.341 |

*Median (range)

(3) Day 1.

Figure 5B:
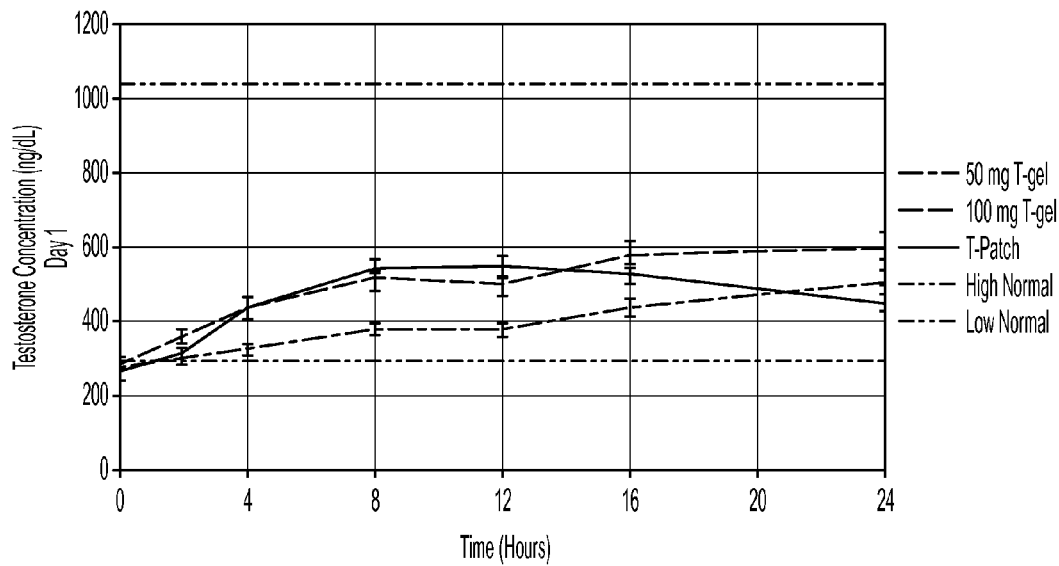

FIG. 5(b) and Tables 8(c)-(d) show the pharmacokinetic profile for all three initial treatment groups after the first application of transdermal testosterone. In general, treatment with ANDROGEL® (testosterone gel) and the testosterone patch produced increases in testosterone concentrations sufficiently large to bring the patients into the normal range in just a few hours. However, even on day 1, the pharmacokinetic profiles were markedly different in the ANDROGEL® (testosterone gel) and patch groups. Serum testosterone rose most rapidly in the testosterone patch group reaching a maximum concentration (Cmax) at about 12 hours (Tmax). In contrast, serum testosterone rose steadily to the normal range after ANDROGEL® (testosterone gel) application with Cmax levels achieved by 22 and 16 hours in the 5.0 g/day ANDROGEL® (testosterone gel) group and the 10.0 g/day ANDROGEL® (testosterone gel) group, respectively.

TABLE 8(c)

Testosterone Pharmacokinetic Parameters on Day 1 by Initial Treatment Group (Mean ± SD)

|  | 5.0 g/day T-Gel | 10.0 g/day T-gel | T-patch |
|---|---|---|---|
| N | 73 | 76 | 74 |
| $C_{avg}$ (ng/dL) | 398 ± 156 | 514 ± 227 | 482 ± 204 |
| $C_{max}$ (ng/dL) | 560 ± 269 | 748 ± 349 | 645 ± 280 |
| $T_{max}$* (hr) | 22.1 (0.0-25.3) | 16.0 (0.0-24.3) | 11.8 (1.8-24.0) |
| $C_{min}$ (ng/dL) | 228 ± 122 | 250 ± 143 | 232 ± 132 |
| $T_{min}$* (hr) | 1.9 (0.0-24.0) | 0.0 (0.0-24.2) | 1.5 (0.0-24.0) |

*Median (Range)

TABLE 8(d)

Testosterone Phamacokinetic Parameters on Day 1 by Final Treatment Group (Mean ± SD)

| | Doses Received During Initial => Extended Treatment Phases | | | | |
|---|---|---|---|---|---|
| | 5.0 g/day T-gel | 5.0 => 7.5 g/day T-gel | 10.0 => 7.5 g/day T-gel | 10.0 g/day T-gel | T-patch |
| N | 53 | 20 | 19 | 57 | 74 |
| $C_{avg}$ (ng/dL) | 411 ± 160 | 363 ± 143 | 554 ± 243 | 500 ± 223 | 482 ± 204 |
| $C_{max}$ (ng/dL) | 573 ± 285 | 525 ± 223 | 819 ± 359 | 724 ± 346 | 645 ± 280 |
| $T_{max}$* (hr) | 22.1 (0.0-25.3) | 19.5 (1.8-24.3) | 15.7 (3.9-24.0) | 23.0 (0.0-24.3) | 11.8 (1.8-24.0) |
| $C_{min}$ (ng/dL) | 237 ± 125 | 204 ± 112 | 265 ± 154 | 245 ± 140 | 232 ± 132 |
| $T_{min}$* (hr) | 1.8 (0.0-24.0) | 3.5 (0.0-24.0) | 1.9 (0.0-24.2) | 0.0 (0.0-23.8) | 1.5 (0.0-24.0) |
| Fluc Index (ratio) | 0.600 ± 0.471 | 0.699 ± 0.503 | 0.678 ± 0.580 | 0.514 ± 0.284 | 0.576 ± 0.341 |

*Median (range)

(4) Days 30, 90, and 180.

Figure 5C:
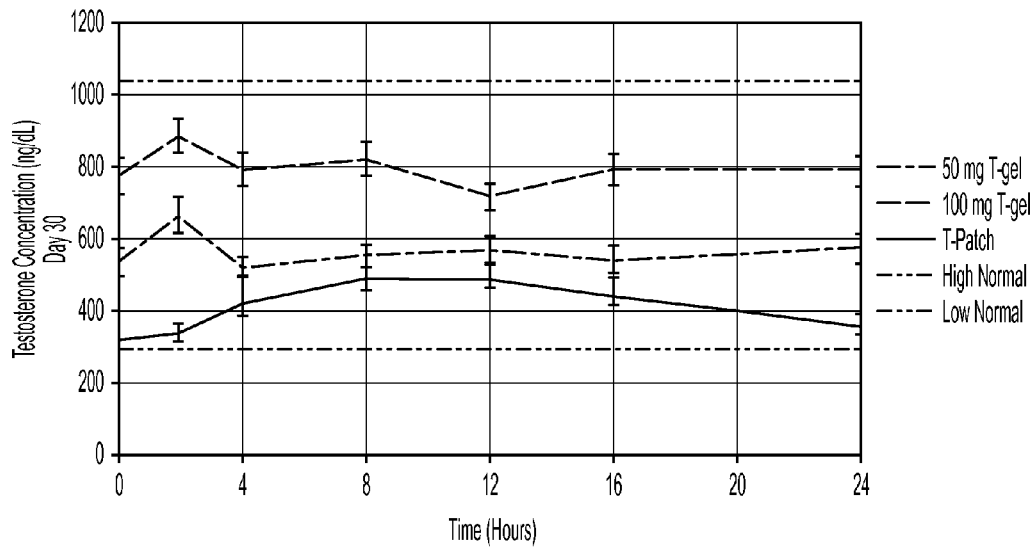
Figure 5D:
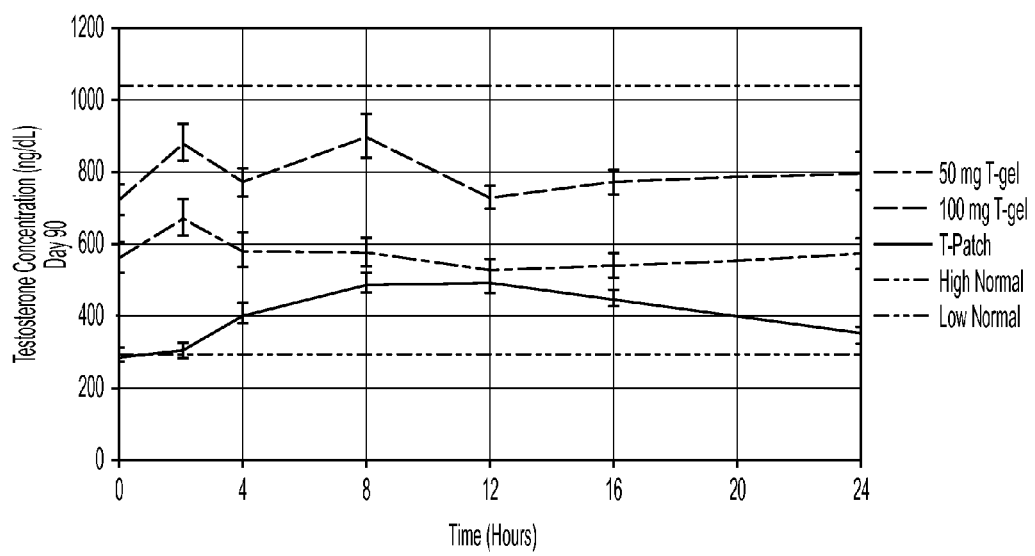

FIGS. 5(c) and 5(d) show the unique 24-hour pharmacokinetic profile of ANDROGEL® (testosterone gel)-treated patients on days 30 and 90. In the ANDROGEL® (testosterone gel) groups, serum testosterone levels showed small and variable increases shortly after dosing. The levels then returned to a relatively constant level. In contrast, in the testosterone patch group, patients exhibited a rise over the first 8 to 12 hours, a plateau for another 8 hours, and then a decline to the baseline of the prior day. Further, after gel application on both days 30 and 90, the Cavg in the 10.0 g/day ANDROGEL® (testosterone gel) group was 1.4 fold higher than in the 5.0 g/day ANDROGEL® (testosterone gel) group and 1.9 fold higher than the testosterone patch group. The testosterone patch group also had a Cmin substantially below the lower limit of the normal range. On day 30, the accumulation ratio was 0.94 for testosterone patch group, showing no accumulation. The accumulation ratios at 1.54 and 1.9 were significantly higher in the 5.0 g/day ANDROGEL® (testosterone gel) group and 10.0 g/day ANDROGEL® (testosterone gel) group, respectively. The differences in accumulation ratio among the groups persisted on day 90. This data indicates that the ANDROGEL® (testosterone gel) preparations had a longer effective half-life than testosterone patch.

Figure 5E:
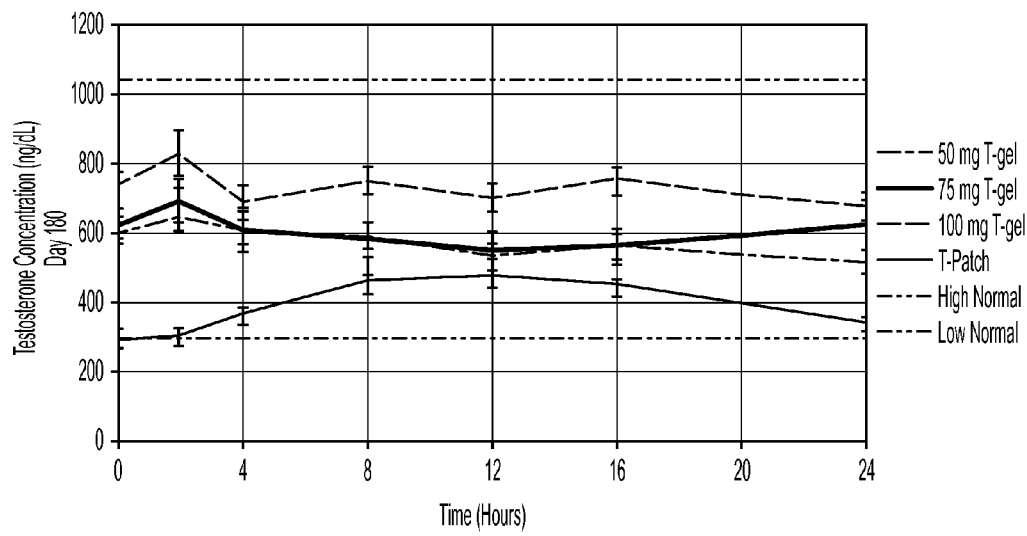

FIG. 5(e) shows the 24-hour pharmacokinetic profile for the treatment groups on day 180. In general, as Table 8(e) shows, the serum testosterone concentrations achieved and the pharmacokinetic parameters were similar to those on days 30 and 90 in those patients who continued on their initial randomized treatment groups. Table 8(f) shows that the patients titrated to the 7.5 g/day ANDROGEL® (testosterone gel) group were not homogeneous. The patients that were previously in the 10.0 g/day group tended to have higher serum testosterone levels than those previously receiving 5.0 g/day. On day 180, the Cavg in the patients in the 10.0 g/day group who converted to 7.5 g/day on day 90 was 744 ng/dL, which was 1.7 fold higher than the Cavg of 450 in the patients titrated to 7.5 g/day from 5.0 g/day. Despite adjusting the dose up by 2.5 g/day in the 5.0 to 7.5 g/day group, the Cavg remained lower than those remaining in the 5.0 group. In the 10.0 to 7.5 g/day group, the Cavg became similar to those achieved by patients remaining in the 10.0 g/day group without dose titration. These results suggest that many of the under-responders may actually be poorly compliant patients. For example, if a patient does not apply ANDROGEL® (testosterone gel) properly (e.g., preferentially from the placebo container or shortly before bathing), then increasing the dose will not provide any added benefit.

Figure 5F:
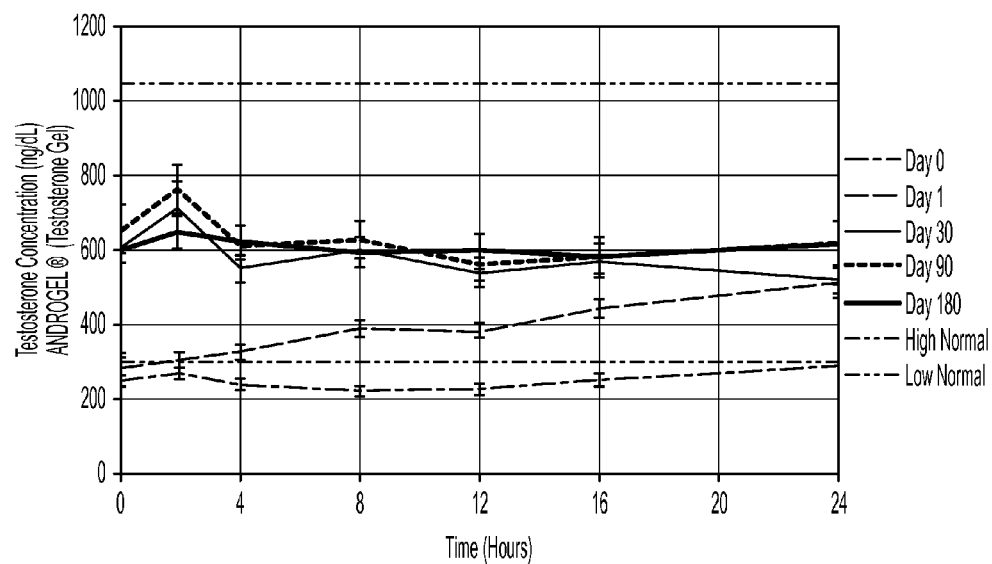
Figure 5G:
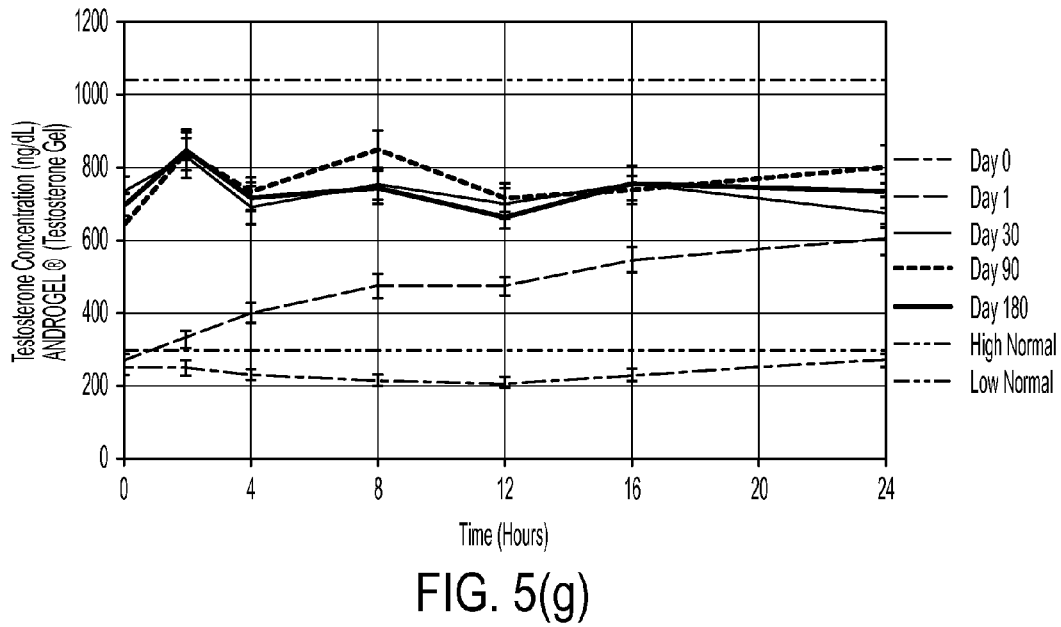
Figure 5H:
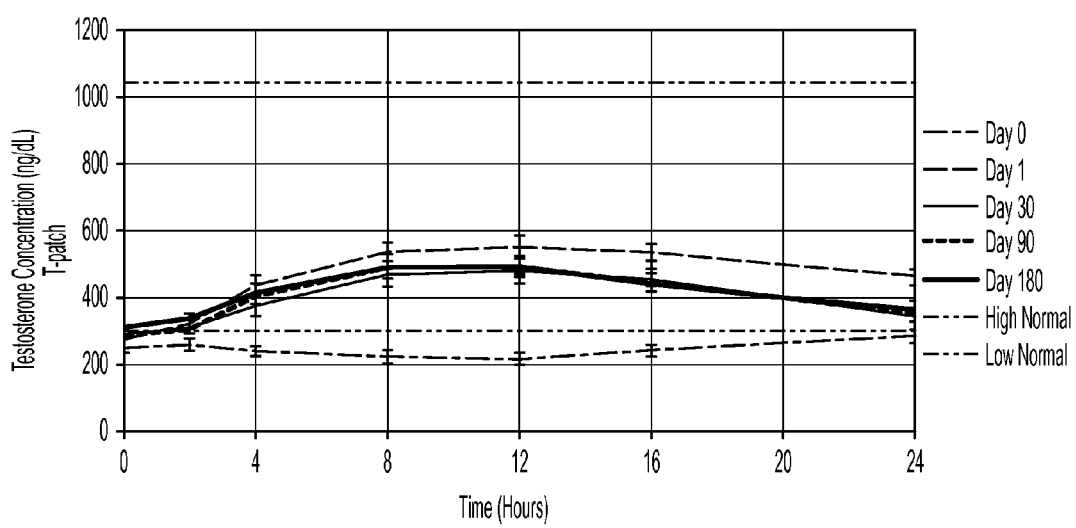

FIGS. 5(f)-(h) compare the pharmacokinetic profiles for the 5.0 g/day ANDROGEL® (testosterone gel) group, the 10.0 g/day ANDROGEL® (testosterone gel) g/day group, and the testosterone patch group at days 0, 1, 30, 90, and 180, respectively. In general, the mean serum testosterone levels in the testosterone patch group remained at the lower limit of the normal range throughout the treatment period. In contrast, the mean serum testosterone levels remained at about 490-570 ng/dL for the 5.0 g/day ANDROGEL® (testosterone gel) group and about 630-860 ng/dL ANDROGEL® (testosterone gel) for the 10.0 g/day group.

TABLE 8(e)

Testosterone Phamacokinetic Parameters on Day 1 by Initial Treatment Group (Mean ± SD)

|  | 5.0 g/day T-Gel | 10.0 g/day T-gel | T-patch |
|---|---|---|---|
| Day 30 | N = 66 | N = 74 | N = 70 |
| $C_{avg}$ (ng/dL) | 566 ± 262 | 792 ± 294 | 419 ± 163 |
| $C_{max}$ (ng/dL) | 876 ± 466 | 1200 ± 482 | 576 ± 223 |
| $T_{max}$*(hr) | 7.9 (0.0-24.0) | 7.8 (0.0-24.3) | 11.3 (0.0-24.0) |
| $C_{min}$ (ng/dL) | 361 ± 149 | 505 ± 233 | 235 ± 122 |
| $T_{min}$* (hr) | 8.0 (0.0-24.1) | 8.0 (0.0-25.8) | 2.0 (0.0-24.2) |
| Fluc Index (ratio) | 0.857 ± 0.331 | 0.895 ± 0.434 | 0.823 ± 0.289 |
| Accum Ratio (ratio) | 1.529 ± 0.726 | 1.911 ± 1.588 | 0.937 ± 0.354 |
| Day 90 | N = 65 | N = 73 | N = 64 |
| $C_{avg}$ (ng/dL) | 553 ± 247 | 792 ± 276 | 417 ± 157 |
| $C_{max}$ (ng/dL) | 846 ± 444 | 1204 ± 570 | 597 ± 242 |
| $T_{max}$*(hr) | 4.0 (0.0-24.1) | 7.9 (0.0-25.2) | 8.1 (0.0-25.0) |
| $C_{min}$ (ng/dL) | 354 ± 147 | 501 ± 193 | 213 ± 105 |
| $T_{min}$* (hr) | 4.0 (0.0-25.3) | 8.0 (0.0-24.8) | 2.0 (0.0-24.0) |
| Fluc Index (ratio) | 0.851 ± 0.402 | 0.859 ± 0.399 | 0.937 ± 0.442 |
| Accum Ratio (ratio) | 1.615 ± 0.859 | 1.927 ± 1.310 | 0.971 ± 0.453 |
| Day 180 | N = 63 | N = 68 | N = 45 |
| $C_{avg}$ (ng/dL) | 520 ± 227 | 722 ± 242 | 403 ± 163 |
| $C_{max}$ (ng/dL) | 779 ± 359 | 1091 ± 437 | 580 ± 240 |
| $T_{max}$*(hr) | 4.0 (0.0-24.0) | 7.9 (0.0-24.0) | 10.0 (0.0-24.0) |
| $C_{min}$ (ng/dL) | 348 ± 164 | 485 ± 184 | 223 ± 114 |
| $T_{min}$* (hr) | 11.9 (0.0-24.0) | 11.8 (0.0-27.4) | 2.0 (0.0-25.7) |
| Fluc Index (ratio) | 0.845 ± 0.379 | 0.829 ± 0.392 | 0.891 ± 0.319 |
| Accum Ratio (ratio) | 1.523 ± 1.024 | 1.897 ± 2.123 | 0.954 ± 0.4105 |

*Median (Range)

(5) Dose Proportionality for ANDROGEL® (Testosterone Gel).

Table 8(g) shows the increase in AUC0-24 on days 30, 90, and 180 from the pretreatment baseline (net AUC0-24). In order to assess dose-proportionality, the bioequivalence assessment was performed on the log-transformed AUCs using "treatment" as the only factor. The AUCs were compared after subtracting away the AUC contribution from the endogenous secretion of testosterone (the AUC on day 0) and adjusting for the two-fold difference in applied doses. The AUC ratio on day 30 was 0.95 (90% C.I.: 0.75-1.19) and on day 90 was 0.92 (90% C.I.: 0.73-1.17). When the day 30 and day 90 data was combined, the AUC ratio was 0.93 (90% C.I.: 0.79-1.10).

The data shows dose proportionality for ANDROGEL® (testosterone gel) treatment. The geometric mean for the increase in AUC0-24 from day 0 to day 30 or day 90 was twice as great for the 10.0 g/day group as for the 5.0 g/day group. A 125 ng/dL mean increase in serum testosterone Cavg level was produced by each 2.5 g/day of ANDROGEL® (testosterone gel). In other words, the data shows that 0.1 g/day of ANDROGEL® (testosterone gel) produced, on the average, a 5 ng/dL increase in serum testosterone concentration. This dose proportionality aids dosing adjustment by the physician. Because ANDROGEL® (testosterone gel) is provided in 2.5 g packets (containing 25 mg of testosterone), each 2.5 g packet will produce, on average, a 125 ng/dL increase in the Cavg for serum total testosterone.

TABLE 8(f)

Testosterone Phamacokinetic Parameters on Days 30, 90, 180 by Final Treatment Group (Mean ± SD)

| | Doses Received During Initial => Extended Treatment Phases | | | | |
|---|---|---|---|---|---|
| | 5.0 g/day T-gel | 5.0 => 7.5 g/day T-gel | 10.0 => 7.5 g/day T-gel | 10.0 g/day T-gel | T-patch |
| Day 30 | N = 47 | N = 19 | N = 19 | N = 55 | N = 70 |
| $C_{avg}$ (ng/dL) | 604 ± 288 | 472 ± 148 | 946 ± 399 | 739 ± 230 | 419 ± 163 |
| $C_{max}$ (ng/dL) | 941 ± 509 | 716 ± 294 | 1409 ± 556 | 1128 ± 436 | 576 ± 223 |
| $T_{max}$* (hr) | 7.9 (0.0-24.0) | 8.0 (0.0-24.0) | 8.0 (0.0-24.3) | 7.8 (0.0-24.3) | 11.3 (0.0-24.0) |
| $C_{min}$ (ng/dL) | 387 ± 159 | 296 ± 97 | 600 ± 339 | 471 ± 175 | 235 ± 122 |
| $T_{min}$* (hr) | 8.1 (0.0-24.1) | 1.7 (0.0-24.1) | 11.4 (0.0-24.1) | 8.0 (0.0-25.8) | 2.0 (0.0-24.2) |
| Fluc Index (ratio) | 0.861 ± 0.341 | 0.846 ± 0.315 | 0.927 ± 0.409 | 0.884 ± 0.445 | 0.823 ± 0.289 |
| Accum Ratio (ratio) | 1.543 ± 0.747 | 1.494 ± 0.691 | 2.053 ± 1.393 | 1.864 ± 1.657 | 0.937 ± 0.354 |
| Day 90 | N = 45 | N = 20 | N = 18 | N = 55 | N = 64 |
| $C_{avg}$ (ng/dL) | 596 ± 266 | 455 ± 164 | 859 ± 298 | 771 ± 268 | 417 ± 157 |
| $C_{max}$ (ng/dL) | 931 ± 455 | 654 ± 359 | 1398 ± 733 | 1141 ± 498 | 597 ± 242 |
| $T_{max}$* (hr) | 3.8 (0.0-24.1) | 7.7 (0.0-24.0) | 7.9 (0.0-24.0) | 7.9 (0.0-25.2) | 8.1 (0.0-25.0) |
| $C_{min}$ (ng/dL) | 384 ± 147 | 286 ± 125 | 532 ± 181 | 492 ± 197 | 213 ± 105 |
| $T_{min}$* (hr) | 7.9 (0.0-25.3) | 0.0 (0.0-24.0) | 12.0 (0.0-24.1) | 4.0 (0.0-24.8) | 2.0 (0.0-24.0) |
| Fluc Index (ratio) | 0.886 ± 0.391 | 0.771 ± 0.425 | 0.959 ± 0.490 | 0.826 ± 0.363 | 0.937 ± 0.442 |
| Accum Ratio (ratio) | 1.593 ± 0.813 | 1.737 ± 1.145 | 1.752 ± 0.700 | 1.952 ± 1.380 | 0.971 ± 0.453 |
| Day 180 | N = 44 | N = 18 | N = 19 | N = 48 | N = 41 |
| $C_{avg}$ (ng/dL) | 555 ± 225 | 450 ± 219 | 744 ± 320 | 713 ± 209 | 408 ± 165 |
| $C_{max}$ (ng/dL) | 803 ± 347 | 680 ± 369 | 1110 ± 468 | 1083 ± 434 | 578 ± 245 |
| $T_{max}$* (hr) | 5.8 (0.0-24.0) | 2.0 (0.0-24.0) | 7.8 (0.0-24.0) | 7.7 (0.0-24.0) | 10.6 (0.0-24.0) |
| $C_{min}$ (ng/dL) | 371 ± 165 | 302 ± 150 | 505 ± 233 | 485 ± 156 | 222 ± 116 |
| $T_{min}$* (hr) | 11.9 (0.0-24.0) | 9.9 (0.0-24.0) | 12.0 (0.0-24.0) | 8.0 (0.0-27.4) | 2.0 (0.0-25.7) |
| Fluc Index (ratio) | 0.853 ± 0.402 | 0.833 ± 0.335 | 0.824 ± 0.298 | 0.818 ± 0.421 | 0.866 ± 0.311 |
| Accum Ratio (ratio) | 1.541 ± 0.917 | NA | NA | 2.061 ± 2.445 | 0.969 ± 0.415 |

*Median (range)

TABLE 8(g)

Net $AUC_{0-24}$ (nmol*h/L) on Days 30, 90, and 180 after Transdermal Testosterone Application

|  | T Patch | T gel 5.0 g/day | T gel 10.0 g/day |
|---|---|---|---|
| Day 30 | 154 ± 18 | 268 ± 28 | 446 ± 30 |
| Day 90 | 157 ± 20 | 263 ± 29 | 461 ± 28 |
| Day 180 | 160 ± 25 | 250 ± 32 | 401 ± 27 |

The increase in AUC0-24 from pretreatment baseline achieved by the 10.0 g/day and the 5.0 g/day groups were approximately 2.7 and 1.7 fold higher than that resulting from application of the testosterone patch.

b. Pharmacokinetics of Serum Free Testosterone Concentration:

(1) Methods.

Serum free testosterone was measured by RIA of the dialysate, after an overnight equilibrium dialysis, using the same RIA reagents as the testosterone assay. The LLQ of serum free testosterone, using the equilibrium dialysis method, was estimated to be 22 pmol/L. When steroid free serum was spiked with increasing doses of testosterone in the adult male range, increasing amounts of free testosterone were recovered with a coefficient of variation that ranged from 11.0-18.5%. The intra- and interassay coefficients of free testosterone were 15% and 16.8% for adult normal male values, respectively. As estimated by the UCLA-Harbor Medical Center, free testosterone concentrations range from 3.48-17.9 ng/dL (121-620 pmol/L) in normal adult men.

(2) Pharmacokinetic Results.

In general, as shown in Table 9, the pharmacokinetic parameters of serum free testosterone mirrored that of serum total testosterone as described above. At baseline (day 0), the mean serum free testosterone concentrations (Cavg) were similar in all three groups which were at the lower limit of the adult male range. The maximum serum free testosterone concentration occurred between 8 and 10 a.m., and the minimum about 8 to 16 hours later. This data is consistent with the mild diurnal variation of serum testosterone.

Figure 6A:
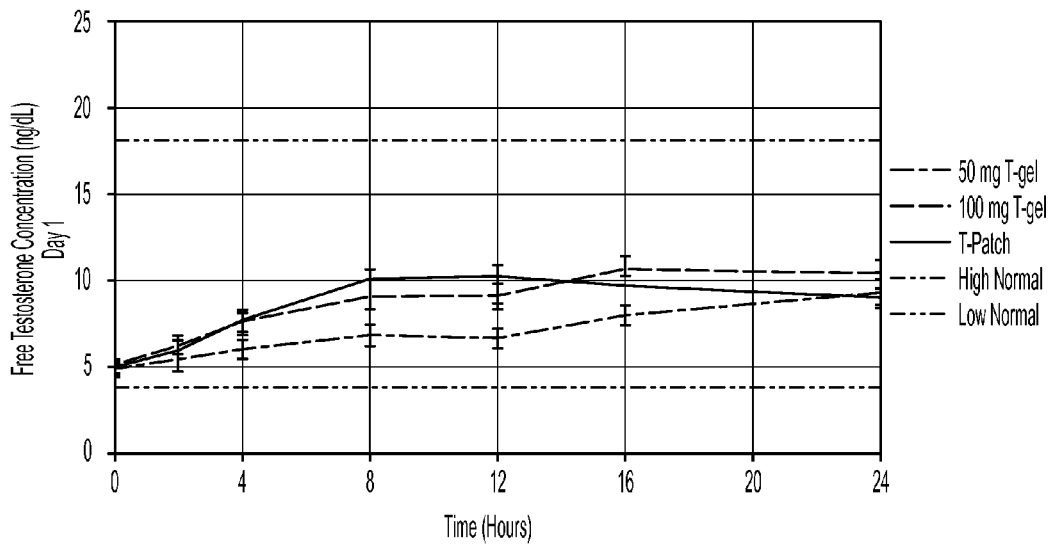
FIG. 6(a) is a graph showing the 24-hour free testosterone pharmacokinetic profile for hypogonadal men on day 1 of treatment with either 5.0 g/day of ANDROGEL® (testosterone gel), 10.0 g/day of ANDROGEL® (testosterone gel), or the testosterone patch (by initial treatment group).

FIG. 6(a) shows the 24-hour pharmacokinetic profiles for the three treatment groups on day 1. After application of the testosterone patch, the serum free testosterone levels peaked at about 4 hours earlier than those achieved by the ANDROGEL® (testosterone gel) groups. The serum free testosterone levels then declined in the testosterone patch group whereas in the ANDROGEL® (testosterone gel) groups, the serum free testosterone levels continued to rise.

Figure 6B:
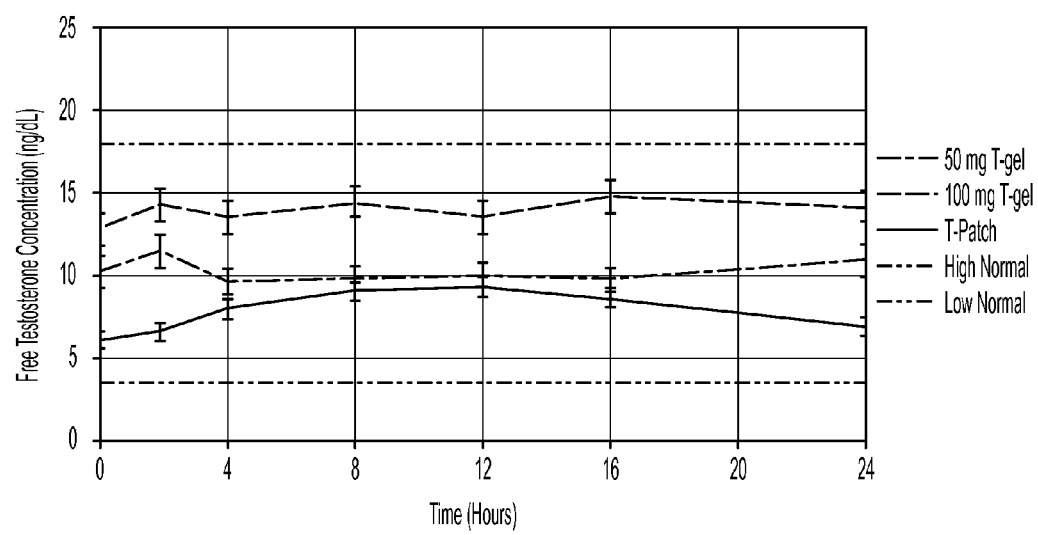
FIG. 6(b) is a graph showing the 24-hour free testosterone pharmacokinetic profile for hypogonadal men on day 30 of treatment with either 5.0 g/day of ANDROGEL® (testosterone gel), 10.0 g/day of ANDROGEL® (testosterone gel), or the testosterone patch (by initial treatment group).
Figure 6C:
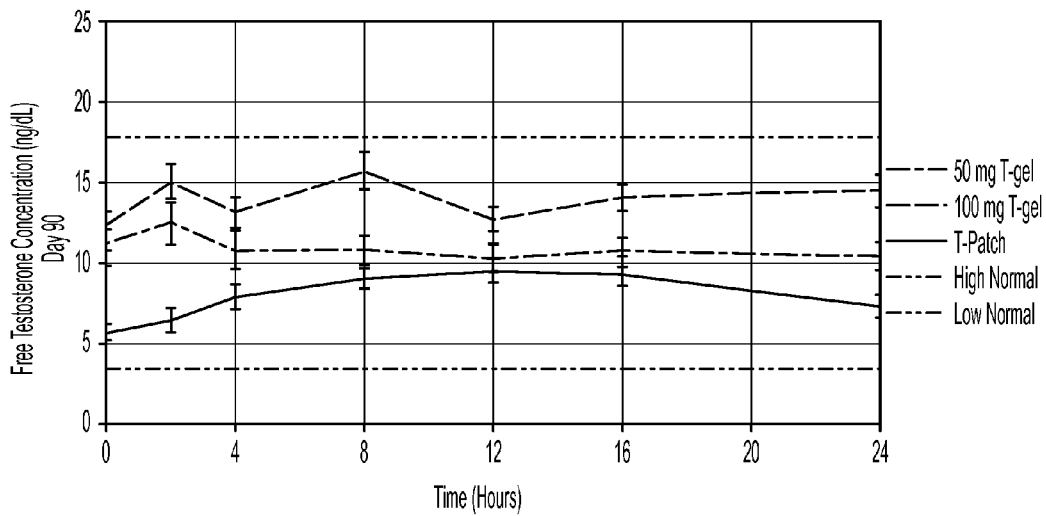
FIG. 6(c) is a graph showing the 24-hour free testosterone pharmacokinetic profile for hypogonadal men on day 90 of treatment with either 5.0 g/day of ANDROGEL® (testosterone gel), 10.0 g/day of ANDROGEL® (testosterone gel), or the testosterone patch (by initial treatment group).

FIGS. 6(b) and 6(c) show the pharmacokinetic profiles of free testosterone in the ANDROGEL® (testosterone gel)-treated groups resembled the unique testosterone profiles on days 30 and 90. After ANDROGEL® (testosterone gel) application, the mean serum free testosterone levels in the three groups were within normal range. Similar to the total testosterone results, the free testosterone Cavg achieved by the 10.0 g/day group was 1.4 fold higher than the 5.0 g/day group and 1.7 fold higher than the testosterone patch group. Moreover, the accumulation ratio for the testosterone patch was significantly less than that of the 5.0 g/day ANDROGEL® (testosterone gel) group and the 10.0 g/day ANDROGEL® (testosterone gel) group.

Figure 6D:
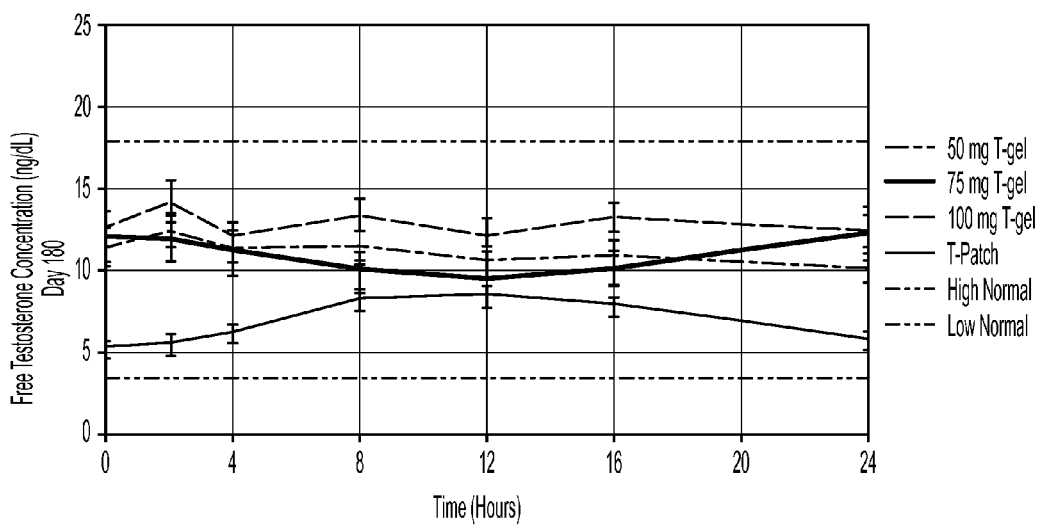
FIG. 6(d) is a graph showing the 24-hour free testosterone pharmacokinetic profile for hypogonadal men on day 180 of treatment with either 5.0 g/day of ANDROGEL® (testosterone gel), 10.0 g/day of ANDROGEL® (testosterone gel), or the testosterone patch (by final treatment group).

FIG. 6(d) shows the free testosterone concentrations by final treatment groups on day 180. In general, the free testosterone concentrations exhibited a similar pattern as serum testosterone. The 24-hour pharmacokinetic parameters were similar to those on days 30 and 90 in those subjects who remained in the three original randomized groups. Again, in the subjects titrated to receive 7.5 g/day of ANDROGEL® (testosterone gel), the group was not homogenous. The free testosterone Cavg in the patients with doses adjusted upwards from 5.0 to 7.5 g/day remained 29% lower than those of subjects remaining in the 5.0 g/day group. The free testosterone Cavg in the patients whose doses were decreased from 10.0 to 7.5 g/day was 11% higher than those in remaining in the 10.0 g/day group.

Figure 6E:
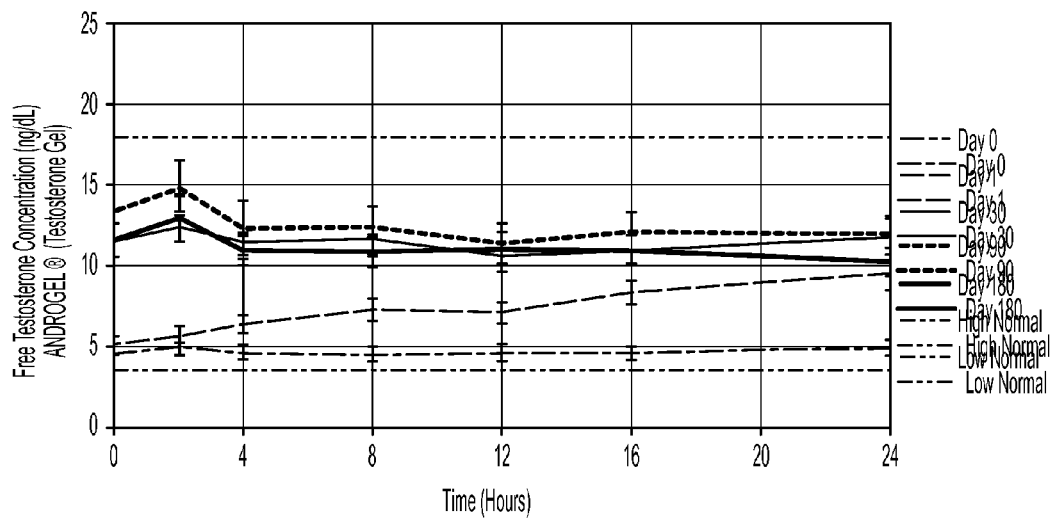
FIG. 6(e) is a graph showing the 24-hour free testosterone pharmacokinetic profile for hypogonadal men on day 0, 1, 30, 90, and 180 of treatment with 5.0 g/day of ANDROGEL® (testosterone gel).
Figure 6F:
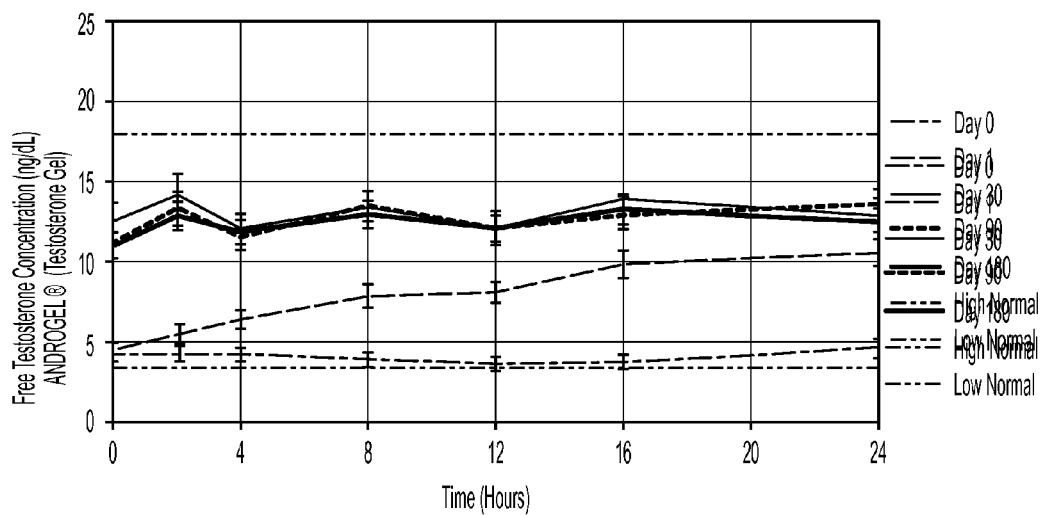
FIG. 6(f) is a graph showing the 24-hour free testosterone pharmacokinetic profile for hypogonadal men on day 0, 1, 30, 90, and 180 of treatment with 10.0 g/day of ANDROGEL® (testosterone gel).
Figure 6G:
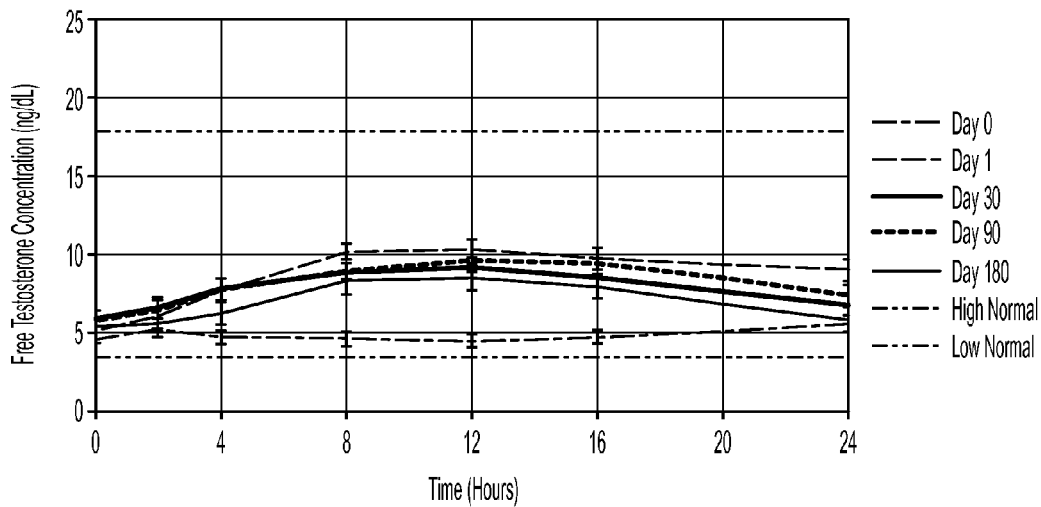
FIG. 6(g) is a graph showing the 24-hour free testosterone pharmacokinetic profile for hypogonadal men on day 0, 1, 30, 90, and 180 of treatment with the testosterone patch.

FIGS. 6(e)-(g) show the free testosterone concentrations in the three groups of subjects throughout the 180-day treatment period. Again, the free testosterone levels followed that of testosterone. The mean free testosterone levels in all three groups were within the normal range with the 10.0 g/day group maintaining higher free testosterone levels than both the 5.0 g/day and the testosterone patch groups.

TABLE 9

Free Testosterone Pharmacokinetic Parameters by Final Treatment (Mean ± SD)

Doses Received During Initial => Extended Treatment Phases

|  | 5.0 g/day T-gel | 5.0 => 7.5 g/day T-gel | 10.0 => 7.5 g/day T-gel | 10/0 g/day T-gel | T-patch |
|---|---|---|---|---|---|
| Day 0 | N = 53 | N = 20 | N = 20 | N = 58 | N = 76 |
| Cavg (ng/dL) | 4.52 ± 3.35 | 4.27 ± 3.45 | 4.64 ± 3.10 | 4.20 ± 3.33 | 4.82 ± 3.64 |
| Cmax (ng/dL) | 5.98 ± 4.25 | 6.06 ± 5.05 | 6.91 ± 4.66 | 5.84 ± 4.36 | 6.57 ± 4.90 |
| Tmax* (hr) | 4.0 (0.0-24.5) | 2.0 (0.0-24.0) | 13.5 (0.0-24.2) | 2.1 (0.0-24.1) | 3.8 (0.0-24.0) |
| Cmin (ng/dL) | 3.23 ± 2.74 | 3.10 ± 2.62 | 3.14 ± 2.14 | 3.12 ± 2.68 | 3.56 ± 2.88 |
| Tmin* (hr) | 8.0 (0.0-24.2) | 9.9 (0.0-24.0) | 4.0 (0.0-23.3) | 8.0 (0.0-24.0) | 7.9 (0.0-24.0) |
| Fluc Index (ratio) | 0.604 ± 0.342 | 0.674 ± 0.512 | 0.756 ± 0.597 | 0.634 ± 0.420 | 0.614 ± 0.362 |
| Day 1 | N = 53 | N = 20 | N = 19 | N = 57 | N = 74 |
| Cavg (ng/dL) | 7.50 ± 4.83 | 6.80 ± 4.82 | 9.94 ± 5.04 | 8.93 ± 6.09 | 9.04 ± 4.81 |
| Cmax (ng/dL) | 10.86 ± 7.45 | 10.10 ± 7.79 | 15.36 ± 7.31 | 13.20 ± 8.61 | 12.02 ± 6.14 |
| Tmax* (hr) | 16.0 (0.0-25.3) | 13.9 (0.0-24.3) | 15.7 (2.0-24.0) | 23.5 (1.8-24.3) | 12.0 (1.8-24.0) |
| Cmin (ng/dL) | 4.30 ± 3.33 | 3.69 ± 3.24 | 3.88 ± 2.73 | 4.40 ± 3.94 | 4.67 ± 3.52 |
| Tmin* (hr) | 0.0 (0.0-24.1) | 1.8 (0.0-24.0) | 0.0 (0.0-24.2) | 0.0 (0.0-23.9) | 0.0 (0.0-24.0) |
| Day 30 | N = 47 | N = 19 | N = 19 | N = 55 | N = 70 |
| Cavg (ng/dL) | 11.12 ± 6.22 | 7.81 ± 3.94 | 16.18 ± 8.18 | 13.37 ± 7.13 | 8.12 ± 4.15 |
| Cmax (ng/dL) | 16.93 ± 10.47 | 11.62 ± 6.34 | 25.14 ± 10.80 | 19.36 ± 9.75 | 11.48 ± 5.78 |
| Tmax* (hr) | 8.0 (0.0-27.8) | 8.0 (0.0-26.3) | 8.0 (0.0-24.3) | 8.0 (0.0-24.3) | 8.0 (0.0-24.0) |
| Cmin (ng/dL) | 6.99 ± 3.82 | 4.78 ± 3.10 | 9.99 ± 7.19 | 8.25 ± 5.22 | 4.31 ± 3.20 |
| Tmin* (hr) | 4.0 (0.0-24.1) | 3.5 (0.0-24.1) | 11.4 (0.0-24.1) | 7.8 (0.0-25.8) | 2.0 (0.0-24.8) |
| Fluc Index (ratio) | 0.853 ± 0.331 | 0.872 ± 0.510 | 1.051 ± 0.449 | 0.861 ± 0.412 | 0.929 ± 0.311 |

TABLE 9-continued

Free Testosterone Pharmacokinetic Parameters by Final Treatment (Mean ± SD)

| | Doses Received During Initial => Extended Treatment Phases | | | | |
|---|---|---|---|---|---|
| | 5.0 g/day T-gel | 5.0 => 7.5 g/day T-gel | 10.0 => 7.5 g/day T-gel | 10/0 g/day T-gel | T-patch |
| Accum Ratio (ratio) | 1.635 ± 0.820 | 1.479 ± 0.925 | 2.065 ± 1.523 | 1.953 ± 1.626 | 0.980 ± 0.387 |
| Day 90 | N = 45 | N = 20 | N = 18 | N = 55 | N = 64 |
| Cavg (ng/dL) | 12.12 ± 7.78 | 8.06 ± 3.78 | 17.65 ± 8.62 | 13.11 ± 5.97 | 8.50 ± 5.04 |
| Cmax (ng/dL) | 18.75 ± 12.90 | 10.76 ± 4.48 | 25.29 ± 12.42 | 18.61 ± 8.20 | 12.04 ± 6.81 |
| Tmax* (hr) | 4.0 (0.0-24.0) | 9.7 (0.0-24.0) | 8.0 (0.0-24.0) | 8.0 (0.0-25.2) | 11.6 (0.0-25.0) |
| Cmin (ng/dL) | 7.65 ± 4.74 | 4.75 ± 2.86 | 10.56 ± 6.07 | 8.40 ± 4.57 | 4.38 ± 3.70 |
| Tmin* (hr) | 8.0 (0.0-24.0) | 1.9 (0.0-24.0) | 5.9 (0.0-24.1) | 4.0 (0.0-24.8) | 2.0 (0.0-24.1) |
| Fluc Index (ratio) | 0.913 ± 0.492 | 0.815 ± 0.292 | 0.870 ± 0.401 | 0.812 ± 0.335 | 0.968 ± 0.402 |
| Accum Ratio (ratio) | 1.755 ± 0.983 | 1.916 ± 1.816 | 1.843 ± 0.742 | 2.075 ± 1.866 | 1.054 ± 0.498 |
| Day 180 | N = 44 | N = 18 | N = 19 | N = 48 | N = 41 |
| Cavg (ng/dL) | 11.01 ± 5.24 | 7.80 ± 4.63 | 14.14 ± 7.73 | 12.77 ± 5.70 | 7.25 ± 4.90 |
| Cmax (ng/dL) | 16.21 ± 7.32 | 11.36 ± 6.36 | 22.56 ± 12.62 | 18.58 ± 9.31 | 10.17 ± 5.90 |
| Tmax* (hr) | 7.9 (0.0-24.0) | 2.0 (0.0-23.9) | 7.8 (0.0-24.0) | 8.0 (0.0-24.0) | 11.1 (0.0-24.0) |
| Cmin (ng/dL) | 7.18 ± 3.96 | 5.32 ± 4.06 | 9.54 ± 6.45 | 8.23 ± 4.01 | 3.90 ± 4.20 |
| Tmin* (hr) | 9.9 (0.0-24.2) | 7.9 (0.0-24.0) | 8.0 (0.0-23.2) | 11.8 (0.0-27.4) | 2.5 (0.0-25.7) |
| Fluc Index (ratio) | 0.897 ± 0.502 | 0.838 ± 0.378 | 0.950 ± 0.501 | 0.815 ± 0.397 | 0.967 ± 0.370 |
| Accum Ratio (ratio) | 1.712 ± 1.071 | NA | NA | 2.134 ± 1.989 | 1.001 ± 0.580 |

*Median (Range)

c. Serum DHT Concentrations.

Serum DHT was measured by RIA after potassium permanganate treatment of the sample followed by extraction. The methods and reagents of the DHT assay were provided by DSL (Webster, Tex.). The cross reactivities of the antiserum used in the RIA for DHT were 6.5% for 3-β-androstanediol, 1.2% for 3-α-androstanediol, 0.4% for 3-α-androstanediol glucuronide, and 0.4% for testosterone (after potassium permanganate treatment and extraction), and less than 0.01% for other steroids tested. This low cross-reactivity against testosterone was further confirmed by spiking steroid free serum with 35 nmol/L (1,000 pg/dL) of testosterone and taking the samples through the DHT assay. The results even on spiking with over 35 nmol/L of testosterone was measured as less than 0.1 nmol/L of DHT. The LLQ of serum DHT in the assay was 0.43 nmol/L. The mean accuracy (recovery) of the DHT assay determined by spiking steroid free serum with varying amounts of DHT from 0.43 nmol/L to 9 nmol/L was 101% and ranged from 83 to 114%. The intra-assay and inter-assay coefficients of variation for the DHT assay were 7.8 and 16.6%, respectively, for the normal adult male range. The normal adult male range of DHT was 30.7-193.2 ng/dL (1.06 to 6.66 nmol/L) as determined by the UCLA-Harbor Medical Center.

As shown in Table 10, the pretreatment mean serum DHT concentrations were between 36 and 42 ng/dL, which were near the lower limit of the normal range in all three initial treatment groups. None of the patients had DHT concentrations above the upper limit of the normal range on the pretreatment day, although almost half (103 patients) had concentrations less than the lower limit.

Figure 7:
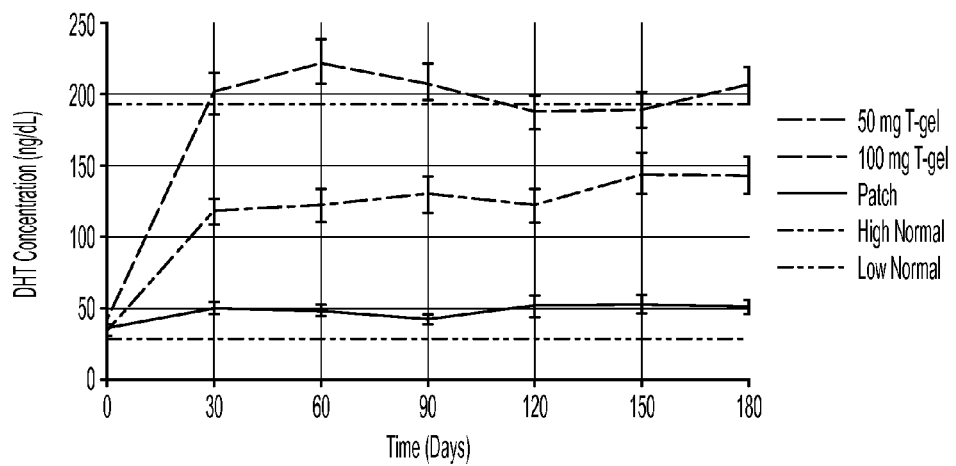
FIG. 7 is a graph showing the DHT concentrations on days 0 through 180 for hypogonadal men receiving either 5.0 g/day of ANDROGEL® (testosterone gel), 10.0 g/day of ANDROGEL® (testosterone gel), or the testosterone patch (by initial treatment group).

FIG. 7 shows that after treatment, the differences between the mean DHT concentrations associated with the different treatment groups were statistically significant, with patients receiving ANDROGEL® (testosterone gel) having a higher mean DHT concentration than the patients using the patch and showing dose-dependence in the mean serum DHT concentrations. Specifically, after testosterone patch application mean serum DHT levels rose to about 1.3 fold above the baseline. In contrast, serum DHT increased to 3.6 and 4.8 fold above baseline after application of 5.0 and 10.0 g/day of ANDROGEL® (testosterone gel), respectively.

TABLE 10

DHT Concentrations (ng/dL) on Each of the Observation Days By Initial Treatment (Mean ± SD)

| | Day 0 | Day 30 | Day 60 | Day 90 | Day 120 | Day 150 | Day 180 |
|---|---|---|---|---|---|---|---|
| 5.0 g/day | N = 73 | N = 69 | N = 70 | N = 67 | N = 65 | N = 63 | N = 65 |
| T-gel | 36.0 ± 19.9 | 117.6 ± 74.9 | 122.4 ± 99.4 | 130.1 ± 99.2 | 121.8 ± 89.2 | 144.7 ± 110.5 | 143.7 ± 105.9 |
| 10.0 g/day | N = 78 | N = 78 | N = 74 | N = 75 | N = 68 | N = 67 | N = 71 |
| T-gel | 42.0 ± 29.4 | 200.4 ± 127.8 | 222.0 ± 126.6 | 207.7 ± 111.0 | 187.3 ± 97.3 | 189.1 ± 102.4 | 206.1 ± 105.9 |
| T-Patch | N = 76 | N = 73 | N = 66 | N = 68 | N = 49 | N = 46 | N = 49 |
| | 37.4 ± 21.4 | 50.8 ± 34.6 | 49.3 ± 27.2 | 43.6 ± 26.9 | 53.0 ± 52.8 | 54.0 ± 42.5 | 52.1 ± 34.3 |
| Across RX | 0.6041 | 0.0001 | 0.0001 | 0.0001 | 0.0001 | 0.0001 | 0.0001 |

The increase in DHT concentrations are likely attributed to the concentration and location of 5α-reductase in the skin. For example, the large amounts of 5α-reductase in the scrotal skin presumably causes an increase in DHT concentrations in the TESTODERM® (testosterone transdermal) patch. In contrast, the ANDRODERM® (testosterone transdermal system) and TESTODERM® TTS (testosterone transdermal) patches create little change in DTH levels because the surface area of the patch is small and little 5α-reductase is located in nonscrotal skin. ANDROGEL® (testosterone gel) presumably causes an increase in DHT levels because the gel is applied to a relatively large skin area and thus exposes testosterone to greater amounts of the enzyme.

To date, elevated DHT levels have not been reported to have any adverse clinical effects. Moreover, there is some evidence to suggest that increased DHT levels may inhibit prostate cancer.

d. DHT/T Ratio.

Figure 8:
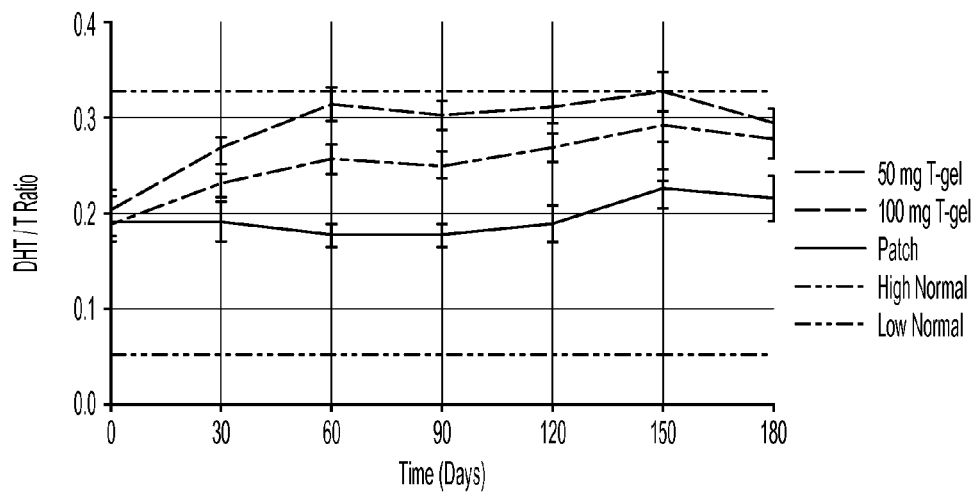
FIG. 8 is a graph showing the DHT/T ratio on days 0 through 180 for hypogonadal men receiving either 5.0 g/day of ANDROGEL® (testosterone gel), 10.0 g/day of ANDROGEL® (testosterone gel), or the testosterone patch (by initial treatment group).

The UCLA-Harbor Medical Center reports a DHT/T ratio of 0.052-0.328 for normal adult men. In this example, the mean ratios for all three treatments were within the normal range on day 0. As shown in FIG. 8 and Table 11, there were treatment and concentration-dependent increases observed over the 180-day period. Specifically, the ANDROGEL® (testosterone gel) treatment groups showed the largest increase in DHT/T ratio. However, the mean ratios for all of the treatment groups remained within the normal range on all observation days.

f. E2 Concentrations.

Serum E2 levels were measured by a direct assay without extraction with reagents from ICN (Costa Mesa, Calif.). The intra-assay and inter-assay coefficients of variation of E2 were 6.5 and 7.1% respectively. The UCLA-Harbor Medical Center reported an average E2 concentration ranging from 7.1 to 46.1 pg/mL (63 to 169 pmol/L) for normal adult male range. The LLQ of the E2 was 18 pmol/L. The cross reactivities of the E2 antibody were 6.9% for estrone, 0.4% for equilenin, and less than 0.01% for all other steroids tested. The accuracy of the E2 assay was assessed by spiking steroid free serum with increasing amount of E2 (18 to 275 pmol/L).

TABLE 11

DHT/T Ratio on Each of the Observation Days By Initial Treatment (Mean ± SD)

|  | Day 0 | Day 30 | Day 60 | Day 90 | Day 120 | Day 150 | Day 180 |
|---|---|---|---|---|---|---|---|
| 5.0 g/day T-gel | N = 73<br>0.198 ± 0.137 | N = 68<br>0.230 ± 0.104 | N = 70<br>0.256 ± 0.132 | N = 67<br>0.248 ± 0.121 | N = 65<br>0.266 ± 0.119 | N = 62<br>0.290 ± 0.145 | N = 64<br>0.273 ± 0.160 |
| 10.0 g/day T-gel | N = 78<br>0.206 ± 0.163 | N = 77<br>0.266 ± 0.124 | N = 74<br>0.313 ± 0.160 | N = 74<br>0.300 ± 0.131 | N = 68<br>0.308 ± 0.145 | N = 67<br>0.325 ± 0.142 | N = 71<br>0.291 ± 0.124 |
| T-Patch | N = 76<br>0.204 ± 0.135 | N = 73<br>0.192 ± 0.182 | N = 68<br>0.175 ± 0.102 | N = 65<br>0.175 ± 0.092 | N = 49<br>0.186 ± 0.134 | N = 46<br>0.223 ± 0.147 | N = 46<br>0.212 ± 0.160 |
| Across RX | 0.7922 | 0.0001 | 0.0001 | 0.0001 | 0.0001 | 0.0001 | 0.0002 | e. Total Androgen (DHT+T).

Figure 9:
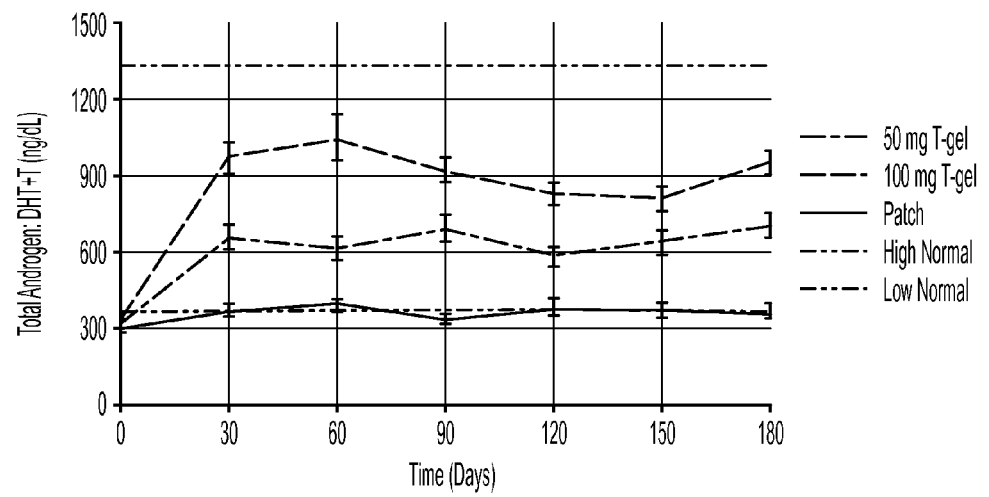
FIG. 9 is a graph showing the total androgen concentrations (DHT+T) on days 0 through 180 for hypogonadal men receiving either 5.0 g/day of ANDROGEL® (testosterone gel), 10.0 g/day of ANDROGEL® (testosterone gel), or the testosterone patch (by initial treatment group).

The UCLA-Harbor Medical Center has determined that the normal total androgen concentration is 372 to 1,350 ng/dL. As shown in FIG. 9 and Table 12, the mean pre-dose total androgen concentrations for all three treatments were below the lower limit of the normal range on pretreatment day 0. The total androgen concentrations for both ANDROGEL® (testosterone gel) groups were within the normal range on all treatment observation days. In contrast, the mean concentrations for patients receiving the testosterone patch was barely within the normal range on day 60 and 120, but were below the lower normal limit on days 30, 90, 150, and 180.

The mean recovery of E2 compared to the amount added was 99.1% and ranged from 95 to 101%.

Figure 10:
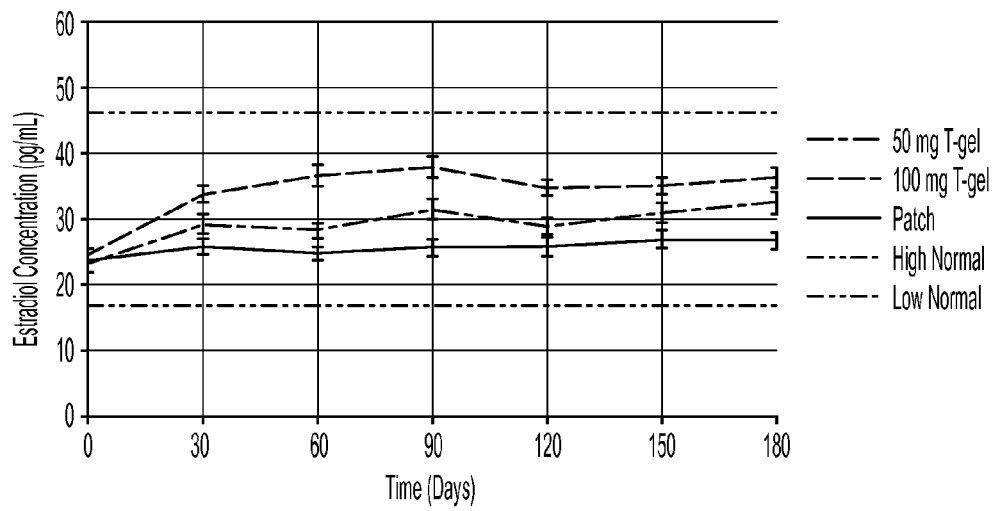
FIG. 10 is a graph showing the E2 concentrations on days 0 through 180 for hypogonadal men receiving either 5.0 g/day of ANDROGEL® (testosterone gel), 10.0 g/day of ANDROGEL® (testosterone gel), or the testosterone patch (by initial treatment group).

FIG. 10 depicts the E2 concentrations throughout the 180-day study. The pretreatment mean E2 concentrations for all three treatment groups were 23-24 pg/mL. During the study, the E2 levels increased by an average 9.2% in the testosterone patch during the treatment period, 30.9% in the 5.0 g/day ANDROGEL® (testosterone gel) group, and 45.5% in the 10.0 g/day ANDROGEL® (testosterone gel) group. All of the mean concentrations fell within the normal range.

TABLE 12

Total Androgen (DHT + T) (ng/dL) on Each of the Observation Days By Initial Treatment (Mean ± SD)

|  | Day 0 | Day 30 | Day 60 | Day 90 | Day 120 | Day 150 | Day 180 |
|---|---|---|---|---|---|---|---|
| 5.0 g/day T-gel | N = 73<br>281 ± 150 | N = 68<br>659 ± 398 | N = 70<br>617 ± 429 | N = 67<br>690 ± 431 | N = 65<br>574 ± 331 | N = 62<br>631 ± 384 | N = 64<br>694 ± 412 |
| 10.0 g/day T-gel | N = 78<br>307 ± 180 | N = 77<br>974 ± 532 | N = 74<br>1052 ± 806 | N = 74<br>921 ± 420 | N = 68<br>827 ± 361 | N = 67<br>805 ± 383 | N = 71<br>944 ± 432 |
| T-Patch | N = 76<br>282 ± 159 | N = 73<br>369 ± 206 | N = 68<br>392 ± 229 | N = 65<br>330 ± 173 | N = 49<br>378 ± 250 | N = 46<br>364 ± 220 | N = 46<br>355 ± 202 |
| Across RX | 0.7395 | 0.0001 | 0.0001 | 0.0001 | 0.0001 | 0.0001 | 0.0001 |

TABLE 13

Estradiol Concentration (pg/mL) on Each of the Observation Days By Initial Treatment (Mean ± SD)

|  | Day 0 | Day 30 | Day 60 | Day 90 | Day 120 | Day 150 | Day 180 |
|---|---|---|---|---|---|---|---|
| 5.0 g/day T-gel | N = 73<br>23.0 ± 9.2 | N = 69<br>29.2 ± 11.0 | N = 68<br>28.1 ± 10.0 | N = 67<br>31.4 ± 11.9 | N = 64<br>28.8 ± 9.9 | N = 65<br>30.8 ± 12.5 | N = 65<br>32.3 ± 13.8 |
| 10.0 g/day T-gel | N = 78<br>24.5 ± 9.5 | N = 78<br>33.7 ± 11.5 | N = 74<br>36.5 ± 13.5 | N = 75<br>37.8 ± 13.3 | N = 71<br>34.6 ± 10.4 | N = 66<br>35.0 ± 11.1 | N = 71<br>36.3 ± 13.9 |
| T-Patch | N = 76<br>23.8 ± 8.2 | N = 72<br>25.8 ± 9.8 | N = 68<br>24.8 ± 8.0 | N = 66<br>25.7 ± 9.8 | N = 50<br>25.7 ± 9.4 | N = 49<br>27.0 ± 9.2 | N = 49<br>26.9 ± 9.5 |
| Across RX | 0.6259 | 0.0001 | 0.0001 | 0.0001 | 0.0001 | 0.0009 | 0.0006 |

E2 is believed to be important for the maintenance of normal bone. In addition, E2 has a positive effect on serum lipid profiles.

g. Serum SHBG Concentrations.

Serum SHBG levels were measured with a fluoroimmunometric assay ("FIA") obtained from Delfia (Wallac, Gaithersberg, Md.). The intra- and interassay coefficients were 5% and 12% respectively. The LLQ was 0.5 nmol/L. The UCLA-Harbor Medical Center determined that the adult normal male range for the SHBG assay is 0.8 to 46.6 nmol/L.

Figure 11:
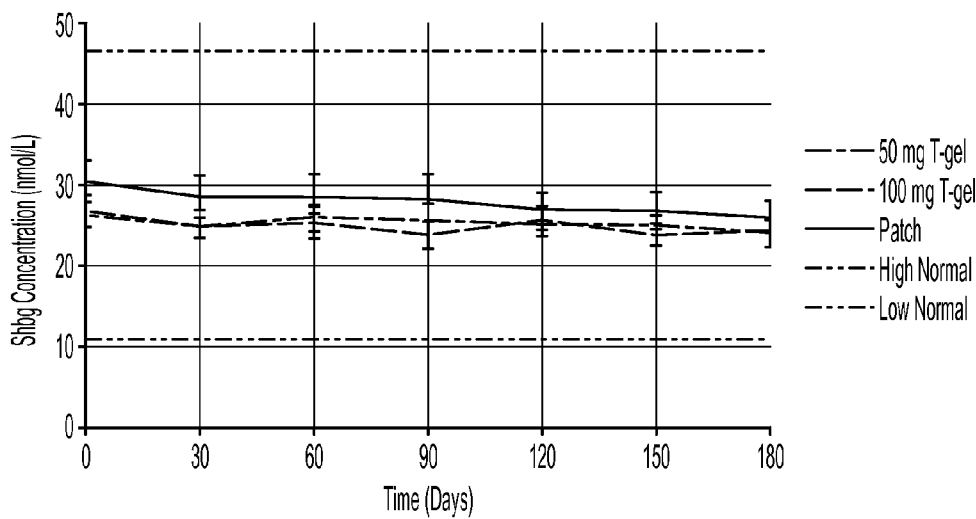
FIG. 11 is a graph showing the SHBG concentrations on days 0 through 180 for hypogonadal men receiving either 5.0 g/day of ANDROGEL® (testosterone gel), 10.0 g/day of ANDROGEL® (testosterone gel), or the testosterone patch (by initial treatment group).
Figure 12A:
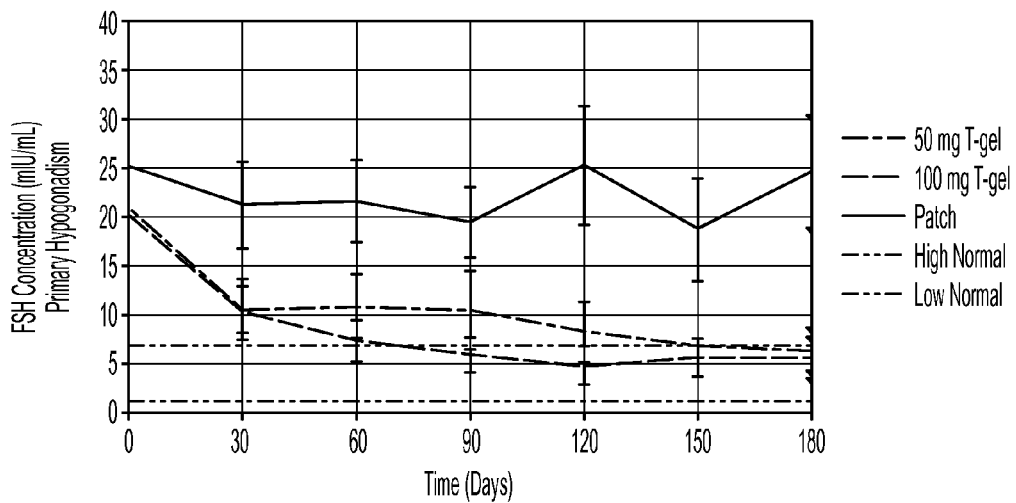
FIG. 12(a) is a graph showing the FSH concentrations on days 0 through 180 for men having primary hypogonadism and receiving either 5.0 g/day of ANDROGEL® (testosterone gel), 10.0 g/day of ANDROGEL® (testosterone gel), or the testosterone patch (by initial treatment group).

As shown in FIG. 11 and Table 11, the serum SHBG levels were similar and within the normal adult male range in the three treatment groups at baseline. None of the treatment groups showed major changes from the baseline on any of the treatment visit days. After testosterone replacement, serum SHBG levels showed a small decrease in all three groups. The most marked change occurred in the 10.0 g/day ANDROGEL® (testosterone gel) group.

identified as having primary hypogonadism. For these patients, the mean FSH concentrations in the three treatment groups on day 0 were 21-26 mIU/mL, above the upper limit of the normal range. As shown in FIG. 12(a) and Table 15(a), the mean FSH concentrations decreased during treatment in all three treatment regimens. However, only the 10.0 g/day ANDROGEL® (testosterone gel) group reduced the mean concentrations to within the normal range during the first 90 days of treatment. Treatment with the 10.0 g/day ANDROGEL® (testosterone gel) group required approximately 120 days to reach steady state. The mean FSH concentration in patients applying 5.0 g/day of ANDROGEL® (testosterone gel) showed an initial decline that was completed by day 30 and another declining phase at day 120 and continuing until the end of treatment. Mean FSH concentrations in the patients receiving the testosterone patch appeared to reach steady state after 30 days but were significantly higher than the normal range.

TABLE 14

SHBG Concentration (nmol/L) on Each of the Observation Days By Initial Treatment (Mean ± SD)

|  | Day 0 | Day 30 | Day 60 | Day 90 | Day 120 | Day 150 | Day 180 |
|---|---|---|---|---|---|---|---|
| 5.0 g/day T-gel | N = 73<br>26.2 ± 14.9 | N = 69<br>24.9 ± 14.0 | N = 69<br>25.9 ± 14.4 | N = 67<br>25.5 ± 14.7 | N = 66<br>25.2 ± 14.1 | N = 65<br>24.9 ± 12.9 | N = 65<br>24.2 ± 13.6 |
| 10.0 g/day T-gel | N = 78<br>26.6 ± 17.8 | N = 78<br>24.8 ± 14.5 | N = 75<br>25.2 ± 15.5 | N = 75<br>23.6 ± 14.7 | N = 72<br>25.5 ± 16.5 | N = 68<br>23.8 ± 12.5 | N = 71<br>24.0 ± 14.5 |
| T-Patch | N = 76<br>30.2 ± 22.6 | N = 72<br>28.4 ± 21.3 | N = 68<br>28.2 ± 23.8 | N = 66<br>28.0 ± 23.6 | N = 50<br>26.7 ± 16.0 | N = 49<br>26.7 ± 16.4 | N = 49<br>25.8 ± 15.1 |
| Across RX | 0.3565 | 0.3434 | 0.5933 | 0.3459 | 0.8578 | 0.5280 | 0.7668 | h. Gonadotropins.

Serum FSH and LH were measured by highly sensitive and specific solid-phase FIA assays with reagents provided by Delfia (Wallac, Gaithersburg, Md.). The intra-assay coefficient of variations for LH and FSH fluroimrnunometric assays were 4.3 and 5.2%, respectively; and the interassay variations for LH and FSH were 11.0% and 12.0%, respectively. For both LH and FSH assays, the LLQ was determined to be 0.2 IU/L. All samples obtained from the same subject were measured in the same assay. The UCLA-Harbor Medical Center reports that the adult normal male range for LH is 1.0-8.1 U/L and for FSH is 1.0-6.90/L.

(1) FSH.

Table 15(a)-(d) shows the concentrations of FSH throughout the 180-day treatment depending on the cause of hypogonadism: (1) primary, (2) secondary, (3) age-associated, or (4) unknown.

As discussed above, patients with primary hypogonadism have an intact feedback inhibition pathway, but the testes do not secrete testosterone. As a result, increasing serum testosterone levels should lead to a decrease in the serum FSH concentrations. In this example, a total of 94 patients were TABLE 15(a)

FSH Concentrations (mIU/mL) on Each of the Observation Days by Initial Treatment Group for Patients Having Primary Hypogonadism (Mean ± SD)

|  | N | 5 g/day | N | 10 g/day | N | T-patch |
|---|---|---|---|---|---|---|
| Day 0 | 26 | 21.6 ± 21.0 | 33 | 20.9 ± 15.9 | 34 | 25.5 ± 25.5 |
| Day 30 | 23 | 10.6 ± 15.0 | 34 | 10.6 ± 14.1 | 31 | 21.4 ± 24.6 |
| Day 60 | 24 | 10.8 ± 16.9 | 32 | 7.2 ± 12.6 | 31 | 21.7 ± 23.4 |
| Day 90 | 24 | 10.4 ± 19.7 | 31 | 5.7 ± 10.1 | 30 | 19.5 ± 20.0 |
| Day 120 | 24 | 8.1 ± 15.2 | 28 | 4.6 ± 10.2 | 21 | 25.3 ± 28.4 |
| Day 150 | 22 | 6.7 ± 15.0 | 29 | 5.3 ± 11.0 | 21 | 18.6 ± 24.0 |
| Day 180 | 24 | 6.2 ± 11.3 | 28 | 5.3 ± 11.2 | 22 | 24.5 ± 27.4 |

Figure 12B:
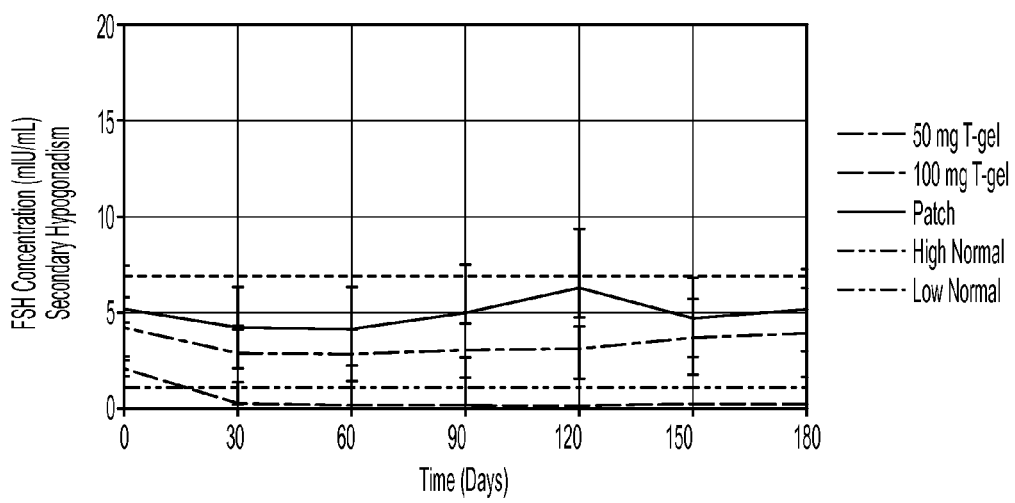
FIG. 12(b) is a graph showing the FSH concentrations on days 0 through 180 for men having secondary hypogonadism and receiving either 5.0 g/day of ANDROGEL® (testosterone gel), 10.0 g/day of ANDROGEL® (testosterone gel), or the testosterone patch (by initial treatment group).

Patients with secondary hypogonadism have a deficient testosterone negative feedback system. As shown in FIG. 12(b), of 44 patients identified as having secondary hypogonadism, the mean FSH concentrations decreased during treatment, although the decrease over time was not statistically significant for the testosterone patch. The patients in the 5.0 g/day ANDROGEL® (testosterone gel) group showed a decrease in the mean FSH concentration by about 35% by day 30, with no further decrease evident by day 60. Beyond day 90, the mean FSH concentration in the patients appeared to slowly return toward the pretreatment value. By day 30, all of the 10.0 g/day ANDROGEL® (testosterone gel) group had FSH concentrations less than the lower limit.

TABLE 15(b)

FSH Concentrations (mIU/mL) on Each of the Observation Days by Initial Treatment Group for Patients Having Secondary Hypogonadism (Mean ± SD)

|  | N | 5 g/day | N | 10 g/day | N | T-patch |
|---|---|---|---|---|---|---|
| Day 0 | 17 | 4.2 ± 6.6 | 12 | 2.1 ± 1.9 | 15 | 5.1 ± 9.0 |
| Day 30 | 16 | 2.8 ± 5.9 | 12 | 0.2 ± 0.1 | 14 | 4.2 ± 8.0 |
| Day 60 | 17 | 2.8 ± 6.1 | 12 | 0.2 ± 0.1 | 13 | 4.2 ± 7.4 |
| Day 90 | 15 | 2.9 ± 5.6 | 12 | 0.2 ± 0.1 | 14 | 4.9 ± 9.0 |
| Day 120 | 14 | 3.0 ± 6.1 | 12 | 0.1 ± 0.1 | 12 | 6.1 ± 10.7 |
| Day 150 | 14 | 3.5 ± 7.5 | 12 | 0.2 ± 0.2 | 11 | 4.6 ± 6.5 |
| Day 180 | 14 | 3.7 ± 8.6 | 12 | 0.1 ± 0.1 | 12 | 4.9 ± 7.4 |

Figure 12C:
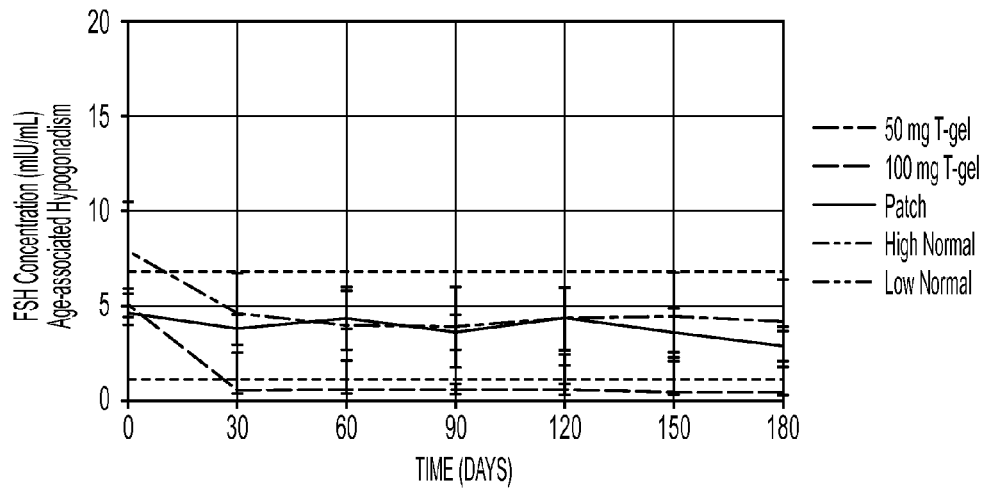
FIG. 12(c) is a graph showing the FSH concentrations on days 0 through 180 for men having age-associated hypogonadism and receiving either 5.0 g/day of ANDROGEL® (testosterone gel), 10.0 g/day of ANDROGEL® (testosterone gel), or the testosterone patch (by initial treatment group).

Twenty-five patients were diagnosed with age-associated hypogonadism. As shown in FIG. 12(c), the 5.0 g/day ANDROGEL® (testosterone gel) group had a mean pretreatment FSH concentration above the normal range. The mean concentration for this group was within the normal range by day 30 and had decreased more than 50% on days 90 and 180. The decrease in FSH mean concentration in the 10.0 g/day ANDROGEL® (testosterone gel) group showed a more rapid response. The concentrations in all six patients decreased to below the lower normal limit by day 30 and remained there for the duration of the study. The six patients who received the testosterone patch exhibited no consistent pattern in the mean FSH level; however, there was an overall trend towards lower FHS levels with continued treatment.

TABLE 15(c)

FSH Concentrations (mIU/mL) on Each of the Observation Days by Initial Treatment Group for Patients Having Age-Related Hypogonadism (Mean ± SD)

|  | N | 5 g/day | N | 10 g/day | N | T-patch |
|---|---|---|---|---|---|---|
| Day 0 | 13 | 8.0 ± 9.1 | 6 | 5.2 ± 1.9 | 6 | 4.7 ± 1.7 |
| Day 30 | 12 | 4.6 ± 7.4 | 6 | 0.4 ± 0.3 | 6 | 3.7 ± 2.0 |
| Day 60 | 12 | 3.9 ± 6.6 | 6 | 0.3 ± 0.3 | 4 | 4.3 ± 3.3 |
| Day 90 | 11 | 3.8 ± 7.0 | 6 | 0.4 ± 0.7 | 4 | 3.5 ± 1.9 |
| Day 120 | 11 | 4.2 ± 8.3 | 6 | 0.4 ± 0.7 | 4 | 4.2 ± 3.3 |
| Day 150 | 11 | 4.3 ± 8.1 | 5 | 0.2 ± 0.2 | 4 | 3.4 ± 2.7 |
| Day 180 | 11 | 4.0 ± 7.2 | 6 | 0.2 ± 0.2 | 4 | 2.7 ± 2.1 |

Figure 12D:
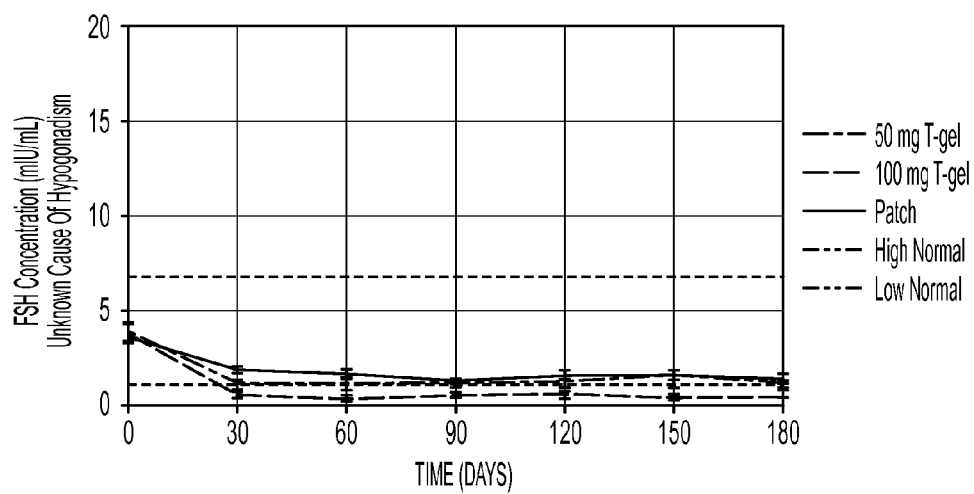
FIG. 12(d) is a graph showing the FSH concentrations on days 0 through 180 for men having hypogonadism of an unknown origin and receiving either 5.0 g/day of ANDROGEL® (testosterone gel), 10.0 of ANDROGEL® (testosterone gel), or the testosterone patch (by initial treatment group).

Sixty-four patients in the study suffered from unclassified hypogonadism. As shown in FIG. 12(d), the patients showed a marked and comparatively rapid FSH concentration decrease in all three groups, with the greatest decrease being in the 10.0 g/day ANDROGEL® (testosterone gel) group. The 10.0 ANDROGEL® (testosterone gel) group produced nearly a 90% decrease in the mean FSH concentration by day 30 and maintained the effect today 180. The 5.0 g/day ANDROGEL® (testosterone gel) group produced about a 75% drop in mean FSH concentration by day 30 and stayed at that level for the remainder of treatment. The 21 patients receiving the testosterone patch had a 50% decrease in the mean FSH concentration by day 30, a trend that continued to day 90 when the concentration was about one-third of its pretreatment value.

TABLE 15(d)

Concentrations (mIU/mL) for FSH on Each of the Observation Days by Initial Treatment Group for Patients Having Unknown-Related Hypogonadism (Mean ± SD)

|  | N | 5 g/day | N | 10 g/day | N | T-patch |
|---|---|---|---|---|---|---|
| Day 0 | 17 | 4.0 ± 1.8 | 26 | 4.1 ± 1.6 | 21 | 3.7 ± 1.4 |
| Day 30 | 17 | 1.1 ± 1.0 | 26 | 0.5 ± 0.5 | 21 | 1.8 ± 0.8 |
| Day 60 | 16 | 1.1 ± 1.1 | 26 | 0.3 ± 0.3 | 18 | 1.6 ± 1.0 |
| Day 90 | 17 | 1.1 ± 1.1 | 25 | 0.4 ± 0.7 | 18 | 1.2 ± 0.9 |
| Day 120 | 16 | 1.2 ± 1.4 | 26 | 0.4 ± 0.6 | 12 | 1.4 ± 1.0 |
| Day 150 | 17 | 1.4 ± 1.4 | 23 | 0.3 ± 0.5 | 13 | 1.4 ± 1.2 |
| Day 180 | 16 | 1.0 ± 0.9 | 24 | 0.4 ± 0.4 | 11 | 1.3 ± 0.9 |

This data shows that feedback inhibition of FSH secretion functioned to some extent in all four subpopulations. The primary hypogonadal population showed a dose-dependency in both the extent and rate of the decline in FSH levels. The sensitivity of the feedback process appeared to be reduced in the secondary and age-associated groups in that only the highest testosterone doses had a significant and prolonged impact on FSH secretion. In contrast, the feedback inhibition pathway in the patients in the unclassified group was quite responsive at even the lowest dose of exogenous testosterone.

(2) LH.

The response of LH to testosterone was also examined separately for the same four subpopulations. Tables 16(a)-(d) shows the LH concentrations throughout the treatment period.

Figure 13A:
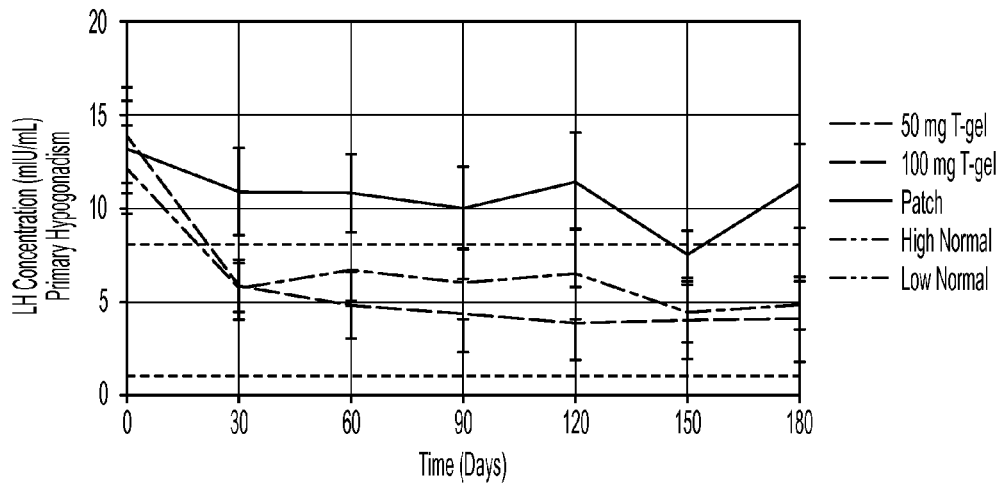
FIG. 13(a) is a graph showing the LH concentrations on days 0 through 180 for men having primary hypogonadism and receiving either 5.0 g/day of ANDROGEL® (testosterone gel), 10.0 g/day of ANDROGEL® (testosterone gel), or the testosterone patch (by initial treatment group).

As shown in FIG. 13(a) and Table 16(a), the LH concentrations prior to treatment were about 175% of the upper limit of the normal range in primary hypogonadal patients. The mean LH concentrations decreased during treatment in all groups. However, only the ANDROGEL® (testosterone gel) groups decreased the mean LH concentrations enough to fall within the normal range. As with FSH, the primary hypogonadal men receiving ANDROGEL® (testosterone gel) showed dose-dependence in both the rate and extent of the LH response.

TABLE 16(a)

Concentrations for LH (mIU/mL) on Each of the Observation Days for Patients Having Primary Hypogonadism (Summary of Mean ± SD)

|  | N | 5 g/day | N | 10 g/day | N | T-patch |
|---|---|---|---|---|---|---|
| Day 0 | 26 | 12.2 ± 12.1 | 33 | 13.9 ± 14.9 | 33 | 13.3 ± 14.3 |
| Day 30 | 23 | 5.6 ± 7.6 | 34 | 5.9 ± 8.1 | 31 | 10.9 ± 12.9 |
| Day 60 | 24 | 6.8 ± 9.0 | 32 | 4.8 ± 10.0 | 31 | 10.8 ± 11.8 |
| Day 90 | 24 | 5.9 ± 9.5 | 31 | 4.2 ± 11.0 | 30 | 10.0 ± 11.7 |
| Day 120 | 24 | 6.4 ± 11.9 | 28 | 3.8 ± 10.4 | 21 | 11.5 ± 11.5 |
| Day 150 | 22 | 4.4 ± 8.5 | 29 | 4.0 ± 11.3 | 21 | 7.4 ± 6.0 |
| Day 180 | 24 | 4.8 ± 6.8 | 28 | 4.0 ± 11.9 | 22 | 11.2 ± 10.5 |

Figure 13B:
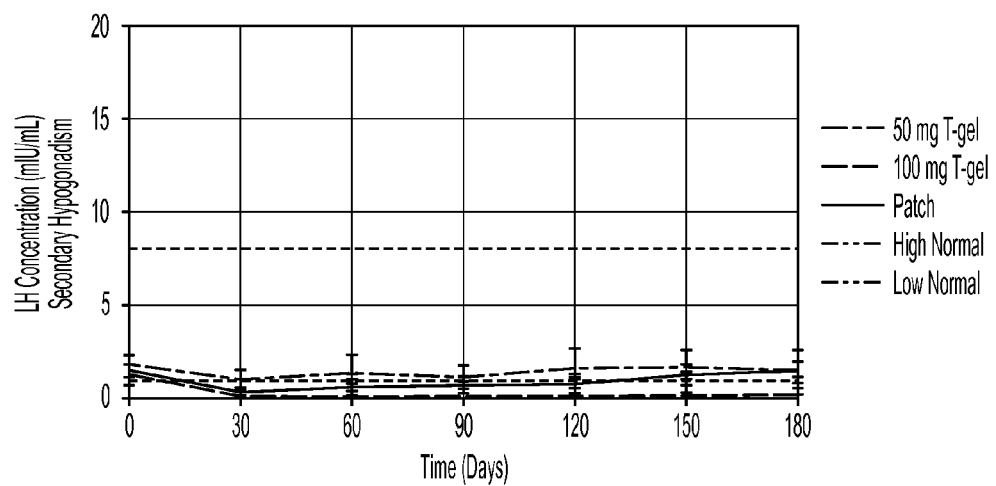
FIG. 13(b) is a graph showing the LH concentrations on days 0 through 180 for men having secondary hypogonadism and receiving either 5.0 g/day of ANDROGEL® (testosterone gel), 10.0 g/day of ANDROGEL® (testosterone gel), or the testosterone patch (by initial treatment group).
Figure 13C:
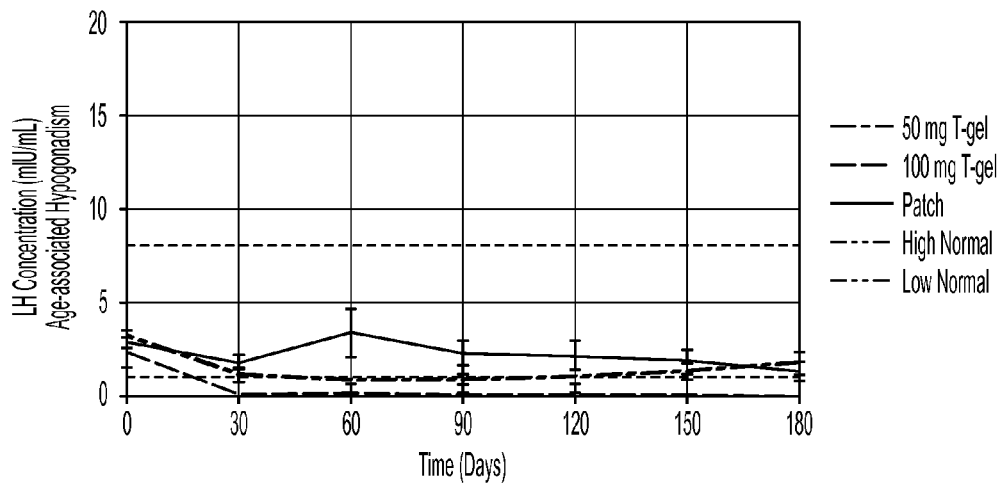
FIG. 13(c) is a graph showing the LH concentrations on days 0 through 180 for men having age-associated hypogonadism and receiving either 5.0 g/day of ANDROGEL® (testosterone gel), 10.0 g/day of ANDROGEL® (testosterone gel), or the testosterone patch (by initial treatment group).
Figure 13D:
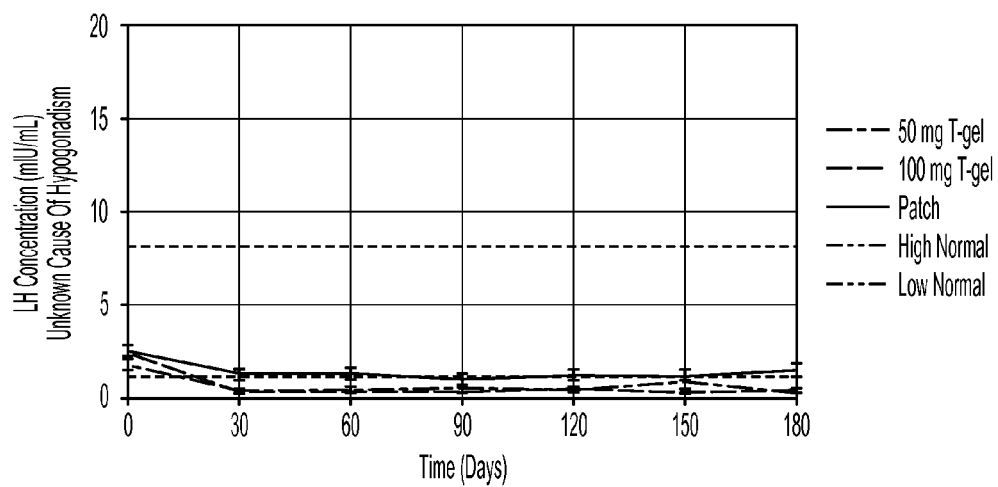
FIG. 13(d) is a graph showing the LH concentrations on days 0 through 180 for men having hypogonadism of an unknown origin and receiving either 5.0 g/day of ANDROGEL® (testosterone gel), 10.0 of ANDROGEL® (testosterone gel), or the testosterone patch (by initial treatment group).

The secondary hypogonadal men were less sensitive to exogenous testosterone. For the 44 patients identified as having secondary hypogonadism, the pretreatment mean concentrations were all within the lower limit normal range. The mean LH concentrations decreased during treatment with all three regimens as shown in FIG. 13(b) and Table 16(b).

TABLE 16(b)

Concentrations for LH (mIU/mL) on Each of the Observation Days for Patients Having Secondary Hypogonadism (Summary of Mean ± SD)

|  | N | 5 g/day | N | 10 g/day | N | T-patch |
|---|---|---|---|---|---|---|
| Day 0 | 17 | 1.8 ± 2.6 | 12 | 1.4 ± 1.8 | 15 | 1.6 ± 3.1 |
| Day 30 | 16 | 1.1 ± 2.2 | 12 | 0.2 ± 0.2 | 14 | 0.4 ± 0.4 |
| Day 60 | 17 | 1.4 ± 3.8 | 12 | 0.2 ± 0.2 | 13 | 0.6 ± 0.5 |
| Day 90 | 15 | 1.2 ± 2.4 | 12 | 0.2 ± 0.2 | 14 | 0.7 ± 1.0 |
| Day 120 | 14 | 1.6 ± 4.0 | 12 | 0.2 ± 0.2 | 12 | 0.8 ± 0.8 |
| Day 150 | 14 | 1.6 ± 3.5 | 12 | 0.2 ± 0.2 | 11 | 1.2 ± 2.0 |
| Day 180 | 14 | 1.5 ± 3.7 | 12 | 0.2 ± 0.2 | 12 | 1.4 ± 2.1 |

None of the 25 patients suffering from age-associated hypogonadism had pretreatment LH concentrations outside of the normal range as shown in FIG. 13(*c*) and Table 16(c). The overall time and treatment effects were significant for the ANDROGEL® (testosterone gel) patients but not those patients using the testosterone patch.

TABLE 16(c)

Concentrations for LH (mIU/mL) on Each of the Observation Days for Patients Having Age-Related Hypogonadism (Summary of Mean ± SD)

|  | N | 5 g/day | N | 10 g/day | N | T-patch |
|---|---|---|---|---|---|---|
| Day 0 | 13 | 3.2 ± 1.1 | 6 | 2.4 ± 1.8 | 6 | 2.9 ± 0.6 |
| Day 30 | 12 | 1.1 ± 1.0 | 6 | 0.1 ± 0.0 | 6 | 1.8 ± 1.1 |
| Day 60 | 12 | 0.8 ± 0.7 | 6 | 0.2 ± 0.3 | 5 | 3.4 ± 2.8 |
| Day 90 | 11 | 0.9 ± 1.2 | 6 | 0.1 ± 0.0 | 4 | 2.3 ± 1.4 |
| Day 120 | 11 | 1.0 ± 1.4 | 6 | 0.1 ± 0.0 | 4 | 2.2 ± 1.4 |
| Day 150 | 11 | 1.3 ± 1.5 | 5 | 0.1 ± 0.0 | 4 | 1.9 ± 1.2 |
| Day 180 | 11 | 1.8 ± 2.1 | 6 | 0.1 ± 0.0 | 4 | 1.4 ± 1.0 |

Of the 64 patients suffering from an unclassified hypogonadism, none of the patients had a pretreatment LH concentration above the upper limit. Fifteen percent, however, had pretreatment concentrations below the normal limit. The unclassified patients showed comparatively rapid LH concentration decreases in all treatment groups as shown in FIG. 13(*d*) and Table 16(d).

TABLE 16(d)

Concentrations for LH (mIU/mL) on Each of the Observation Days for Patients Having Unknown-Related Hypogonadism (Summary of Mean ± SD)

|  | N | 5 g/day | N | 10 g/day | N | T-patch |
|---|---|---|---|---|---|---|
| Day 0 | 17 | 1.8 ± 1.2 | 26 | 2.5 ± 1.5 | 21 | 2.5 ± 1.5 |
| Day 30 | 17 | 0.3 ± 0.3 | 26 | 0.3 ± 0.3 | 21 | 1.3 ± 1.3 |
| Day 60 | 17 | 0.4 ± 0.5 | 26 | 0.3 ± 0.3 | 18 | 1.2 ± 1.4 |
| Day 90 | 17 | 0.5 ± 0.5 | 26 | 0.3 ± 0.4 | 18 | 1.0 ± 1.4 |
| Day 120 | 17 | 0.4 ± 0.4 | 26 | 0.4 ± 0.5 | 12 | 1.2 ± 1.1 |
| Day 150 | 17 | 0.8 ± 1.1 | 23 | 0.3 ± 0.4 | 13 | 1.1 ± 1.1 |
| Day 180 | 15 | 0.3 ± 0.4 | 25 | 0.4 ± 0.4 | 11 | 1.5 ± 1.3 |

(3) Summary: LH and FSH.

Patients receiving ANDROGEL® (testosterone gel) or the testosterone patch achieve "hormonal steady state" only after long-term treatment. Specifically, data involving FSH and LH show that these hormones do not achieve steady-state until many weeks after treatment. Because testosterone concentrations are negatively inhibited by FSH and LH, testosterone levels do not achieve true steady state until these other hormones also achieve steady state. However, because these hormones regulate only endogenous testosterone (which is small to begin with in hypogonadal men) in an intact feedback mechanism (which may not be present depending on the cause of hypogonadism), the level of FSH and/or LH may have little effect on the actual testosterone levels achieved. The net result is that the patients do not achieve a "hormonal steady state" for testosterone even though the Cavg, Cmin, and Cmax for testosterone remains relatively constant after a few days of treatment.

2. Bone Mineral Density ("BMD") and Similar Markers:
a. BMD.

BMD was assessed by dual energy X-ray absorptiometry ("DEXA") using Hologic QDR 2000 or 4500 A (Hologic, Waltham, Mass.) on days 0 and 180 in the lumbar spine and left hip regions. BMD of spine was calculated as the average of BMD at L1 to L4. BMD of the left hip, which included Ward's triangle, was calculated by the average of BMD from neck, trochanter, and intertrochanter regions. The scans were centrally analyzed and processed at Hologic. BMD assessments were performed at 13 out of the 16 centers (206 out of 227 subjects) because of the lack of the specific DEXA equipment at certain sites.

Figure 14A:
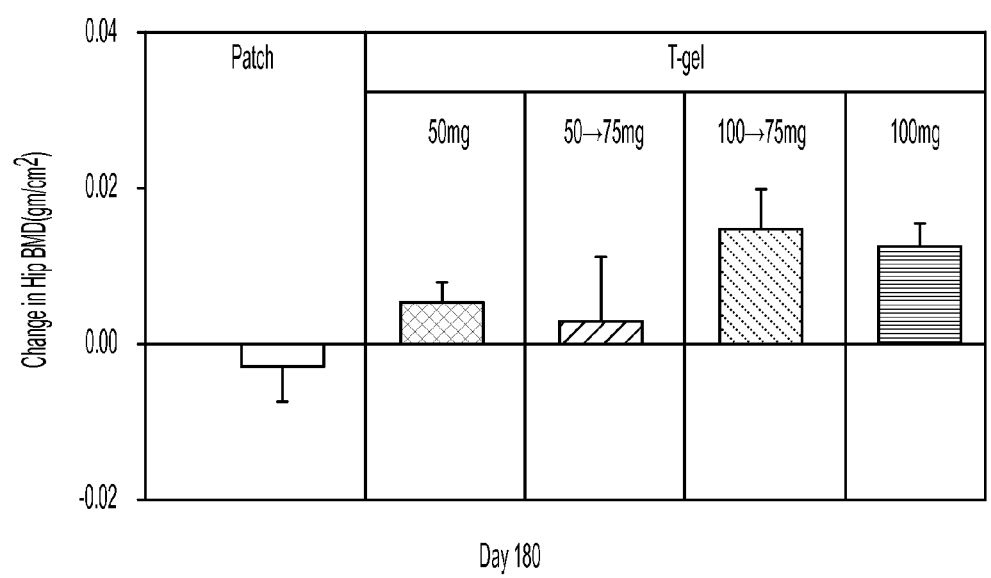
FIG. 14(a) is a bar graph showing the change in hip BMD for hypogonadal men after 180 days of treatment with 5.0 g/day of ANDROGEL® (testosterone gel), 7.5 g/day of ANDROGEL® (testosterone gel), 10.0 g/day of ANDROGEL® (testosterone gel), or the testosterone patch.
Figure 14B:
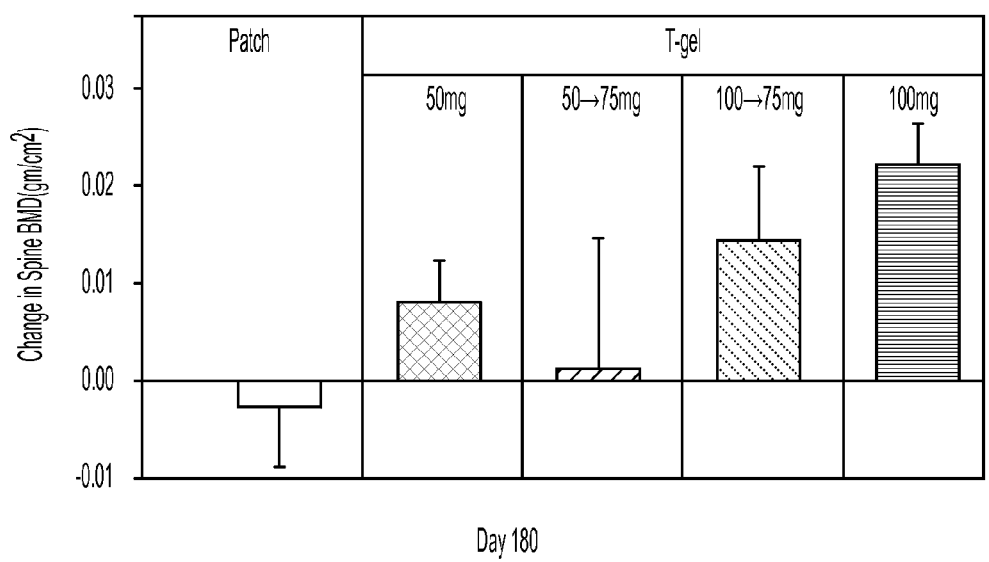

Table 17 and FIGS. 14(*a*)-14(*b*) show that before treatment, the BMD of the hip or the spine was not different among the three treatment groups. Significant increases in BMD occurred only in subjects in the ANDROGEL® (testosterone gel) 10.0 g/day group and those who switched from ANDROGEL® (testosterone gel) 10.0 to 7.5 g/day groups. The increases in BMD were about 1% in the hip and 2% in the spine during the six-month period. Average increases in BMD of 0.6% and 1% in the hip and spine were seen in those receiving 5.0 g/day of ANDROGEL® (testosterone gel) but no increase was observed in the testosterone patch group.

TABLE 17

BMD Concentrations on Day 0 and Day 180 by Final Treatment Group Mean (±SD)

| Final Treatment Group | N | Day 0 | N | Day 180 | N | % Change from Day 0 to Day 180 |
|---|---|---|---|---|---|---|
| Hip |  |  |  |  |  |  |
| 5.0 g/day T-gel | 50 | 1.026 ± 0.145 | 41 | 1.022 ± 0.145 | 41 | 0.7 ± 2.1 |
| 5.0 to 7.5 g/day T-gel | 16 | 1.007 ± 0.233 | 15 | 1.011 ± 0.226 | 15 | 1.0 ± 4.9 |
| 10.0 to 7.5 g/day T-gel | 20 | 1.002 ± 0.135 | 19 | 1.026 ± 0.131 | 19 | 1.3 ± 2.4 |
| 10.0 g/day T-gel | 53 | 0.991 ± 0.115 | 44 | 0.995 ± 0.130 | 44 | 1.1 ± 1.9 |
| T-Patch | 67 | 0.982 ± 0.166 | 37 | 0.992 ± 0.149 | 37 | −0.2 ± 2.9 |

TABLE 17-continued

BMD Concentrations on Day 0 and Day 180 by Final Treatment Group Mean (±SD)

| Final Treatment Group | N | Day 0 | N | Day 180 | N | % Change from Day 0 to Day 180 |
|---|---|---|---|---|---|---|
| Spine | | | | | | |
| 5.0 g/day T-gel | 50 | 1.066 ± 0.203 | 41 | 1.072 ± 0.212 | 41 | 1.0 ± 2.9 |
| 5.0 to 7.5 g/day T-gel | 16 | 1.060 ± 0.229 | 15 | 1.077 ± 0.217 | 15 | 0.4 ± 5.5 |
| 10.0 to 7.5 g/day T-gel | 19 | 1.049 ± 0.175 | 19 | 1.067 ± 0.175 | 18 | 1.4 ± 3.2 |
| 10.0 g/day T-gel | 53 | 1.037 ± 0.126 | 44 | 1.044 ± 0.124 | 44 | 2.2 ± 3.1 |
| T-Patch | 67 | 1.058 ± 0.199 | 36 | 1.064 ± 0.205 | 36 | −0.2 ± 3.4 |

Note:
Day 0 and Day 180 are arithmetic mean, while percent change is a geometric mean.

The baseline hip and spine BMD and the change in BMD on day 180 were not significantly correlated with the average serum testosterone concentration on day 0. The changes in BMD in the hip or spine after testosterone replacement were not significantly different in subjects with hypogonadism due to primary, secondary, aging, or unclassified causes; nor were they different between naive and previously testosterone replaced subjects. The change in BMD in the spine was negatively correlated with baseline BMD values, indicating that the greatest increase in BMD occurred in subjects with the lowest initial BMD. The increase in BMD in the hip (but not in the spine) after testosterone treatment was correlated with the change in serum testosterone levels.

b. Bone Osteoblastic Activity Markers.

The results described above are supported by measurements of a number of serum and urine markers of bone formation. Specifically, the mean concentrations of the serum markers (PTH, SALP, osteocalcin, type I procollagen) generally increase during treatment in all treatment groups. In addition, the ratios of two urine markers of bone formation (N-telopeptide/creatinine ratio and calcium/creatinine ratio) suggests a decrease in bone resorption.

(1) PTH (Parathyroid or Calciotropic Hormone).

Serum intact PTH was measured by two site immunoradiometric assay ("IRMA") kits from Nichol's Institute (San Juan Capistrano, Calif.). The LLC for the PTH assay was 12.5 ng/L. The intra- and inter-assay coefficients of variation were 6.9 and 9.6%, respectively. The UCLA-Harbor Medical Center has reported previously that the normal male adult range of PTH is 6.8 to 66.4 ng/L.

Figure 15:
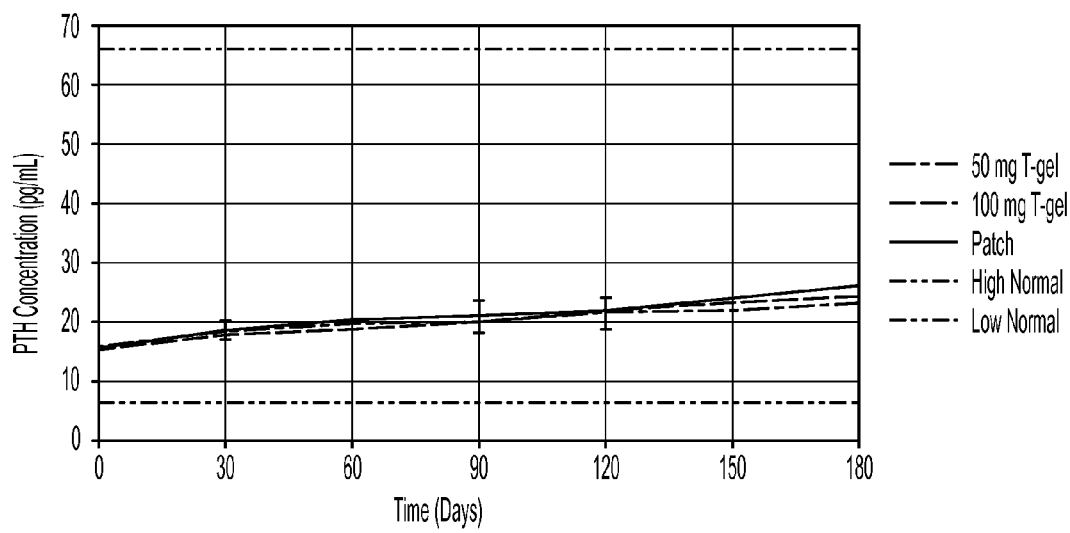
FIG. 15 is a graph showing PTH concentrations on days 0 through 180 for hypogonadal men receiving either 5.0 g/day of ANDROGEL® (testosterone gel), 10.0 g/day of ANDROGEL® (testosterone gel), or the testosterone patch (by initial treatment group).

Table 18 provides the PTH concentrations over the 180-day study. FIG. 15 shows that the mean serum PTH levels were within the normal male range in all treatment groups at baseline. Statistically significant increases in serum PTH were observed in all subjects as a group at day 90 without inter-group differences. These increases in serum PTH were maintained at day 180 in all three groups.

TABLE 18

PTH Concentrations on Each of the Observation Days by Final Treatment Group (Mean ± SD)

| | N | 5 g/day T-gel | N | 5 => 7.5 g/day T-gel | N | 10 => 7.5 g/day T-gel | N | 10 g/day T-gel | N | T-Patch |
|---|---|---|---|---|---|---|---|---|---|---|
| Day 0 | 53 | 16.31 ± 8.81 | 20 | 17.70 ± 9.66 | 20 | 18.02 ± 8.18 | 58 | 14.99 ± 6.11 | 75 | 15.60 ± 6.57 |
| Day 30 | 49 | 17.91 ± 10.36 | 20 | 18.33 ± 8.02 | 20 | 17.45 ± 5.67 | 58 | 18.04 ± 8.95 | 72 | 18.33 ± 10.92 |
| Day 90 | 47 | 21.32 ± 11.47 | 20 | 21.25 ± 10.96 | 19 | 17.10 ± 6.04 | 54 | 20.01 ± 9.77 | 66 | 21.45 ± 13.71 |
| Day 120 | 46 | 21.19 ± 11.42 | 19 | 21.42 ± 13.20 | 20 | 19.62 ± 9..96 | 50 | 22.93 ± 12.57 | 46 | 21.07 ± 11.44 |
| Day 180 | 46 | 22.85 ± 12.89 | 19 | 21.34 ± 11.08 | 19 | 21.02 ± 10.66 | 51 | 25.57 ± 15.59 | 46 | 25.45 ± 16.54 |

(2) SALP.

SALP was quantitated by IRMA using reagents supplied by Hybritech (San Diego, Calif.). The LLQ for the SALP assay was 3.8 µg/L; and the intra- and inter-assay precision coefficients were 2.9 and 6.5%, respectively. The UCLA-Harbor Medical Center reported that the adult normal male concentration of SALP ranges from 2.4 to 16.6 µg/L.

Figure 16:
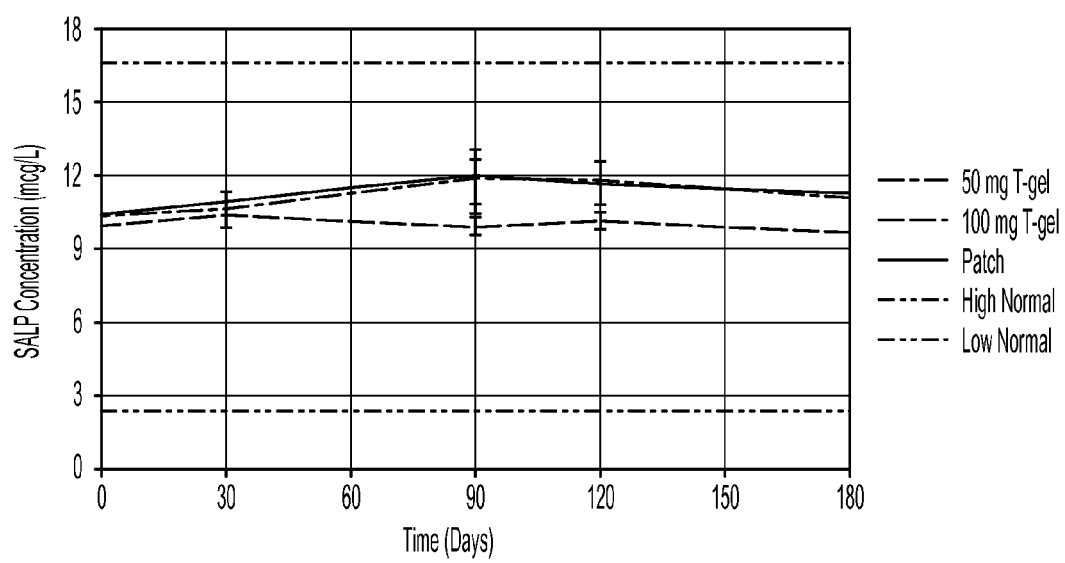
FIG. 16 is a graph showing SALP concentrations on days 0 through 180 for hypogonadal men receiving either 5.0 g/day of ANDROGEL® (testosterone gel), 10.0 g/day of ANDROGEL® (testosterone gel), or the testosterone patch (by initial treatment group).

The pretreatment SALP concentrations were within the normal range. FIG. 16 and Table 19 show that SALP levels increased with testosterone treatment in the first 90 days and reached statistical difference in the testosterone patch group. Thereafter serum SALP plateaued in all treatment groups.

TABLE 19

SALP Concentrations on Each of the Observation Days by final Treatment Group (Mean ± SD)

| | N | 5 g/day T-gel | N | 5 => 7.5 g/day T-gel | N | 10 => 7.5 g/day T-gel | N | 10 g/day T-gel | N | T-Patch |
|---|---|---|---|---|---|---|---|---|---|---|
| Day 0 | 53 | 9.96 ± 5.61 | 20 | 12.36 ± 4.62 | 20 | 10.48 ± 3.68 | 58 | 9.80 ± 3.57 | 76 | 10.44 ± 3.77 |
| Day 30 | 49 | 10.20 ± 6.77 | 20 | 11.38 ± 4.09 | 20 | 11.83 ± 4.32 | 58 | 9.93 ± 3.88 | 71 | 10.86 ± 3.75 |
| Day 90 | 47 | 11.64 ± 7.98 | 20 | 11.97 ± 5.03 | 20 | 10.97 ± 3.18 | 55 | 9.56 ± 3.12 | 65 | 11.99 ± 9.36 |

TABLE 19-continued

SALP Concentrations on Each of the Observation Days by final Treatment Group (Mean ± SD)

| | N | 5 g/day T-gel | N | 5 => 7.5 g/day T-gel | N | 10 => 7.5 g/day T-gel | N | 10 g/day T-gel | N | T-Patch |
|---|---|---|---|---|---|---|---|---|---|---|
| Day 120 | 46 | 11.71 ± 7.85 | 19 | 12.12 ± 5.25 | 20 | 11.61 ± 2.58 | 48 | 9.63 ± 3.58 | 45 | 11.63 ± 4.72 |
| Day 180 | 45 | 11.12 ± 7.58 | 19 | 11.67 ± 5.35 | 19 | 11.22 ± 3.44 | 51 | 9.19 ± 2.42 | 46 | 11.47 ± 3.77 |

(3) Osteocalcin.

Serum osteocalcin was measured by an IRMA from Immutopics (San Clemente, Calif.). The LLQ was 0.45 µg/L. The intra- and inter-assay coefficients were 5.6 and 4.4%, respectively. The UCLA-Harbor Medical Center reports that the normal male adult range for the osteocalcin assay ranges from 2.9 to 12.7 µg/L.

Figure 17:
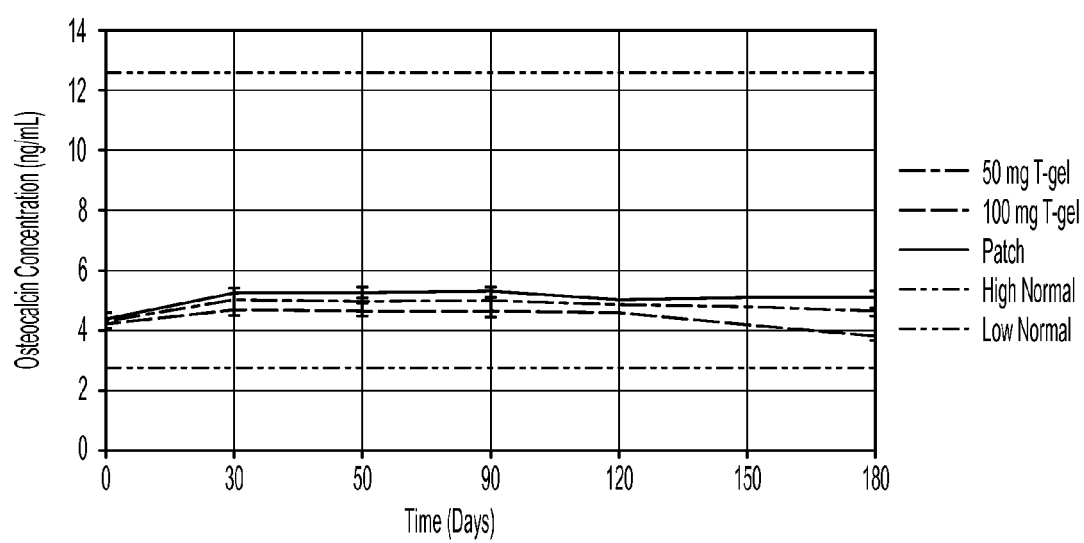
FIG. 17 (b) is a bar graph showing the change in spine BMD for hypogonadal men after 180 days of treatment with 5.0 g/day of ANDROGEL® (testosterone gel), 7.5 g/day of ANDROGEL® (testosterone gel), 10.0 g/day of ANDROGEL® (testosterone gel), or the testosterone patch.

As shown in FIG. 17 and Table 20, the baseline mean serum osteocalcin levels were within the normal range in all treatment groups. During the first 90-day treatment, mean serum osteocalcin increased with testosterone replacement in all subjects as a group without significant differences between the groups. With continued treatment serum osteocalcin either plateaued or showed a decrease by day 180.

c. Urine Bone Turnover Markers: N-telopeptide/Cr and Ca/Cr Ratios.

Urine calcium and creatinine were estimated using standard clinical chemistry procedures by an autoanalyzer operated by the UCLA-Harbor Pathology Laboratory. The procedures were performed using the COBAS MIRA automated chemistry analyzer system manufactured by Roche Diagnostics Systems. The sensitivity of the assay for creatinine was 8.9 mg/dL and the LLQ was 8.9 mg/dL. According to the UCLA-Harbor Medical Center, creatinine levels in normal adult men range from 2.1 mM to 45.1 mM. The sensitivity of the assay for calcium was 0.7 mg/dL and the LLQ was 0.7 mg/dL. The normal range for urine calcium is 0.21 mM to 7.91N-telopeptides were measured by an enzyme-linked immunosorbant assay ("ELISA") from Ostex (Seattle, Wash.). The LLQ for the N-telopeptide assay was 5 nM bone

TABLE 20

Osteocalcin Concentrations on Each of the Observation Days by Final Treatment Group (Mean ± SD)

| | N | 5 g/day T-gel | N | 5 => 7.5 g/day T-gel | N | 10 => 7.5 g/day T-gel | N | 10 g/day T-gel | N | T-Patch |
|---|---|---|---|---|---|---|---|---|---|---|
| Day 0 | 53 | 4.62 ± 1.55 | 20 | 5.01 ± 2.03 | 20 | 4.30 ± 1.28 | 58 | 4.58 ± 1.92 | 76 | 4.53 ± 1.54 |
| Day 30 | 49 | 4.63 ± 1.65 | 20 | 5.35 ± 2.06 | 20 | 4.48 ± 1.72 | 58 | 4.91 ± 2.08 | 72 | 5.17 ± 1.61 |
| Day 90 | 47 | 4.91 ± 2.15 | 20 | 5.29 ± 1.87 | 19 | 4.76 ± 1.50 | 55 | 4.83 ± 2.13 | 66 | 5.18 ± 1.53 |
| Day 120 | 46 | 4.95 ± 1.97 | 18 | 4.97 ± 1.60 | 20 | 4.71 ± 1.39 | 49 | 4.61 ± 2.01 | 47 | 4.98 ± 1.87 |
| Day 180 | 45 | 4.79 ± 1.82 | 19 | 4.89 ± 1.54 | 19 | 4.47 ± 1.49 | 51 | 3.76 ± 1.60 | 46 | 5.15 ± 2.18 |

(4) Type I Procollagen.

Serum type I procollagen was measured using a RIA kit from Incstar Corp (Stillwater, Minn.). The LLQ of the procollagen assay was 5 µg/L, and the intra- and inter-assay precisions were 6.6 and 3.6%, respectively. The UCLA-Harbor Medical Center reports that the normal adult male concentration of type I procollagen ranges from 56 to 310 µg/L.

Figure 18:
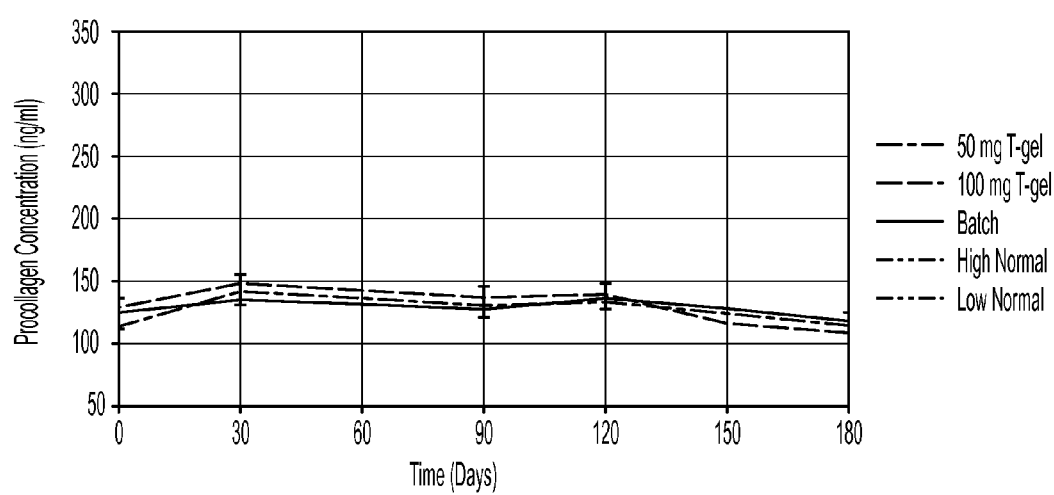
FIG. 18 is a graph showing the type I procollagen concentrations on days 0 through 180 for hypogonadal men receiving either 5.0 g/day of ANDROGEL® (testosterone gel), 10.0 g/day of ANDROGEL® (testosterone gel), or the testosterone patch (by initial treatment group).

FIG. 18 and Table 21 show that serum procollagen generally followed the same pattern as serum osteocalcin. At baseline the mean levels were similar and within the normal range in all treatment groups. With transdermal treatment, serum procollagen increased significantly in all subjects as a group without treatment group differences. The increase in procollagen was highest on day 30 and then plateaued until day 120. By day 180, the serum procollagen levels returned to baseline levels.

collagen equivalent ("BCE"). The intra- and inter-assay had a precision of 4.6 and 8.9%, respectively. The normal range for the N-telopeptide assay was 48-2529 nM BCE. Samples containing low or high serum/urine bone marker levels were reassayed after adjusting sample volume or dilution to ensure all samples would be assayed within acceptable precision and accuracy.

Figure 19:
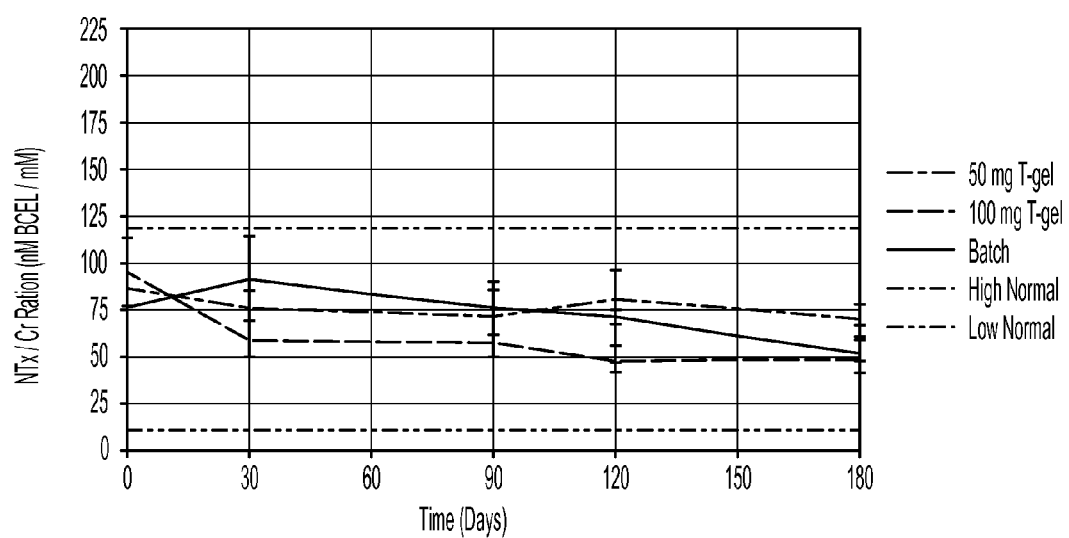
FIG. 19 is a graph showing the N-telopeptide/Cr ratio on days 0 through 180 for hypogonadal men receiving either 5.0 g/day of ANDROGEL® (testosterone gel), 10.0 g/day of ANDROGEL® (testosterone gel), or the testosterone patch (by initial treatment group).

The normal adult male range for the N-telopeptide/Cr ratio is 13 to 119 nM BCE/nM Cr. As shown in FIG. 19 and Table 22, urinary N-telopeptide/Cr ratios were similar in all three treatment groups at baseline but decreased significantly in the ANDROGEL® (testosterone gel) 10.0 g/day group but not in the ANDROGEL® (testosterone gel) 5.0 g/day or testosterone patch group during the first 90 days of treatment. The decrease was maintained such that urinary N-telopeptide/Cr ratio remained lower than baseline in ANDROGEL® (test-

TABLE 21

Procollagen Concentrations on Each of the Observation Days by Final Treatment Group (Mean ± SD)

| | N | 5 g/day T-gel | N | 5 => 7.5 g/day T-gel | N | 10 => 7.5 g/day T-gel | N | 10 g/day T-gel | N | T-Patch |
|---|---|---|---|---|---|---|---|---|---|---|
| Day 0 | 53 | 115.94 ± 43.68 | 20 | 109.27 ± 32.70 | 20 | 120.93 ± 28.16 | 58 | 125.33 ± 57.57 | 76 | 122.08 ± 51.74 |
| Day 30 | 49 | 141.09 ± 64.02 | 20 | 141.41 ± 77.35 | 20 | 147.25 ± 49.85 | 58 | 149.37 ± 60.61 | 71 | 139.26 ± 59.12 |
| Day 90 | 47 | 137.68 ± 68.51 | 20 | 129.02 ± 60.20 | 29 | 144.60 ± 58.20 | 55 | 135.59 ± 51.54 | 66 | 130.87 ± 49.91 |
| Day 120 | 46 | 140 07 ± 81.48 | 19 | 133.61 ± 54.09 | 20 | 139.00 ± 64.96 | 50 | 128.48 ± 45.56 | 46 | 130.39 ± 42.22 |
| Day 180 | 45 | 119.78 ± 49.02 | 19 | 108.78 ± 35.29 | 19 | 123.51 ± 39.30 | 51 | 108.52 ± 38.98 | 45 | 120.74 ± 56.10 | osterone gel) 10.0 g/day and in those subjects adjusted to 7.5 g/day from 10.0 g/day group at day 180. This ratio also decreased in the testosterone patch treatment group by day 180.

TABLE 22

N-Telopeptide/Cr Ratio on Each of the Observation Days by Initial Treatment Group (Mean ± SD)

| Initial Treatment Group | N | 5.0 g/day T-gel | N | 10.0 g/day T-gel | N | T-Patch | Across-group p-value |
|---|---|---|---|---|---|---|---|
| Day 0   | 71 | 90.3 ± 170.3 | 75 | 98.0 ± 128.2 | 75 | 78.5 ± 82.5  | 0.6986 |
| Day 30  | 65 | 74.6 ± 79.3  | 73 | 58.4 ± 66.4  | 66 | 91.6 ± 183.6 | 0.3273 |
| Day 90  | 62 | 70.4 ± 92.6  | 73 | 55.2 ± 49.1  | 63 | 75.0 ± 113.5 | 0.5348 |
| Day 120 | 35 | 78.8 ± 88.2  | 36 | 46.6 ± 36.4  | 21 | 71.2 ± 108.8 | 0.2866 |
| Day 180 | 64 | 68.2 ± 81.1  | 70 | 46.9 ± 43.1  | 47 | 49.4 ± 40.8  | 0.2285 |

Figure 20:
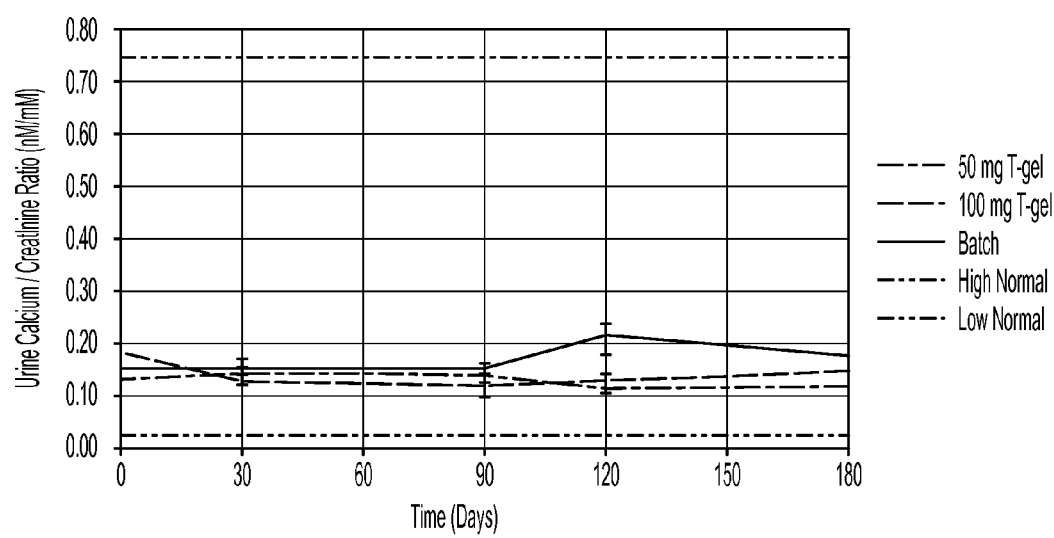
FIG. 20 is a graph showing the Ca/Cr ratio on days 0 through 180 for hypogonadal men receiving either 5.0 g/day of ANDROGEL® (testosterone gel), 10.0 g/day of ANDROGEL® (testosterone gel), or the testosterone patch (by initial treatment group).

The normal range for Ca/Cr ratio is 0.022 to 0.745 mM/mM. FIG. 20 shows no significant difference in baseline urinary Ca/Cr ratios in the three groups. With transdermal testosterone replacement therapy, urinary Ca/Cr ratios did not show a significant decrease in any treatment group at day 90. With continued testosterone replacement to day 180, urinary Ca/Cr showed marked variation without significant changes in any treatment groups.

TABLE 23

Ca/Cr Ratio on Each of the Observation Days by Initial Treatment Group (Mean ± SD)

| Initial Treatment Group | N | 5.0 g/day T-gel | N | 10.0 g/day T-gel | N | T-Patch | Across-group p-value |
|---|---|---|---|---|---|---|---|
| Day 0   | 71 | 0.150 ± 0.113 | 75 | 0.174 ± 0.222 | 75 | 0.158 ± 0.137 | 0.6925 |
| Day 30  | 65 | 0.153 ± 0.182 | 73 | 0.128 ± 0.104 | 66 | 0.152 ± 0.098 | 0.3384 |
| Day 90  | 63 | 0.136 ± 0.122 | 73 | 0.113 ± 0.075 | 63 | 0.146 ± 0.099 | 0.2531 |
| Day 120 | 36 | 0.108 ± 0.073 | 36 | 0.117 ± 0.090 | 21 | 0.220 ± 0.194 | 0.0518 |
| Day 180 | 64 | 0.114 ± 0.088 | 70 | 0.144 ± 0.113 | 47 | 0.173 ± 0.108 | 0.0398 |

Interestingly, the change in Ca/Cr ratio from baseline at day 90 was inversely related to the baseline Ca/Cr ratios. Similarly, the change in urine N-telopeptide/Cr ratio was also inversely proportional to the baseline N telopeptide/Cr ratio (r=−0.80, p=0.001). Thus subjects with the highest bone resorption markers at baseline showed the largest decreases of these markers during transdermal testosterone replacement. The decreases in urinary bone resorption markers were most prominent in subjects who had highest baseline values, suggesting that hypogonadal subjects with the most severe metabolic bone disease responded most to testosterone replacement therapy.

d. Serum Calcium.

Serum calcium showed no significant inter-group differences at baseline, nor significant changes after testosterone replacement. Serum calcium levels showed insignificant changes during testosterone replacement.

3. Libido, Sexual Performance, and Mood.

Sexual function and mood were assessed by questionnaires the patients answered daily for seven consecutive days before clinic visits on day 0 and on days 30, 60, 90, 120, 150, and 180 days during gel and patch application. The subjects recorded whether they had sexual day dreams, anticipation of sex, flirting, sexual interaction (e.g., sexual motivation parameters) and orgasm, erection, masturbation, ejaculation, intercourse (e.g., sexual performance parameters) on each of the seven days. The value was recorded as 0 (none) or 1 (any) for analyses and the number of days the subjects noted a parameter was summed for the seven day period. The average of the four sexual motivation parameters was taken as the sexual motivation score and that of the five sexual motivation parameters as the sexual motivation mean score (0 to 7). The subjects also assessed their level of sexual desire, sexual enjoyment, and satisfaction of erection using a seven-point Likert-type scale (0 to 7) and the percent of full erection from 0 to 100%. The subjects rated their mood using a 0 to 7 score. The parameters assessed included positive mood responses: alert, friendly, full of energy, well/good feelings and negative mood responses: angry, irritable, sad, tired, nervous. Weekly average scores were calculated. The details of this questionnaire had been described previously and are fully incorporated by reference. See Wang et al., "Testosterone Replacement Therapy Improves Mood in Hypogonadal Men A Clinical Research Center Study," 81 *J. Clinical Endocrinology & Metabolism* 3578-3583 (1996).

a. Libido.

Figure 21A:
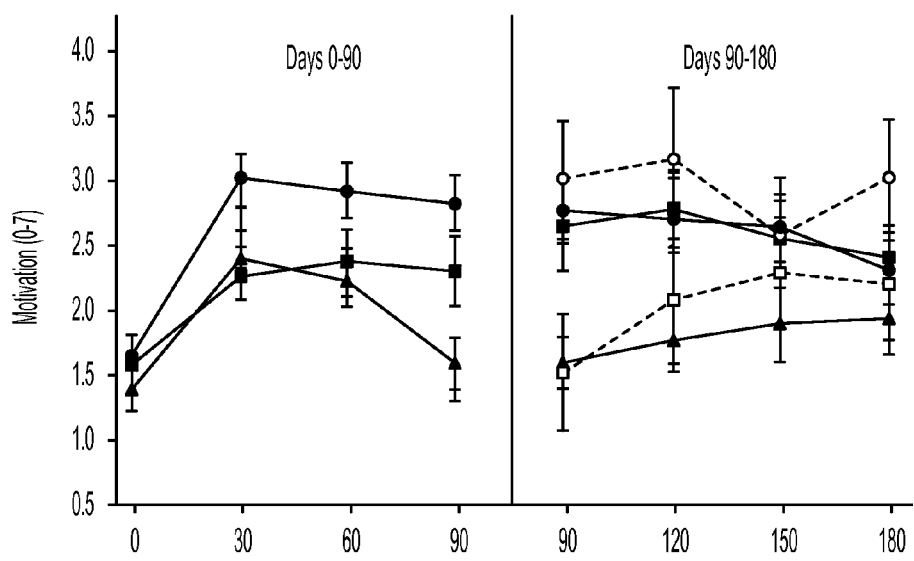
FIG. 21(a) is a graph showing sexual motivation scores on days 0 through 180 for hypogonadal men receiving either 5.0 g/day of ANDROGEL® (testosterone gel), 7.5 g/day of ANDROGEL® (testosterone gel), 10.0 g/day of ANDROGEL® (testosterone gel), or the testosterone patch.
Figure 21B:
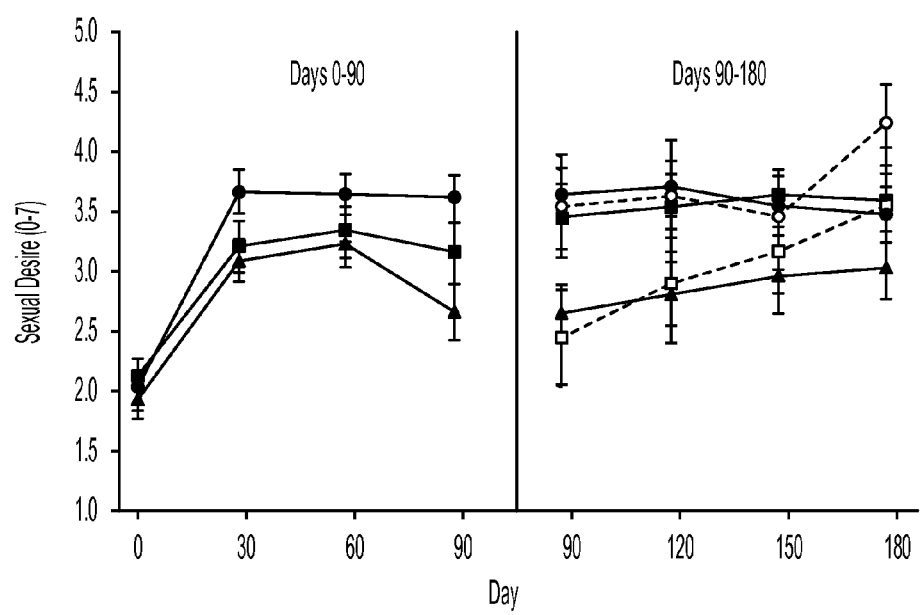
FIG. 21(b) is a graph showing overall sexual desire scores on days 0 through 180 for hypogonadal men receiving either 5.0 g/day of ANDROGEL® (testosterone gel), 7.5 g/day of ANDROGEL® (testosterone gel), 10.0/g/day of ANDROGEL® (testosterone gel), or the testosterone patch.
Figure 21C:
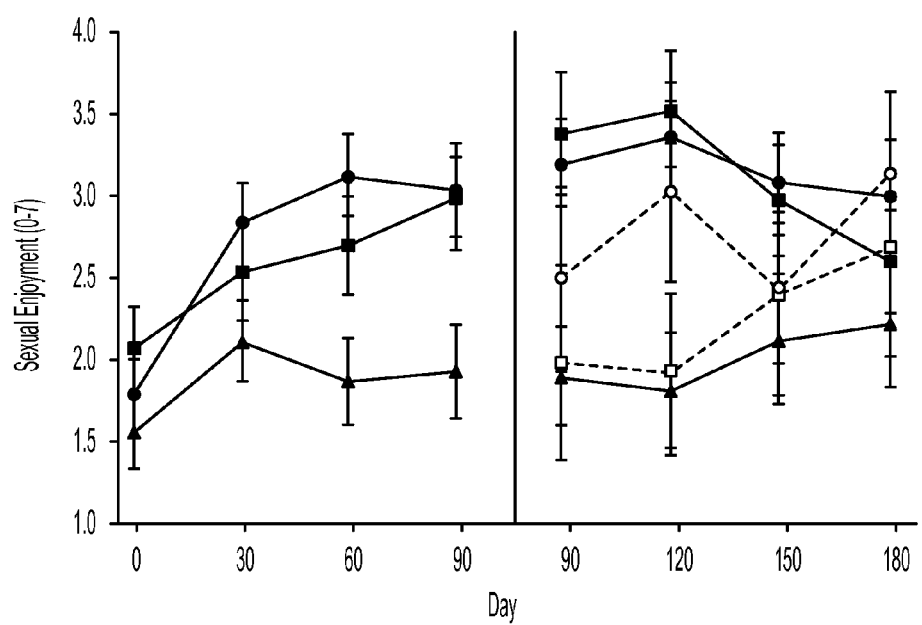
FIG. 21(c) is a graph showing sexual enjoyment (with a partner) scores on days 0 through 180 for hypogonadal men receiving either 5.0 g/day of ANDROGEL® (testosterone gel), 7.5 g/day of ANDROGEL® (testosterone gel), 10.0 g/day of ANDROGEL® (testosterone gel), or the testosterone patch.

As shown in FIG. 21(*a*), at baseline, sexual motivation was the same in all treatment groups. After transdermal testosterone treatment, overall sexual motivation showed significant improvement. The change in the summary score from baseline, however, was not different among the three treatment groups.

Libido was assessed from responses on a linear scale of: (1) overall sexual desire, (2) of sexual activity without a partner, and (3) enjoyment of sexual activity with a partner. As shown in FIG. 21(*b*) and Table 24, as a group, overall sexual desire increased after transdermal testosterone treatment without inter-group difference. Sexual enjoyment with and without a partner (FIG. 21(*c*) and Tables 25 and 26) also increased as a group.

Similarly the sexual performance score improved significantly in all subjects as a group. The improvement in sexual performance from baseline values was not different between transdermal preparations.

TABLE 24

Overall Sexual Desire Changes From Day 0 to Day 180 by Initial Treatment Group (Mean ± SD)

| Initial Treatment Group | N | Day 0 | N | Day 180 | N | Change From Day 0 to Day 180 | Within-Group p-value |
|---|---|---|---|---|---|---|---|
| 5.0 g/day T-gel | 69 | 2.1 ± 1.6 | 63 | 3.5 ± 1.6 | 60 | 1.4 ± 1.9 | 0.0001 |
| 10.0 g/day T-gel | 77 | 2.0 ± 1.4 | 68 | 3.6 ± 1.6 | 67 | 1.5 ± 1.9 | 0.0001 |
| T-Patch | 72 | 2.0 ± 1.6 | 47 | 3.1 ± 1.9 | 45 | 1.6 ± 2.1 | 0.0001 |
| Across-Groups p-value | | 0.8955 | | 0.2247 | | 0.8579 | |

TABLE 25

Level of Sexual Enjoyment Without a Partner Changes From Day 0 to Day 180 by Initial Treatment Group (Mean ± SD)

| Initial Treatment Group | N | Day 0 | N | Day 180 | N | Change From Day 0 to Day 180 | Within-Group p-value |
|---|---|---|---|---|---|---|---|
| 5.0 g/day T-gel | 60 | 1.5 ± 1.9 | 51 | 1.9 ± 1.9 | 44 | 0.8 ± 1.4 | 0.0051 |
| 10.0 g/day T-gel | 63 | 1.2 ± 1.4 | 53 | 2.2 ± 1.9 | 48 | 1.1 ± 1.6 | 0.0001 |
| T-Patch | 66 | 1.4 ± 1.8 | 44 | 2.2 ± 2.3 | 40 | 1.0 ± 1.9 | 0.0026 |
| Across-Groups p-value | | 0.6506 | | 0.7461 | | 0.6126 | |

TABLE 26

Level of Sexual Enjoyment With a Partner Change from Day 0 to Day 180 by Initial Treatment Group (Mean ± SD)

| Initial Treatment Group | N | Day 0 | N | Day 180 | N | Change From Day 0 to Day 180 | Within-Group p-value |
|---|---|---|---|---|---|---|---|
| 5.0 g/day T-gel | 64 | 2.1 ± 2.1 | 55 | 2.6 ± 2.2 | 48 | 0.4 ± 2.2 | 0.0148 |
| 10.0 g/day T-gel | 66 | 1.8 ± 1.7 | 58 | 3.0 ± 2.2 | 52 | 1.0 ± 2.3 | 0.0053 |
| T-Patch | 61 | 1.5 ± 1.7 | 40 | 2.2 ± 2.4 | 35 | 0.7 ± 2.3 | 0.1170 |
| Across-Groups p-value | | 0.2914 | | 0.1738 | | 0.3911 | | b. Sexual Performance.

Figure 22A:
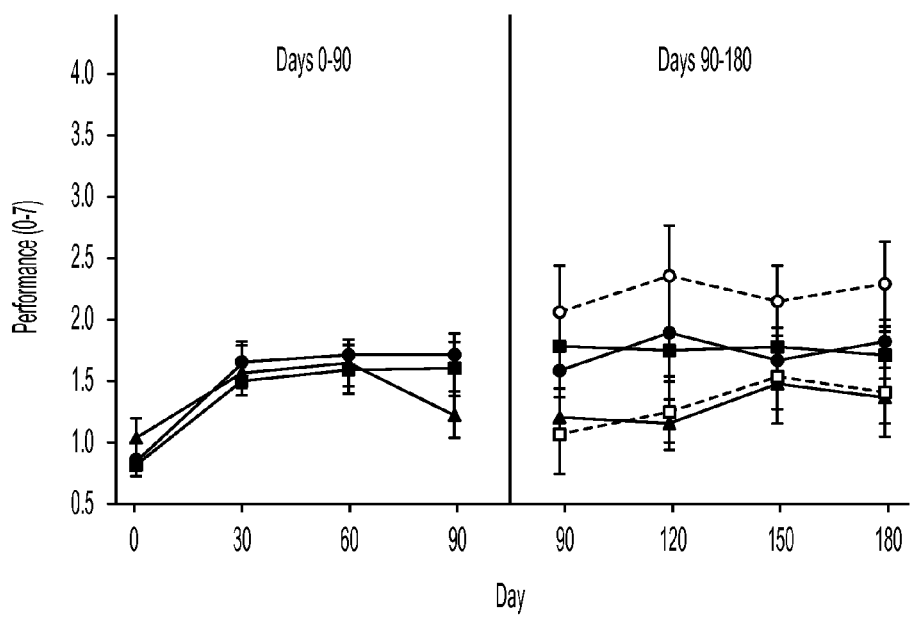
FIG. 22(a) is a graph showing sexual performance scores on days 0 through 180 for hypogonadal men receiving either 5.0 g/day of ANDROGEL® (testosterone gel), 7.5 g/day of ANDROGEL® (testosterone gel), 10.0 g/day of ANDROGEL® (testosterone gel), or the testosterone patch.
Figure 22B:
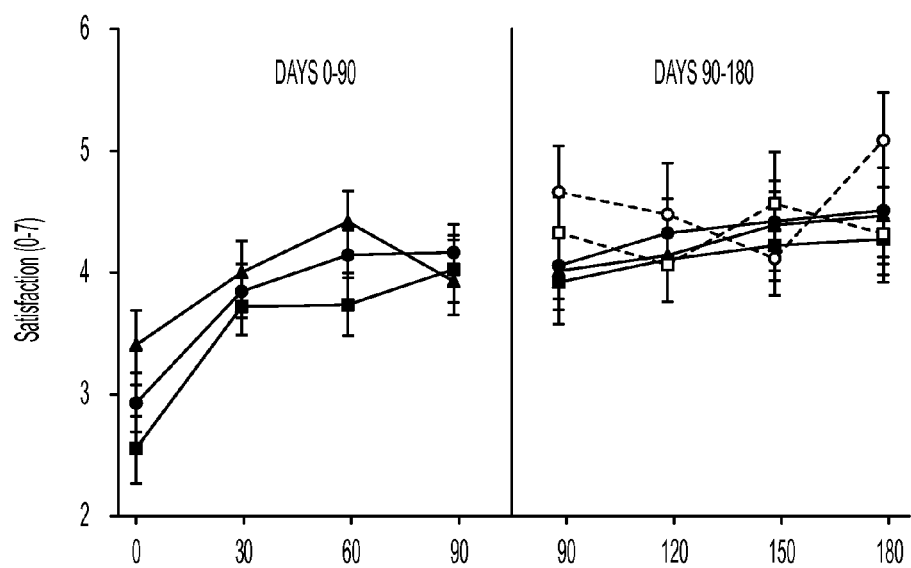
FIG. 22(b) is a graph showing erection satisfaction performance scores on days 0 through 180 for hypogonadal men receiving either 5.0 g/day of ANDROGEL® (testosterone gel), 7.5 g/day of ANDROGEL® (testosterone gel), 10.0 g/day of ANDROGEL® (testosterone gel), or the testosterone patch.
Figure 22C:
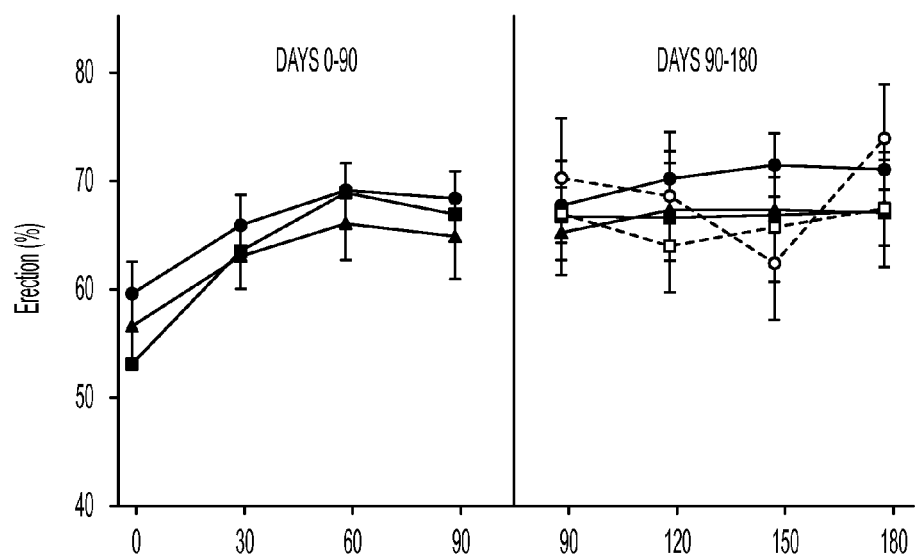
FIG. 22(c) is a graph showing percent erection scores on days 0 through 180 for hypogonadal men receiving either 5.0 g/day of ANDROGEL® (testosterone gel), 7.5 g/day of ANDROGEL® (testosterone gel), 10.0 g/day of ANDROGEL® (testosterone gel), or the testosterone patch.

FIG. 22(a) shows that while all treatment groups had the same baseline sexual performance rating, the rating improved with transdermal testosterone treatment in all groups. In addition, as a group, the subjects' self-assessment of satisfaction of erection (FIG. 22(b) and Table 27) and percent full erection (FIG. 22(c) and Table 28) were also increased with testosterone replacement without significant differences between groups.

The improvement in sexual function was not related to the dose or the delivery method of testosterone. Nor was the improvement related to the serum testosterone levels achieved by the various testosterone preparations. The data suggest that once a threshold (serum testosterone level probably at the low normal range) is achieved, normalization of sexual function occurs. Increasing serum testosterone levels higher to the upper normal range does not further improve sexual motivation or performance.

TABLE 27

Satisfaction with Duration of Erection Change from Day 0 to Day 180 by Initial Treatment Group (Mean ± SD)

| Initial Treatment Group | N | Day 0 | N | Day 180 | N | Change From Day 0 to Day 180 | Within-Group p-value |
|---|---|---|---|---|---|---|---|
| 5.0 g/day T-gel | 55 | 2.5 ± 2.1 | 57 | 4.3 ± 1.8 | 44 | 1.9 ± 2.0 | 0.0001 |
| 10.0 g/day T-gel | 64 | 2.9 ± 1.9 | 58 | 4.5 ± 1.7 | 53 | 1.5 ± 2.0 | 0.0001 |
| T-Patch | 45 | 3.4 ± 2.1 | 34 | 4.5 ± 2.0 | 20 | 1.3 ± 2.1 | 0.0524 |
| Across-Groups p-value | | 0.1117 | | 0.7093 | | 0.5090 | |

TABLE 28

Percentage of Full Erection Change from Day 0 to
Day 180 by Initial Treatment Group (Mean ± SD)

| Initial Treatment Group | N | Day 0 | N | Day 180 | N | Change From Day 0 to Day 180 | Within-Group p-value |
|---|---|---|---|---|---|---|---|
| 5.0 g/day T-gel | 53 | 53.1 ± 24.1 | 57 | 67.4 ± 22.5 | 43 | 18.7 ± 22.1 | 0.0001 |
| 10.0 g/day T-gel | 62 | 59.6 ± 22.1 | 59 | 72.0 ± 20.2 | 52 | 10.4 ± 23.4 | 0.0001 |
| T-Patch | 47 | 56.5 ± 24.7 | 33 | 66.7 ± 26.7 | 19 | 12.7 ± 20.3 | 0.0064 |
| Across-Groups p-value | | 0.3360 | | 0.4360 | | 0.1947 | | c. Mood.

Figure 23A:
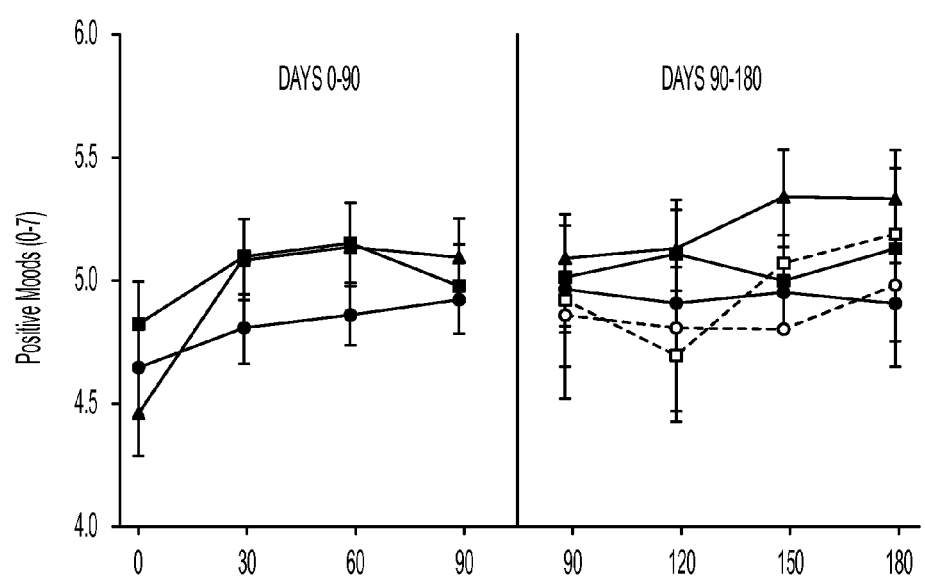
FIG. 23(a) is a graph showing positive mood scores on days 0 through 180 for hypogonadal men receiving either 5.0 g/day of ANDROGEL® (testosterone gel), 7.5 g/day of ANDROGEL® (testosterone gel), 10.0 g/day of ANDROGEL® (testosterone gel), or the testosterone patch.
Figure 23B:
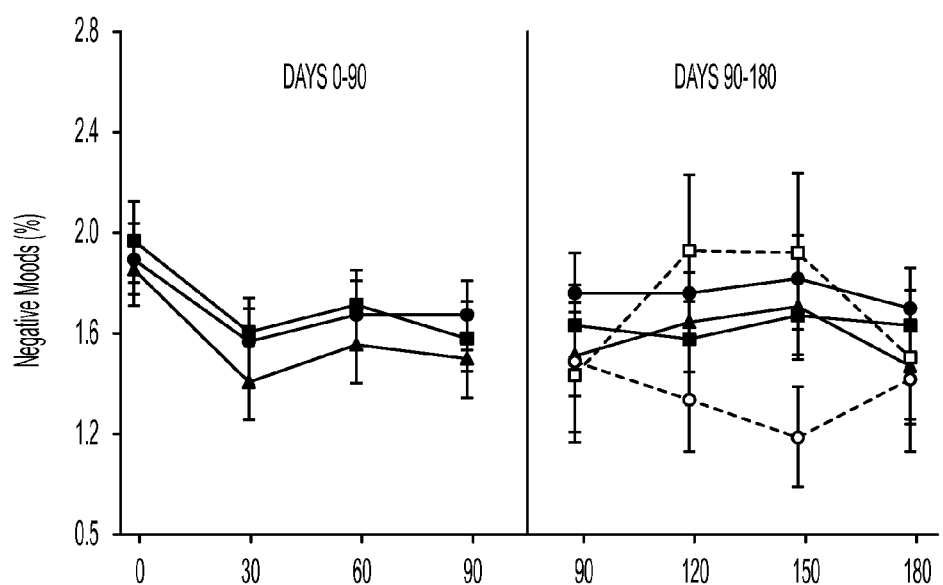
FIG. 23(b) is a graph showing negative mood scores on days 0 through 180 for hypogonadal men receiving either 5.0 g/day of ANDROGEL® (testosterone gel), 7.5 g/day of ANDROGEL® (testosterone gel), 10.0 g/day of ANDROGEL® (testosterone gel), or the testosterone patch.

The positive and negative mood summary responses to testosterone replacement therapy are shown in FIGS. 23(a) and 23(b). All three treatment groups had similar scores at baseline and all subjects as a group showed improvement in positive mood. Similarly, the negative mood summary scores were similar in the three groups at baseline and as a group the responses to transdermal testosterone applications showed significant decreases without showing between group differences. Specifically, positive mood parameters, such as sense of well being and energy level, improved and negative mood parameters, such as sadness and irritability, decreased. The improvement in mood was observed at day 30 and was maintained with continued treatment. The improvement in mood parameters was not dependent on the magnitude of increase in the serum testosterone levels. Once the serum testosterone increased into the low normal range, maximal improvement in mood parameters occurred. Thus, the responsiveness in sexual function and mood in hypogonadal men in response to testosterone therapy appeared to be dependent on reaching a threshold of serum testosterone at the low normal range.

4. Muscle Strength.

Muscle strength was assessed on days 0, 90, and 180. The one-repetitive maximum ("1-RM") technique was used to measure muscle mass in bench press and seated leg press exercises. The muscle groups tested included those in the hips, legs, shoulders, arms, and chest. The 1-RM technique assesses the maximal force generating capacity of the muscles used to perform the test. After a 5-10 minute walking and stretching period, the test began with a weight believed likely to represent the patient's maximum strength. The test was repeated using increments of about 2-10 pounds until the patient was unable to lift additional weight with acceptable form. Muscle strength was assessed in 167 out of the 227 patients. Four out of 16 centers did not participate in the muscle strength testing because of lack of the required equipment.

Figure 24A:
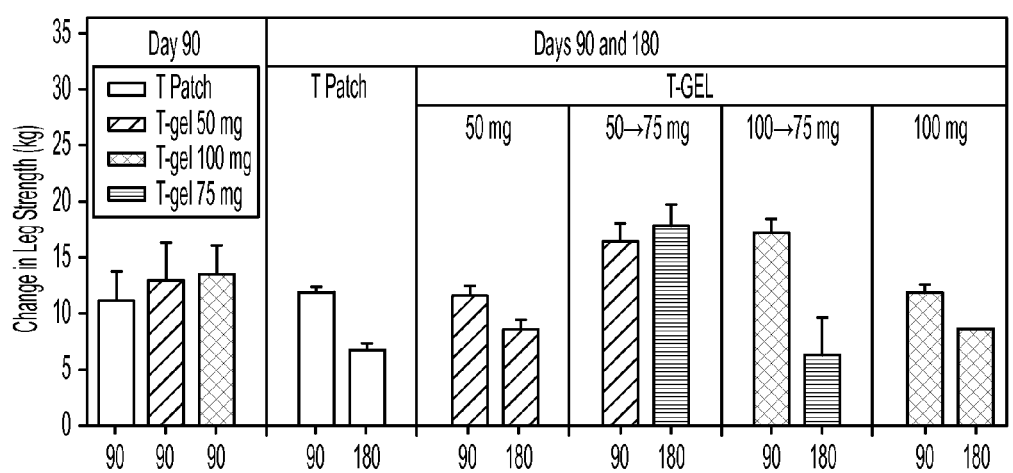
FIG. 24(a) is a bar graph showing the change in leg strength on days 90 and 180 for hypogonadal men receiving either 5.0 g/day of ANDROGEL® (testosterone gel), 7.5 g/day of ANDROGEL® (testosterone gel), 10.0 g/day of ANDROGEL® (testosterone gel), or the testosterone patch.
Figure 24B:
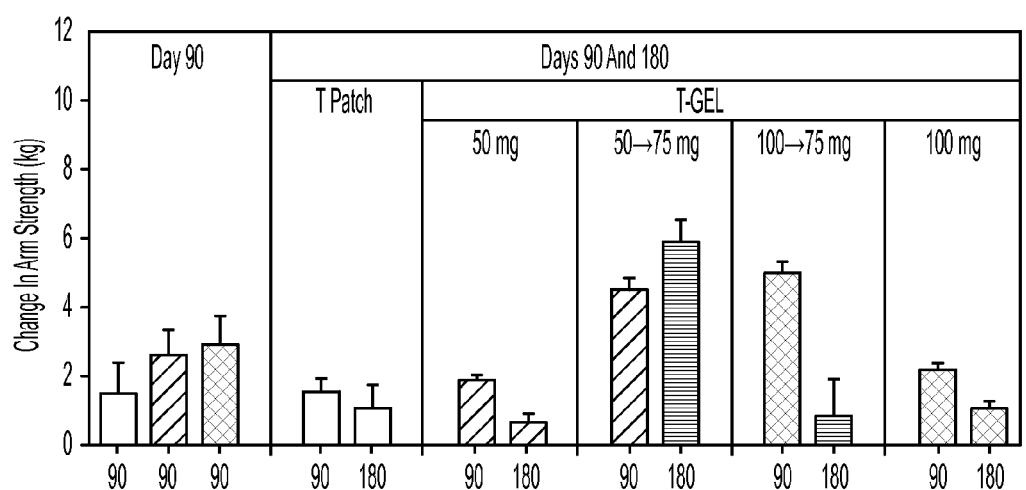
FIG. 24(b) is a bar graph showing the change in arm strength on days 90 and 180 for hypogonadal men receiving either 5.0 g/day of ANDROGEL® (testosterone gel), 7.5 g/day of ANDROGEL® (testosterone gel), 10.0 g/day of ANDROGEL® (testosterone gel), or the testosterone patch.

The responses of muscle strength testing by the arm/chest and leg press tests are shown in FIGS. 24(a) and 24(b) and Table 29. There were no statistical significant differences in arm/chest or leg muscle strength among the three groups at baseline. In general, muscle strength improved in both the arms and legs in all three treatment groups without inter-group differences at both day 90 and 180. The results showed an improvement in muscle strength at 90 and 180 days, more in the legs than the arms, which was not different across treatment groups nor on the different days of assessment. Adjustment of the dose at day 90 did not significantly affect the muscle strength responses to transdermal testosterone preparations.

TABLE 29

Muscle Strength - Days 0, 90, and 180 Levels
and Change (lbs.) from Day 0 to Day 90 and from
Day 0 to Day 180 by Final Treatment Group

| Final Treatment Group | Study Day | Seated Leg Press | | Arm/Chest (Bench Press) | |
|---|---|---|---|---|---|
| | | N | Mean ± SD (lbs.) | N | Mean ± SD (lbs.) |
| 5.0 g/day T-gel | 0 | 37 | 356.8 ± 170.0 | 37 | 100.5 ± 37.4 |
| | 90 | 30 | 396.4 ± 194.3 | 31 | 101.2 ± 30.7 |
| | Δ 0-90 | 30 | 25.8 ± 49.2 | 31 | 4.0 ± 10.0 |
| | 180 | 31 | 393.4 ± 196.6 | 31 | 99.7 ± 31.4 |
| | Δ 0-180 | 31 | 19.9 ± 62.4 | 31 | 1.3 ± 13.0 |
| 7.5 g/day T-gel (from 5.0 g/day) | 0 | 16 | 302.8 ± 206.5 | 16 | 102.8 ± 48.9 |
| | 90 | 15 | 299.8 ± 193.9 | 15 | 109.5 ± 47.6 |
| | Δ 0-90 | 15 | 17.0 ± 88.4 | 15 | 5.0 ± 21.3 |
| | 180 | 14 | 300.6 ± 203.0 | 14 | 108.5 ± 49.3 |
| | Δ 0-180 | 14 | −0.1 ± 110.2 | 14 | 5.6 ± 30.4 |
| 7.5 g/day T-gel (From 10.0 g/day) | 0 | 14 | 363.4 ± 173.8 | 14 | 123.3 ± 54.7 |
| | 90 | 14 | 401.6 ± 176.6 | 14 | 134.6 ± 57.5 |
| | Δ 0-90 | 14 | 38.2 ± 42.9 | 14 | 11.3 ± 10.5 |
| | 180 | 12 | 409.9 ± 180.2 | 14 | 132.3 ± 61.5 |
| | Δ 0-180 | 12 | 33.9 ± 67.3 | 14 | 9.0 ± 18.7 |
| 10.0 g/day T-gel | 0 | 45 | 345.9 ± 186.9 | 43 | 114.7 ± 55.1 |
| | 90 | 43 | 373.5 ± 194.8 | 41 | 119.8 ± 54.2 |
| | Δ 0-90 | 43 | 27.6 ± 45.1 | 41 | 4.6 ± 12.8 |
| | 180 | 36 | 364.4 ± 189.1 | 34 | 112.0 ± 45.5 |
| | Δ 0-180 | 36 | 32.2 ± 72.3 | 34 | 1.9 ± 14.8 |
| T-Patch | 0 | 55 | 310.4 ± 169.7 | 54 | 99.2 ± 43.1 |
| | 90 | 46 | 344.9 ± 183.9 | 46 | 106.2 ± 44.0 |
| | Δ 0-90 | 46 | 25.4 ± 37.0 | 46 | 3.2 ± 12.0 |
| | 180 | 36 | 324.8 ± 199.0 | 35 | 104.8 ± 44.8 |
| | Δ 0-180 | 36 | 15.2 ± 54.7 | 35 | 2.3 ± 15.7 |

5. Body Composition.

Body composition was measured by DEXA with Hologic 2000 or 4500A series on days 0, 90, and 180. These assessments were done in 168 out of 227 subjects because the Hologic DEXA equipment was not available at 3 out of 16 study centers. All body composition measurements were centrally analyzed and processed by Hologic (Waltham, Mass.).

Figure 25A:
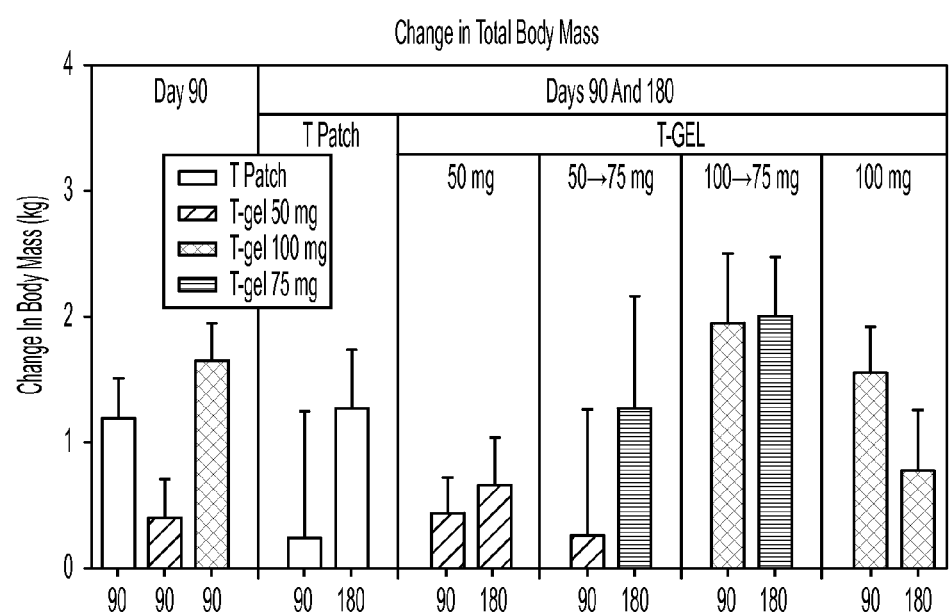
FIG. 25(a) is a bar graph showing the change in total body mass on days 90 and 180 for hypogonadal men receiving either 5.0 g/day of ANDROGEL® (testosterone gel), 7.5 g/day of ANDROGEL® (testosterone gel), 10.0 g/day of ANDROGEL® (testosterone gel), or the testosterone patch.
Figure 25B:
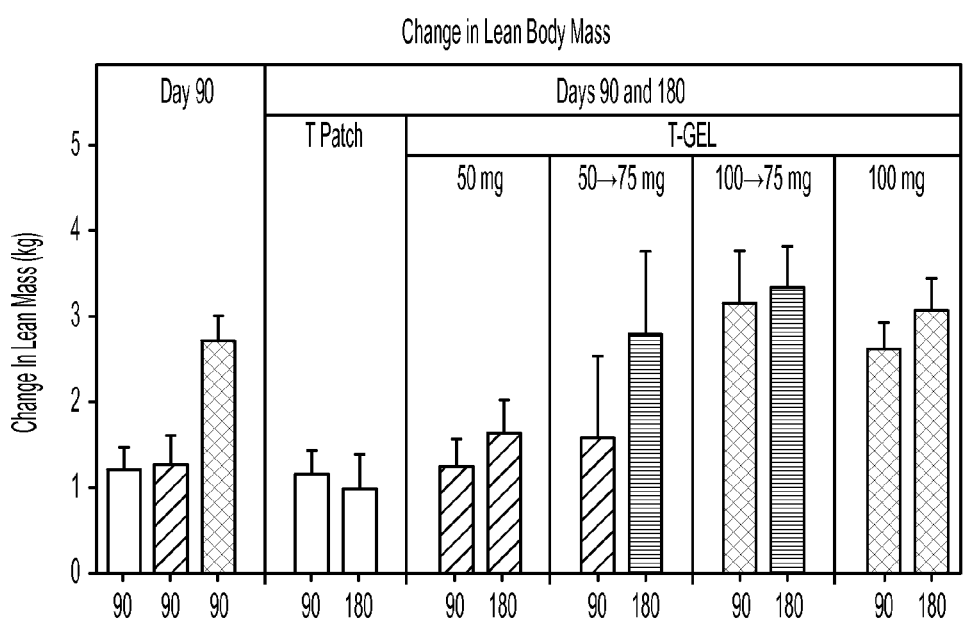
FIG. 25(b) is a bar graph showing the change in lean body mass on days 90 and 180 for hypogonadal men receiving either 5.0 g/day of ANDROGEL® (testosterone gel), 7.5 g/day of ANDROGEL® (testosterone gel), 10.0 g/day of ANDROGEL® (testosterone gel), or the testosterone patch.

At baseline, there were no significant differences in total body mass ("TBM"), total body lean mass ("TLN"), percent fat ("PFT"), and total body fat mass ("TFT") in the three treatment groups. As shown in FIG. 25(a) and Table 30, all treatment groups incurred an overall increase in TBM. The increase in TBM was mainly due to the increases in TLN. FIG. 25(b) and Table 30 show that after 90 days of testosterone replacement the increase in TLN was significantly higher in the 10.0 g/day ANDROGEL® (testosterone gel) group than in the other two groups. At day 180, the increases in TLN were further enhanced or maintained in all ANDROGEL® (testosterone gel) treated groups, as well as in the testosterone patch group.

Figure 25C:
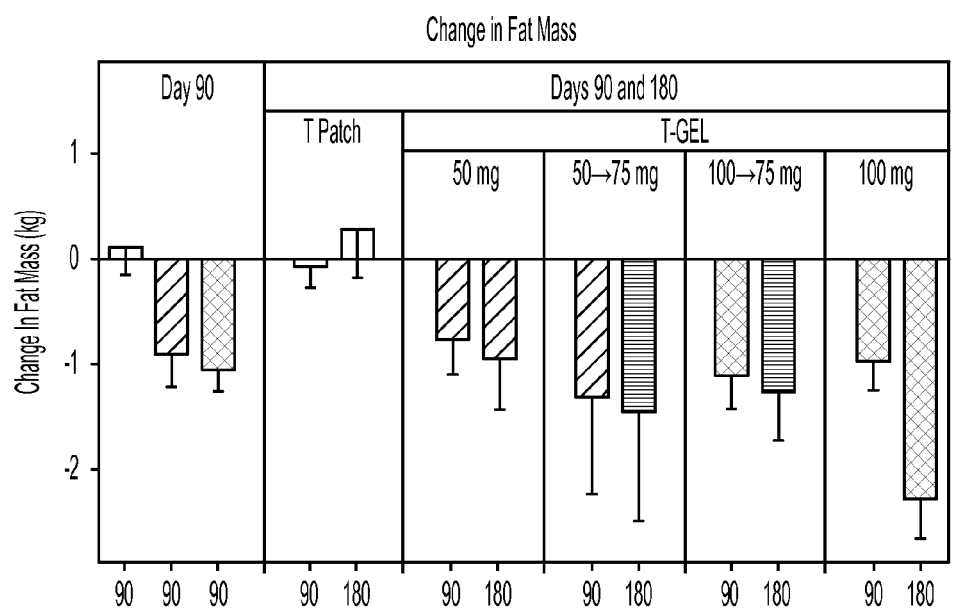
FIG. 25(c) is a bar graph showing the change in fat mass on days 90 and 180 for hypogonadal men receiving either 5.0 g/day of ANDROGEL® (testosterone gel), 7.5 g/day of ANDROGEL® (testosterone gel), 10.0 g/day of ANDROGEL® (testosterone gel), or the testosterone patch.
Figure 25D:
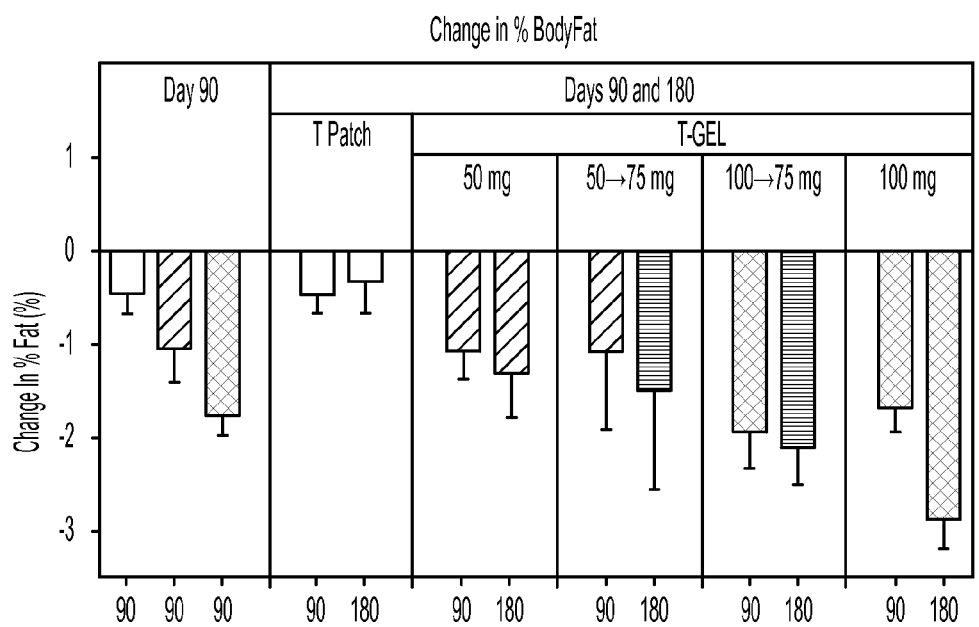
FIG. 25(d) is a bar graph showing the change in percent body fat on days 90 and 180 for hypogonadal men receiving either 5.0 g/day of ANDROGEL® (testosterone gel), 7.5 g/day of ANDROGEL® (testosterone gel), 10.0 g/day of ANDROGEL® (testosterone gel), or the testosterone patch.

FIGS. 25(c) and (d) show that the TFT and the PFT decreased in all transdermal ANDROGEL® (testosterone gel) treatment groups. At 90 days of treatment, TFT was significantly reduced in the 5.0 g/day and 10.0 g/day ANDROGEL® (testosterone gel) groups, but was not changed in the testosterone patch group. This decrease was maintained at day 180. Correspondingly, at day 90 and 180, the decrease in PFT remained significantly lower in all ANDROGEL® (testosterone gel) treated groups but not significantly reduced in the testosterone patch group.

The increase in TLN and the decrease in TFT associated with testosterone replacement therapy showed significant correlations with the serum testosterone level attained by the testosterone patch and the different doses of ANDROGEL® (testosterone gel). Testosterone gel administered at 10.0 increased lean mass more than the testosterone patch and the 5.0 g/day ANDROGEL® (testosterone gel) groups. The changes were apparent on day 90 after treatment and were maintained or enhanced at day 180. Such changes in body composition was significant even though the subjects were withdrawn from prior testosterone therapy for six weeks. The decrease in TFT and PFT was also related to the serum testosterone achieved and were different across the treatment groups. The testosterone patch group did not show a decrease in PFT or TFT after 180 days of treatment. Treatment with ANDROGEL® (testosterone gel) (5.0 to 10.0 g/day) for 90 days reduced PFT and TFT. This decrease was maintained in the 5.0 and 7.5 g/day groups at 180 days but were further lowered with continued treatment with the higher dose of the ANDROGEL® (testosterone gel).

ter's laboratory) at day 180 in 17.2, 20.4, and 12.2% of subjects on testosterone patch, ANDROGEL® (testosterone gel) 5.0 g/day and ANDROGEL® (testosterone gel) 10.0 g/day, respectively. Serum HDL-cholesterol levels (initially normal) were reduced to below the normal range (of each center's laboratory) in 9.8, 4.0, 9.1, and 12.5% of subjects at day 180 in the testosterone patch, ANDROGEL® (testosterone gel) 5.0, 7.5, and 10.0 g/day groups, respectively. There was no clinically significant changes in renal or liver function tests in any treatment group.

7. Skin Irritations.

Skin irritation assessments were performed at every clinic visit using the following scale: 0=no erythema; 1=minimal erythema; 2=moderate erythema with sharply defined borders; 3=intense erythema with edema; and 4=intense erythema with edema and blistering/erosion.

Tolerability of the daily application of ANDROGEL® (testosterone gel) at the tested dosages was much better than with the permeation-enhanced testosterone patch. Minimal skin irritation (erythema) at the application site was noted in three patients in the ANDROGEL® (testosterone gel) 5.0 g/day group (5.7%) and another three in the ANDROGEL® (testosterone gel) 10.0 g/day group (5.3%). Skin irritation varying in intensity from minimal to severe (mild erythema to intense edema with blisters) occurred in 65.8% of patients in the patch group. Because of the skin irritation with the testosterone patch, 16 subjects discontinued the study; 14 of these had

TABLE 30

Mean Change in Body Composition Parameters (DEXA) From Baseline to Day 90 and Baseline to Day 180 By Final Treatment Groups

| Final Treatment Group | Mean Change from Day 0-Day 90 | | | | |
|---|---|---|---|---|---|
| | N | TFT (g) | TLN (g) | TBM (g) | PFT |
| 5.0 g/day T-gel | 43 | −782 ± 2105 | 1218 ± 2114 | 447 ± 1971 | −1.0 ± 2.2 |
| 7.5 g/day (from 5.0 g/day) | 12 | −1342 ± 3212 | 1562 ± 3321 | 241 ± 3545 | −1.0 ± 3.1 |
| 7.5 g/day (from 10.0 g/day) | 16 | −1183 ± 1323 | 3359 ± 2425 | 2176 ± 2213 | −2.0 ± 1.5 |
| 10.0 g/day T-gel | 45 | −999 ± 1849 | 2517 ± 2042 | 1519 ± 2320 | −1.7 ± 1.8 |
| T-Patch | 52 | 11 ± 1769 | 1205 ± 1913 | 1222 ± 2290 | −0.4 ± 1.6 |

| Final Treatment Group | Mean Change from Day 0-Day 180 | | | | |
|---|---|---|---|---|---|
| | N | TFT (g) | TLN (g) | TBM (g) | PFT |
| 5.0 g/day T-gel | 38 | −972 ± 3191 | 1670 ± 2469 | 725 ± 2357 | −1.3 ± 3.1 |
| 7.5 g/day (from 5.0 g/day) | 13 | −1467 ± 3851 | 2761 ± 3513 | 1303 ± 3202 | −1.5 ± 3.9 |
| 7.5 g/day (from 10.0 g/day) | 16 | −1333 ± 1954 | 3503 ± 1726 | 2167 ± 1997 | −2.2 ± 1.7 |
| 10.0 g/day T-gel | 42 | −2293 ± 2509 | 3048 ± 2284 | 771 ± 3141 | −2.9 ± 2.1 |
| T-Patch | 34 | 293 ± 2695 | 997 ± 2224 | 1294 ± 2764 | −0.3 ± 2.2 |

6. Lipid Profile and Blood Chemistry.

The serum total, HDL, and LDL cholesterol levels at baseline were not significantly different in all treatment groups. With transdermal testosterone replacement, there were no overall treatment effects nor inter-group differences in serum concentrations of total, HDL- and LDL-cholesterol (FIG. 5(d)) and triglycerides (data not shown). There was a significant change of serum total cholesterol concentrations as a group with time (p=0.0001), the concentrations on day 30, 90, and 180 were significantly lower than day 0.

Approximately 70 to 95% of the subjects had no significant change in their serum lipid profile during testosterone replacement therapy. Total cholesterol levels which were initially high were lowered into the normal range (of each cenmoderate to severe skin reactions at the medication sites. No patients who received ANDROGEL® (testosterone gel) discontinued the study because of adverse skin reactions. The open system and the lower concentration of alcohol in the ANDROGEL® (testosterone gel) formulation markedly reduced skin irritation resulting in better tolerability and continuation rate on testosterone replacement therapy.

Moreover, based on the difference in the weight of the dispensed and returned ANDROGEL® (testosterone gel) bottles, the mean compliance was 93.1% and 96.0% for the 5.0 g/day and 10.0 g/day ANDROGEL® (testosterone gel) groups during days 1-90, respectively. Compliance remained at over 93% for the three ANDROGEL® (testosterone gel) groups from days 91-180. In contrast, based on counting the patches returned by the subjects, the testosterone patch compliance was 65% during days 1-90 and 74% during days 91-180. The lower compliance in the testosterone patch group was mostly due to skin reactions from the subjects' records.

TABLE 31

Incidence of Skin-Associated Adverse Events: Day 1 to Day 180 in Patients Who Remained on Initial Treatment

|  | 5.0 g/day T-gel N = 53 | 10.0 g/day T-gel N = 57 | T-Patch N = 73 |
|---|---|---|---|
| Total | 16 (30.2%) | 18 (31.6%) | 50 (68.5%) |
| Application Site Reaction | 3 (5.7% | 3 (5.3%) | 48 (65.8%) |
| Acne | 1 (1.9%) | 7 (12.3%) | 3 (4.1%) |
| Rash | 4 (7.5%) | 4 (7.0%) | 2 (2.7%) |
| Skin Disorder | 2 (3.8%) | 1 (1.8%) | 1 (1.4%) |
| Skin Dry | 2 (3.8) | 0 (0.0%) | 1 (1.4%) |
| Sweat | 0 (0.0%) | 2 (3.5%) | 0 (0.0%) |
| Reaction Unevaluable | 2 (3.6%) | 1 (1.7%) | 0 (0.0%) |
| Cyst | 0 (0.0%) | 0 (0.0%) | 2 (2.7%) |

Example 2

Gel Delivery Dosage Forms and Devices

The present invention is also directed to a method for dispensing and packaging the gel. In one embodiment, the invention comprises a hand-held pump capable of delivering about 2.5 g of testosterone gel with each actuation. In another embodiment, the gel is packaged in foil packets comprising a polyethylene liner. Each packet holds about 2.5 g of testosterone gel. The patient simply tears the packet along a perforated edge to remove the gel. However, because isopropyl myristate binds to the polyethylene liner, additional isopropyl myristate is added to the gel in order to obtain a pharmaceutically effective gel when using this delivery embodiment. Specifically, when dispensing the gel via the foil packet, about 41% more isopropyl myristate is used in the gel composition (i.e., about 0.705 g instead of about 0.5 g in Table 5), to compensate for this phenomenon.

The composition can also be dispensed from a rigid multi-dose container (e.g., with a hand pump) having a larger foil packet of the composition inside the container. Such larger packets also comprise a polyethylene liner as above.

Both embodiments permit a patient to deliver accurate but incremental amounts of gel (e.g., either 2.5 g, 5.0 g, 7.5 g, etc.) to the body. These delivery mechanisms thus permit the gel to be administered in unit dose form depending on the particular needs and characteristics of the patient.

Although the invention has been described with respect to specific embodiments and examples, it should be appreciated that other embodiments utilizing the concept of the present invention are possible without departing from the scope of the invention. The present invention is defined by the claimed elements, and any and all modifications, variations, or equivalents that fall within the true spirit and scope of the underlying principles.

The invention claimed is:

1. A method of treating hypogonadism in a human male, the method comprising the steps of:
    applying, once per day, a therapeutically effective dose of a pharmaceutical composition to an area of skin of the human male, the pharmaceutical composition consisting of:
    (i) 0.1% to 10% (w/w) testosterone;
    (ii) 0.10% to 5.0% (w/w) isopropyl myristate;
    (iii) 30.0% to 98.0% (w/w) of ethanol, isopropanol or combinations thereof;
    (iv) 0.1% to 5.0% of a polyacrylic acid, wherein the polyacrylic acid is neutralized with sodium hydroxide; and
    (v) water;
    wherein the administration of the pharmaceutical composition is as a gel and not as part of a patch, and
    further wherein the administration once per day is sufficient for the testosterone to reach the bloodstream of the human male to achieve a steady state profile in which there is an increase in serum testosterone levels of the human male for a period of time of 4 hours or less before returning to an approximately constant level.

2. The method of claim 1, wherein the sodium hydroxide is 0.1 N NaOH.

3. The method of claim 1, wherein the composition consists of testosterone, isopropyl myristate, ethanol, polyacrylic acid neutralized with sodium hydroxide and water.

4. The method of claim 3, wherein the ethanol is 95% (v/v) ethanol.

5. The method of claim 1, wherein the hypogonadism is primary hypogonadism, secondary hypogonadism or age-related hypogonadism.

6. The method of claim 1, wherein the pharmaceutical composition is administered to the left upper arm, the right upper arm, the left shoulder or the right shoulder.

7. The method of claim 1, wherein the administration once per day is sufficient for the testosterone to reach the bloodstream of the human male to achieve a steady state profile in which there is an increase in serum testosterone levels of the human male for a period of time of 2 hours or less before returning to a relatively constant level.

\* \* \* \* \*